US012697304B2

(12) United States Patent
Alhnan

(10) Patent No.: US 12,697,304 B2
(45) Date of Patent: Aug. 4, 2026

(54) SOLID DOSAGE FORM PRODUCTION

(71) Applicant: University of Lancashire, Preston (GB)

(72) Inventor: Mohamed Albed Alhnan, Preston (GB)

(73) Assignee: University of Lancashire, Preston (GB)

( * ) Notice: Subject to any disclaimer, the term of this patent is extended or adjusted under 35 U.S.C. 154(b) by 0 days.

(21) Appl. No.: 18/231,027

(22) Filed: Aug. 7, 2023

(65) Prior Publication Data

US 2024/0148657 A1 May 9, 2024

Related U.S. Application Data

(63) Continuation of application No. 15/508,538, filed as application No. PCT/GB2015/052595 on Sep. 8, 2015, now Pat. No. 11,771,655.

(30) Foreign Application Priority Data

Sep. 8, 2014 (GB) ..................................... 1415811
Feb. 6, 2015 (GB) ..................................... 1502041

(51) Int. Cl.
  *B33Y 70/00* (2020.01)
  *A61K 9/00* (2006.01)
  (Continued)

(52) U.S. Cl.
  CPC .......... *A61K 9/2095* (2013.01); *A61K 9/0087* (2013.01); *A61K 47/10* (2013.01);
  (Continued)

(58) Field of Classification Search
  None
  See application file for complete search history.

(56) References Cited

U.S. PATENT DOCUMENTS 5,121,329 A    6/1992   Crump
5,204,055 A    4/1993   Sachs et al.
(Continued)

FOREIGN PATENT DOCUMENTS

CN    1386089 A    12/2002
CN    1709222 A    12/2005
(Continued)

OTHER PUBLICATIONS

M. M. Crowley et al., "Pharmaceutical Applications of Hot-Melt Extrusion: Part I", in Drug Development and Industrial Pharmacy, 33: 9, pp. 909-926, 2007 (Year: 2207).*
(Continued)

*Primary Examiner* — Mohammad M Ameen
(74) *Attorney, Agent, or Firm* — ArentFox Schiff LLP

(57) ABSTRACT

The present invention utilizes 3D printing technology, specifically fused filament fabrication (FFF) 3D printing, to produce solid dosage forms, such as pharmaceutical tablets. The production process utilizes novel printing filaments, typically on a spool, which contain the active ingredient. Such active-containing filaments have proved to be extremely robust and the principles outlined in the present disclosure provide access to a variety of viable formulations directly from a 3D printer. This, for the first time, affords a viable means for the in situ (e.g. within a pharmacy) 3D printing of personalized medicines tailored to a patient's needs. The invention also relates to purpose-built software for operating the printing apparatus, as well as local, national and global systems for monitoring the real time operation of a plurality of printing apparati to enable facile detection of malfunctions, thereby making regulatory approval viable and facilitating regulatory compliance.

22 Claims, 35 Drawing Sheets

(51) Int. Cl.

| | |
|---|---|
| *A61K 9/20* | (2006.01) |
| *A61K 47/10* | (2017.01) |
| *A61K 47/32* | (2006.01) |
| *A61K 47/38* | (2006.01) |
| *B29C 64/118* | (2017.01) |
| *B29C 64/209* | (2017.01) |
| *B29C 64/245* | (2017.01) |
| *B29C 64/314* | (2017.01) |
| *B29C 64/393* | (2017.01) |
| *B33Y 50/02* | (2015.01) |
| *B29K 105/00* | (2006.01) |
| *B29L 31/00* | (2006.01) |
| *B33Y 30/00* | (2015.01) |

(52) U.S. Cl.
CPC .............. *A61K 47/32* (2013.01); *A61K 47/38* (2013.01); *B29C 64/118* (2017.08); *B29C 64/209* (2017.08); *B29C 64/245* (2017.08); *B29C 64/314* (2017.08); *B29C 64/393* (2017.08); *B33Y 50/02* (2014.12); *B33Y 70/00* (2014.12); *B29K 2105/0035* (2013.01); *B29L 2031/753* (2013.01)

(56) References Cited

U.S. PATENT DOCUMENTS

| | | | | |
|---|---|---|---|---|
| 5,340,433 A | * | 8/1994 | Crump | B22F 3/115 |
| | | | | 156/218 |
| 5,490,962 A | * | 2/1996 | Cima | A61K 9/1647 |
| | | | | 264/41 |
| 7,374,712 B2 | | 5/2008 | Swanson et al. | |
| 7,892,221 B2 | | 2/2011 | Santini et al. | |
| 2003/0198677 A1 | | 10/2003 | Pryce-Lewis et al. | |
| 2004/0005360 A1 | | 1/2004 | Wang et al. | |
| 2007/0071813 A1 | * | 3/2007 | Ahmed | A61P 25/22 |
| | | | | 264/109 |
| 2008/0111282 A1 | * | 5/2008 | Xie | B33Y 10/00 |
| | | | | 264/401 |
| 2013/0209600 A1 | | 8/2013 | Tow | |
| 2014/0117585 A1 | | 5/2014 | Douglas et al. | |
| 2014/0252684 A1 | | 9/2014 | Swanson et al. | |
| 2014/0259652 A1 | | 9/2014 | Pushpala et al. | |

FOREIGN PATENT DOCUMENTS

| | | | |
|---|---|---|---|
| CN | 101199497 A | 6/2008 | |
| CN | 103877053 A | 6/2014 | |
| WO | 1995011007 A1 | 4/1995 | |
| WO | 2009088995 A1 | 7/2009 | |
| WO | WO - 2014/075185 A1 * | 5/2014 | |

OTHER PUBLICATIONS

S.A. Khaled et al., "Desktop 3D printing of controlled release pharmaceutical bilayer tablets", in International Journal of Pharmaceutics, vol. 461 (2014), pp. 105-111 (Year: 2014).*

Safety Data Sheet Cat# BTNM-0023, G-Bioscience, 2012 (Year: 2012).*

Chen et al., "Preparation and characterization of biodegradable PLA polymeric blends," Biomaterials, vol. 24, pp. 1167-1173 (2003).

Cho et al., "Methods for Distributed Design and Fabrication of Parts with Local Composition Control," Proceedings of the NSF Design and Manufacturing Grantees Conference (2000).

Crowley et al., "Pharmaceutical Applications of Hot-Melt Extrusion: Part I," Drug Development and Industrial Pharmacy, vol. 33:9, pp. 909-926 (2007).

Dash et al., "Solid-State Properties of Tobramycin," Pharmaceutical Research, vol. 8, No. 9, pp. 1159-1165 (1991).

Dierickz et al., "Co-Extrusion as Manufacturing Technique for Fixed-Dose Combination Mini-Matrices," European Journal of Pharmaceutics and Biopharmaceutics, vol. 81(3), pp. 683-689 (2012).

Forster et al., "Characterization of Glass Solutions of Poorly Water-Soluble Drugs Produced by Melt Extrusion with Hydrophilic Amorphous Polymers," Journal of Pharmacy and Pharmacology, vol. 53, pp. 303-315 (2001).

Goyanes, A., "Fused-Filament 3D Printing (3DP) for Fabrication of Tablets," International Journal of Pharmaceutics, vol. 476, pp. 88-92, (2014).

Hsiao et al., "3D printing of oral drugs: a new reality or hype?" Expert Opinion on Drug Delivery, 15:1, 1-4 pages (2018).

Interlocutory decision in Opposition proceedings (Art. 101(3)(a) and 106(2) EPC), issued Dec. 23, 2021.

Kastra et al., "Oral dosage forms fabricated by three dimensional printing," J Control Release 66(1):1-9 pages, (May 2000).

Khaled et al., "Desktop 3D printing of controlled release pharmaceutical bilayer tablets," International Journal of Pharmaceutics, vol. 461, pp. 105-111 (2014).

Maniruzzaman et al., "Dissolution Enhancement of Poorly Water-Soluble APIs Processed by Hot-Melt Extrusion Using Hydrophilic Polymers," Drug Development and Industrial Pharmacy 39(2), pp. 218-227 (2013).

Masood, S.H., "Application of Fused Deposition Modelling in Controlled Drug Delivery Devices," Assembly Automation, vol. 27, iss. 3, pp. 215-221 (2007).

Miller et al., "Physical Characterization of Tobramycin Inhalation Powder: I. Rational Design of a Stable Engineered-Particle Formulation for Delivery to the Lungs," Mol Pharmaceutics, vol. 12, pp. 2582-2593 (2015).

MIT News (Sep. 14, 2011) "Printing off the paper", 5 pages.

Notice of Opposition to the grant of European Patent EP3191084B1 titled "Solid Dosage Form Production," dated Aug. 27, 2019.

Park et al., "Integration of surface modification and 3D fabrication techniques to prepare patterned poly L-lactide) substrates allowing regionally selective cell adhesion," J Biomater Sci Polym Ed. 9(2):89-110 pages (1998).

Pietrzak et al., "A flexible-dose dispenser for immediate and extended release 3D printed tablets," Eur. J. Pharma. & Biopharma, vol. 96, pp. 380-387, (Oct. 2015).

Rowe et al., "Multimechanism oral dosage forms fabricated by three dimensional printing," J Control Release 66(1):11-17 pages (May 2000).

Safety Data Sheet Cat# BTNM-0023, G-Bioscience (2012).

Sandler et al., "Towards Fabrication of 3D Printed Medical Devices to Prevent Biofilm Formation," International Journal of Pharmaceutics 459(1-2):62-64 (2014).

Summons to Attend Oral Proceedings, dated Feb. 1, 2021, in connection with EP Patent No. 3191084B1, (15 pages).

Zhang et al., "Open-Source 3D-Printable Optics Equipment," in PLOS one 8(3):e59840, DOI:10.1371/journal.pone.0059840 (2013).

Shah et al., "Amorphous Solid Dispersions, Theory and Practice," Springer (2014).

Manual of "UP!"-printer used in N. Sandler ("Sandler") et al., "Towards Fabrication of 3D Printed Medical Devices to Prevent Biofilm Formation," International Journal of Pharmaceutics, vol. 459, pp. 62-64 (2014).

Wikipedia, "Fluorescein," URL: https://en.wikipedia.org/wiki/Fluorescein, 18:32 (Aug. 26, 2019).

Wikipedia, "Guaifenesin," URL: https://de.wikipedia.org/wiki/Guaifenesin, 18:34 (Aug. 26, 2019).

Wikipedia, "Nitrofurantoin," URL: https://en.wikipedia.org/wiki/Nitrofurantoin, 18:35 (Aug. 26, 2019).

Guerin, D., "Louisiana Tech researchers use 3D printers to create custom medical implants," Louisiana Tech University, [online] Retrieved from URL: http://news.latech.edu/2014/08/20/louisiana-tech-researchers-use-3d-printers-to-create-custom-medial-implants/ (accessed: May 3, 2015), 3 pages.

* cited by examiner

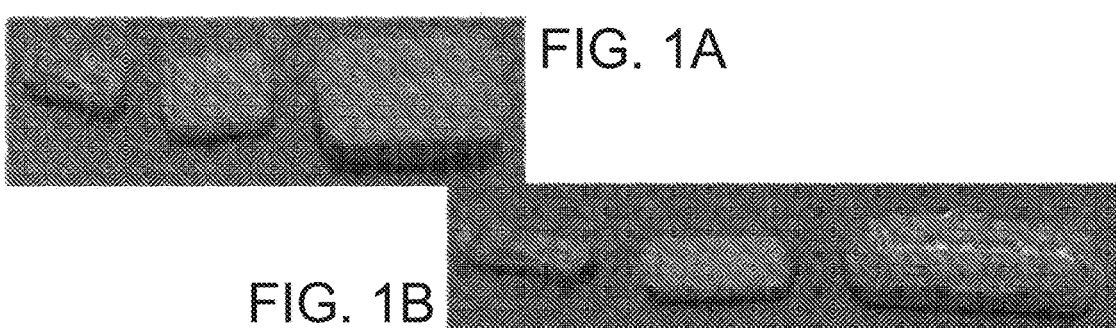
FIG. 1A
FIG. 1B
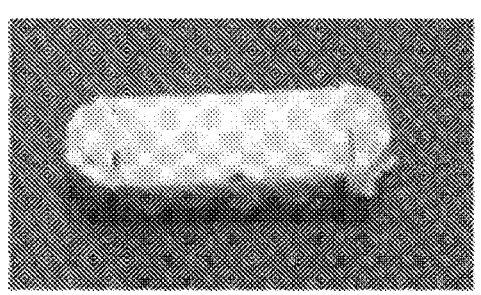
FIG. 2A
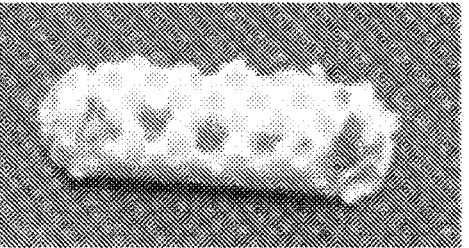
FIG. 2B
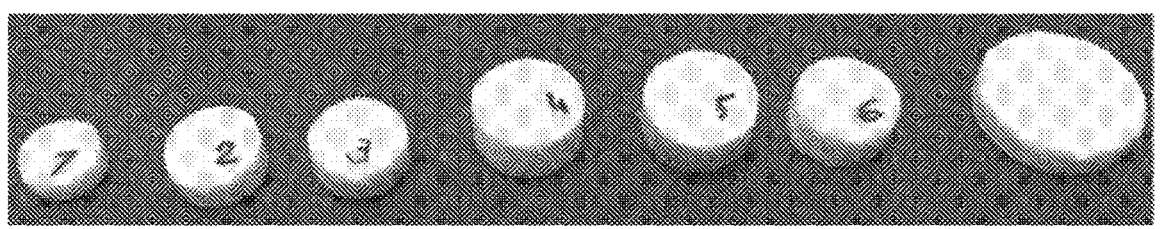
FIG. 3
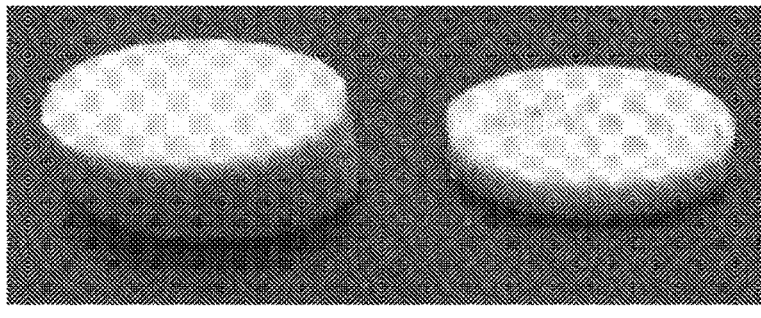
FIG. 4

FIG. 5A
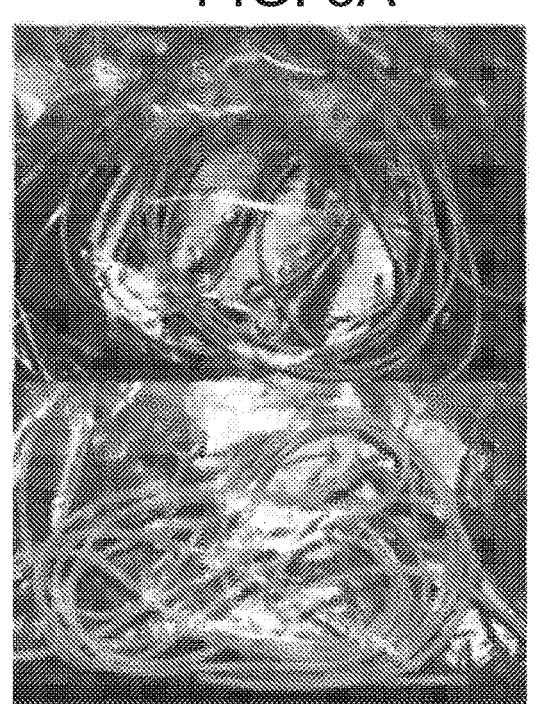
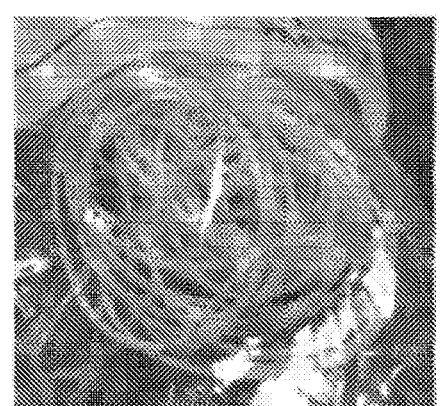
FIG. 5C
FIG. 5B
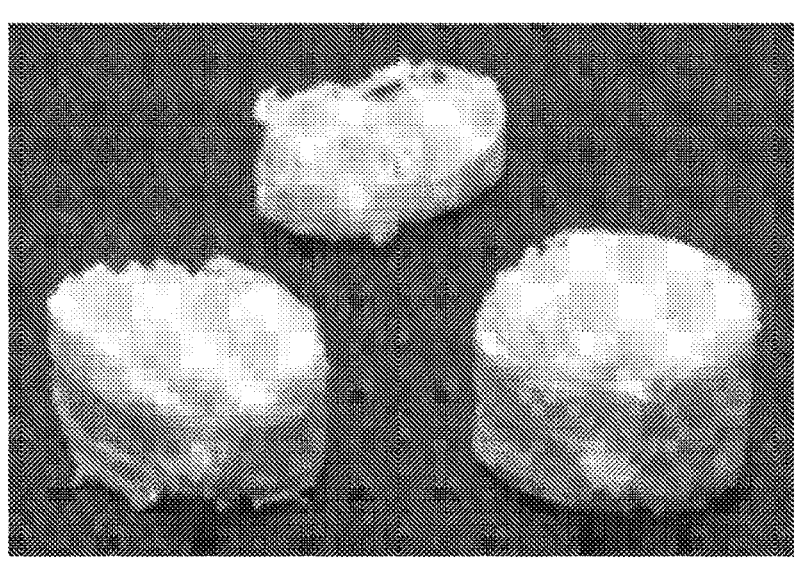
FIG. 6

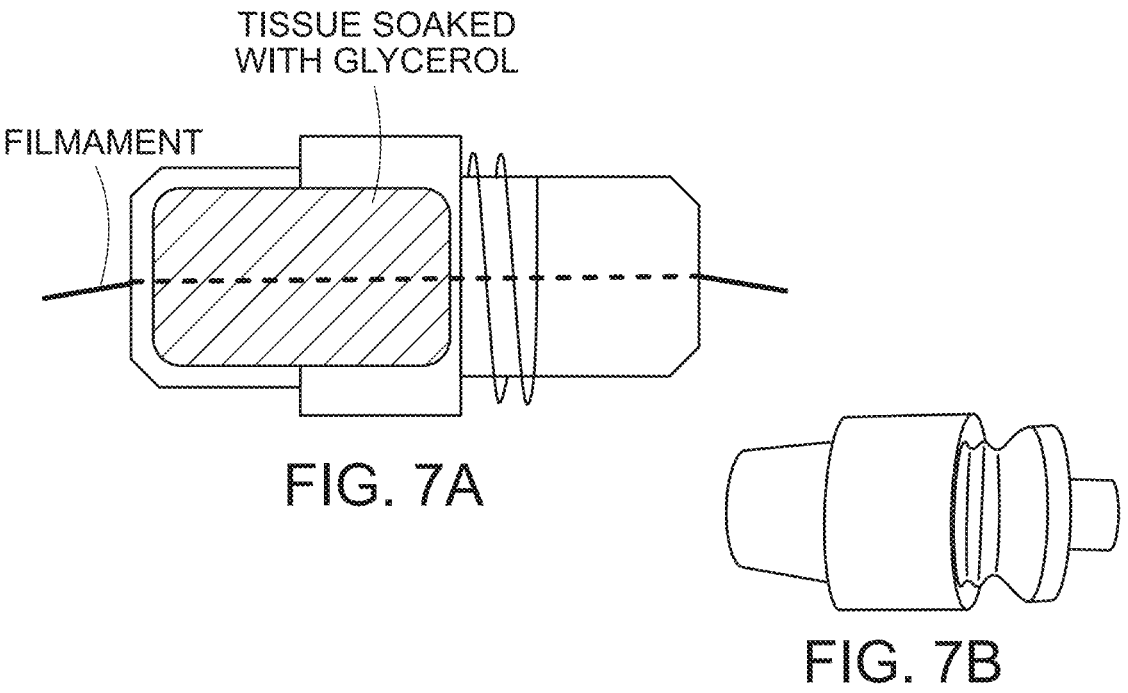
FIG. 7A
FIG. 7B
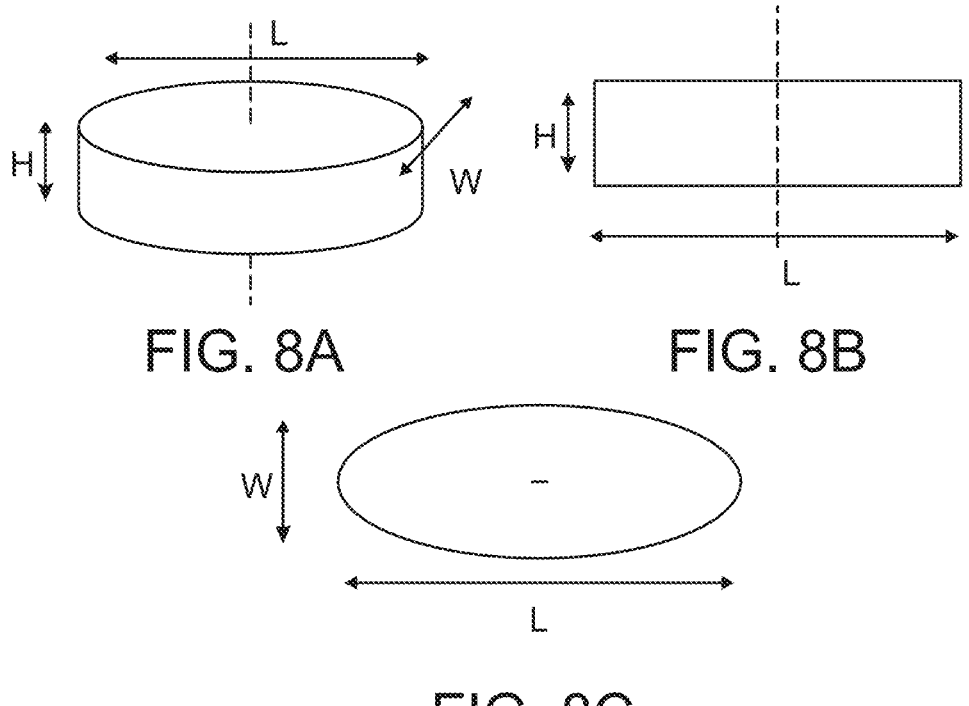
FIG. 8A                    FIG. 8B
FIG. 8C FIG. 13A 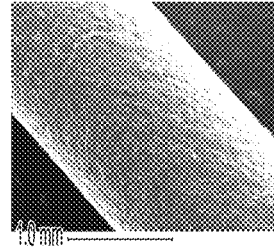 FIG. 13B
FIG. 13C 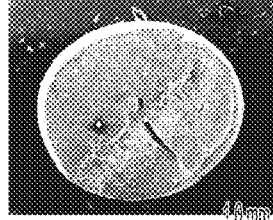 FIG. 13D
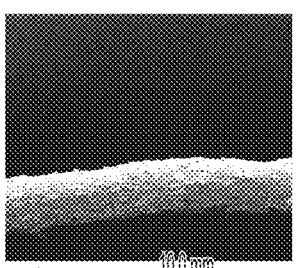
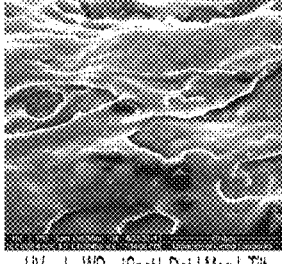
FIG. 14A         FIG. 14B
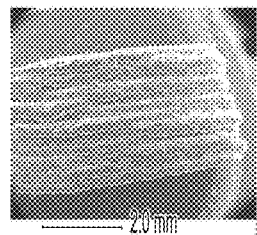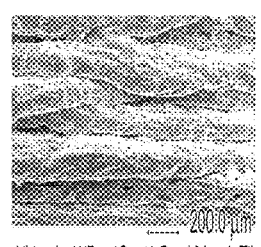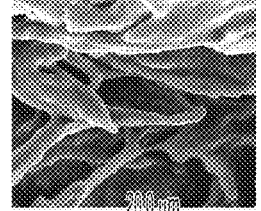
FIG. 15A      FIG. 15B      FIG. 15C

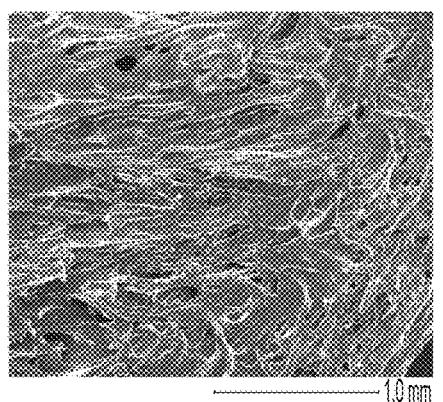

| HV | WD | Spot | Det | Mag | Tilt |
|---|---|---|---|---|---|
| 20.0 kV | 6.9 mm | 4.0 | ETD | 50x | -0.9° |
| 6/18/2014 | | | University of | | |
| 11:37:55 AM | | | Central Lancashire | | |

FIG. 16A

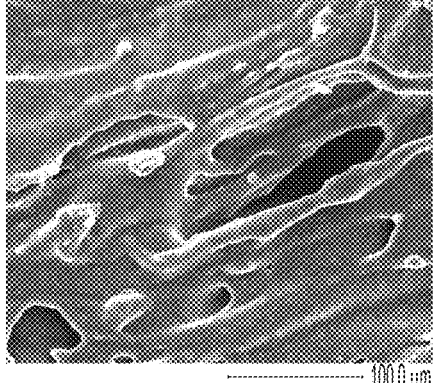

| HV | WD | Spot | Det | Mag | Tilt |
|---|---|---|---|---|---|
| 20.0 kV | 7.1 mm | 4.0 | ETD | 400x | -0.9° |
| 6/18/2014 | | | University of | | |
| 11:40:53 AM | | | Central Lancashire | | |

FIG. 16B

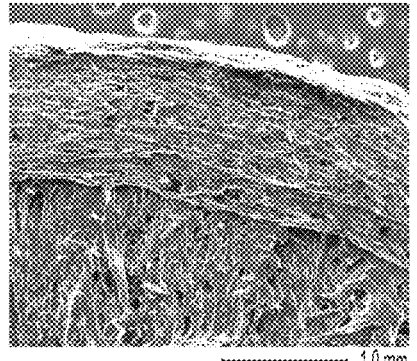

| HV | WD | Spot | Det | Mag | Tilt |
|---|---|---|---|---|---|
| 20.0 kV | 9.1 mm | 4.0 | ETD | 40x | -0.9° |
| 6/18/2014 | | | University of | | |
| 10:26:53 AM | | | Central Lancashire | | |

FIG. 17A

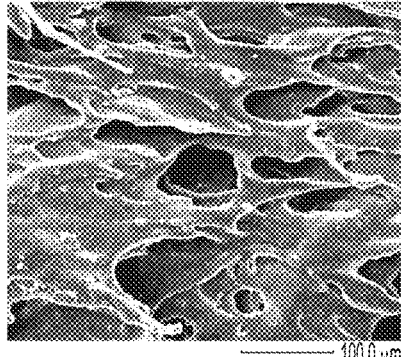

| HV | WD | Spot | Det | Mag | Tilt |
|---|---|---|---|---|---|
| 20.0 kV | 9.7 mm | 4.0 | ETD | 300x | -0.9° |
| 6/18/2014 | | | University of | | |
| 10:34:32 AM | | | Central Lancashire | | |

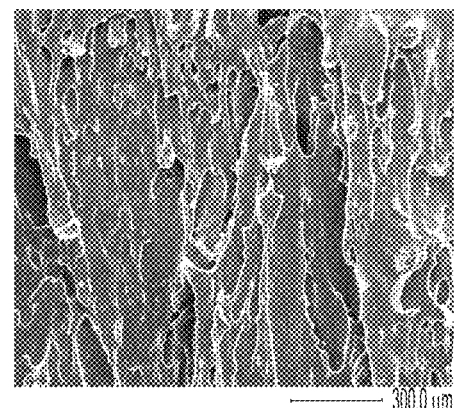

| HV | WD | Spot | Det | Mag | Tilt |
|---|---|---|---|---|---|
| 20.0 kV | 9.4 mm | 4.0 | ETD | 15x | -0.9° |
| 6/18/2014 | | | University of | | |
| 10:39:29 PM | | | Central Lancashire | | |

FIG. 51                    FIG. 52

2Theta (Coupled TwoTheta/Theta) WL=1.54060

FIG. 69A  FIG. 69B
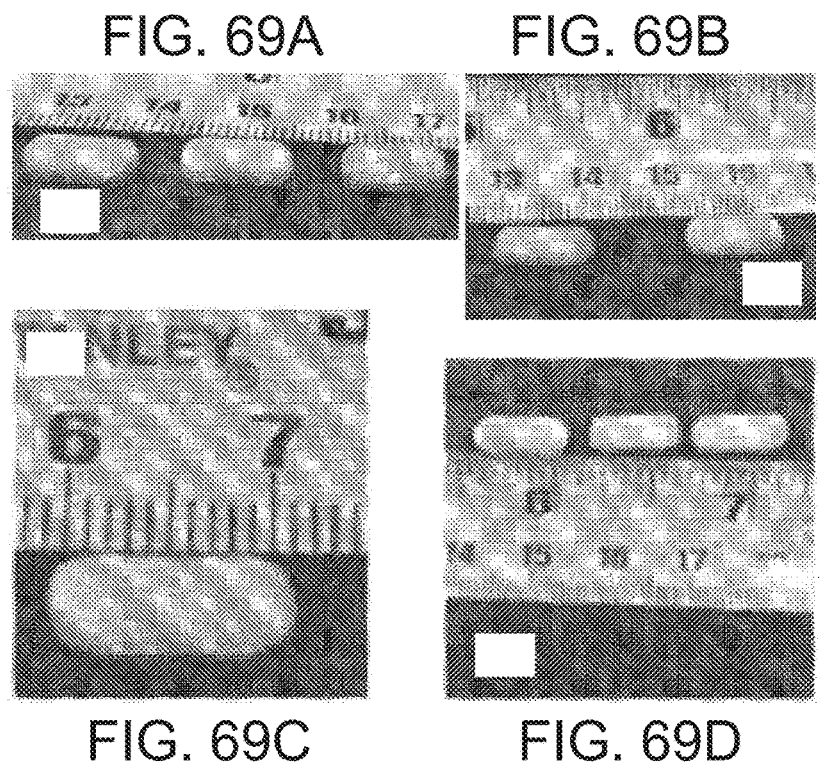
FIG. 69C  FIG. 69D
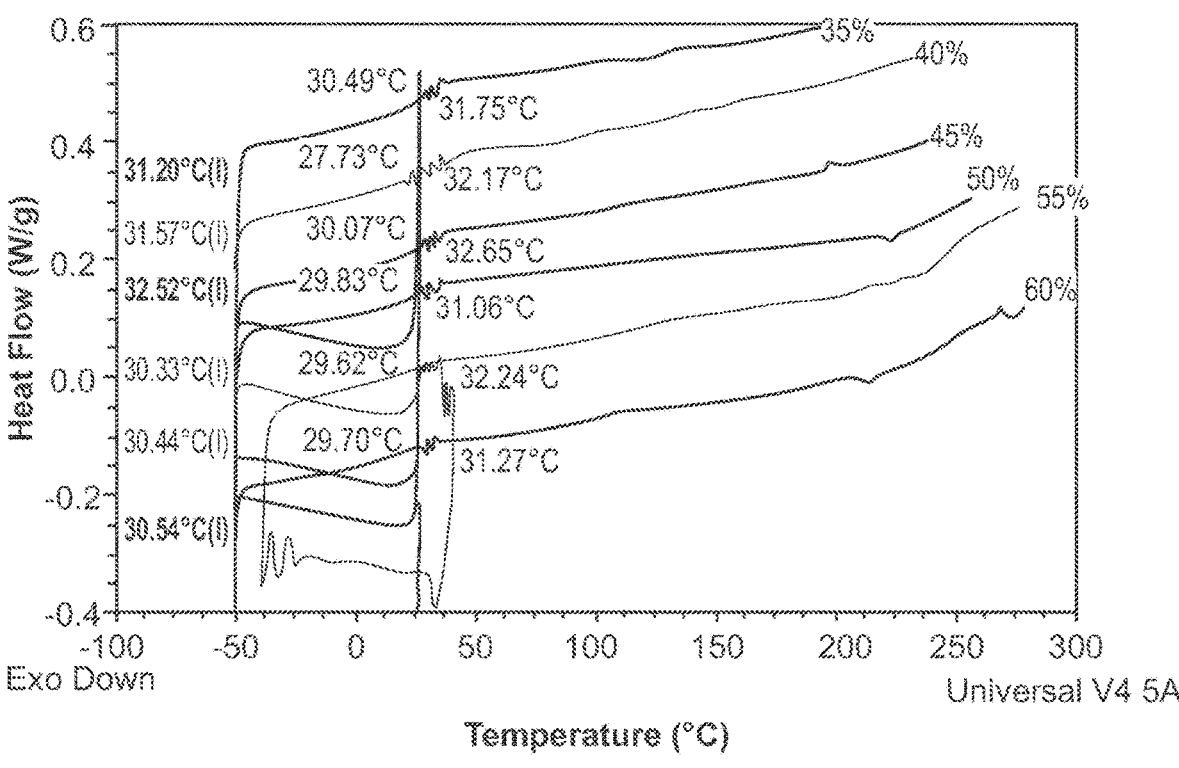
FIG. 70

FIG. 71A
FIG. 71B
FIG. 71C
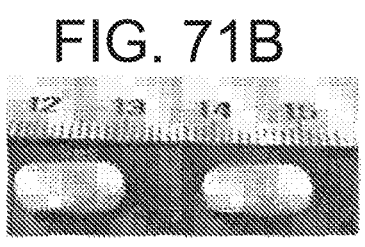
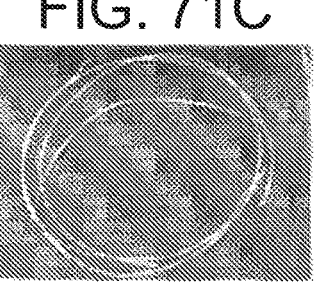
FIG. 71D
FIG. 71E
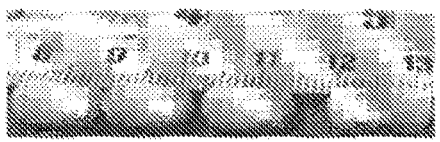
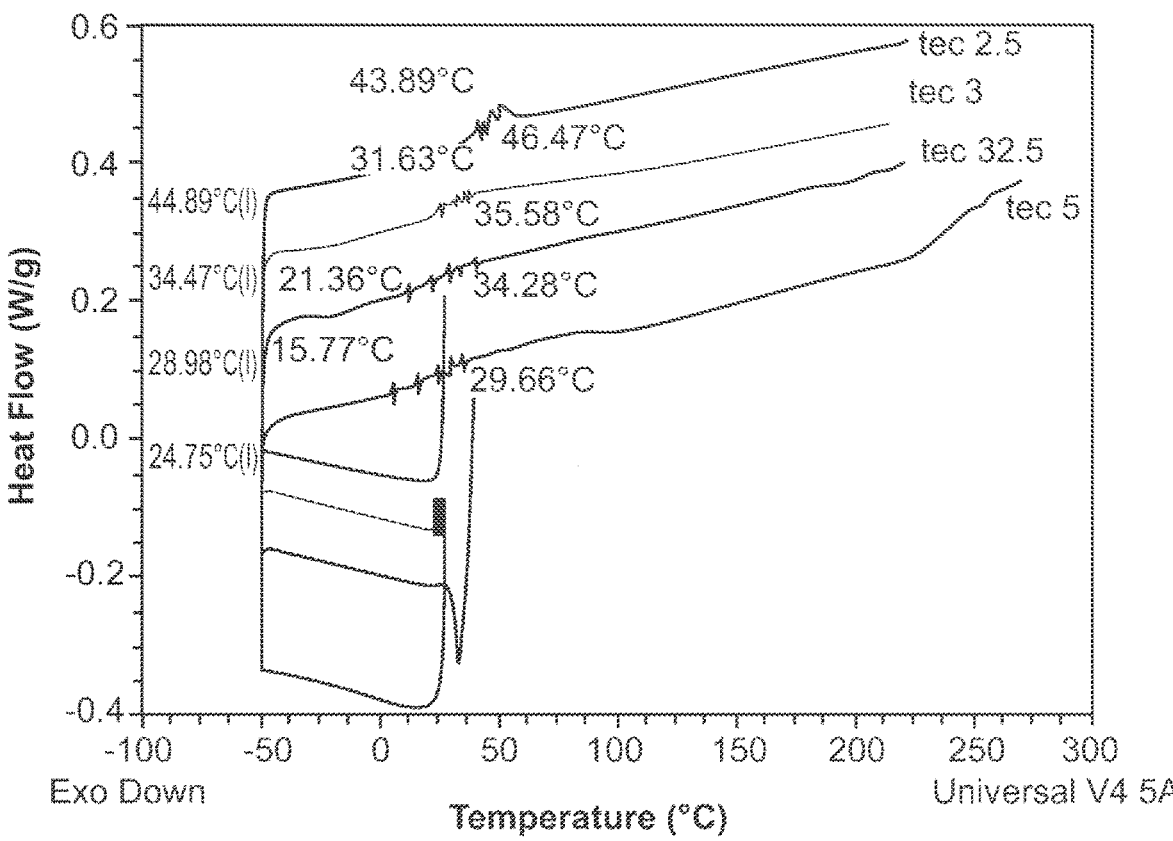
FIG. 72

FIG. 73A     FIG. 73B     FIG. 73C
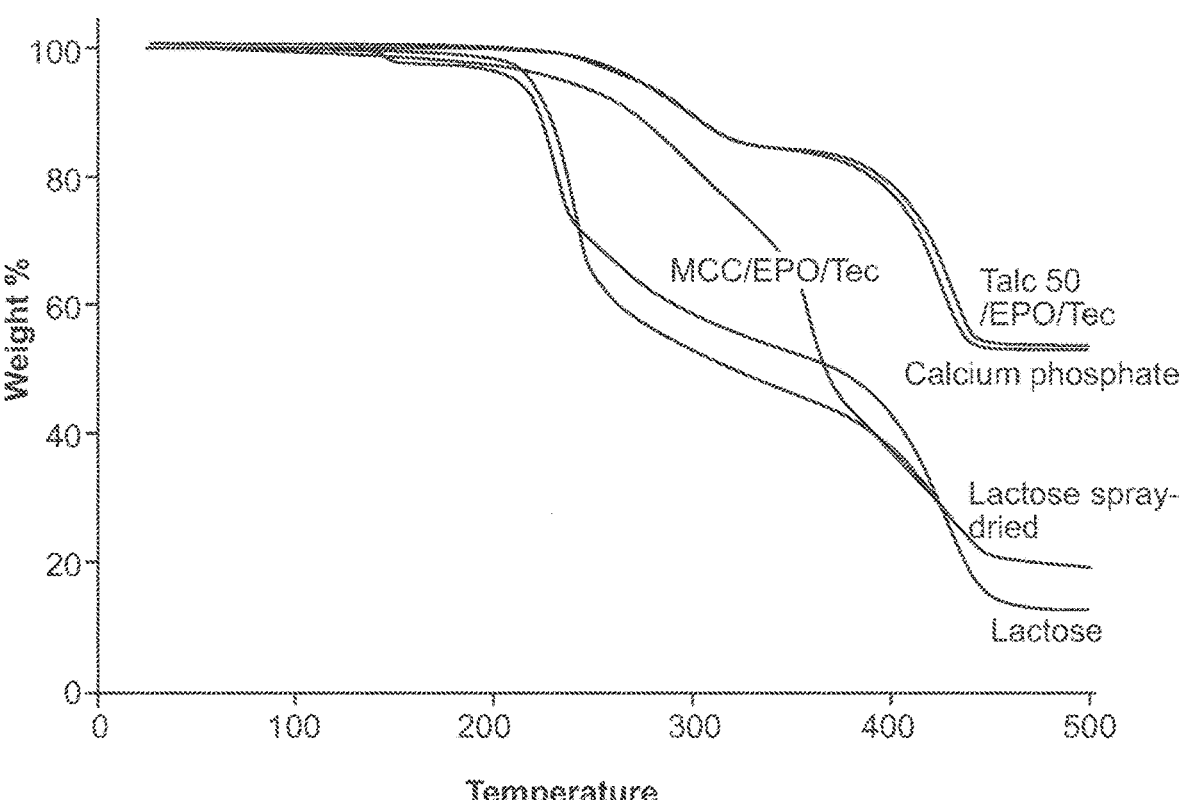
FIG. 74

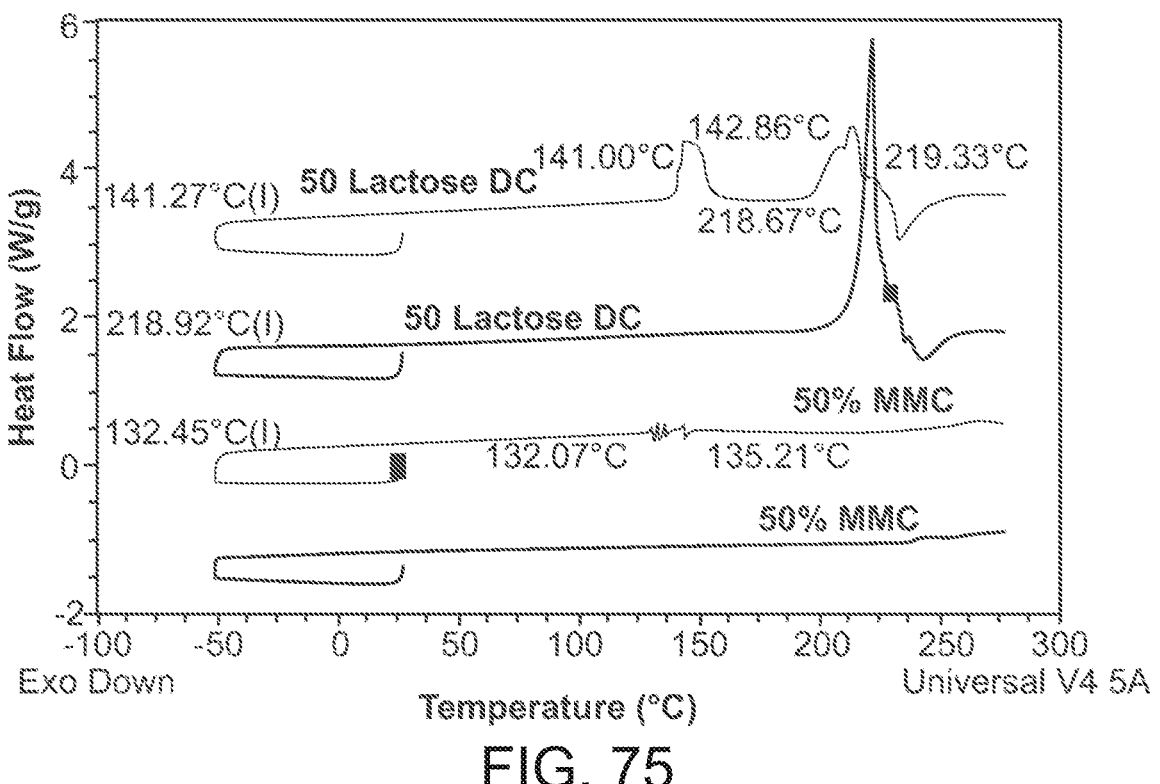
FIG. 75
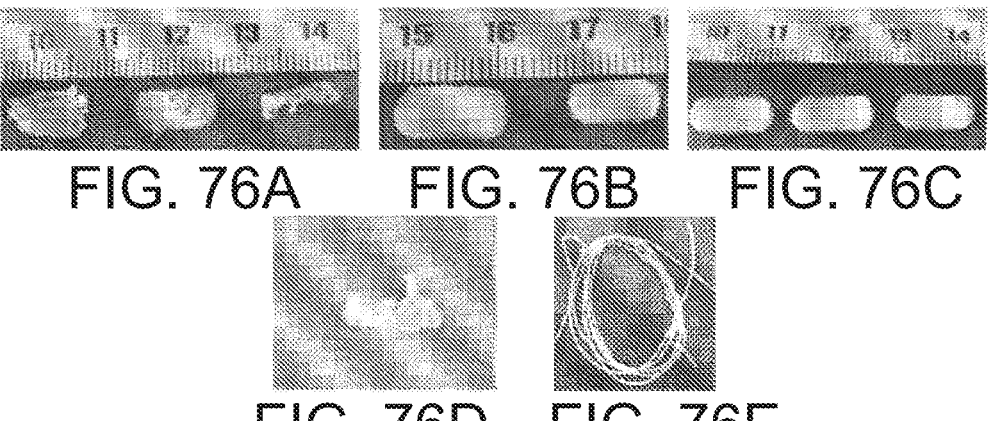
FIG. 76A     FIG. 76B     FIG. 76C
FIG. 76D    FIG. 76E 10.00 mm                    3.64 mm 3.96 mm

SOLID DOSAGE FORM PRODUCTION

CROSS-REFERENCE TO RELATED APPLICATIONS

This U.S. application is a continuation of U.S. application Ser. No. 15/508,538 filed Mar. 3, 2017, which is a U.S. national stage application under 35 U.S.C. 371 of International Application No. PCT/GB2015/052595 filed on Sep. 8, 2015, which in turn claims priority to Great Britain Patent Application No. 1502041.5 filed on Feb. 6, 2015, and claims priority to Great Britain Patent Application No. 1415811.7 filed on Sep. 8, 2014. Each of the above-described applications is hereby incorporated herein by reference in their entirety.

INTRODUCTION

The present invention relates to a solid dosage form printing apparatus (and method for its use) in the production of solid dosage forms, such as tablets. The invention also relates to solid dosage forms obtainable by such printing methods and apparatus, a solid dosage form package, relevant active-containing printing elements and other printing elements (and processes for their manufacture), a kit of parts, a computer for controlling the relevant printing process (and software and computer-implemented methods connected therewith), and a system for collecting data relating to the solid dosage form production process (and databases associated therewith).

BACKGROUND

The production and consumption of medicines, nutraceuticals, and food supplements (collectively referred to herein as "healthcare dosage forms"), in solid dosage form (e.g. tablets, implants, etc.) is ever increasing, not least due to an increased reliance on such products by national health services and the like in an increasingly health-conscious society. Where possible, solid dosage forms tend to be most preferred, relative to other formulations (e.g. injectable liquid formulations), due to their ease of administration (i.e. usually orally) which gives rise to better patient compliance, storability and transportability (low space requirements and ease of packaging), high stability (longer lifetimes—less degradation). However, despite the significant advantages of solid dosage forms over other dosage forms, they are often more onerous to manufacture (in terms of the number of both ingredients and processing steps) and are generally only cost effective to produce on large scale, meaning large manufacturing facilities with sophisticated equipment is usually required. These manufacturing limitations have a detrimental impact on consumer choice and/or the customizability of healthcare dosage forms since, for example, it is impractical and non-cost effective to mass produce a wide variety of different dosages for a given medicament via conventional manufacturing techniques. Consumers (e.g. patients) and healthcare professionals (e.g. doctors, pharmacists) must therefore make the best of the limited variety of dosages available, as dictated by the suppliers rather than a consumer's need.

Since the advent of 3-dimensional (3D) printing in the early 1980s, a number of researchers have attempted to make viable use of 3D printing technology to fabricate healthcare solid dosage forms. For instance, for well over a decade, MIT and Therics, Inc. have collaborated in the development of viable pill printing machines which utilize 3D printers to print solid pharmaceutical dosage forms in situ. The technology forms pills via a multi-layered 3D printing process involving precise printing of doses of a liquid drug solution onto thin layers of fine powder before further layers are then applied (e.g. further powder, binder, etc.). Examples of such processes are disclosed in earlier publications, such as WO95/11007 (MASSACHUSETTS INSTITUTE OF TECHNOLOGY) and WO03/092633 (THERICS, INC.), which describe inter alia the production of solid dosage forms having various structures and drug release profiles. However, regulatory approval (e.g. by the FDA or MHRA) for such 3D drug printing systems still remains elusive, and for the time being they are suitable only for low dose drug products, partly owing to the limited solubility of many drugs within the relevant ink solutions. As such, patient choice would still be very limited, as would the options of a doctor or pharmacist in providing specifically-tailored treatments. Furthermore, resolution and shape of the solid dosage form still remains an issue. However, a particular issue with prior art 3D printing systems such as these is that the large number of different ingredients (and thus different printing cartridges etc.) needed to produce viable dosage forms imparts a high degree of complexity, user-unfriendliness, which in turn increases the likelihood of manufacturing errors, machine breakdown and malfunction, quality control variation, and regulatory viability (i.e. the FDA is less likely to approve drug printing systems which are prone to too many variables that may impact on the quality of the drug product). A further issue is the poor stability of some drug substances in liquid ink formulations. This can severely limit the shelf-life of the drug source, thus posing large regulatory and cost issues.

It is therefore an object of the invention to provide improved methods of producing solid dosage forms, and to suitable solve at least one problem inherent in the prior art.

Another object is to provide a method of producing dose customizable solid dosage forms on-demand, with one or more advantages selected from: high dose of actives (or higher concentrations in the solid dosage form), minimal input and output variables, minimal input ingredients or elements, minimal complexity, customizable drug release profiles, maximum storage stability for both input materials (especially anything containing the active substance, e.g. drug) and products, and a system that is suitable for regulatory approval and which may be used in pharmacies (and reduce the workload or manual operations of a pharmacy) or other approved customized drug manufacturing facilities.

Another object of the invention is to provide a means to allow more aesthetic customization of solid dosage forms (e.g. colour and shape) without loss of resolution or functional and structural integrity (e.g. novelty shapes for children may facilitate patient compliance).

Another object is to provide a method of producing solid dosage forms to facilitate prototyping and formulation research and development (e.g. as a development tool in the pharmaceutical industry).

SUMMARY OF THE INVENTION

According to a first aspect of the present invention there is provided a solid dosage form printing apparatus for printing a solid dosage form comprising an active ingredient, the apparatus comprising:
  a fused filament fabrication (FFF) 3D printer;
  a build platform upon which the solid dosage form is printable (i.e. upon which the solid dosage form may be built);

an active ingredient-containing printing filament, wherein the active ingredient-containing printing filament consists of, consists essentially of, or comprises an active ingredient-containing filament composition comprising the active ingredient (or a precursor thereof—e.g. a precursor which is transformed into the active ingredient during 3D printing and/or further processing) and optionally (and most suitably) an active ingredient carrier;

optionally one or more further printing filaments, each suitably independently consisting of, consisting essentially of, or comprising a further filament composition; and a computer for controlling the FFF 3D printer and optionally also the build platform.

(wherein the FFF 3D printer is suitably operable via the computer, suitably a computer running pursuant to specialist solid dosage form printing software, and optionally also to one or more databases, to print the solid dosage form upon the build platform, suitably via a process involving the printing and/or extrusion of the active ingredient-containing printing filament and optionally also involving the printing and/or extrusion of one or more further printing filaments). Any one or more of the build platform, active ingredient-containing printing filament, further printing filaments, and/or computer, and/or any part thereof, may suitably be integrated within or form a part of the FFF 3D printer.

According to a further aspect of the present invention there is provided a method of printing a solid dosage form (or method of using the apparatus as defined herein) comprising an active ingredient, the method comprising:

a) providing a solid dosage form printing apparatus (suitably as defined herein, or suitable variation thereof) for printing a solid dosage form comprising an active ingredient, the apparatus comprising:

a fused filament fabrication (FFF) 3D printer;

a build platform upon which the solid dosage form is printable;

an active ingredient-containing printing filament, wherein the active ingredient-containing printing filament consists of, consists essentially of, or comprises an active ingredient-containing filament composition comprising the active ingredient (or a precursor thereof—e.g. a precursor which is transformed into the active ingredient during 3D printing and/or further processing) and optionally (and most suitably) an active ingredient carrier;

optionally one or more further printing filaments, each suitably independently consisting of, consisting essentially of, or comprising a further filament composition;

a computer for controlling the FFF 3D printer and optionally also the build platform;

b) operating the FFF 3D printer to print the solid dosage form (or precursor therefor) upon the build platform via a process (suitably computer-implemented) comprising:

i) printing (and/or extruding) the active ingredient-containing printing filament (or printing/extruding an active ingredient-containing filament composition derived from the active ingredient-containing printing filament); and ii) optionally printing (and/or extruding) one or more further printing filaments (or printing/extruding one or more further filament compositions derived from the one or more further printing filaments);

c) optionally performing one or more further processing steps (with or without the FFF 3D printer; e.g. coating or otherwise modifying the surface, shape, or properties of the solid dosage form).

According to a further aspect of the invention, there is provided, a solid dosage form obtainable by, obtained by, or directly obtained by the method of printing a solid dosage form as defined herein.

According to a further aspect of the invention, there is provided a solid dosage form comprising an active ingredient-containing filament composition, and optionally one or more further filament compositions.

According to a further aspect of the invention, there is provided a multilayered solid dosage form comprising one or more layers of an active ingredient-containing filament composition, and optionally one or more layers of one or more further filament compositions.

According to a further aspect of the invention, there is provided a solid dosage form comprising extruded active ingredient-containing printing filament, and optionally extruded one or more further printing filaments.

According to a further aspect of the invention, there is provided a solid dosage form comprising one or more layers of extruded active ingredient-containing printing filament, and optionally one or more layers of extruded one or more further printing filaments.

According to a further aspect of the invention, there is provided a method of producing a solid dosage form package, the method comprising packaging one or more solid dosage forms as defined herein, wherein the one or more solid dosage forms are optionally the same or different.

According to a further aspect of the invention, there is provided a solid dosage form package, obtainable by, obtained by, or directly obtained by the method of producing a solid dosage form package as defined herein.

According to a further aspect of the invention, there is provided a solid dosage form package, comprising one or more solid dosage forms, as defined herein, within a packaging.

According to a further aspect of the invention, there is provided an active ingredient-containing printing filament (suitably for fused filament fabrication 3D printing), wherein the active ingredient-containing printing filament consists of, consists essentially of, or comprises an active ingredient-containing filament composition comprising an active ingredient (or a precursor thereof—e.g. a precursor which is transformed into the active ingredient during 3D printing and/or further processing) and optionally (and most suitably) an active ingredient carrier;

suitably wherein the active ingredient is selected from a pharmaceutical, a nutraceutical, or a food supplement;

suitably wherein the active ingredient carrier is or comprises one or more pharmaceutically or nutraceutically acceptable polymeric carriers.

According to a further aspect of the invention, there is provided an active ingredient-containing filament composition comprising an active ingredient (or a precursor thereof—e.g. a precursor which is transformed into the active ingredient during 3D printing and/or further processing) and optionally (and most suitably) an active ingredient carrier;

suitably wherein the active ingredient is selected from a pharmaceutical, a nutraceutical, or a food supplement;

suitably wherein the active ingredient carrier is or comprises one or more pharmaceutically or nutraceutically acceptable polymeric carriers.

According to a further aspect of the invention, there is provided an active ingredient-containing printing filament (suitably for fused filament fabrication 3D printing), comprising an active ingredient and optionally (and most suitably) an active ingredient carrier;

suitably wherein the active ingredient is selected from a pharmaceutical, a nutraceutical, or a food supplement;

suitably wherein the active ingredient carrier is or comprises one or more pharmaceutically or nutraceutically acceptable polymeric carriers.

According to a further aspect of the invention, there is provided a printing filament, a filament composition, or a solid dosage form comprising a meltable component and a non-meltable component. Suitably the meltable component has a melting point (or glass transition temperature) at or below 150° C., suitably at or below 100° C., suitably at or below 80° C. Suitably, the non-meltable component has a melting point at or above 150° C., suitably at or above 200° C., suitably at or above 500° C., suitably at or above 1000° C.

According to a further aspect of the invention, there is provided an active filament spool (suitably for fused filament fabrication 3D printing), comprising an active ingredient-containing printing filament as defined herein.

According to a further aspect of the invention, there is provided a method of preparing an active ingredient-containing filament composition, the method comprising mixing together (and optionally additionally melting or liquidizing together) an active ingredient and optionally (and most suitably) an active ingredient carrier.

According to a further aspect of the invention, there is provided an active ingredient-containing filament composition obtainable by, obtained by, or directly obtained by the method of preparing an active ingredient-containing filament composition as defined herein.

According to a further aspect of the invention, there is provided a method of preparing an active ingredient-containing printing filament, the method comprising mixing together an active ingredient and optionally (and most suitably) an active ingredient carrier to produce a premixture; melting (or liquidizing) the premixture to produce a melted (or liquidized) premixture; and extruding the melted (or liquidized) premixture to produce the active ingredient-containing printing filament.

According to a further aspect of the invention, there is provided an active ingredient-containing printing filament obtainable by, obtained by, or directly obtained by the method of preparing an active ingredient-containing printing filament as defined herein.

According to a further aspect of the invention, there is provided a method of preparing an active filament spool, the method comprising providing an active ingredient-containing printing filament as defined herein or preparing an active ingredient-containing printing filament by a method as defined herein; and coiling the active ingredient-containing printing filament around a spool.

According to a further aspect of the invention, there is provided an active filament spool obtainable by, obtained by, or directly obtained by the method of preparing an active filament spool as defined herein.

According to a further aspect of the invention, there is provided a further printing filament (suitably for fused filament fabrication 3D printing), wherein the further printing filament consists of, consists essentially of, or comprises a further filament composition comprising an active ingredient carrier for an active ingredient, and optionally one or more pharmaceutically or nutraceutically acceptable diluents or carriers;

suitably wherein the active ingredient is selected from a pharmaceutical, a nutraceutical, or a food supplement;

suitably wherein the active ingredient carrier is or comprises one or more pharmaceutically or nutraceutically acceptable polymeric carriers.

According to a further aspect of the invention, there is provided a further filament composition comprising an active ingredient carrier for an active ingredient, and optionally one or more pharmaceutically or nutraceutically acceptable diluents or carriers;

suitably wherein the active ingredient is selected from a pharmaceutical, a nutraceutical, or a food supplement;

suitably wherein the active ingredient carrier is or comprises one or more pharmaceutically or nutraceutically acceptable polymeric carriers.

According to a further aspect of the invention, there is provided a further printing filament (suitably for fused filament fabrication 3D printing), comprising an active ingredient carrier for an active ingredient, and optionally one or more pharmaceutically or nutraceutically acceptable diluents or carriers;

suitably wherein the active ingredient is selected from a pharmaceutical, a nutraceutical, or a food supplement;

suitably wherein the active ingredient carrier is or comprises one or more pharmaceutically or nutraceutically acceptable polymeric carriers.

According to a further aspect of the invention, there is provided a further filament spool (suitably for fused filament fabrication 3D printing), comprising a further printing filament as defined herein.

According to a further aspect of the invention, there is provided a method of preparing a further filament composition, the method comprising mixing together (and optionally additionally melting or liquidizing together) an active ingredient carrier for an active ingredient, and optionally one or more pharmaceutically or nutraceutically acceptable diluents or carriers.

According to a further aspect of the invention, there is provided a further filament composition obtainable by, obtained by, or directly obtained by the method of preparing a further filament composition as defined herein.

According to a further aspect of the invention, there is provided a method of preparing a further printing filament, the method comprising mixing together (and optionally additionally melting or liquidizing together) an active ingredient carrier for an active ingredient, and optionally one or more pharmaceutically or nutraceutically acceptable diluents or carriers, to produce a pre-mixture; melting (or liquidizing) the premixture to produce a melted (or liquidized) premixture; and extruding the melted (or liquidized) premixture to produce the further printing filament.

According to a further aspect of the invention, there is provided a further printing filament obtainable by, obtained by, or directly obtained by the method of preparing a further printing filament as defined herein.

According to a further aspect of the invention, there is provided a method of preparing a further filament spool, the method comprising providing a further printing filament as defined herein or preparing a further printing filament by a method as defined herein; and coiling the further printing filament around a spool.

According to a further aspect of the invention, there is provided a further filament spool obtainable by, obtained by, or directly obtained by the method of preparing a further filament spool as defined herein.

According to a further aspect of the invention, there is provided a kit of parts comprising an active ingredient-containing printing filament as defined herein, and optionally one or more further printing filaments as defined herein.

According to a further aspect of the invention, there is provided a kit of parts comprising an active filament spool as defined herein, and optionally one or more further filament spools as defined herein.

According to a first aspect of the present invention there is provided a solid dosage form printing apparatus for printing a solid dosage form comprising an active ingredient, the apparatus comprising:

a fused filament fabrication (FFF) 3D printer with a computer interface (whether for wired or wireless connection to a computer operable to control the FFF 3D printer);

a build platform upon which the solid dosage form is printable (i.e. upon which the solid dosage form may be built);

an active ingredient-containing printing filament, wherein the active ingredient-containing printing filament consists of, consists essentially of, or comprises an active ingredient-containing filament composition comprising the active ingredient (or a precursor thereof—e.g. a precursor which is transformed into the active ingredient during 3D printing and/or further processing) and optionally (and most suitably) an active ingredient carrier;

optionally one or more further printing filaments, each suitably independently consisting of, consisting essentially of, or comprising a further filament composition.

According to a further aspect of the invention, there is provided a fused filament fabrication (FFF) 3D printer or printing apparatus, for printing a solid dosage form comprising an active ingredient, the FFF 3D printer or printing apparatus comprising:

a computer interface (whether for wired or wireless connection to a computer operable to control the FFF 3D printer or printing apparatus);

an active filament spool comprising an active ingredient-containing printing filament as defined herein;

optionally one or more further filament spools independently comprising one or more further printing filaments as defined herein;

at least one extrusion nozzle through and from which a filament (or part thereof) can be extruded; and a conveyor for conveying the active ingredient-containing printing filament and any optional one or more further printing filaments to and/or through the at least one extrusion nozzle;

an extrusion nozzle heating element (for heating the at least one extrusion nozzle to melt (or otherwise liquidize) the or part of the active ingredient-containing printing filament and any optional one or more further printing filaments;

a build platform upon which the solid dosage form is printable (i.e. upon which the solid dosage form may be built).

Methods, and judicious variations thereof, of using an apparatus may be applied (as appropriate) to any of the apparati defined herein.

According to a further aspect of the present invention, there is provided a computer for operating a solid dosage form printing apparatus, a fused filament fabrication (FFF) 3D printer, or printing apparatus as defined herein, wherein the computer comprises:

an interface connecting or enabling connection of (whether wirelessly or wired) the computer to or within a solid dosage form printing apparatus, a fused filament fabrication (FFF) 3D printer, or printing apparatus as defined herein (suitably to allow the computer to control and/or operate the aforesaid); wherein the computer runs pursuant to solid dosage form printing software (and optionally also to one or more databases), which configures the computer to carry out the steps of:

i) obtaining information (e.g. through manual user input or via one or more databases, optionally in response to a user-inputted reference, such as a patient's name) regarding one or more parameters pertaining to the solid dosage form to be printed (e.g. the active ingredient, active loading/dose, shape, release profile, etc.);

ii) calculating the mass and/or volume of the solid dosage form to be printed based on the information obtained in step (i);

iii) controlling printing of and relative proportions of ingredients within (i.e. make up of the solid dosage form) the solid dosage form by, on the basis of the information obtained in step (i) and calculations performed in step (ii):

a. controlling printing, deposition, and/or extrusion, of an active ingredient-containing printing filament (or part thereof);

b. optionally controlling printing, deposition, and/or extrusion, of one or more further printing filaments (or part(s) thereof);

c. optionally controlling performance of one or more further processing steps).

According to a further aspect of the present invention, there is provided a computer-implemented method of operating a solid dosage form printing apparatus, a fused filament fabrication (FFF) 3D printer, or printing apparatus as defined herein, the method comprising:

operating a computer (with suitable data connections to the relevant printing apparatus, be them wired or wireless) running pursuant to solid dosage form printing software (and optionally also to one or more databases) to:

i) obtain information (e.g. through manual user input or via one or more databases, optionally in response to a user-inputted reference, such as a patient's name) regarding one or more parameters pertaining to the solid dosage form to be printed (e.g. the active ingredient, active loading/dose, shape, release profile, shape, colour, etc.);

ii) calculate the mass and/or volume of the solid dosage form to be printed based on the information obtained in step (i);

iii) control printing of and relative proportions of ingredients within (i.e. make up of the solid dosage form) the solid dosage form by, on the basis of the information obtained in step (i) and calculations performed in step (ii):

a. controlling printing, deposition, and/or extrusion, of an active ingredient-containing printing filament (or part thereof);

b. optionally controlling printing, deposition, and/or extrusion, of one or more further printing filaments (or part(s) thereof);

c. optionally controlling performance of one or more further processing steps).

According to a further aspect of the present invention, there is provided a computer program, comprising solid dosage form printing software code for performing the computer-implemented method defined herein (i.e. methods of operating a solid dosage form printing apparatus, a fused filament fabrication (FFF) 3D printer, or printing apparatus as defined herein) when the computer program is run on a computer.

According to a further aspect of the present invention, there is provided a computer-readable medium comprising solid dosage form printing software code executable otto cause a computer to perform the computer-implemented method defined herein (i.e. methods of operating a solid dosage form printing apparatus, a fused filament fabrication (FFF) 3D printer, or printing apparatus as defined herein) when the software code is executed on a computer.

According to a further aspect of the present invention, there is provided a system for collecting data relating to solid dosage form production (suitably with a solid dosage form printing apparatus, a fused filament fabrication (FFF) 3D printer, or printing apparatus as defined herein), the system comprising:

a network computer system;

a central production database associated with the network computer system;

one or more monitoring computers (whether they correspond with or are different from the computer(s) associated with and mediating the operation of respective printing apparati, be them local or remote from the associated printing apparatus) in communication with one or more solid dosage form printing apparati (or FFF 3D printers thereof), each of said monitoring computers being configured to collect production data relating to the operation of the one or more solid dosage form printing apparati (or FFF 3D printers) (optionally via sensors associated with the relevant printing apparatus or FFF 3D printers, which are configured to detect operational parameters and feedback (or transmit) said operational parameters to the relevant monitoring computer(s)), to enable monitoring of production of respective solid dosage forms;

associated with each of the one or more monitoring computers a communicator for communicating (or transmitting/receiving), via the network computer system, with the central production database to enable the central production database to log (or collect and/or store) collected production data (from the or each monitoring computer) relating to the operation of some or all of the one or more solid dosage form printing apprati (or FFF 3D printers) to enable central monitoring of production of some or all solid dosage forms;

optionally one or more analytical computers (optionally the same as one or more of the monitoring computers) configured or operable to analyse data communicated to the central production database and optionally trigger a response (e.g. data transfers and/or actions) based on an analysis of the data (e.g. alerts where an operational malfunction is recognised).

Any features, including optional, suitable, and preferred features, described in relation to any particular aspect of the invention may also be features, including optional, suitable and preferred features, of any other aspect of the present invention.

BRIEF DESCRIPTION OF THE DRAWINGS

For a better understanding of the invention, and to show how embodiments of the same are put into effect, reference is now made, by way of example, to the following diagrammatic drawings, in which:

FIG. 1A and FIG. 1B show top and bottom projection views of ABS-based model tablets produced using an ABS filament.

FIG. 2A and FIG. 2B show top and bottom projection views of ABS-based core-shell model tablets produced using white and red ABS filaments.

FIG. 3 shows top projection views of several PVA-based disc-shaped uniform model tablets produced using PVA filaments.

FIG. 4 shows a top projection view of a PVA-based disc-shaped core-shell model tablet, and an open cross-section thereof, produced using PVA filaments.

FIG. 5A, FIG. 5B, and FIG. 5C respectively show projection views of PVA filament treated with methanol, prednisolone-loaded PVA filament; and dipyridamole-loaded PVA filament.

FIG. 6 shows a top projection view of prednisolone-loaded PVA model tablets.

FIG. 7A and FIG. 7B show a special lid (or plasticizing station) which dispenses plasticizer, from a tissue pre-soaked in plasticizer, to a filament as the filament passes therethrough towards a printing nozzle within a 3D printer.

FIG. 8A, FIG. 8B, and FIG. 8C respectively show schematic top projection, side, and plan views of the tablet design.

FIG. 13 shows SEM images of: FIG. 13A shows a surface view, and FIG. 13B shows a cross-sectional view of a default PVA filament (PVA only); and FIG. 13C shows a surface view, and FIG. 13D shows a cross-sectional view of a prednisolone-loaded PVA filament.

FIG. 14A and FIG. 14B show SEM images of PVA after extrusion from nozzle of fused deposition modelling 3D printer at 1000 μm magnification, and 50 μm magnification, respectively.

FIG. 15 shows SEM images of the side surface of prednisolone-loaded PVA tablets at different magnifications: FIG. 15A at 2000 μm; FIG. 15B at 200 μm; FIG. 15C at 20 μm.

FIG. 16 shows SEM images of the top surface of prednisolone-loaded PVA tablets at different magnifications: FIG. 16A at 1000 μm; and FIG. 16B at 100 μm.

FIG. 17 shows SEM images of a cross section of prednisolone-loaded PVA tablets: FIG. 17A general view; FIG. 17B magnification of peripheral domain; and FIG. 17C magnification of central domain.

FIG. 51 shows SEM images of Theophylline Eudragit® RL 3D printed tablet at low resolution.

FIG. 52 shows SEM images of Theophylline Eudragit® RL 3D printed tablet at standard resolution.

FIG. 55B 3D printed tablets of drugs formulated with Eudrafit RL:E (solid squares), Eudragit® RL:RS 1:1 (solid diamonds), Eudragit® RL (solid triangle), Eudragit® RS (solid circle).

FIG. 69A, FIG. 69B, FIG. 69C and FIG. 69D show photographs of filaments formed with calcium tribasic phosphate fillers.

FIG. 70 is a DSC thermograph showing thermal analysis of various filaments containing calcium tribasic phosphate fillers.

FIG. 71A, FIG. 71B, FIG. 71C, FIG. 71D and FIG. 71E show photographs of filaments and tablets formed with varying levels of plasticizer.

FIG. 72 is a DSC thermograph showing thermal analysis of various filaments containing different levels of plasticizer.

FIG. 73A, FIG. 73B, and FIG. 73C show photographs of tablets formed with varying levels of plasticizer.

FIG. 74 shows a TGA graph of different filler combinations used with Eudragit® E.

FIG. 75 shows DSC thermographs of different fillers combinations used with Eudragit® E.

FIG. 76A, FIG. 76B, FIG. 76C, FIG. 76D and FIG. 76E show photographs of filaments and tablets formed with varying levels of different disintegrants.

DETAILED DESCRIPTION OF THE INVENTION

Definitions

Figure 9:
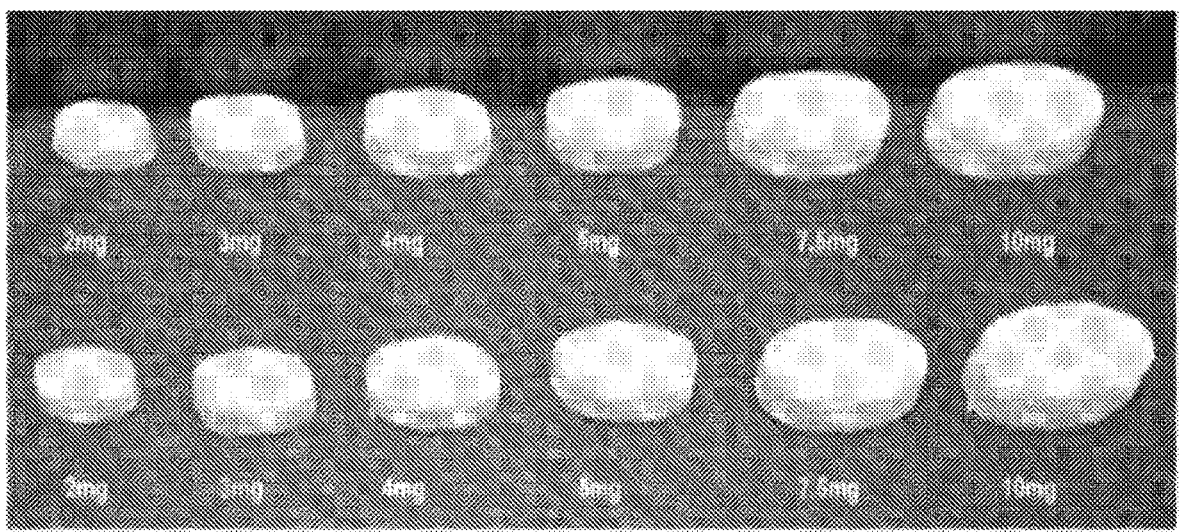
FIG. 9 shows a top projection view of several tablets, with the top row showing prednisolone-loaded PVA tablets at respective prednisolone doses of 2 mg, 3 mg, 4 mg, 5 mg, 7.5 mg and 10 mg; and the bottom row showing blank PVA-only tablets of the same size as the tablets corresponding to the 2 mg, 3 mg, 4 mg, 5 mg, 7.5 mg and 10 mg doses in the top row.

Unless otherwise stated, the following terms used in the specification and claims have the following meanings set out below.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

For the avoidance of doubt, it is hereby stated that the information disclosed earlier in this specification under the heading "Background" is relevant to the invention and is to be read as part of the disclosure of the invention.

Unless stated otherwise, any reference herein to the term "melt" (or its derivatives), especially in the context of melting filaments, suitably includes a glass transition or softening of a given material, suitably to allow extrusions thereof (e.g. through a nozzle). However, the term "melt" in the context of a defined "melting point" of a substance is as defined as per the art—a phase transition from solid to liquid.

Herein, references to "glass transition temperature" or "$T_g$" suitably refers to the temperature at which a material softens (e.g. to allow extrusion thereof). Suitably, glass transition temperatures (Tg) of materials described herein may be determined by a standard test method, suitably using dynamic mechanical analysis—a suitable test includes the testing protocol defined by ASTM E1640. Differential Scanning calorimetry (DSC-) may also be utilized. For instance, glass transition temperatures may be discerned using the protocols set forth in ASTM E1356 and ASTM D7426. It will be understood by those skilled in the art that references herein to a particular material's glass transition temperature falling within a certain temperature range is intended to mean that at least one glass transition temperature of said material (which may or may not have multiple glass transition temperatures) falls within said temperature range. Suitably unqualified references to a "glass transition temperature" means at least one, suitably means the lowest glass transition temperature, and may suitably mean the glass transition temperature which absorbs the most thermal energy (or is most endothermic). The key, which is self-evident to those skilled in the art, is that sufficient softening of said material occurs under a particular set of circumstances (e.g. at the printing nozzle, where a filament needs to be softened in order to be extruded during the printing process, after which resolidification or rehardening may take place).

Unless stated otherwise, the term "viscosity" as used herein refers to a viscosity determined by means of a Brookfield viscometer (UL adapter/30 rpm/20° C.) in accordance with testing protocols defined by Ph. Eur. 2.2.10 or USP <912> method II.

Unless stated otherwise, any reference herein to an "average" value is intended to relate to the mean value.

Where a composition is said to comprise a plurality of stipulated ingredients (optionally in stipulated amounts of concentrations), said composition may optionally include additional ingredients other than those stipulated. However, in certain embodiments, a composition said to comprise a plurality of stipulated ingredients may in fact consist essentially of or consist of all the stipulated ingredients.

Herein, where a composition is said to "consists essentially of" a particular component, said composition suitably comprises at least 70 wt % of said component, suitably at least 90 wt % thereof, suitably at least 95 wt % thereof, most suitably at least 99 wt % thereof. Suitably, a composition said to "consist essentially of" a particular component consists of said component save for one or more trace impurities.

Where the quantity or concentration of a particular component of a given composition is specified as a weight percentage (wt % or % w/w), said weight percentage refers to the percentage of said component by weight relative to the total weight of the composition as a whole. It will be understood by those skilled in the art that the sum of weight percentages of all components of a composition will total 100 wt %. However, where not all components are listed (e.g. where compositions are said to "comprise" one or more particular components), the weight percentage balance may optionally be made up to 100 wt % by unspecified ingredients (e.g. a diluent, such as water, or other non-essentially but suitable additives).

Herein, unless stated otherwise, the term "parts" (e.g. parts by weight, pbw) when used in relation to multiple ingredients/components, refers to relative ratios between said multiple ingredients/components. Expressing molar or weight ratios of two, three or more components gives rise to the same effect (e.g. a molar ratio of x, y, and z is $x_1{:}y_1{:}z_1$ respectively, or a range $x_1{-}x_2{:}y_1{-}y_2{:}z_1{-}z_2$). Though in many embodiments the amounts of individual components within a composition may be given as a "wt %" value, in alternative embodiments any or all such wt % values may be converted to parts by weight (or relative ratios) to define a multi-component composition. This is so because the relative ratios between components is often more important than the absolute concentrations thereof in the liquid pharmaceutical compositions of the invention. Where a composition comprising multiple ingredients is described in terms of parts by weight alone (i.e. to indicate only relative ratios of ingredients), it is not necessary to stipulate the absolute amounts or concentrations of said ingredients (whether in toto or individually) because the advantages of the invention can stem from the relative ratios of the respective ingredients rather than their absolute quantities or concentrations. However, in certain embodiments, such compositions consists essentially of or consist of the stipulated ingredients and a diluents (e.g. water).

The term "mole percent" (i.e. mol %) is well understood by those skilled in the art, and the mol % of a particular constituent means the amount of the particular constituent (expressed in moles) divided by the total amount of all constituents (including the particular constituent) converted into a percentage (i.e. by multiplying by 100). The concept of mol % is directly related to mole fraction.

The term "substantially free", when used in relation to a given component of a composition (e.g. "a liquid pharmaceutical composition substantially free of compound X"), refers to a composition to which essentially none of said component has been added. When a composition is "substantially free" of a given component, said composition suitably comprises no more than 0.001 wt % of said component, suitably no more than 0.0001 wt % of said component, suitably no more than 0.00001 wt %, suitably no more than 0.000001 wt %, suitably no more than 0.0000001 wt % thereof, most suitably no more than 0.0001 parts per billion (by weight).

The term "entirely free", when used in relation to a given component of a composition (e.g. "a liquid pharmaceutical composition entirely free of compound X"), refers to a composition containing none of said component.

Suitably, unless stated otherwise, where reference is made to a parameter (e.g. pH, pKa, etc.) or state of a material (e.g. liquid, gas, etc.) which may depend on pressure and/or temperature, suitably in the absence of further clarification such a reference refers to said parameter at standard ambient temperature and pressure (SATP). SATP is a temperature of 298.15 K (25° C., 77° F.) and an absolute pressure of 100 kPa (14.504 psi, 0.987 atm).

Herein, the term "particle size" or "pore size" refers respectively to the length of the longest dimension of a given particle or pore. Particle and pore sizes may be measured using methods well known in the art, including a laser particle size analyser and/or electron microscopes (e.g. transmission electron microscope, TEM, or scanning electron microscope, SEM).

General Points and Advantages Relating to the Invention

The present invention utilizes 3D printing technology, specifically fused filament fabrication (FFF) 3D printing, to produce solid dosage forms, most particularly in relation to pharmaceuticals, though the skilled person will readily appreciate that the principles of the invention are readily applicable to nutraceuticals and food supplements. The production process utilizes novel printing filaments (typically a spool of filament), which contain the relevant active ingredient and/or other ingredients (e.g. excipients), to actually print the relevant solid dosage form. Such printing filaments, by virtue of being in a substantially solid form, are highly stable on storage and transport, and can be used in printing without degrading the materials contained therein. This makes it ideal for printing solid pharmaceutical dosage forms, the production of which is heavily regulated to ensure patients are injecting a consistent drug product that meets the required regulatory standards for marketing authorisation.

The inventors found that their active ingredient-containing filaments provided not only a viable source of an active ingredient in the printing process, but an ideal source given that such filaments keep the active ingredient "safe" (i.e. stable on storage and in use, e.g. when exposed to higher printing temperatures) can be judiciously formulated, using the principles outlined in the disclosure, to customize dosage forms in terms of their composite, shape, and active release profile, whilst also allowing production of a consistent consumable product. This renders the invention useful in both final production and also research and development, where relevant printing apparati of the invention may be utilized for prototyping. The versatility of the invention makes it ideal for both purposes.

Having established a process for the 3D printing of solid dosage forms, consumers will have more choice (in terms of the dose within the solid dosage form, its aesthetics, and drug release profile) products are more readily customizable and dispensible by a pharmacist with limited labour (because minimal pre-fabricated input elements may be used) without the need for complex and expensive equipment, production can be tracked/logged (at a central point if necessary) to ensure quality control and react to batch failures and machine maintenance issues, high dose products may be produced, high resolution is achievable, and minimal machine breakdowns will occur due to minimal printing nozzle blockages. Moreover, the fact that everything in the process is solid (e.g. both filament and dosage form), except during printing, ensures ease of handling.

It is expected that the present invention will make a significant contribution to the art in terms of the production, dispensing, and consumption of pharmaceutical products, and this will have positive health impacts for all concerned.

Solid Dosage Form Printing Apparatus

The present invention provides a solid dosage form printing apparatus, suitably as defined herein. The printing apparatus suitably allows the printing of a solid dosage form (e.g. tablet or implant) via fused filament fabrication (FFF). As such, the apparatus suitably employs pre-fabricated filament(s) (at least one of which suitably contains an active ingredient) that are selectively extruded and deposited in a layer-by-layer printing process.

The apparatus is suitably for printing a solid dosage form, where the solid dosage form suitably comprises an active ingredient.

The apparatus suitably comprises a fused filament fabrication 3-dimensional printer (an FFF 3D printer). Such printers are often referred to as fabrication deposition Modelling™ (FDM) 3D printers.

The apparatus suitably comprises a build platform (or built plate) upon which the solid dosage form is printable (i.e. upon which the solid dosage form may be built). The build platform suitably provides a (substantially flat) surface which supports the solid dosage form throughout the printing process. In a particular embodiment, the build platform comprises a surface, tape layer (i.e. a layer of tape at the surface) or surface coating which promotes adhesion of the solid dosage form to the build platform during the printing process (i.e. promoting adhesion of a first layer of the solid dosage form to be printed upon the build plate, suitably after the first layer hardens upon cooling), though suitably the solid dosage form is (readily) removable from the build platform following its production.

Suitably, the apparatus comprises a computer interface (whether for wired or wireless connection to a computer operable to control the FFF 3D printer or printing apparatus).

The apparatus suitably comprises a computer for controlling the FFF 3D printer and optionally also the build platform.

Suitably, the apparatus comprises at least one extrusion nozzle through and from which a filament (or part thereof) can be extruded. Suitably the or each extrusion nozzle may be a heated extrusion nozzle, suitably a heated extrusion nozzle with a variable temperature control (e.g. to allow the extrusion nozzle to be selectively heated at a desired temperature). As such, the apparatus may comprise an extrusion nozzle heating element, suitably for heating the extrusion nozzle to melt (or otherwise liquidize) the or part of the relevant filament. Suitably, the apparatus may comprise a plurality of the aforementioned extrusion nozzles, each of which may be assigned to one or more filaments.

Suitably, the apparatus comprises a conveyor for conveying the active ingredient-containing printing filament and any optional one or more further printing filaments to and/or through the at least one extrusion nozzle. Suitably the conveyor grips the relevant filament and feeds it through itself towards and/or through the relevant extrusion nozzle. Suitably the conveyor is controlled to deliver the relevant filament at a rate and/or at intervals suitable to provide the desired solid dosage form. The conveyor, or a part thereof (e.g. "a feeder") (preferably a part en route to the extrusion nozzle) may be heated, suitably via an heating element associated therewith, optionally a separate and/or separately controllable heating element from any heating elements associated with the extrusion nozzle. Where the apparatus comprises more than one nozzle, suitably the apparatus comprises more than one feeder, one associated with each extrusion nozzle.

The apparatus suitably comprises an active ingredient-containing printing filament, suitably consisting of, consisting essentially of, or comprising comprises an active ingredient-containing filament composition comprising an active ingredient and optionally (and most suitably) an active ingredient carrier. Optionally the active ingredient-containing printing filament may comprise an excipient, diluent and/or an excipient carrier. In a particular embodiment, the active ingredient-containing printing filament is provided as an active filament spool as defined herein. As such, the apparatus suitably comprises an active filament spool as defined herein.

Suitably, the active ingredient-containing printing filament consists essentially of (and most suitably consists of) the active ingredient-containing filament composition, though in some embodiments, the filament may be further treated (e.g. coated) to enhance stability thereof (e.g. on storage), suitably without compromising printability.

The apparatus may suitably comprise one or more further printing filaments, each suitably independently consisting of, consisting essentially of, or comprising a further filament composition. Suitably, where present, the, each, or at least one of the one or more further printing filaments comprise an active ingredient carrier (e.g. one or more pharmaceutically or nutraceutically acceptable polymeric carriers), whether or not it or they comprise an active ingredient. Alternatively or additionally, where present, the, each, or at least one of the one or more further printing filaments comprise an excipient carrier (e.g. one or more pharmaceutically or nutraceutically acceptable polymeric carriers), whether or not it or they comprise an excipient. Alternatively or additionally, where present, the, each, or at least one of the one or more further printing filaments comprise an excipient (e.g. one or more pharmaceutically acceptable excipients), whether or not it or they comprise an active ingredient. Alternatively or additionally, where present, the, each, or at least one of the one or more further printing filaments comprise a diluent (e.g. one or more pharmaceutically or nutraceutically acceptable diluents), whether or not it or they comprise an excipient or active ingredient. In a particular embodiment, the, each, or some of the one or more further printing filaments are provided as further filament spools as defined herein. As such, the apparatus may suitably comprise one or more further filament spools as defined herein.

Suitably, the or each of the one or more further printing filaments consists essentially of (and most suitably consists of) the further filament composition, though in some embodiments, the filament may be further treated (e.g. coated) to enhance stability thereof (e.g. on storage), suitably without compromising printability.

Suitably, the active ingredient may be selected from a pharmaceutical, nutraceutical, or food supplement. In some embodiments, the solid dosage form may comprise more than one active ingredients (suitably of the same class, be it a pharmaceutical, nutraceutical, or food supplement), though most suitably only a single active ingredient is present within the solid dosage form. Where the solid dosage form comprises a plurality of active ingredients, the active ingredient-containing printing filament used in its production may comprise a plurality of active ingredients (suitably of the same class, be it a pharmaceutical, nutraceutical, or food supplement), though most suitably only a single active ingredient is present within the active ingredient-containing printing filament. Alternatively or additionally, where the solid dosage form comprises a plurality of active ingredients, one or more further printing filaments may comprise one or more active ingredients (suitably of the same class, be it a pharmaceutical, nutraceutical, or food supplement) in addition to any active ingredient(s) present within the active ingredient-containing printing filament.

Suitably, an active ingredient carrier is a substance or mixture of substances which acts as a vehicle for the active ingredient within the solid dosage form and/or serves as a suitable solid matrix for retaining the active ingredient within a relevant filament prior to printing therewith. Suitably, the active ingredient is dispersible or even soluble within the active ingredient carrier.

Suitably, any excipients may be selected from those well known in the art, especially those suitable for use in oral dosage forms, particularly solid dosage forms for oral administration.

Suitably, an excipient carrier is a substance or mixture of substances which acts as a vehicle for any excipient(s) present within the solid dosage form and/or serves as a suitable solid matrix for retaining the excipient(s) within a relevant filament prior to printing therewith. Suitably, the excipient(s) is dispersible or even soluble within the relevant excipient carrier(s).

Suitably, a diluent is a substance or mixture of substances which act as an inert diluent for any active ingredient(s) and/or excipient(s) present within the solid dosage form. Such diluents may be particularly useful when customizing the active ingredient loading level, which may be judiciously varied in line with the present invention. The diluent is suitably a solid diluent and is suitably a pharmaceutically and/or nutraceutically acceptable diluent. The diluent may be selected from any substance defined herein in relation to a carrier (be it for the active ingredient or any excipients) or may be one of a number well known in the art.

The FFF 3D printer (and optionally the build platform) is suitably operable via the computer, suitably a computer running pursuant to specialist solid dosage form printing software, and optionally also to one or more databases, to print the solid dosage form upon the build platform, suitably via a process involving the printing and/or extrusion of the active ingredient-containing printing filament and optionally also involving the printing and/or extrusion of one or more further printing filaments.

It will be readily understood by those skilled in the art that any one or more of the build platform, active ingredient-containing printing filament, further printing filaments, and/or computer, and/or any part thereof, may suitably be integrated within or form a part of the FFF 3D printer. In an embodiment, the printing apparatus is essentially an FFF 3D print or printing apparatus.

In an aspect of the invention, the apparatus comprises an active ingredient-containing printing filament and optionally any one or more of the features defined herein in relation to the apparatus. However, for the apparatus to function, suitably a computer and an FFF 3D printer should be present in addition to this filament, and most suitably further filament(s) are present to enable greater flexibility and customizability with respect to the ultimate solid dosage form being produced. Furthermore, the apparatus may comprise a plurality of active ingredient-containing printing filaments, each suitably comprising a different active ingredient, in order that different solid dosage forms may be produced, each with a different function. As such, an FFF 3D printer may be configured for printing a variety of different solid dosage forms containing different active ingredients.

Method of Printing Solid Dosage Form and/or Using the Apparatus

The present invention also provides a method of printing a solid dosage form, suitably as defined herein. Suitably this method is a method of using the aforesaid apparatus.

The method suitably comprises providing a solid dosage form printing apparatus, FFF 3D printer, or printing apparatus as defined herein.

The method suitably comprises operating the FFF 3D printer or printing apparatus to print the solid dosage form, suitably upon the build platform. Suitably, such printing is performed via a computer-implemented process (i.e. where printing is controlled and suitably initiated by a computer that is connected or connectable to or within the printing apparatus, be it in a wired or wireless fashion.

Suitably, the printing of the solid dosage form involves printing (and/or extruding) the active ingredient-containing printing filament (or printing/extruding an active ingredient-containing filament composition derived from the active ingredient-containing printing filament).

Suitably, the printing may involve printing (and/or extruding) one or more further printing filaments (or printing/extruding one or more further filament compositions derived from the one or more further printing filaments).

Suitably the method may involve performing one or more further processing steps (with or without the FFF 3D printer; e.g. coating or otherwise modifying the surface, shape, or properties of the solid dosage form).

Computer-Implemented Method of Printing

The present invention provides a method of operating a solid dosage form printing apparatus (or such like, suitably as defined herein), suitably a computer-implemented method of operating a solid dosage form printing apparatus, suitably as defined herein.

The method suitably involves providing a solid dosage form printing apparatus, suitably as defined herein, and operating said apparatus to print the solid dosage form. Suitably the apparatus includes or is otherwise connected to a computer. Operating the apparatus suitably involves operating a computer, which is suitably connected (be it in a wired or wireless fashion) with or within the relevant printing apparatus (so as to allow the computer to control and co-ordinate other parts of the apparatus, suitably including an FFF 3D printer), to cause printing of a solid dosage form.

Features described in relation to a method of printing are (where applicable) suitably equally applicable to an apparatus or a part thereof (e.g. filament).

Computer

The printing apparatus suitably includes or is otherwise connected to a computer. The printing apparatus (or 3D printer) are suitably connected to the computer via an interface (suitably a digital interface), which may be wired (e.g. a port-to-port connection via an appropriate data lead, e.g. a USB lead) or wireless. The computer may be located at the site of the relevant printing apparatus or 3D printer (i.e. a local computer). However, the invention is equally applicable where the relevant computer (or computers) is located remote from the site of the relevant printing apparatus or 3D printer, but both the printing apparatus (or 3D printer) and remote computer comprise or are otherwise connected to respective communicators allowing the remote computer and printing apparatus (or 3D printer) to communicate with one another. In this manner, a remote computer may be caused to operate the printing apparatus. In a particular embodiment, the printing apparatus (or 3D printer) may be connected to a network so that multiple remote computers (and/or local computers) may communicate therewith to cause the operation of the printing apparatus (or 3D printer).

The computer associated or otherwise connected with the printing apparatus suitably controls printing of the relevant filament(s) in accordance with a solid dosage form design and/or solid dosage form parameters (e.g. relative amounts and juxtaposition of ingredients) set forth in a given solid dosage form data file (e.g. in a CAD or a .STL file), suitably as interpreted by relevant software pursuant to which the computer runs.

In a particular embodiment, the printing apparatus comprises or is connected to a local computer, and both printing apparatus and the local computer are located on site at a pharmacy, most suitably in a purpose-build printing area or room (which may be suitably have regulatory approval).

Suitably the method and/or apparatus involves a computer running pursuant to solid dosage form printing software (and optionally one or more internal and/or external databases).

Suitably, a computer running pursuant to said to solid dosage form printing software is configured to obtain information regarding one or more parameters (optionally including physical design parameters, such as shape) pertaining to the solid dosage form to be printed (e.g. be it from information inputted manually by a user or information obtained automatically from another data source). Suitably the computer pursuant to said to solid dosage form printing software is configured to request manual user input via a user interface (e.g. keyboard/screen) regarding one or more parameters pertaining to the solid dosage form to be printed. For example, a user (which may be a pharmacist acting under instruction from a patient and/or doctor) may be requested to input information regarding patient name, patient reference number (e.g. healthcare number), and/or another reference name or number, following which the computer may communicate (via relevant communicators associated therewith) with one or more databases (be it local or remote, wired or wirelessly, e.g. via a network such as the internet) to automatically call further information and/or options corresponding with said name or reference (e.g. personal patient data, medication history, repeat prescriptions, data or partial data relating to solid dosage forms to be printed, including solid dosage form data files containing designs and/or other relevant parameters). Thereafter, the user may be requested to manually input or manually select further information (e.g. drug, drug dose, release profile, etc.) and/or options to allow the computer to obtain all relevant information pertaining to the printing of the desired solid dosage form. Alternatively or additionally, the user may be requested to manually input or call information relating to one or more specific parameters pertaining to the solid dosage form (e.g. drug name/reference, drug dose, drug release requirements, colour, size, shape, solubility, packaging labelling information, etc.). Suitably, any user input may be logged and/or stored for future reference or for repeat prescriptions, etc.

There are a variety of ways the computer may be configured to obtain the relevant information to allow a solid dosage form to be printed, but it is likely that a variety of pre-set information may be used (e.g. certain approved formulations/filament combinations for producing a give solid dosage form). As such, the computer may suitably be associated with or connected/connectable with a solid dosage form database (suitably a central database accessible via a network, such as the internet) which provides all necessary pre-set information (e.g. data files relating to the solid dosage form and details of variable parameters such as drug dose levels/limits).

Suitably, a solid dosage form design for printing (and optionally parameters connected therewith) may be recorded in a solid dosage form data file, which may be read by a computer running pursuant to the solid dosage form printing software.

Suitably, a computer running pursuant to said to solid dosage form printing software is configured to calculate the mass and/or volume of the solid dosage form to be printed based on the information obtained. Suitably once the computer has obtained all required information (be it information manually inputed by a user, information imported automatically, or a combination of both) it is configured to perform calculations to allow finalisation of printing instructions before the computer controls printing. At this stage, further input may be required or requested (e.g. via a user interface), for instance dimension(s) and/or shape modifications may be optionally selected. Calculations typically relate to the mass and/or volume of a given solid dosage form required to provide a given active dosage per dosage form. Though it may be possible to increase the concentration of a given active relative to other ingredients (e.g. excipients), typically formulations are optimized and relative proportions fixed/pre-set, whereas overall mass/volume may be varied whilst retaining the same relative proportions of ingredients.

Suitably, a computer running pursuant to said to solid dosage form printing software is configured to control printing of and relative proportions of ingredients within the solid dosage form, suitably based on the information obtained and suitably based on the calculations performed. Suitably "controlling printing" includes initiating printing a terminating printing and any or all printing operations therebetween.

Suitably during printing, operational data is collected (optionally by one or more local and/or remote computers and/or databases) and suitably stored (most suitably at a central computer which may analyse such data, e.g. for quality control monitoring, monitoring of malfunctions, monitoring of batches, monitoring of dosage forms dispensed to a given patient, etc.). Suitably the printing apparatus comprises or is otherwise associated with one or more operational sensors (e.g. nozzle temperature sensors, filament feed rate sensors or conveyor sensors, overall temperature sensors, build platform sensors which may, for example, monitor surface temperature and/or rate of post-print cooling, etc.) which feedback operational parameters/information to a computer, database, or data storage facility, relating to the operation of the printing apparatus and elements associated therewith during the printing of each dosage form. Most preferably, such operational data is collected, stored, and/or otherwise transmitted to a central computer or database to enable independent auditing of any given printing apparatus. This may be important in order to maintain quality control, and maintain appropriate records in order to retain regulatory approval of any given 3D printing system.

Suitably, a computer running pursuant to said to solid dosage form printing software is configured to control performance of one or more further processing steps.

FFF 3D Printer

In the context of the present invention, an FFF 3D printer may be any device or association of parts which enables a 3D-shaped object (i.e. suitably with a depth at its deepest or thickest point of at least 100 μm, suitably at least 1 mm, suitably at least 2 mm) to be deposited form one or more printing filaments. Conventional FFF 3D printers are well known in the art, and are generally suitable for use with the present invention, though they may be judiciously modified based on the principles outlined herein to optimize printing of solid dosage forms. For the skilled persons reference, the following research articles describe a viable operation of FFF 3D printers—S. H. Masood, "Application of fused deposition modelling in controlled drug delivery devices", *Assembly Automation*, 27/3 (2007), p. 215-221 and Khaled et al, "Desktop 3D printing of controlled release pharmaceutical bilayer tablets", *International Journal of Pharmaceutics*, 461 (2014), p. 105-111—describe printing with FFF 3D printers of filaments, albeit there are no active ingredients contained within the filaments being printed (drug compounds are infused at a later stage).

FFF 3D printers suitable for use with the invention generally comprise a heated/heatable extruder nozzle which melts and deposits (suitably onto a build platform) molten filament in a layer-by-layer fashion. The deposited molten filament suitably hardens rapidly following deposition. Maintaining a build platform with a relatively low surface temperature may facilitate such cooling/hardening to improve the final structure of the solid dosage form being printed. The FFF 3D printer also suitably includes one or more nozzle heaters (suitably one associated with each nozzle but optionally one serving multiple nozzles) and suitably one or more conveyors (suitably one associated with each filament and/or nozzle) as defined above. Suitably the FFF 3D printer comprises one or more filament spool zones (or filament spool attachment points) for holding the relevant filament spool(s).

Nozzle(s)

Suitably the printing apparatus or 3D printer comprises one or more extrusion nozzles through and from which a filament (or part thereof) can be extruded. Suitably the or each extrusion nozzle may be a heated extrusion nozzle, suitably a heated extrusion nozzle with which may be selectively heated via a variable temperature control to obtain a desired temperature (suitably to suit the properties of the filament in question). As such, the printing apparatus or 3D printer may comprise one or more extrusion nozzle heating elements associated with the or each extrusion nozzle, suitably for heating the extrusion nozzle to melt (or otherwise liquidize) the or part of the relevant filament. Suitably, the apparatus may comprise a plurality of the aforementioned extrusion nozzles, each of which may be assigned to one or more filaments.

The temperature of the nozzle(s) are suitably set and controlled by the computer according to the properties of the filament in question (which the computer knows after obtaining all relevant information). In particular, it is important to balance factors such as filament extrudability (typically linked to glass transition temperature), desired resolution, and degradation properties (especially with respect to an active or excipient which yields potentially toxic heat-degradation products). For instance, a filament having a relatively low glass transition temperature may be extruded from its respective nozzle at lower temperatures than a filament having a relatively higher glass transition temperature. These parameters are suitably part of the information obtained by the computer (reference may be made to information held in a particular database about a particular filament and the required nozzle temperature settings and feed rate). Conceivably, where multiple filaments are used to print a solid dosage form (e.g. in core-shell arrangements), different nozzles (for each filament) may have a different operating temperature depending on the respective properties of the relevant filament.

Suitably, the operating temperature of an extrusion nozzle through which an active ingredient-containing printing filament passes is high enough to enable filament extrusion but low enough to avoid (pharmaceutically) unacceptable degradation of the active ingredient(s) and/or any excipient(s) at the relevant filament feed rate (it will be appreciated by those skilled in the art that the active ingredient will generally tolerate higher temperatures if heat exposure times are short, as they generally are in the printing processes of the invention). Suitably, the operating temperature of an extrusion nozzle through which an active ingredient-containing printing filament passes is between 90 and 220° C., more suitably between 120 and 190° C., suitably between 165 and 190° C. However, the operating temperature of an extrusion nozzle may be as low as 65° C., especially in systems that employ low-melting polymers (e.g. PEG) or polymers with low glass transition temperatures. Most suitably, the extrusion nozzle temperature is set to at least 65° C., more suitably at least 70° C. In a particular embodiment, the nozzle temperature is 70-220° C., suitably 100-160° C., suitably 130-150° C., suitably 135-145° C.

Suitably, the operating temperature of an extrusion nozzle through which a further printing filament passes is high enough to enable filament extrusion but low enough to avoid (pharmaceutically) unacceptable degradation of the excipient(s) at the relevant filament feed rate. Suitably, the operating temperature of an extrusion nozzle through which an active ingredient-containing printing filament is between 80 and 300° C., more suitably between 100 and 220° C., suitably between 120 and 190° C.

Most suitably, the operating temperature of an extrusion nozzle through which a given filament passes is set or controlled (during printing) at a temperature or within a temperature range at which at least one of the components/ingredients ("melting ingredient(s)") of the given filament melts so as to allow extrusion of the filament through the nozzle (i.e. suitably onto the build platform) and at which at least one of the components/ingredients ("non-melting ingredients") of the given filament (suitably a component constituting at least 0.1 wt % of the filament, suitably at least 1 wt % of the filament, suitably at least 5 wt % of the filament, suitably at least 10 wt % of the filament, suitably at most 30 wt % of the filament, suitably at most 20 wt % of the filament, suitably at most 15 wt % of the filament) remains in or is otherwise transformed into a solid and/or particulate form. The melting ingredient(s) may suitably include diluents(s), carrier(s), and/or excipient(s), and may suitably melt as a composite—the combination of a carrier/diluent and plasticizer may, for example, constitute "melting ingredient(s)". The non-melting ingredient(s) may suitably include excipient(s) and/or an active ingredient, suitably which has a melting point (or composite melting point) higher than the nozzle operating temperature, and suitably higher than a melting point, composite melting point, or glass transition temperature of the corresponding non-melting ingredient(s). The non-melting ingredient(s) are suitably still co-extruded from the relevant nozzle along with any melting ingredient(s). However, the presence of non-melting ingredient(s), especially when in particulate form at the operating temperature of the relevant nozzle, surprisingly reduces nozzle blockages and may additionally or alternatively improve overall resolution of the solid dosage form.

Suitably each extrusion nozzle comprises an input opening (into which a filament is fed) and an output opening (out of which molten filament is deposited). The output opening is suitably smaller than the input opening. The input opening is suitably dimensioned to receive a corresponding filament therethrough. Suitably the input opening has a diameter of 1.0 to 2.5 mm, more suitably 1.5 to 2.0 mm, most preferably about 1.75 mm. The output opening is suitably dimensioned for the properties of the corresponding filament to allow molten filament to be deposited therefrom (e.g. onto a build platform). Suitably the output opening has a diameter of 50 to 400 μm, more suitably 100 to 300 μm, more suitably 150 to 250 μm, most suitably about 200 μm. In an embodiment, the nozzle has an output opening with a diameter between 200 and 500 μm.

Suitably the or each nozzle may be movable (suitably in an automated fashion or in a manner controlled by a computer or by the printer under instruction from the computer) to extrude filament at different locations upon the build platform (or upon the partially formed solid dosage form printed thereon). The nozzle may be moveable in any or all of the X, Y, and Z direction, though in some embodiments (e.g. where the build platform is movable in the Z direction, i.e. up and down relative to the nozzle) it is constrained to move in only X and Y directions.

Suitably the or each extrude nozzle is operable to move at a speed of between 50 and 150 mm/s whilst extruding (i.e. when the nozzle is "on"—this may be the nozzle extrusion speed), more suitably between 70 and 110 mm/s, more suitably between 80 and 100 mm/s. Suitably the or each extrude nozzle is operable to move at a speed of between 100 and 200 mm/s when not extruding (i.e. when the nozzle is "off"—this may be the nozzle travelling speed), more suitably between 120 and 180 mm/s, more suitably between 140 and 160 mm/s.

It will be understood by those skilled in the art that the, each, or any nozzle may be adapted to suit the properties a corresponding filament configured to print thereto. The nozzle properties/design and filament properties/composition suitably complement one another so as to facilitate controlled extrusion of said filament (be it continuous or intermittent, e.g. where more than one filament is used in the printing of a solid dosage form), suitably without any nozzle blockages or impedance, and suitably without any unacceptable degradation of ingredients within the filament during the printing process.

As described below in relation to cartridges, the printer nozzle may be replaced by a cartridge nozzle. As such, a cartridge nozzle may serve as the printer nozzle and may thus, where appropriate, have any of the properties ascribed herein to a printer nozzle.

Build Platform

The printing apparatus or 3D printer suitably comprises a build platform. This provides a platform upon which the solid dosage form(s) may be printed.

Suitably, during printing (e.g. at the relevant printing operating temperature), the surface of the build platform onto which the solid dosage form is to be printed adheres to the solid dosage form (or at least to the layer thereof in contact with the build platform) sufficiently to prevent movement of the developing solid dosage form during printing. Suitably, however, after printing (e.g. optionally at a different temperature to the printing operating temperature) the printed solid dosage form(s) may be removed from the build platform without being damaged (e.g. the build platform is non-adherent enough to allow the solid dosage forms to be removed or is selectively tunable, e.g. by changing the operating temperature, to allow the solid dosage forms to be removed therefrom). As such, the surface of the build platform may comprise a surface coating or surface tape which imparts the required surface properties (e.g. adhesive but not too adhesive that the solid dosage forms are permanently adhered).

The build platform is suitably configured or operable to maintain a surface temperature (i.e. for the surface in contact with the solid dosage form) during printing of less than or equal to 50° C., suitably less than or equal to 40° C., suitably less than or equal to 30° C., suitably greater than or equal to 5° C., suitably greater than or equal to 15° C. In other embodiments, the build platform is operable to maintain a surface temperature of less than or equal to 150° C., suitably less than or equal to 100° C., suitably greater than or equal to 15° C. This may be achieved through selective operation of heating and/or cooling elements associated with (e.g. lying beneath) the surface of the build platform. In a particular embodiment, the build platform is operable and preferably operated to maintain a surface temperature of between 20 and 90° C., suitably between 20 and 60° C., suitably between 30 and 50° C., most suitably about 40° C.

The build platform may be movable (suitably in an automated fashion or in a manner controlled by a computer or by the printer under instruction from the computer) to control the position or height of extrusion of a relevant filament upon the build platform. The build platform may be moveable in any or all of the X, Y, and Z direction, though in some embodiments the build platform is movable in the Z direction only, i.e. up and down. Movement in the Z direction allows the gap (or height) between the nozzle and the printing point to be kept substantially constant throughout the printing process to maintain layer-by-layer consistency.

Software and Data Files

The computer operating the printing apparatus or 3D printer suitably runs pursuant to solid dosage form printing software (and optionally also to one or more databases). As explained herein, this software may configure the computer to obtain information and perform calculations before it then configures the computer to control printing via an interface with the printing apparatus or 3D printer.

Once the computer has obtained the relevant information and performed the relevant calculation, suitably the software configures the computer to control printing of a solid dosage form, suitably based on a design (shape and dimensions, texture, layer structure, internal structure, porosity, colour(s), etc.) and/or parameters (relative amounts of ingredients, such as drug dose) relating to said solid dosage form contained within one or more solid dosage form data files. The solid dosage form data files may include a design file (e.g. containing data and/or images relating to the physical design of the solid dosage form, including its dimensions, shape, layered structure, core-shell structure, etc.) and/or a parameter file (e.g. containing data relating to the chemical composition of the solid dosage form, including drug type, excipient type(s), drug dose level, excipients to control drug release, etc.). A single solid dosage form data file may contain all data pertaining to the physical design and chemical composition. However, the physical design and chemical composition may be modified pursuant to information obtained following user input.

In some embodiments, the design file may be a CAD file depicting a solid dosage form. However, such file formats are likely to require conversion to a file format compatible with the printing apparatus or 3D printer. Conventional 3D printers generally read design files in a .STL format. As such, the design file is suitably a .STL design file depicting the solid dosage form (or at least the physical design thereof).

The design file may include or be linked with a parameter file containing chemical composition details, or the two may be independent. Alternatively there may be no parameter file as such and instead the relevant parameter information may be called from a database, for instance, in response to user input (e.g. patient reference, or drug reference, etc.).

The software may additionally configure the computer to collect, store, and/or transmit (e.g. to a central database) operational data fed back to the computer from the printing apparatus or 3D printer during printing. The software may configure the computer to detect and/or respond to any (or a pre-set level of) deviation in expected operational data (e.g. if nozzle temperatures exceed a maximum pre-set temperature level), for instance alerting the user/operator or any other interested party that a malfunction has occurred and that the solid dosage forms produced during malfunctional printing should be disposed or otherwise tested.

Databases

The printing apparatus and/or computer(s) associated therewith may be configured (e.g. by the solid dosage form printing software) to communicate with (suitably via relevant communicator(s), and suitably via a network such as the internet) one or more solid dosage form databases and/or patient databases to obtain information regarding one or more parameters pertaining to the solid dosage form to be printed. For example, such database(s) may be consulted in response to a user input (e.g. patient reference number) to furnish the computer with the relevant information (or relevant information to be supplemented by further user input) to enable calculations and printing to be performed.

By way of example, a patient database comprising patient records for multiple patients (which records may include, for example, patient name, patient reference number, medical data, medical history, etc.) suitably contains information (which may merely be a cross-reference or reference number relating to information residing in another database, such as a solid dosage form database) regarding the solid dosage forms to be printed for each patient. Where the "information" is a cross-reference to a solid dosage form database, this solid dosage form database may then be consulted for further information regarding the solid dosage form. This information may be any of the information defined herein, though optionally the printing apparatus or computer(s) associate therewith may be instructed (e.g. via a user interface) to modify the information (e.g. drug dose level) prior to calculations and/or printing. Any of these databases may be accessible to interested parties, preferably securely accessible (to maintain confidentiality of certain data), to enable the relevant information (be it in a patient database, solid dosage form database, or both) to be retrieved and/or amended as required (e.g. if a patient needs an increased dose in the printed solid dosage forms or a different active release profile). Suitably such database(s) may be wirelessly accessible via a network, such as the internet. Such database architectures are well known in the art.

The or each printing apparatus and/or computer(s) associated therewith may be configured (e.g. by the solid dosage form printing software) to communicate with (suitably via relevant communicator(s), and suitably via a network such as the internet) one or more apparatus-monitoring databases configured to transmit to and store within said database (and optionally analyse and/or report upon) operational data collected (optionally by one or more local and/or remote computers and/or databases) during each printing operation (i.e. each time a printing apparatus prints). As described herein, such operational data is suitably obtained/delivered by sensors associated with each given printing apparatus, suitably sensors associated with key parts of the printing apparatus that could affect the quality of the ultimate solid dosage forms. The operational data may be transmitted to said database in real time, following printing, or at any suitable time (e.g. at night to avoid unnecessary overloading communication networks during work hours). Such apparatus-monitoring databases may be organised with a record for each printing apparatus, and may suitably maintain a log of operational data each time said printing apparatus is operated. Suitably each set of operational data is cross-reference to a given patient a solid dosage form, suitably so that if any operational data is deemed malfunctional, the relevant interested parties can be alerted. In this manner, each printing apparatus may be monitored (whether in real time or otherwise, whether automatically or otherwise) and data periodically submitted to satisfy regulatory requirements. Moreover, central apparatus-monitoring databases may trigger a response to any perceived malfunction of a given printing apparatus. Moreover, a response may be triggered which prevents the relevant malfunctional printing apparatus from being used until its performance can be revalidated.

Again, any of the one or more apparatus-monitoring databases may be accessible to interested parties, preferably securely accessible (to maintain confidentiality of certain data), to enable the relevant information to be retrieved and/or analysed as required (e.g. if regulatory bodies wish to check that a given printing apparatus has been in good order throughout a given period, or if machine maintenance professionals which to use the data to diagnose a problem in order to restore the performance of a given printing apparatus). Suitably such database(s) may be wirelessly accessible via a network, such as the internet. Such database architectures are well known in the art.

Controlling Printing

It will be understood that features relating to the control of printing may (where appropriate) be deemed equally pertinent in the absence of computer-implementation, but computer-implemented methods are most preferred. A computer that is comprised of or otherwise associated with a printing apparatus or the FFF 3D printer thereof is or may be suitably referred to as a printing control computer (or printing computer). The printing control computer may serve a different function (and may be a distinct entity) to other "computers" referred to herein, such as monitoring computers and analytical computers, though a single computer may perform the function(s) of one or more of any combination of these computers.

Printing of solid dosage forms is suitably controlled by a computer, running pursuant to solid dosage form printing software, suitably based on information provided to the computer by user input(s) (drug type, drug dose level), databases (e.g. patient database and/or solid dosage form databases), and/or data files (e.g. design and/or parameter files), as described herein. Suitably an FFF 3D printer is configured to print pursuant to instructions provided by the computer by: feeding filament(s) to and through their respective nozzle(s) at the appropriate intervals and/or at the appropriate rates; heating the relevant nozzle(s) at the appropriate temperature(s) for the appropriate time; and by moving the nozzle(s) and/or build platform to enable systematic layer-by-layer printing in accordance with the relevant information obtained and calculations made by the computer.

The feeding of filament(s) to and through their respective nozzle(s) is suitably facilitated by a conveyor (or roller) as described elsewhere herein. Such a conveyor is suitably situated along a filament flow path of a given filament, suitably between a filament source (e.g. a filament spool or cartridge) and an extrusion nozzle to and through which the given filament is assigned to flow.

The extrusion nozzle(s) are suitably controlled by the computer according to the "obtained information" regarding the solid dosage form (e.g. design and/or other parameters). Nozzles are suitably controlled to extrude a given filament upon a build platform (or upon a partially build solid dosage form upon the build platform) to a pattern pre-defined by the "obtained information". As such, the or each nozzle may be controlled to switch "on" and "off" in accordance with a pre-defined schedule to deliver the required pattern in the construction of the solid dosage form. A nozzle may be switched "on" by causing an output opening to open, by adjusting the nozzle's operating temperature (e.g. increasing it so as to cause melting of the relevant filament), by operating the a conveyor to feed filament through the nozzle, or a combination of any or all of the aforementioned.

Naturally, a nozzle may be switched off by causing an output opening to close, by adjusting the nozzle's operating temperature (e.g. decreasing it to a temperature which does not cause melting of the relevant filament), by operating the a conveyor to restrict or cease feeding of a filament through the nozzle, or a combination of any or all of the aforementioned. The temperature of the nozzle(s) are suitably set and controlled by the computer according to the properties of the filament in question, as described elsewhere herein. Suitably, the operating temperature of an extrusion nozzle through which an active ingredient-containing printing filament passes is between 90 and 220° C., more suitably between 120 and 190° C., suitably between 165 and 190° C., suitably between 140 and 170° C. Suitably, the operating temperature of an extrusion nozzle through which an active ingredient-containing printing filament is between 80 and 300° C., more suitably between 100 and 220° C., suitably between 120 and 190° C. However, the operating temperature of an extrusion nozzle may be as low as 65° C., especially in systems that employ low-melting polymers (e.g. PEG) or polymers with low glass transition temperatures. Most suitably, the extrusion nozzle temperature is set to at least 70° C. In a particular embodiment, the nozzle temperature is 110-160° C., suitably 110-130° C., suitably 130-150° C., suitably 135-145° C. Suitably the operating temperature of an extrusion nozzle assigned to a given filament is higher than any corresponding hotmelt extrusion temperatures used in the formation (i.e. via extrusion) of the given filament, suitably between 30 and 90° C. higher, more suitably between 50 and 70° C. higher.

The build platform is suitably controlled by the computer according to the "obtained information" regarding the solid dosage form (e.g. design and/or other parameters), suitably as described elsewhere herein. This may include controlling the operating temperature of the build platform, in particular the operating temperature of the surface of the build platform. Suitably, during printing, the operating temperature of the build platform or surface thereof is maintained substantially constant, suitably at a constant temperature +/−5° C. Such temperature control may facilitate cooling and/or hardening of post-deposited molten filament(s) to thereby secure the structural integrity of the solid dosage form as it is being printed. Such temperature control may facilitate adhesion of the developing solid dosage form to the surface of the build platform during printing. Such temperature control may facilitate release (i.e. unsticking) of a solid dosage form after printing (e.g. the surface of the build platform may be heated or cooled, as appropriate, to reduce adhesion of the solid dosage form(s) thereto). During printing, the build platform is suitably configured or operable to maintain a surface temperature (i.e. for the surface in contact with the solid dosage form) of less than or equal to 50° C., suitably less than or equal to 40° C., suitably less than or equal to 30° C., suitably greater than or equal to 5° C., suitably greater than or equal to 15° C.

Printing of the solid dosage form(s) is suitably performed by the printing apparatus or FFF 3D printer in a layer-by-layer fashion. Each layer is suitably a plane (substantially) parallel to that of the surface of the build platform. Any given layer may be of a uniform or non-uniform nature. Likewise, a solid dosage form may itself be of a uniform or non-uniform nature, be it on an intra-layer or inter-layer basis or both (i.e. different layers may have a different nature). Uniformity of any given layer (or layer-to-layer) suitably relates to one or more of the layer(s)' composition (e.g. distribution of ingredient(s) throughout the layer—a core-shell solid dosage form may inevitably lead to some natures comprising zone(s) of core material and zone(s) of shell material), density (e.g. the % infill), porosity (the distribution of pores throughout the layer), patterning (e.g. where multiple filaments may give rise to particular patterns).

Suitably filament(s) are printed/extruded onto the build platform (or onto a partially-formed solid dosage form thereon) at a pre-defined "layer height" (i.e. the distance in the "Z" direction between the top and bottom of a given layer, as opposed to the length or width of the layer in the X or Y direction). The layer height may be determined/controlled, for instance, by the size/diameter of the output opening of the corresponding nozzle (which in some embodiments may be variable, though it is suitably a fixed size), the nozzle extrusion speed (i.e. the slower the nozzle travels during extrusions, the more filament is deposited in a given place for a given filament feed rate), the filament feed rate. Suitably, the layer height is set or controlled between 10 and 1,000 μm, suitably between 50 and 500 μm, more suitably between 100 and 300 μm, most suitably between 150 and 250 μm.

Suitably, different designs of solid dosage form (as dictated by the "obtained information", including the relevant data files containing a given design) will require different intra-layer and/or inter-layer patterns. For example, a design which uses a single filament to produce a controlled release solid dosage form may print/extrude said filament to produce density gradients either across individual layer(s) or between individual layer(s). Alternatively, for example, a design which uses two or more filaments (e.g. an active ingredient-containing printing filament and one or more further printing filaments) to produce a core-shell solid dosage form may print/extrude said filaments such that each layer is printed as a certain pattern of extruded filaments so that together the combination of layers afford a core-shell design. Suitably in such core-shell designs, the core comprises or consists essentially of one of the filaments (or the corresponding filament composition), most suitably an active-ingredient containing printing filament, and the shell (or one of the shells—since multiple shells are perfectly feasible) comprises or consists essentially of a different filament (or the corresponding filament composition), most suitably a further printing filament. In a particular embodiment, a core-shell-based solid dosage form comprises a core (suitably comprising the active ingredient), a first shell (suitably controlling or delaying release of the active ingredient, e.g. an enteric coating), and optionally a second shell. Suitably the first shell (and suitably any other shells) is substantially or entirely free of the active ingredient. In a particular embodiment, a core-shell-based solid dosage form comprises a core comprising the active ingredient, a first shell comprising or consisting essentially of an enteric polymer and/or extended release polymer (suitably controlling, extending, or delaying release of the active ingredient, e.g. an enteric coating), wherein the first shell is free of the active ingredient. Suitably the first shell (and suitably any other shells) is substantially or entirely free of the active ingredient.

Depending on the shape and dimensions of the solid dosage form to be printed, sacrificial supports or rafts (which can be removed after fabrication of the solid dosage form(s), e.g. by dissolving them after printing) may be used during printing. Such sacrificial supports or rafts are suitably themselves printed from corresponding filament(s). However, in preferred embodiments, no such supports or rafts are required.

Generally, overall mass of a solid dosage form is controlled by controlling the volume of the solid dosage form printed. As such, producing a solid dosage form comprising a desired dose (i.e. weight concentration) of an active ingredient suitably involves tailoring the volume accordingly (i.e. if a higher dose is required, a larger solid dosage form is produced, and vice versa). Suitably calculations performed by the computer on the basis of the obtained information include calculating the final volume of the solid dosage form. Printing is then suitably controlled on this basis.

Where more than one filament is being used to produce a given dosage form, the filament(s) suitably comprise carriers (e.g. melting ingredient(s)) with lower glass transition temperatures (Tg) than may be used with single filament printing. This may help avoid nozzle blockages, since dual filament printing inevitably requires each of the nozzle(s) to be "off" for some of the time, during which blockages may occur if the filament hardens therein.

Further Processing Steps

It will be understood that features relating to further processing steps may (where appropriate) be deemed equally pertinent in the absence of computer-implementation. In fact, any, some, or all further processing steps may be implemented without a computer, and even without an FFF 3D printer.

By way of example, a solid dosage form produced via methods of the invention may be subsequently treated in a variety of ways to afford a further-processed solid dosage form. For instance, a solid dosage form may be enterically coated by standard enteric coating treatments known in the art. Likewise, other release-controlling properties may be imparted to a solid dosage form by further processing which, for example, provides the solid dosage form with one or more shells.

Most suitably, however, all steps (including any further processing steps) are performed by the printing apparatus, and are suitably controlled by the same computer.

Packaging of Solid Dosage Forms

Solid dosage form(s) of the invention may be packaged by any one of a number of methods well known in the art. Where, for example, pharmaceutical solid dosage forms according to the invention are produced via printing apparatus situated in a pharmacy (e.g. to provide a patient with customized medicaments on-demand), the pharmacist may package the solid dosage forms in a number of ways, including in tablet bottles, or even monitored dosing systems which may be subsequently dispatched to hospitals, care homes, and the like for ultimate dispensation to a patient.

In some embodiments, the packaging may be formed by the same or a different printing apparatus. In some examples, the packaging and solid dosage forms may be produced simultaneously, whereby the printing operation utilizes one or more filament(s) pertaining to the solid dosage form, and one or more filament(s) pertaining to the packaging, and the packaging may be built around the solid dosage form(s) during printing.

Database, Collecting Data, and Monitoring Operation/Production

Figure 45:
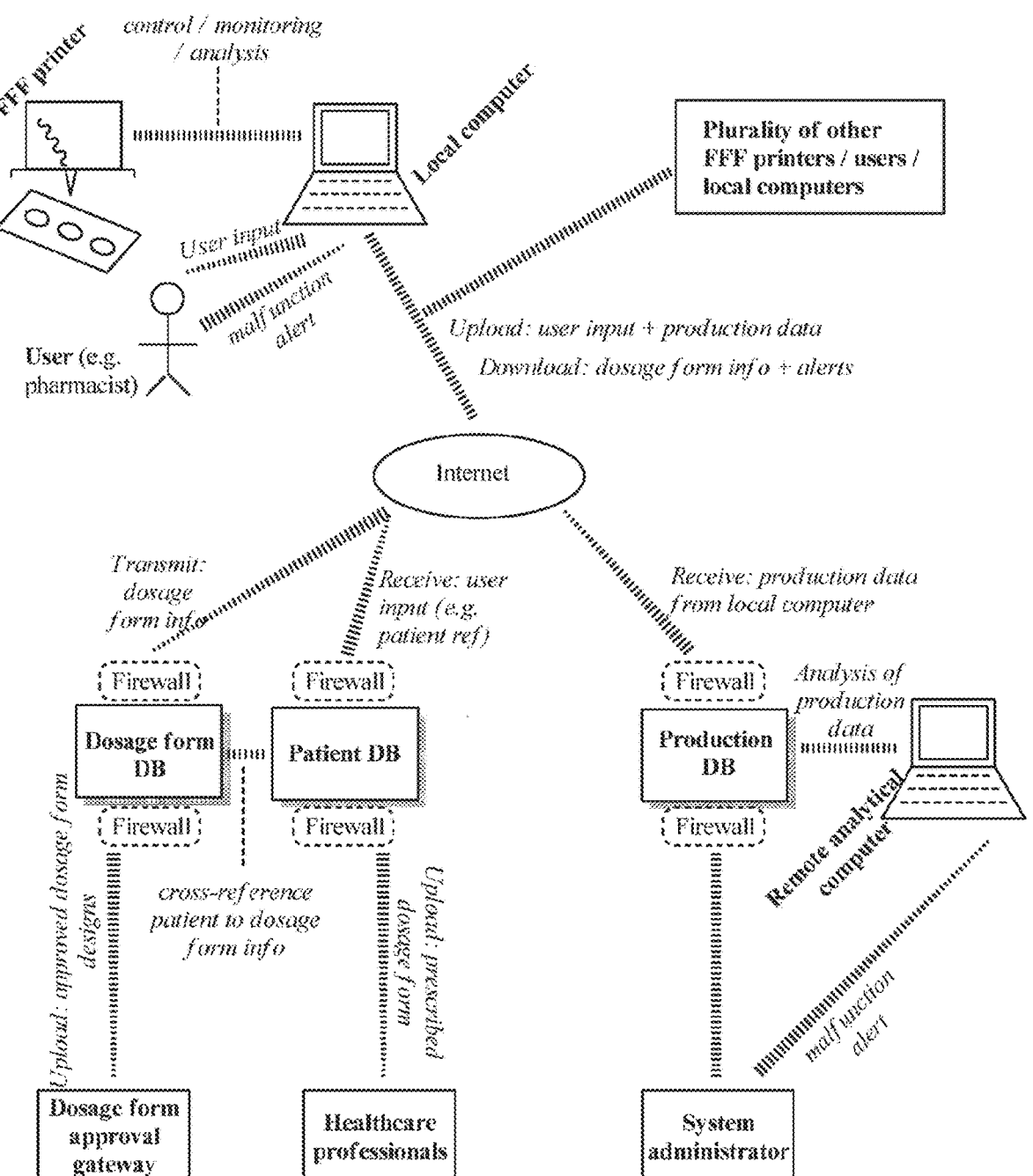
FIG. 45 is a schematic diagram depicting an example of a system of producing and collecting production data relating to solid dosage forms, and details the flow of data and information within the system.

The present invention provides a system for collecting data relating to solid dosage form production (be it in relation to a single printing apparatus/3D printer, or a plurality thereof), suitably as defined herein. An example of such a system is depicted in FIG. 45.

Suitably, the system comprises one or more printing apparati (or FFF 3D printers), most suitably a plurality thereof, suitably as defined herein.

Though each individual printing apparatus may comprise or be otherwise associated with a different (and/or specific) printing control computer, ultimately each individual printing apparatus is suitably associated with or otherwise in communication with one or more (preferably one) monitoring computer each configured to collect production data relating to the operation of one or more of said one or more printing apparati. Suitably, each monitoring computer is the same as each printing control computer (i.e. that which controls printing of the printing apparatus), and most suitably each monitoring computer is a computer located locally to the corresponding printing apparatus (or 3D printer). However, in some embodiments, each monitoring computer is distinct from the printing control computer, and the printing apparatus (or 3D printer) communicated production data to the relevant monitoring computer(s) either via their respective printing control computer (using appropriate communicators associated therewith) and/or directly (again using appropriate communicators).

Suitably, production data relating to the operation of a given printing apparatus (or 3D printer) includes data that is generated by one or more sensors associated with (or comprised of) a given printing apparatus or FFF 3D printer. Such sensors are suitably configured to detect operational parameters (e.g. nozzle temperatures, filament flow rates, nozzle and/or build platform movement speeds, etc.) during the solid dosage form printing process, and suitably configured to correspond each set of operational parameters/production data to specific solid dosage forms or batches thereof, and feedback or transmit said operational parameters to the relevant monitoring computer(s). As such, the production data may include other data, including some of the "obtained information" described herein in relation to the specific solid dosage forms and/or patients in questions, and also dates, times, and other information.

Suitably, the system may comprise one or more analytical computers (optionally the same as one or more of the monitoring computers) configured or operable to analyse the production data. In a particular embodiment, the monitoring and analytical computers are the same computer and may be situated locally to a given printing apparatus. The analytical computer may optionally trigger a response (e.g. data transfers and/or actions) based on an analysis of the data (e.g. alerts where an operational malfunction is recognised).

The system suitably comprises a central production database, which is suitably configured to log (or collect and/or store) production data collected by the monitoring computer(s). As such, the respective monitoring computer(s) suitably comprise or are otherwise associated with a communicator for communicating (or transmitting/receiving, preferably via the network computer system) with the central production database to enable the central production database to log (or collect and/or store) the collected production data. This allows for central monitoring of production of some or all solid dosage forms. Optionally, one or more analytical computers (which as mentioned above may be the same as or different from the one or more monitoring computer(s)) may be configured or operable to analyse data communicated to the central production database and optionally trigger a response (e.g. data transfers and/or actions) based on an analysis of the data (e.g. alerts where an operational malfunction is recognised). Suitably, a detected malfunction relating to a given printing apparatus will be reported (preferably immediately) to a person responsible for the operation and/or maintenance of the given printing apparatus. In certain embodiments, a detected malfunction may trigger a response which prevents any more solid dosage forms being printed by the given printing apparatus.

The system suitably comprises a network computer system (which may suitably include one or more of the internet, one or more local area networks, one or more local or remote servers, and/or one or more associated gateways and/or routers), suitably in operable communication with (or otherwise associated with) the one or more printing apparati, the one or more monitoring computers, one or more optional analytical computers (e.g. if different from the monitoring computers), optional central production database.

The central production database may be any suitable database known in the art.

The production data itself, at least part of which is obtained from the sensors associated with the respective printing apparatus (or 3D printer), may include one or more of:

Time and date of the data collection;

Printing apparatus identification information (e.g. license number, location, etc.)

Batch number(s) of solid dosage form number(s);

At least some of the "obtained Information" relating to the solid dosage form, as defined herein (e.g. design/parameters relating to the dosage form, patient or other relevant information);

Printing apparatus (or 3D printer) operational parameters, for example selected from one or more of extruder nozzle operating temperature(s) (whether measured at the relevant nozzle input, nozzle output, or whether measuring the input current of the nozzle heating element required to maintain a particular temperature), filament feed/flow rate(s) (whether measured at a conveyor, a nozzle input opening, and/or nozzle output opening, or elsewhere), nozzle and/or build platform movement/translation speeds, appearance of solid dosage form during printing (suitably measured via optical techniques, such as photographs), power fluctuations, overall internal (within printing apparatus) and external (ambient outside printing apparatus) temperatures, any other parameters which may impact on the quality and/or consistency of the solid dosage form(s) being printed.

In order to feedback or transmit the above-mentioned operational parameters, the printing apparatus (or 3D printer) may comprise one or more sensors associated with (and configured to detect operational parameters relating to) one or more extruder nozzles or their corresponding heating element(s) (i.e. to monitoring nozzle temperature(s)); one or more filament sources (e.g. spool or cartridge), one or more corresponding conveyor(s), or the input or output(s) of one or more nozzles (i.e. to monitoring filament feed rate(s)) feed/flow rate(s); one or more nozzle or build platform translation elements (i.e. to monitor movement of nozzle(s)/build platform); the build platform (e.g. a camera to monitor the appearance of solid dosage forms during printing); electrical circuitry (to monitor any power fluctuations or electrical parameters), etc. As such, the sensor(s) may be heat detectors, movement detectors, electrical detectors, and/or optical detectors, amongst other things. Each sensor is suitably configured (either wirelessly or wired) to convey sensory data (or production data) to the monitoring computer. Suitably all sensors are configured to convey their respective sensory data in a substantially simultaneous manner such that the relevant printing apparatus (or 3D printer) can be monitored (and/or analysed) in real time.

The production data may be analysed (e.g. via a computer using appropriate monitoring/analytical software, which may be integrated with the solid dosage form printing software) or compared against expected pre-set values (e.g. expected nozzle temperatures or temperature fluctuations for a given filament/solid dosage form; expected physical appearance of solid dosage form at a particular point in the printing cycle; expected filament feed rates, etc.), which may be predetermined based on the design and parameters of the solid dosage form in question (as such the pre-set values may be provided as part of the "obtained information" described herein). A favourable response (indicating the printing apparatus and/or 3D printer is operating within allowed limits of quality control) to the analysis of the production data against expected pre-set values may be issued where the actual production data (or operational parameters thereof) corresponds with the expected pre-set values within a defined tolerance limit. This may trigger a response indicative of satisfactory operation or trigger no response (e.g. if no response is indicative of satisfactory operation). However, an unfavourable response (indicating a malfunctional printing apparatus and/or 3D printer, be it temporary, intermittent, or permanent) to the analysis of the production data against pre-set values may be issued where the actual production data (or operational parameters thereof) deviate from the expected pre-set values by a defined degree. This may trigger a response indicative of unsatisfactory operation (e.g. to alert the relevant parties), optionally along with relevant information allowing the malfunction to be rectified, optionally along with relevant information identifying the solid dosage forms that were produced during (or a certain defined time before or after) the malfunction, and may even trigger the shutdown of the printing apparatus to ensure no more solid dosage forms are produced until satisfactory quality control is restored. For this reason, it is desirable that the operation of the printing apparatus (or 3D printer) be monitored in real time to allow for appropriate responses from the monitoring and/or analytical computer in real time.

Conceivably, collected production data relating to a given printing apparatus (or 3D printer) may be used to obtain or retain regulatory approval for printing solid dosage forms.

Solid Dosage Form

The present invention provides a solid dosage form as defined herein. The solid dosage forms of the invention are generally discernible by chemical and/or microscopic analysis, which suitably reveals the solid dosage form to have been generated by extruded filaments in a layer-by-layer fashion.

The solid dosage form(s) of the invention are suitably for oral administration. Examples of solid dosage forms are tablets, capsules, granules, powders, beads and microcapsules. Most suitably the solid dosage form is a tablet or implant, most suitably a pharmaceutical tablet or medical implant (e.g. an implant which allows for sustained and/or controlled release of an active ingredient).

The solid dosage forms of the invention are advantageously customizable in terms of the type/nature of active ingredient dose, the dose of the active ingredient within the solid dosage form (be it an absolute dose per solid dosage form or the concentration of the active within the dosage form), the mass/volume of the solid dosage form (which is typically adaptable to vary the absolute dose of the active without changing the concentration of the active within the dosage form), the active release profile (which may be varied through judicious use and/or distribution of appropriate excipients, e.g. core-shell arrangements for delayed or sustained release), or shape and appearance (including novelty shapes, colours, and patterns, such as those that may help encourage medication compliance for particular patients).

Many of the features preferred of the solid dosage form are described elsewhere herein. For instance, features described in relation to the method of producing the solid dosage form may suitably reflect a feature of the solid dosage form itself (e.g. layer height). Inevitably the solid dosage form comprises ingredients provided by the filament(s) used in its formation, and may be considered to comprise relevant filament compositions. Since the printing conditions suitably do not (substantially) alter or degrade the ingredients of the respective filament(s), the ensuing descriptions relating to the filament(s) are equally applicable to the solid dosage form.

The solid dosage form may be an immediate release, extended release, or and/or delayed release solid dosage form (where "release" relates to the release of the active ingredient). Typically an immediate release formulation is a substantially uniform solid dosage form. However, extended and/or delayed release formulations are suitably non-uniform solid dosage form, typically comprising a core matrix (which suitably contains the active) and at least one shell matrix surrounding the core (which suitably delays and/or controls release of the active from the core). The shell matrix may essentially be an enteric coating, albeit this may be produced using the printing methods of the invention. Alternatively, a solid dosage form produced according to the invention may be further processed outside the printing apparatus to produce a shell or coating thereon (e.g. an enteric coating around a substantially uniform core).

Suitably, solid dosage forms of the invention comprise greater than or equal to 0.5 wt % active ingredient, suitably greater than or equal to 1 wt % active ingredient, suitably greater than or equal to 5 wt % active ingredient, suitably greater than or equal to 9 wt % active ingredient, suitably greater than or equal to 19 wt %, suitably greater than or equal to 39 wt %. Suitably, solid dosage forms of the invention comprise less than or equal to 60 wt % active ingredient, suitably less than or equal to 50 wt % active ingredient, suitably less than or equal to 30 wt % active ingredient. Suitably, after the active ingredient, the weight balance of solid dosage form consists essentially of carrier(s), diluent(s), and/or excipient(s) (all of which may be deemed to constitute "excipients").

Suitably, solid dosage forms of the invention comprise greater than or equal to 10 wt % excipient(s) and/or active ingredient carrier (suitably excluding any plasticizer(s)), suitably greater than or equal to 20 wt %, suitably greater than or equal to 30 wt %, suitably greater than 50 wt %, suitably greater than or equal to 79 wt %. Suitably, solid dosage forms of the invention comprise less than or equal to 99 wt % excipient(s) and/or active ingredient carrier (suitably excluding any plasticizer(s)), suitably less than or equal to 90 wt %, suitably less than or equal to 80 wt %, suitably less than or equal to 60 wt %. In a particular embodiment, the solid dosage form comprises 40-60 wt % excipient(s) and/or active ingredient carrier (suitably excluding any plasticizer(s)), suitably 45-55 wt %.

Suitably, solid dosage forms of the invention comprise greater than or equal to 0.1 wt % plasticizer(s), suitably greater than or equal to 1 wt %, suitably greater than or equal to 4 wt %, suitably greater than 9 wt %. Suitably, solid dosage forms of the invention comprise less than or equal to 50 wt % plasticizer(s), suitably less than or equal to 30 wt %, suitably less than or equal to 15 wt %, suitably less than or equal to 11 wt %.

Suitably, solid dosage forms of the invention comprise one or more fillers, where a filler is suitably a different component to any carrier ingredients/polymers. The one or more fillers are suitably selected from organic or inorganic compounds, suitably compounds having a melting point of at least 150° C., suitably at least 200° C., suitably at least 500° C., suitably at least 1000° C. The one or more fillers are suitably fillers approved for pharmaceutical and/or nutraceutical use, or are at least GRAS approved. Suitably the one or more fillers constitute or form a part of a non-melting or non-meltable component of a solid dosage form (which suitably refers to the component's meltability under prevailing 3D printing conditions). Suitably the solid dosage form (and/or filament) comprises at least 10 wt % filler(s), suitably at least 25 wt % thereof, more suitably at least 40 wt % thereof. Suitably the solid dosage form (and/or filament) comprises no more than 70 wt % filler(s), suitably no more than 60 wt % thereof. The presence of fillers can significantly improve the structure of corresponding filaments and/or printed dosage forms, and can also facilitate printing itself, especially where the filler(s) are non-melting (or do not undergo any glass transitions) within a heated extrusion nozzle.

Active Ingredient-Containing Printing Filament and Composition

The solid dosage forms of the invention are produced using active ingredient-containing printing filament(s). As such, the solid dosage forms suitably comprise or consist essentially of an active ingredient-containing filament composition. Alternatively, where the solid dosage form is formed from a multiplicity of different filaments, suitably the resulting dosage form is a composite of all filaments in the relevant ratios. In a particular embodiment, a core of a solid dosage form consists essentially of an active ingredient-containing filament composition.

In an aspect of the invention, there is provided a filament or filament composition (and suitably a corresponding solid dosage form or corresponding part/layer of a solid dosage form) comprising a meltable component and a non-meltable component. Suitably the "meltable" component is a component that melts (or undergoes a glass transition to thereby soften) at the designated operating temperature of any corresponding 3D printer extrusion nozzle configured to process said filament, whereas the "non-meltable" component is suitably a component that does not melt (or undergo a glass transition) at the same temperature. Suitably, the "meltable" component may be a mixture of components, which collectively melt or undergo glass transitions together as a mixture—e.g. carrier polymer and plasticizers. However, "non-meltable" components are more likely to be individual components with different melting points or glass transition temperatures. Suitably the meltable component has a melting point (or $T_g$) at or below 220° C., suitably at or below 150° C., suitably at or below 100° C., suitably at or below 80° C., suitably at or below 60° C. Suitably the meltable component has a melting point (or $T_g$—i.e. at least one $T_g$) greater than or equal to 20° C., suitably greater than or equal to 30° C., suitably between 30 and 65° C., suitably between 30 and 35° C. Suitably, the non-meltable component has a melting point (or $T_g$) at or above 150° C., suitably at or above 200° C., suitably at or above 500° C., suitably at or above 1000° C.

As explained above, references to "meltable" and "non-meltable" components encompasses "softenable" and "nonsoftenable" components respectively, where instead of "melting" at a particular temperature the component "softens". As such, references in this context to a melting point may additionally or alternatively relate to a glass transition temperature. Such glass transitions are particularly applicable to thermoplastic component(s). As such, a "meltable" component may be a thermoplastic component, suitably who glass transition temperature (temperature at which the thermoplastic component softens rather than melts) is lower than the temperature to which said component is exposed (e.g. during printing).

Each of the various filament ingredients described herein are suitably either a meltable or a non-meltable component (not both). For instance, typically a carrier polymer, such as an active ingredient carrier is suitably a meltable component and is suitably selected to undergo melting or a glass transition during printing. A filler (e.g. calcium tribasic phosphate, talc, etc.), by contrast, is suitably a non-meltable component and is suitably selected so as to remain solid during printing. Notwithstanding the contrasting melting/glass-transition properties of the various ingredients, suitably the filament itself has a characteristic glass transition temperature. Suitably this characteristic glass transition temperature is measurable using the well-known techniques described herein and elsewhere, and is a consequence of the combination of ingredients. Various concentration (wt %) ratios of meltable:non-meltable components may afford viable filaments for 3D printing. Suitably the ratio of meltable:non-meltable components is between 1:10 and 10:1, more suitably between 3:7 and 7:3, suitably between 4:6 and 6:4, where suitably the meltable component(s) collectively include all relevant meltable components (e.g. carrier polymers, plasticizers, etc.) and the non-meltable component(s) include all relevant non-meltable components (e.g. filler(s), lubricants, active ingredient(s), etc.). Suitably the active ingredient is itself a non-meltable component.

The active ingredient is suitably distributed (substantially) uniformly within the active ingredient-containing printing filament (suitably within an active ingredient carrier(s)). Having the active ingredient distributed within the relevant filament before printing generally allows for higher active loadings and reduces overall processing.

However, in some embodiments, the active ingredient may be distributed (substantially) non-uniformly within the active ingredient-containing printing filament (suitably within an active ingredient carrier(s)). In some cases, such embodiments may contain a gradient of the active through the thickness of the filament.

The active ingredient-containing printing filament is suitably sufficiently stiff to enable it to be viably fed (at a consistent rate) to and through a corresponding extrusion nozzle within the printing apparatus or 3D printer. The active ingredient-containing printing filament is suitably sufficiently stiff to avoid the filament becoming stretched during printing. However, the filament is suitably not so stiff that the nozzle operating temperature required to extrude the filament will degrade the contents of the ingredient (e.g. causing a change in composition of greater than or equal to 1 wt %).

The active ingredient-containing printing filament is suitably sufficiently flexible and/or soft to enable it to be extruded (at a consistent rate) from a corresponding extrusion nozzle within the printing apparatus or 3D printer. The active ingredient-containing printing filament is suitably sufficiently flexible and/or soft to allow the filament to be viably spooled/coiled around a filament spool.

The active ingredient-containing printing filament is suitably neither too brittle (and breakable during printing/spooling) or too flexible (precluding its viable conveyance through the printing apparatus or 3D printer). The composition (e.g. active loading, concentration and type of excipients) and dimensions (e.g. thickness) of the filament can be judiciously altered, using the principles taught in the present disclosure, to obtain an optimal filament structure.

The active ingredient-containing printing filament suitably has a thickness (i.e. diameter or maximum thickness) of between 0.1 mm and 5 mm, suitably between 0.5 mm and 4 mm, more suitably between 1 mm and 3 mm, most suitably between 1.5 mm and 2 mm. In a particular embodiment, the active ingredient-containing printing filament has a thickness of about 1.75 mm. However, the filament thickness may be adjusted to suit the extrusion nozzles (in particular the size/diameter of the respective openings thereof) through which they are to be extruded.

Suitably, the active ingredient-containing printing filament is capable of being coiled (or spooled) around a spool, suitably a spool having a hub diameter of about 20 cm, suitably a hub diameter of about 10 cm, suitably about 5 cm, suitably about 2.5 cm, suitably about 1 cm, suitably without breaking and/or stretching.

Suitably, the active ingredient-containing printing filament comprises at least one ingredient ("melting ingredient(s)") that melts at a respective nozzle operating temperature (which may be a temperature defined herein, suitably so as to allow extrusion of the filament through the nozzle) and at least one ingredient ("non-melting ingredients") that remains in or is otherwise transformed into a solid and/or particulate form at a respective nozzle operating temperature (suitably so that solids and/or particulates are present within the nozzle during extrusion of the filament through the nozzle). The melting ingredient(s) suitably at least comprises the active ingredient carrier(s). However, the melting ingredient(s) may suitably include diluents(s), carrier(s), and/or excipient(s), and may suitably melt as a composite—the combination of a carrier/diluent and plasticizer may, for example, constitute "melting ingredient(s)". The non-melting ingredient(s) suitably at least comprises the active ingredient itself (preferably this does not melt during printing so that its polymorphic form is duly retained). However, the non-melting ingredient(s) may suitably include excipient(s) and/or an active ingredient, suitably which has a melting point (or composite melting point) higher than the nozzle operating temperature, and suitably higher than a melting point, composite melting point, or glass transition temperature of the corresponding non-melting ingredient(s). The non-melting ingredient(s) are suitably still co-extruded from the relevant nozzle along with any melting ingredient(s). However, the presence of non-melting ingredient(s), especially when in particulate form at the operating temperature of the relevant nozzle, surprisingly reduces nozzle blockages and may additionally or alternatively improve overall resolution of the solid dosage form. Moreover, non-melting ingredient(s) also help reduce the formation of bubbles during printing, and degradation of excipients and the active ingredient. Particularly useful non-melting ingredients include lubricants, such as talk.

The invention is applicable to any FFF printing filaments in that an aspect of the invention provides a FFF printing filament comprising a material which melts at a given nozzle operating temperature and a material which remains in or is otherwise transformed into a solid and/or particulate form at the given nozzle operating temperature (suitably so that solids and/or particulates are present within the nozzle during extrusion of the filament through the nozzle).

The active ingredient-containing printing filament suitably has a glass transition temperature ($T_g$) between 20 and 200° C., suitably between 45° C. and 165° C., or suitably between −10° C. and 165° C. The glass transition temperature of a filament typically needs to be higher in the absence of any non-meltable component(s). Suitably the ingredient-containing printing filament suitably has a glass transition temperature ($T_g$) between 30 and 65° C. (especially where a non-meltable component is present, be it a filler, a drug, and/or both or some other). In an embodiment the active ingredient-containing printing filament has a glass transition temperature between 30 and 35° C. The active ingredient-containing printing filament suitably has a glass transition temperature lower than the melting point of the active ingredient, suitably at least 20° C. below, more suitably at least 50° C. below, more suitably at least 80° C. below.

Suitably, the active ingredient-containing printing filament is judiciously tailored with appropriate proportions and types of active(s) and carrier(s)/excipient(s) to produce filaments with a desired $T_g$ and/or melting point to minimise the corresponding nozzle operating temperature required for extrusion.

Suitably, the active ingredient-containing printing filament of the invention comprises greater than or equal to 0.001 wt % active ingredient, suitably greater than or equal to 0.01 wt % active ingredient, suitably greater than or equal to 0.005 wt % active ingredient, suitably greater than or equal to 0.1 wt % active ingredient, suitably greater than or equal to 0.5 wt % active ingredient, suitably greater than or equal to 1 wt % active ingredient, suitably greater than or equal to 5 wt % active ingredient, suitably greater than or equal to 9 wt % active ingredient, suitably greater than or equal to 19 wt %, suitably greater than or equal to 39 wt %. Suitably, the active ingredient-containing printing filament of the invention comprises less than or equal to 60 wt % active ingredient, suitably less than or equal to 50 wt % active ingredient, suitably less than or equal to 30 wt % active ingredient. Suitably, after the active ingredient, the weight balance of the active ingredient-containing printing filament consists essentially of carrier(s), diluent(s), and/or excipient(s) (all of which may be deemed to constitute "excipients").

Suitably, the active ingredient-containing printing filament of the invention comprises greater than or equal to 10 wt % excipient(s) and/or active ingredient carrier (suitably excluding any plasticizer(s)), suitably greater than or equal to 20 wt %, suitably greater than or equal to 30 wt %, suitably greater than 50 wt %, suitably greater than or equal to 70 wt %, suitably greater than or equal to 79 wt %. Suitably, the active ingredient-containing printing filament of the invention comprises less than or equal to 99 wt % excipient(s) and/or active ingredient carrier (suitably excluding any plasticizer(s)), suitably less than or equal to 95 wt %, suitably less than or equal to 80 wt %, suitably less than or equal to 60 wt %.

Suitably, the active ingredient-containing printing filament of the invention comprises greater than or equal to 0.1 wt % plasticizer(s), suitably greater than or equal to 1 wt %, suitably greater than or equal to 3 wt %, suitably greater than or equal to 4 wt %, suitably greater than 9 wt %. Suitably, the active ingredient-containing printing filament of the invention comprises less than or equal to 50 wt % plasticizer(s), suitably less than or equal to 40 wt %, suitably less than or equal to 30 wt %, suitably less than or equal to 15 wt %, suitably less than or equal to 11 wt %.

Suitably the combined concentration of active ingredient carrier(s) and plasticizer(s) is between 30 and 80 wt %, suitably between 40 and 60 wt %, most suitably between 45 and 55 wt %.

As mentioned in relation to the solid dosage form, the composition of which substantially reflects that of the filament where only a single filament is used, the filament suitably comprises one or more fillers, suitably a single filler. Where multiple filaments are used during printing (e.g. core-shell tablets), suitably the core of any resulting printed dosage form has a composition which substantially reflects that of the active-ingredient-containing filament. Such fillers, however, may equally be present in any non-active-ingredient-containing filaments. Suitably the one or more fillers are present within the solid dosage form, core, or active-ingredient-containing filament (and where relevant any non-active-ingredient-containing filaments) at a concentration of at least 10 wt % filler(s), suitably at least 25 wt % thereof, more suitably at least 40 wt % thereof. Suitably the solid dosage form, core, or active-ingredient-containing filament (and where relevant any non-active-ingredient-containing filaments) comprises no more than 70 wt % filler(s), suitably no more than 60 wt % thereof.

In a particular embodiment, the active ingredient-containing printing filament comprises:
0.01-50 wt % active ingredient;
20-99.99 wt % excipient(s) and/or active ingredient carrier;
optionally 1-30 wt % plasticizer.
In a particular embodiment, the active ingredient-containing printing filament comprises:
0.01-50 wt % active ingredient;
20-99.99 wt % active ingredient carrier;
10-70 wt % filler(s);
optionally 1-30 wt % plasticizer.
In a particular embodiment, the active ingredient-containing printing filament comprises:
5-30 wt % active ingredient;
55-95 wt % excipient(s) and/or active ingredient carrier;
Optionally 1-15 wt % plasticizer.
In a particular embodiment, the active ingredient-containing printing filament comprises:
5-30 wt % active ingredient;
55-90 wt % excipient(s) and/or active ingredient carrier;
5-15 wt % plasticizer.
In a particular embodiment, the active ingredient-containing printing filament comprises:
15-60 wt % active ingredient;
25-85 wt % excipient(s) and/or active ingredient carrier (in this case, most suitably an acrylate-based polymer as defined herein);
optionally (and preferably) 1-15 wt % plasticizer.
In a particular embodiment, the active ingredient-containing printing filament comprises:
40-60 wt % active ingredient;
35-55 wt % excipient(s) and/or active ingredient carrier (in this case, most suitably an acrylate-based polymer as defined herein);
1-15 wt % plasticizer.
In a particular embodiment, the active ingredient-containing printing filament comprises:
0.1-40 wt % active ingredient;
35-65 wt active ingredient carrier;
35-65 wt % filler(s);
Optionally 1-20 wt % plasticizer.

Active Ingredient

The present invention is suitably applicable to any active ingredient. The present disclosure allows the skilled person to readily develop viable active-ingredient containing printing filaments for FFF 3D printing through the judicious selection of appropriate active ingredient carrier(s) and/or excipient(s), which may accompany the active ingredient within the filament.

The active ingredient is most suitably a pharmaceutical drug substance (which may be any suitable pharmaceutical compound or pharmaceutically acceptable salt, solvate, prodrug, or polymorph thereof). As such, any carriers, diluents, and/or excipients used within the active ingredient-containing printing filament, or indeed any further printing filaments that may be used in the manufacture of a corresponding solid dosage form, are suitably pharmaceutically acceptable carriers, diluents, and/or excipients.

The active ingredient is suitably in the same form as the active ingredient is in approved drug products. The active ingredient is suitably in the same form (and has substantially the same purity) as the active ingredient before it is incorporated into the filament.

In a particular embodiment, the active ingredient is very soluble, freely soluble, or soluble in accordance with the standard USP (United States Pharmacopeia) definitions for solubility. In another embodiment, the active ingredient is sparingly soluble, slightly soluble, or very slightly soluble in accordance with the standard USP definitions for solubility.

In a particular embodiment, the active ingredient is very soluble in accordance with the standard USP definitions for solubility.

In a particular embodiment, the active ingredient is freely soluble in accordance with the standard USP definitions for solubility.

In a particular embodiment, the active ingredient is soluble in accordance with the standard USP definitions for solubility.

In some embodiments, the active ingredient is sparingly soluble in accordance with the standard USP definitions.

In some embodiments, the active ingredient is slightly soluble in accordance with the standard USP definitions.

In some embodiments, the active ingredient is very slightly soluble in accordance with the standard USP definitions.

In some embodiments, the active ingredient is practically insoluble in accordance with the standard USP definitions.

The active ingredient suitably has a higher melting point than the melting point or glass transition temperature (softening temperature) of the active-ingredient containing printing filament as a whole.

The active ingredient suitably has a higher melting point than the melting point or glass transition temperature (softening temperature) of the active-ingredient carrier or active-ingredient-excipient combination within the filament.

The active ingredient suitably has a higher melting point than the operating temperature of the extrusion nozzle used in the printing of the relevant filament during the formation of the solid dosage form. This is preferred to avoid a transition in form (e.g. polymorphic form) of the active ingredient during the formation of the solid dosage form. This is also preferred to reduce the risk of nozzle blockage. This is also preferred in order to afford high resolution printing of solid dosage forms. Finally, an active ingredient satisfying this condition is likely to be stable (e.g. to degradation) at the given nozzle operating temperature, at least for the period of time the filament is exposed to such temperatures during 3D printing.

The active ingredient suitably has a higher melting point than the operating temperature of the extrusion nozzle used in the initial formation of the active ingredient-containing filament.

Suitably, the active ingredient has a melting point greater than or equal to 150° C., more suitably greater than or equal to 190° C., more suitably greater than or equal to 250° C.

In a particular embodiment, the active ingredient is selected from theophylline, dipyridamole, prednisolone, or diclofenac potassium. In a particular embodiment, the active ingredient is theophylline or dipyridamole.

The same parameters suitably apply where the solid dosage form is a nutraceutical or food supplement solid dosage form.

Active Ingredient Carrier

The active ingredient-containing printing filament suitably comprises an active ingredient carrier, and may suitably comprise one or more active ingredient carriers. Suitably one active ingredient carrier predominates over all others in filaments containing more than one.

Any suitably carrier(s) may be used. In the context of pharmaceuticals, carriers are customarily used in the compounding of solid dosage forms such as tablets and capsules. A solid oral dosage form may be designed to release the active portion of the formulation at the point in the gastro-intestinal tract where bioavailability is maximized and pre-systemic degradation is minimized. At least one additional agent may be included to facilitate absorption of an active of the disclosure and/or any additional therapeutic agents. In such solid dosage forms, the active compound is typically mixed with at least one inert, pharmaceutically acceptable excipient or carrier such as lactose, sodium citrate or dicalcium phosphate and/or one or more: a) fillers or extenders for example starches, lactose, sucrose, glucose, mannitol and silicic acid; b) binders for example carboxymethylcellulose, alginates, gelatin, polyvinylpyrrolidone, sucrose and acacia; c) humectants for example glycerol; d) disintegrating agents for example agar-agar, calcium carbonate, potato or tapioca starch, alginic acid, certain silicates and sodium carbonate; e) solution retarding agents for example paraffin; f) absorption accelerators for example quaternary ammonium compounds; g) wetting agents for example cetyl alcohol and glycerol monostearate; h) absorbents for example kaolin and bentonite clay and i) lubricants for example talc, calcium stearate, magnesium stearate, solid polyethylene glycols, sodium lauryl sulfate and mixtures thereof. Solid compositions of a similar type may also be employed as fillers in soft and hard-filled gelatin capsules using such excipients as lactose or high molecular weight polyethylene glycol, for example.

The melting point (or glass transition temperature) of the active ingredient carrier is suitably less than the active ingredient, suitably by at least 20° C., more suitably by at least 40° C., more suitably by at least 50° C. The active ingredient carrier suitably has a melting point between 140 and 250° C., more suitably between 150 and 200° C., most suitably between 155 and 175° C.

Suitably the active ingredient carrier has a specific heat of between 0.1 and 1 cal/g° C., most suitably between 0.3 and 0.5.

The active ingredient carrier suitably has a density between 1.1 and 1.6 g/mL, most suitably between 1.2 and 1.4.

The active ingredient carrier suitably has a glass transition temperature lower than the melting point of the active ingredient, suitably at least 20° C. lower, more suitably at least 40° C. lower, more suitably at least 50° C. lower.

The active ingredient carrier(s), especially where an immediate release solid dosage form is desired, is suitably selected from a carrier (suitably a cationic polymer or neutral polymer or copolymer) having a viscosity of no more than 50 mPa·s, suitably no more than 30 mPa·s, suitably no more than 10 mPa·s, though suitably having a viscosity of at least 1 mPa·s—most suitably a viscosity between 2 and 8 mPa·s. The active ingredient carrier(s), especially where an immediate release solid dosage form is desired, is suitably selected from a carrier having a molecular weight of at least 20,000 g/mol, more suitably at least 35,000, more suitably at least 45,000, though suitably less than 1,000,000 g/mol, more suitably less than 100,000 g/mol—most suitably a molecular weight between 35,000 and 65,000 g/mol. The active ingredient carrier(s), especially where an immediate release solid dosage form is desired, is suitably selected from a carrier having a glass transition temperature ($T_g$) of at most 100° C., suitably at most 80° C., suitably at most 50° C., though suitably at least −10° C., more suitably at least 35° C.—most suitably a $T_g$ between 30 and 60° C. In some embodiments, the active ingredient carrier(s) may not have a glass transition temperature as such, though observed softening may still occur. The active ingredient carrier(s), especially where an immediate release solid dosage form is desired, is suitably an (optionally alkyl-, suitably methyl- or ethyl-) acrylate, methacrylate and/or ethacrylate copolymer (suitably comprising amine-containing monomeric units) suitably having a viscosity between 2 and 8 mPa., suitably having a molecular weight between 35,000 and 65,000 g/mol, and/or suitably having a $T_g$ between 30 and 60° C. In a particular embodiment, the relevant copolymer is poly (butyl methacrylate-co-(2-dimethylaminoethyl) methacrylate-co-methyl methacrylate), suitably in a respective monomeric molar ratio of 1:2:1 (+/−5% for each molar value of the ratio). The active ingredient carrier is suitably Eudragit® E.

The active ingredient carrier(s), especially where an extended release solid dosage form is desired, is suitably selected from a carrier having a viscosity of no more than 30 mPa·s, suitably no more than 20 mPa·s, suitably no more than 16 mPa·s, though suitably having a viscosity of at least 1 mPa·s—most suitably a viscosity between 1 and 15 mPa·s. The active ingredient carrier(s), especially where an extended release solid dosage form is desired, is suitably selected from a carrier having a molecular weight of at least 10,000 g/mol, more suitably at least 250000, more suitably at least 30,000, though suitably less than 100,000 g/mol, more suitably less than 40,000 g/mol—most suitably a molecular weight between 29,000 and 35,000 g/mol. The active ingredient carrier(s), especially where an extended release solid dosage form is desired, is suitably selected from a carrier having a glass transition temperature ($T_g$) of at most 100° C., suitably at most 80° C., suitably at most 70° C., though suitably at least 40° C., more suitably at least 50° C.—most suitably a $T_g$ between 55 and 70° C. In some embodiments, the active ingredient carrier(s) may not have a glass transition temperature as such, though observed softening may still occur. The active ingredient carrier(s), especially where an extended release solid dosage form is desired, is suitably an (optionally alkyl-, suitably methyl- or ethyl-) acrylate, methacrylate and/or ethacrylate copolymer (suitably comprising amine-containing monomeric units) suitably having a viscosity between 1 and 15 mPa., suitably having a molecular weight between 29,000 and 35,000 g/mol, and/or suitably having a $T_g$ between 55 and 70° C. In a particular embodiment, the relevant copolymer is poly (ethyl acrylate-co-methyl methacrylate-co-trimethylammonioethyl methacrylate chloride), suitably in a respective monomeric molar ratio of 1:2:0.2 (+/−5% for each molar value of the ratio). The active ingredient carrier is suitably Eudragit® RL.

The active ingredient carrier(s), especially where a delayed release solid dosage form is desired, is suitably selected from a carrier having a viscosity of at least 20 mPa·s, suitably at least 40 mPa·s, suitably at least 50 mPa·s, though suitably having a viscosity of no more than 300 mPa·s, suitably no more than 210 mPa·s—most suitably a viscosity between 40 and 210 mPa·s. The active ingredient carrier(s), especially where a delayed release solid dosage form is desired, is suitably selected from a carrier having a molecular weight of at least 10,000 g/mol, more suitably at least 15,000, though suitably less than 400,000 g/mol—in a particular embodiment the molecular weight is between 10,000 and 25,000 g/mol, whereas in other embodiments the molecular weight is between 100,000 and 350,000 g/mol. The active ingredient carrier(s), especially where a delayed release solid dosage form is desired, is suitably selected from a carrier having a glass transition temperature ($T_g$) of at least 80° C., suitably at least 90° C., suitably at least 100° C., though suitably at most 200° C., more suitably at most 160° C.—most suitably a $T_g$ between 90 and 160° C. In some embodiments, the active ingredient carrier(s) may not have a glass transition temperature as such, though observed softening may still occur. The active ingredient carrier(s), especially where a delayed release solid dosage form is desired, is suitably selected from:

an (optionally alkyl-, suitably methyl- or ethyl-) acrylate, methacrylate and/or ethacrylate polymer or copolymer (suitably free of any amine-containing monomeric units), suitably with a viscosity between 90 and 210 mPa·s, suitably with a molecular weight between 100,000 and 350,000 g/mol, and/or suitably with a glass transition temperature between 90 and 140° C.; wherein the relevant polymer or copolymer is suitably selected from: poly(methacrylic acid-co-ethyl acrylate), suitably in a respective monomeric molar ratio of 1:1 (+/−5% for each molar value of the ratio); poly (methacrylic acid-co-methyl methacrylate), suitably in a respective monomeric molar ratio of 1:1 (+/−5% for each molar value of the ratio); poly(methacrylic acid-co-methyl methacrylate), suitably in a respective monomeric molar ratio of 1:2 (+/−5% for each molar value of the ratio); or a cellulose or cellulose derivative, suitably a hydroxypropyl methylcellulose (HPMC) derivative, most suitably a hydroxypropyl methylcellulose (HPMC) acetate succinate (HPMCAS), suitably with a molecular weight between 10,000 and 25,000 g/mol and/or suitably with a glass transition temperature between 100 and 145° C. (or suitably between 100 and 165° C.); wherein the relevant HPMCAS is suitably selected from Aqoat LG, Aqoat MG, and/or Aqoat HG. Suitably HPMC derivatives may, however, also include hydroxypropylmethylcellulose phthalate (HPMCP), such as HP-50, HP-55 and HP-55S grades thereof.

In principle any suitably carrier(s) may be used, including any one or more of those selected from an (optionally alkyl-, suitably methyl- or ethyl-) acrylate, methacrylate and/or ethacrylate copolymer (suitably comprising amine-containing monomeric units); an (optionally alkyl-, suitably methyl- or ethyl-) acrylate, methacrylate and/or ethacrylate polymer or copolymer (suitably free of any amine-containing monomeric units); a cellulose or cellulose derivative; polyvinyl alcohol (PVA); poly(lactic-co-glycolic acid) (PLGA); and/or any suitable pharmaceutical acceptable carrier.

(Optionally alkyl-, suitably methyl- or ethyl-) acrylate, methacrylate and/or ethacrylate polymer or copolymers are particularly advantageous at supporting high loadings of the active ingredient.

The active ingredient carrier(s) is suitably selected from Eudragit® E, Eudragit® NE, HPC SSL, Eudragit® RS, Eudragit® RL, HPC SL, HPC M, HPC H, Eudragit® L100-55, Eudragit® L100, Eudragit® S100, Aqoat LG, Aqoat MG, Aqoat HG, and/or polyvinyl alcohol (PVA), or any combination of any of the aforementioned.

In some embodiments, especially where an active ingredient has limited solubility in a target solubilisation medium (e.g. in the body), active ingredient carrier(s) such as poly-vinylpyrrolidone polymers or polyvinylpyrrolidone-derived polymers may be employed. Such polymers can facilitate dissolution of an active ingredient that may otherwise exhibit limited solubility. In a particular embodiment, PVP K29-32 (a povidone) may be used. When present, suitably a PVP or PVP-based carrier is present (e.g. in a filament, solid dosage form, or core) at a concentration of between 20 and 80 wt %, suitably at a concentration between 40 and 60 wt %, suitably 45-55 wt %. PVP and PVP-based carrier polymers may be used alongside one or more filler(s), and optionally with other ingredients such as plasticizer(s). Mixtures of different PVP or PVP-based carriers may also or alternatively be used (e.g. PVPs of different molecular weights).

In some embodiments, polyalkyleneglycol and polyal-kyleneglycol-derived polymers may be employed as a carrier polymer, such as an active ingredient carrier. In a particular embodiment the polyalkyleneglycol or polyal-kyleneglycol-derived carrier polymer is a polyethylenegly-col (PEG) or polyethyleneglycol-derived carrier polymer. Suitably, wherever a PEG or PEG-based carrier polymer is deployed, at least a portion of the PEG or PEG-based carrier polymer has a molecular weight of at least 100,000, though suitably at most 1,000,000. However, a mixture of different polyalkyleneglycol and polyalkyleneglycol-derived poly-mers (e.g. PEG or PEG-based carrier polymers) may be incorporated within filaments and/or corresponding dosage forms. For instance, a high molecular weight PEG may be used alongside a relatively low molecular weight PEG to achieve an optimal balance of properties. Higher molecular weight PEG and PEG-based polymers (e.g. $M_w \geq 80,000$) can serve as carrier molecules, whereas lower molecular weight PEG and PEG-based polymers (e.g. $M_w$ 200-20000) may serve as plasticizers and/or solubility enhancers. Increasing the proportions of lower molecular weight PEGs is likely to lower the $T_g$ of the resulting filament. Moreover, increasing the proportions of lower $M_w$ PEGs also favours accelerated drug release. Suitably any PEG or PEG-based carrier poly-mers are used alongside one or more filler(s), though such polymers may be used with or without non-melting com-ponents.

Fillers

As aforementioned mentioned, suitably filaments of the invention (and their corresponding dosage forms or layers therein) comprise one or more filler(s), suitably in the amounts stated. Suitably filler(s) are included alongside carrier polymer(s) such as those described herein, and optionally also along with other excipients such as plasti-cizer(s), binders, and the like. Achieving an ideal balance between the respective ingredients is possible by following the teachings of the present specification. Typically, the inclusion of one or more filler(s) within a filament or filament composition will strengthen the resulting filaments and thereby facilitate their generation and processing during 3D printing. However, too much filler(s) may lead to a degree of brittleness, which can be mitigated through the judicious use of other ingredients (e.g. plasticizers and the like that may serve to soften the filaments), by lowering the proportions of filler, and/or changing the nature of the filler (e.g. its melting point).

Numerous fillers are known in the art of pharmaceuticals and nutraceuticals, and any of these may be deployed where appropriate or desired for a particular drug or nutraceutical formulation. Suitably, at least one (preferably all) of the filler(s) have a melting point exceeding the relevant oper-ating temperature(s) of components with which the filaments make contact (e.g. printing nozzles, extrusion nozzles, and/or heated conveyors or feeders). Suitably, the filler(s) are substantially inert, and/or suitably have minimal or no interaction with other component(s) of the filament or dos-age form, for instance a drug or polymer. Inclusion of filler(s) is particularly appropriate in systems in which the drug has a relatively low melting point or imparts a plasti-cizing effect. Inclusion of filler(s) may also be appropriate in systems having a drug present in only relatively low con-centrations (e.g. within the filament). In a particular embodi-ment the filler(s) may include lactose and/or calcium tribasic phosphate. Talc is another ideal filler for use in the filaments and dosage forms of the present invention, especially in conjunction with PVP or PEG polymers.

Optional Plasticizer

The active ingredient-containing printing filament may suitably comprise a plasticizer. Such a plasticizer may improve the quality of filament (e.g. in terms of smoothness, flexibility, fluidity on extrusion). The plasticizer may serve to lower the glass transition (or softening) temperature of the filament (or of the carriers), and consequent may allow lower extrusion nozzle operating temperatures to be used during printing and/or formation of the filament.

In general, if a filament has a glass transition temp (Tg) that is too high, it may be too brittle (for instance, to coil onto a filament spool) for an FFF 3D printer to handle (i.e. without breaking the filament), and/or may require extrusion nozzle operating temperatures that are so high that degra-dation of the ingredients within the filament may occur. Where a filament has a glass transition temperature that is too low, the filament may be too soft and/or flexible for an FFF 3D printer to handle, too distortable for consistent printing, and yields poor shape control and incoherent solid dosage form products. A plasticizer can be used as an additive to optimize the performance of a filament by obtaining the optimal glass transition or softening tempera-ture and striking the right balance of properties.

The filament may comprise any suitable plasticizer. Many pharmaceutically acceptable plasticizers are known in the art for use in the formation of pharmaceutical solid dosage forms.

In a particular embodiment, the plasticizer may be selected from one or more of triethylcitrate (TEC), glycerol, castor oil, oleic acid, glycerol, triacetin and polyalkylene glycols (e.g. a polyethylene glycol or polypropylene glycol, such as PEG400).

Certain plasticizers may be more appropriate than others, depending on the particular active ingredient and active ingredient carrier(s). Particular combinations that offer excellent performance include:

TEC and/or triacetin (0.5-10 wt % thereof within the filament as a whole) plasticizer in conjunction with cellulose-based carriers, such as HPC, HPMC, and HPMCAS;

glycerol plasticizer in conjunction with PVA-based carrier;

TEC plasticizer (suitably 0.5-30 wt % thereof within the filament as a whole) in conjunction with (optionally alkyl-, suitably methyl- or ethyl-) acrylate, methacrylate and/or ethacrylate polymer or copolymers.

More than one plasticizer (optionally as defined herein) may be used.

The active ingredient-containing printing filament (and/or optionally the solid dosage form or the core thereof) may suitably comprise between 0.1 wt % and 50 wt % plasticizer(s), more suitably between 2.5 wt % and 40 wt %, more suitably between 5 wt % and 20 wt %, most suitably between 8 and 12 wt %, especially where the glass transition temperature of the filament without the plasticizer(s) is greater than or equal to 180° C.

In an alternative embodiment, instead of incorporating the plasticizer within the filament, the plasticizer may be coated upon the surface of the relevant filament, suitably so as to provide the required malleability and viable nozzle operating temperature. In a particular embodiment, during the printing process a filament (with or without a plasticizer therein) may be conveyed towards a corresponding extrusion nozzle via a plasticizer dispenser which coats the surface (or a part thereof) of said filament with the plasticizer. As such, in a particular embodiment, the active ingredient-containing printing filament may suitably comprise or be contacted with a plasticizer before it is extruded from a corresponding extrusion nozzle.

Other Ingredients

The active ingredient-containing printing filament may contain one or more other ingredients in addition to those aforedescribed. Other ingredients may suitably include one or more excipients, excipient carriers, and/or diluents, all of which may be included in active filament.

In particular, the one or more other ingredients within the active ingredient-containing printing filament may be selected from one or more fillers/diluents, antiadherents, binders, disintegrants, lubricants, glidants, flavourants, preservatives, sweeteners, and coatings.

Suitable antiadherents may include magnesium stearate. Suitable diluents/fillers may include plant cellulose, dibasic calcium phosphate, vegetable fats and oils, lactose, sucrose, glucose, mannitol, sorbitol, calcium carbonate, magnesium stearate, and/or microcrystalline cellulose. Suitable binders may include saccharides; polysaccharides/derivatives thereof, for example, starches, cellulose or modified cellulose such as microcrystalline cellulose and cellulose ethers such as hydroxypropyl cellulose, hydroxypropyl methyl cellulose, and derivatives thereof; sugar alcohols, for example, xylitol, sorbitol or maltitol; synthetic polymers, for example, polyvinylpyrrolidone (PVP), polyethylene glycol (PEG) . . . ). Suitable disintegrants may include crosslinked polyvinylpyrrolidone (crospovidone), crosslinked sodium carboxymethyl cellulose, croscarmellose sodium, modified starch sodium and/or starch glycolate. Suitable lubricants may include silica; fats, e.g. vegetable stearin; magnesium stearate or stearic acid; and/or talc. Suitable glidants may include fumed silica, talc, magnesium carbonate, and/or colloidal silica. Suitable coatings may include tablet coatings to protect tablet ingredients from deterioration by moisture in the air and make large or unpleasant-tasting tablets easier to swallow (e.g. a cellulose ether hydroxypropyl methylcellulose (HPMC) film coating; synthetic polymers, shellac, corn protein zein or other polysaccharides, gelatin; enteric coatings, for example, including fatty acid(s), wax(es), shellac, plastics, plant fibres). The generic classes of excipients are well understood by those skilled in the art.

In particular embodiments, the active ingredient-containing printing filament comprises talc. Talc may serve as non-melting particles which improve the performance of the extrusion nozzle. A filament or a final solid dosage form (or a core thereof) may comprise between 0.5 and 20 wt % talc, though preferably at most 15 wt %, since too much lubricant may lead to poor adhesion of the solid dosage form to the build platform during printing.

Such excipients may be chosen to suit the properties of the final solid dosage form, the properties of a filament, or both, or a judicious compromise between both. For instance, in terms of the solid dosage form, excipient(s) may be chosen for ease of administration to the target patient population(s) by the intended route; improved dosing compliance; consistency and control of drug bioavailability; to enable bioavailability; improved active ingredient stability including protection from degradation; to ensure a robust and reproducible physical product. In terms of a filament (e.g. for use in FFF 3D printing), excipient(s) may be chosen to optimize the physical form and/or stability of the filament; stability of the active ingredient, including protection from degradation; to ensure a robust and reproducible physical products; flexibility and rigidity of the filament (an optimal balance between flexibility and rigidity of a filament is desirable to ensure that the filament can be conveyed successfully to an extrusion nozzle but then easily extruded from the nozzle); to enable production of optimal solid dosage forms (e.g. as per the aforementioned points).

Filament Coating

Filaments of the invention may suitably comprise a protective filament coating, suitably coated upon the outermost surface of said filament. Such filament coatings may be deployed regardless of whether single-head or multi-head (e.g. dual-head) printing is used, though such coatings are perhaps most applicable in multi-head printing scenarios where filaments are at increased risk of prolonged exposure to heat (and consequential filament degradation) whilst temporarily at rest (when not being printed) within their corresponding nozzles.

The protective filament coating(s) are suitably derived from corresponding protective filament coating compositions. Suitably the protective filament coating comprises pharmaceutically and/or nutraceutically acceptable ingredients. Suitably the protective filament coating us a liquid or oil, suitably having a high boiling point (e.g. at least 150° C., suitably at least 170° C., suitably at least 220° C.). The coating suitably reduces degradation of the filament upon exposure to heat. The protective filament coating (or composition) suitably comprises a liquid and/or oil. Suitably the protective filament coating is inert to the active ingredient-containing printing filament and the ingredients thereof. Suitably the protective filament coating does not mix with or dissolve the active ingredient-containing printing filament and/or any of the ingredients thereof. Suitably the protective coating does not prevent the relevant filament from melting or undergoing a glass transition at the operating temperature of the extrusion nozzle.

The inventors found that the use of olive oil BP, oleic acid, arachidonic acid and glycerol helps co-ordination between the two-nozzle and to evade drug-polymer filament degradation. Using such components to coat a filament is thought to provide a protective layer on the surface of the filament. Such components also have relatively high melting points and do not degrade at the processing temperature of the 3D nozzle.

Active Filament Spool

In preferred embodiments of a printing apparatus of the invention, the active ingredient-containing printing filament is suitably provided as an active filament spool (suitably for fused filament fabrication 3D printing) comprising an active ingredient-containing printing filament as defined herein.

Filament spools are well known in the art, and suitable comprise a hub around which the filament is coiled or coilable. The dimensions of the spool and/or hub may vary, though most suitably the hub diameter is between 3 and 30 cm, more suitably between 5 and 25 cm, most suitably between 10 and 20 cm. The length of the hub generally depends on how much filament is intended to be coiled about the spool.

Suitably, the filament spool is attachable (suitably rotatably attachable) to or within an FFF 3D printer to allow filament to be dispensed therefrom and conveyed to the extrusion nozzle during printing.

Cartridges

Any filament spool or spool defined herein may be optionally contained within a cartridge. As such the present invention provides a cartridge comprising a spool as defined herein (e.g. active filament spool comprising an active ingredient-containing printing filament as defined herein; or a further filament spool comprising a further printing filament as defined herein). The cartridge is suitably configured (e.g. with an appropriate shape, profile, and/or attachment mechanisms) for releasable engagement with or installation within the printer (e.g. in a docking position/station within the printer). The cartridge is suitably configured, when engaged with/installed within the printer, to be operable to deliver and print the filament contained therein, suitably via a nozzle which may suitably be associated with (or integral to) the printer or the cartridge itself (which may replace a nozzle associated with the printer).

The cartridge suitably comprises a housing or case, suitably which contains the spool. Suitably the cartridge is configured to preserve a filament coiled around the spool. Suitably the case is (substantially) sealed (or sealable—e.g. with a plug) and/or humidity controlled (or controllable).

The cartridge suitably comprises a conveyor mechanism operable to convey a filament from the spool to a nozzle (e.g. out of which the filament is suitably printed). The conveyor mechanism suitably comprises a feed channel along which the filament is fed during its conveyance to the nozzle. The feed channel suitably comprises one or more conveyor elements which frictional engage or grip the filament as the filament is conveyed. In a particular embodiment, one or more of the conveyor elements may comprise a roller (or set of rollers) which engage with (or grip) the filament whilst feeding the filament therethrough. The conveyor element(s) are suitably coupled to complementary drive elements which, when driven, drive the relevant conveyor element(s).

The conveyor mechanism of the cartridge is suitably engaged or engageable with a mechanical drive mechanism associated with (or integral to) the printer. In this manner, when the mechanical drive mechanism is operated (e.g. under instruction from a computer), it may in turn engageably operate the conveyor mechanism of the cartridge to cause the filament to be conveyed from the spool to the nozzle. As such, the cartridge is suitably configured and/or engageable with the printer to enable operational coupling between the conveyor mechanism of the cartridge and mechanical drive mechanism of the printer. For instance, suitably each of the conveyor mechanism and the mechanical drive mechanism comprise complementary drive elements (e.g. gears), which are mutually engageable (and engaged during use) to enable the conveyor mechanism to be operated by the printer via the mechanical drive mechanism thereof.

Suitably the conveyor mechanism is contained within the cartridge to an extent that permits (suitably unimpeded) operational engagement between complementary drive elements of each of the conveyor mechanism of the cartridge and mechanical drive mechanism of the printer. The drive elements (e.g. gears) of the conveyor mechanism of the cartridge may thus be (partially or entirely) external to the case/housing to enable facile engagement with the drive elements of the mechanical drive mechanism of the printer. The drive elements (e.g. gears) of the conveyor mechanism of the cartridge may be (partially or entirely) located within the case/housing if the case/housing is configured (e.g. with openings) to permit drive elements of the mechanical drive mechanism of the printer to access and engage the drive elements of the conveyor mechanism. In some embodiments, the cartridge and printer are mutually configured such that when the cartridge is engaged with (or installed within) the printer, a cavity (suitably a sealed cavity) is formed therebetween which contains (partially or entirely) both sets of respective drive elements (suitably in mutual engagement with each other).

Most suitably, the cartridge comprises a cartridge nozzle through which the filament is dispensed (and/or printed). When dispensed through the cartridge nozzle, the filament may be subsequently conveyed to a printer nozzle, through which the filament is ultimately printed. Such an arrangement allows handling of the filament within the printer in the interests of the printer durability (e.g. the printer can cut away excess filament residing between the cartridge nozzle and printer nozzle and self-clean its nozzle to thereby mitigate against printer nozzle blockages, whilst allowing the cartridge nozzle to be sacrificed instead). However, in preferred embodiments, the cartridge nozzle replaces the printer nozzle (at least during printing from said cartridge)— i.e. the cartridge nozzle may be the printer nozzle. Such a cartridge may be considered a fully integrated cartridge comprising a spool (with a filament coiled therearound), a conveyor mechanism and a nozzle (through which the filament may be printed).

A cartridge nozzle of a fully integrated cartridge is suitably selectively heatable, suitably via a heat source external to the cartridge (although in some embodiments the cartridge may comprise its own internal heater mechanism). In a particular embodiment, the cartridge and/or printer is/are configured (suitably in a complementary fashion) to enable a heater located within (or associated with) the printer to heat the cartridge nozzle (suitably in a selectively controllable manner to a predesignated temperature). As such, the cartridge nozzle suitably comprises (or is made of) a conductive material (e.g. steel) to facilitate selective heating thereof. In preferred embodiments, the cartridge nozzle is configured to receive a plug which may be inserted thereinto to seal (and optionally treat, e.g. lubricate) the head of the nozzle.

Such cartridges of the invention are particularly advantageous in that they mitigate against inter-filament cross-contamination, and through self-sacrifice mitigate against undesirable wear and tear of components (especially vulnerable components, such as the printer nozzle, which may otherwise become readily blocked with certain filament types) of the printer.

Method of Preparing Active Ingredient-Containing Printing Filament

The active ingredient-containing printing filament is suitably prepared by a method as defined herein.

In some embodiments, the active ingredient-containing printing filament is prepared by first producing a filament without the active ingredient, but comprising an active ingredient carrier, and optionally any further ingredients defined herein in relation to the active ingredient-containing printing filament, and thereafter incorporating the active ingredient within the filament or coating the active ingredient upon (or embedding the active ingredient within) the surface of the filament or within exposed pores of the filament. However, this generally leads to a non-uniform distribution of the active ingredient through the filament, and also often precludes high drug loadings.

In preferred embodiments, the active ingredient-containing printing filament is prepared by mixing all relevant filament ingredients together (with the optional exception of the plasticizer, which may be coated onto the surface of a post-produced filament, optionally in situ during printing) and forming the active ingredient-containing printing filament directly from the mixture, suitably via extrusion, such as hotmelt extrusion.

The method suitably involves loading all relevant ingredients of the active ingredient-containing printing filament to a hotmelt extruder, suitably in powder/solid form, to form a hotmelt mixture. The hotmelt mixture is then suitably heated at a "mixing temperature" ($T_1$) (optionally whilst being mixed or otherwise agitated) for a suitable period of time (e.g. 1-10 minutes) prior to extrusion. The mixing temperature ($T_1$) is typically a temperature between 70 and 150° C. (more suitably 110-130° C. or 115 to 135° C.), thought it will depend on the active ingredient carrier and other ingredients within the hotmelt mixture. The heated hotmelt mixture is then extruded (suitably via an extrusion nozzle) (suitably using counterflow extruders, suitably set a rotation speed of about 50-200 rpm) at a "processing temperature" ($T_2$) suitable to achieve torque of between 0.1 and 2.0 Nm/screw, more suitably between 0.3 and 1.0 Nm/screw, more suitably between 0.5 and 0.7 Nm/screw. The processing temperature ($T_2$) is suitably lower than the mixing temperature ($T_1$), suitably between 10 and 50° C. lower, suitably between 10 and 25° C. lower, more suitably between 20 and 30° C. lower, and as such the processing temperature is suitably between 40 and 130° C. (more suitably 90-110° C.), suitably between 105 and 125° C. Suitably the processing temperature ($T_2$) is between 30 and 90° C. lower, more suitably between 50 and 70° C. lower, than the printing temperature ($T_3$) ultimately used in production of the solid dosage form from the respective filament.

Suitably the hotmelt mixture is extruded via a hotmelt extrusion nozzle. The hotmelt extrusion nozzle suitably has a nozzle size (or output diameter) of between 0.4-3.0 mm, most suitably between 0.9 and 2.1 mm. Since a filament may sometimes expand or contract on cooling, a nozzle size of between 0.9 and 1.4 mm is most preferred (suitably to allow for expansion after extrusion). Most suitably, the nozzle size is selected to give a post-cooled filament with a diameter within the preferred range (see above). The hotmelt extrusion nozzle suitably operates with a torque between 0.1 and 2.0 Nm/screw, more suitably between 0.3 and 1.0 Nm/screw, more suitably between 0.5 and 0.7 Nm/screw, suitably about 0.6. The extruded filament is suitably then received on a non-adhesive surface (e.g. Teflon). The extruded filament is then allowed to cool.

The mixing temperature is suitably high enough to enable filament extrusion but low enough to avoid (pharmaceutically) unacceptable degradation of the active ingredient(s) and/or any excipient(s) at the relevant filament feed rate (it will be appreciated by those skilled in the art that the active ingredient will generally tolerate higher temperatures if heat exposure times are short, as they generally are in the printing processes of the invention).

Further Printing Filaments and Compositions

The relevant printing apparatus may comprise one or more further printing filaments in combination with the active ingredient-containing printing filament. Since the principles applicable to the active ingredient-containing printing filaments are generally equally applicable to the further printing filaments, suitably any further printing filaments may be defined in exactly the same way as per the active ingredient-containing printing filament(s). Any further printing filaments are suitably substantially or entirely free of an active ingredient, though in some embodiments one of the further printing filaments may optionally comprise another active ingredient. As such, any further printing filaments suitably comprise or consist essentially of one or more carrier(s) (including any of those defined herein as active ingredient carriers), diluents(s), and/or excipients (including plasticizers) as defined herein in relation to the active ingredient-containing printing filament(s).

Most suitably, a further printing filament is used in conjunction with an active ingredient-containing filament in order to adjust or augment the properties of the final dosage form. Suitably, a further printing filament provides additional (and optionally different) carrier(s), diluents(s), and/or excipients to those already present within the active ingredient-containing printing filament.

Any further printing filament may comprise any, some, or all of the ingredients (or indeed parameters, e.g. glass transition temperature, filament thickness, etc.) described herein in relation to the active ingredient-containing printing filament, albeit suitably an active ingredient is absent. The skilled person will be readily capable of adjusting specified proportions of ingredients accordingly (the figures given in relation to the active ingredient-containing printing filament may be adjusted proportionately, or weight ratios of ingredients may be readily deduced).

As with the active ingredient-containing printing filament, any further printing filaments may be provided as part of a filament spool, with any or all of the features stated in relation to the active filament spool. Furthermore, any further printing elements may be formed using the same methodology utilized to form the active ingredient-containing printing filament.

Any methods and/or apparati defined herein in relation to the active ingredient-containing printing filament(s) may apply equally to the further printing filament(s), including nozzle operating temperatures and such like. A skilled person is readily able to judiciously modify filament manufacture and/or printing conditions to suit the properties of a given further printing filament.

Suitably, where a further printing filament is involved in the formation of the solid dosage form, the solid dosage form may either still be defined as herein in relation to the solid dosage form as a whole (e.g. in relation to stipulated proportions of ingredients) or else a core of the solid dosage form (e.g. where a core-shell arrangement is produced) may instead be defined as per any or all the definitions set forth herein in relation to the solid dosage form as a whole.

Printing with multiple filaments is much akin to printing with different colours on a 3D printer. As such, the printing apparatus may be operated to print a solid dosage form which incorporates both active ingredient-containing filament composition and one or more further filament compositions. The pattern and/or distribution of the respective filament compositions is suitably determined by the predetermined design being printed.

In a particular embodiment, a further printing filament is used in conjunction with an active ingredient-containing printing filament to produce a core-shell dosage form, suitably with a core formed (predominantly) by printing/extrusion of the active ingredient-containing printing filament and with a shell formed (predominantly) by printing/extrusion of the further printing filament.

Suitably, where the solid dosage form is a core-shell dosage form, the shell is suitably formed from a further printing filament comprising one or more HPMC-AS polymers, optionally in conjunction with a plasticizer.

The further printing filaments may, as such, be utilized in printing to modify the release properties of the active ingredient in the final solid dosage form.

EXAMPLES

Example 1—Experimenting the Printing of Designs of a Tablet Using Commercially Available Dissolvable PVA Filament 1.1 Materials and Equipment Prednisolone was purchased from (Severn Biotech Ltd, UK). Polyvinyl alcohol (PVA) filaments (melting point; 160-170° C., specific heat; 0.4 Cal/g ° C., Density; 1.25-1.35 g/cm 3) were purchased from Reprapcentral (UK). Glycerol, acetonitrile and methanol were supplied by British Drug Houses (BDH) (London, UK). Castor Oil was purchased from Sigma-Aldrich (St. Louis, USA). Oleic acid was obtained from VWR (Radnor, USA). Scotch blue painter's tape 5 mm was supplied by 3M (Bracknell, UK).

MakerBot Replicator® 2X Experimental 3D Printer (MakerBot Industries, LLC, New York, USA) was utilized to print blank PVA tablets (i.e. tablets without any active).

Blank tablets (PVA only) were printed using default settings of the software for PLA filament as follows: type of printer: Replicator 2X; type of filament: PLA; resolution: standard; temperature of nozzle: 230° C.; temperature of building plate: 20° C.; speed of extruder 90 mm/s while extruding and 150 mm/s while traveling; infill: 100%; height of the layer: 200 μm; number of shells: 2. No supports or rafts were utilized in the printing process. No further modifications were implemented.

1.2 Outline of Study

The feasibility of printing tablets for oral administration using 3D printing methods was first explored by way of model studies. These involved the production and study of a variety of uniform and core-shell model tablets. Thereafter, attempts were made to "load" different drug molecules into a model polyvinyl alcohol (PVA) filament.

1.3 Experiment 1A—Experimental Printing of a Uniform Tablet Design Using Default Red Acrylonitrile Butadiene Styrene (ABS) Filament Supplied by Makerbot Blank tablets (ABS only) were printed using default settings of the software for ABS filament as follows: type of printer: Replicator 2X; type of filament: PLA; resolution: standard; temperature of nozzle: 230° C.; temperature of building plate: 20° C.; speed of extruder 90 mm/s while extruding and 150 mm/s while traveling; infill: 100%; height of the layer: 200 μm; number of shells: 2. No supports or rafts were utilized in the printing process. No further modifications were implemented.

FIG. 1A and FIG. 1B show top and bottom projection views of ABS-based model tablets produced using an ABS filament.

1.4 Experiment 1B—Experimental Printing of a Core-Shell Tablet Design, as a Model for Enteric Coated Tablets or Core-Shell Reservoir Systems, Using Red and White ABS Filament Supplied by Makerbot Blank core-shell model tablets (white and red ABS only, with a red core and white shell) were printed using default settings of the software for ABS filament as follows: type of printer: Replicator 2×; type of filament: ABS; resolution: standard; temperature of nozzle: 250° C.; temperature of building plate: 100° C.; speed of extruder 90 mm/s while extruding and 150 mm/s while traveling; infill: 100%; height of the layer: 200 μm; number of shells: 2. No supports or rafts were utilized in the printing process. No further modifications were implemented.

FIG. 2A and FIG. 2B show top and bottom projection views of ABS-based core-shell model tablets produced using white and red ABS filaments. It was noted that ABS filament lacked flexibility when forming thin film layer.

1.5 Experiment 1C—Experimental Printing of a Uniform and Core-Shell Disc-Shaped Tablet Design Using a PVA Filament Blank tablets (PVA only) were printed using default settings of the software for PLA filament as follows: type of printer: Replicator 2X; type of filament: PLA; resolution: standard; temperature of nozzle: 230° C.; temperature of building plate: 20° C.; speed of extruder 90 mm/s while extruding and 150 mm/s while traveling; infill: 100%; height of the layer: 200 μm; number of shells: 2. No supports or rafts were utilized in the printing process. No further modifications were implemented.

FIG. 3 shows top projection views of several PVA-based disc-shaped uniform model tablets produced using PVA filaments.

FIG. 4 shows a top projection view of a PVA-based disc-shaped core-shell model tablet, and an open cross-section thereof, produced using PVA filaments.

1.5 Experiment 1D—Loading of Various Drugs to a PVA Filament with Various Solvents and Printing a Tablet Therewith Before attempting to manufacture various customized drug-loaded filaments for testing, the inventors explored the possibility of using default filaments, such as commercially available PVA filaments, to assess drug release properties. Commercial PVA filament was chosen since PVA is widely used in pharmaceutical industry and was considered a promising model for tablets or extended release implants.

Different drug-loading solvents (i.e. solvents in which the relevant drug was dissolved and into which a drug-free PVA filament is immersed) were used to assess their ability to form drug-loaded filaments. Acetone, ethanol and water led to a complete breakdown of the filament. However, methanol maintained the integrity of the filament. Methanol was thus considered the solvent of choice for loading the PVA filament with the drug.

Different drug compounds were employed to assess their ability to be incorporated within the PVA filament following prolonged incubation. Prednisolone, dipyridamole or diclofenac potassium were selected as model drug candidates. In each case, following immersion/incubation of a PVA filament within a methanolic solution of the respective drug, the drug content was found to be approximately 2% by weight of dry filament.

FIG. 5A, FIG. 5B and FIG. 5C, respectively show projection views of PVA filament treated with methanol, prednisolone-loaded PVA filament; and dipyridamole-loaded PVA filament.

Prednisolone was chosen as a drug model due to its low dose (up to 60 mg daily) and the need of large range of doses. The optimized method of drug loading is summarized in Example 2.

Model tablets were then printed with prednisolone-loaded PVA filaments using the PVA-based printed method outlined herein.

FIG. 6 shows a top projection view of prednisolone-loaded PVA model tablets. It was noted that better tablet finishing was achieved by printing at 250° C. rather than 220° C.

1.6 Conclusions from Example 1

These experiments facilitated optimization of the design and orientation of 3D printing of tablets.

It was recognised that several modifications ideally need to be made in order to successfully print PVA-based tablets, particularly those with a core-shell structure, including increasing nozzle temperature, and potentially plasiticizing with a plasticizer such as glycerol.

It was noted that incubation within a saturated solution with methanol yielded 2% incorporation of drugs within a PVA filament.

A decision was made to use prednisolone in subsequent experimental models used to assess drug release properties.

Example 2—Control of Drug Dose in the 3D Printed Tablet and Physical and In Vitro Characterization of the Product 2.1 Outline of Study In this Example, the inventors examined the ability of the 3D printer to control the drug loading (i.e. the dose) of a tablet by controlling the volume of the printed solid dosage form. Furthermore, the inventors assessed drug loading levels within the tablets formed, as well as the accuracy of drug dosing.

In general, the same materials and equipment was used as those set forth in Example 1, albeit with modifications as described below.

2.2 Experiment 2A—Modification of 3D Printer

Before printing prednisolone loaded PVA tablets, the following modifications were implemented:

a) The default Kapton tape layer provided poor adhesion to the designs to the build platform. As such, this tape was replaced by blue Scotch painters tape applied to the surface of the build platform to improve adhesion to the surface layer.

b) Drug-loaded PVA filaments were relatively less flexible than the corresponding blank PVA filaments from which the drug-loaded filaments were formed. As such, the 3D printer was modified to introduce a plasticizing station upstream from (i.e. before) the filament feed into the extrusion nozzle. Castor oil, oleic acid and glycerol were all tested as a plasticizer. The plasticizing station was constructed, as per FIG. 7A and FIG. 7B, as a special lid through which the filament may pass. FIG. 7A and FIG. 7B show a special lid (or plasticizing station) which dispenses plasticizer, from a tissue pre-soaked in plasticizer, to a filament as the filament passes therethrough towards a printing nozzle within a 3D printer. Within the lid is a tissue (or other suitable absorbent material), that has been pre-soaked in a plasticizer (in this case glycerol), against which the filament must pass en route through the lid. As the filament passes through the lid it makes contact with the pre-soaked tissue and itself become impregnated and/or surface coated with the plasticizer dispensed by the tissue. This may serve to lubricate the filament before it is pulled inside the printer. Quality of tablets was visually compared and glycerol was chosen as a plasticizer.

c) The extrusion nozzle (i.e. printing nozzle) temperature was raised from 230° C. to 250° C. to maintain constant flow of prednisolone loaded PVA filament.

Prednisolone loaded PVA tablets were printed using the protocols previously outlined, except the extrusion nozzle temperature was raised to 250° C.

2.3 Experiment 2B—Preparation of Prednisolone-Loaded PVA Filament

PVA filaments were loaded with prednisolone via incubation with a saturated solution of the drug in methanol at 30° C. for 24 hours. Thereafter the filaments were dried in an oven at 40° C. and weighed every 1 hour until the weight stabilized. Other solvents such as ethanol and acetone had a degrading effect on original filament or poor loading efficiency respectively and were deemed unsuitable for loading process.

Three representative samples of prednisolone-loaded PVA, 100 mg each, were sonicated in 100 ml of methanol and water (using the same process as that set forth in the next section in relation to the assessment of prednisolone content in drug-loaded PVA filaments and the printed tablets) and were thereafter assessed using the same HPLC method as that detailed in the next section (i.e. section 2.4). The drug-loading percentage of the filament was calculated as shown in Table 1 below:

TABLE 1

| | | | | | | |
|---|---|---|---|---|---|---|
| Drug-loading results in triplicate | | | | | | |
| number of sample | Area | concentration [mg/L] | m of pred in 100 ml volumetric flask | m of filament | % w/w | av (% w/w) |
| 1 | 3583.3 | 19.51699422 | 1.951699422 | 100.12 | 1.94936019 | 1.969015848 |
| 2 | 3646 | 19.85890719 | 1.985890719 | 99.84 | 1.989073236 | |
| 3 | 3600.6 | 19.61133384 | 1.961133384 | 99.62 | 1.968614118 | |

2.4 Experiment 2C—Determination of Drug Loading in Tablets

In order to assess the prednisolone content in drug-loaded filaments and printed tablets, the following procedure was used. This procedure may be readily adapted for assessing filaments, as described in the previous section.

Each tablet was weighed and transferred to a 500 ml volumetric flask. Each tablet was then sonicated for 1 h with 150 ml of distilled water, after which time a further 500 mL of methanol was added and the whole mixture subsequently sonicated for an additional 4 hours at 50° C. After cooling to room temperature, samples were filtered through a 0.22 μm Millex-GP syringe filter (Merck Millipore, USA) for HPLC analysis.

Prednisolone concentrations were established via HPLC analysis using an Agilent HPLC 1260 series (Agilent Technologies, Inc., Germany) equipped with Kinetex C18 column (100×2.1 mm, particle size 2.6 μm C18 (Phenomenex, Torrance, USA) were used. The mobile phase consisting of acetonitrile and water were used in gradient concentration (Table 2) with a flow rate of 0.5 ml/min. The injection volume was 40 μl and the UV detector employed an absorbance wavelength of 250 nm. Temperature in the column was 45° C. and stop time for each sample was 14 min.

TABLE 2

Gradient profile of HPLC method for detection of prednisolone

| Step. No. | Time (min) | Water (%) | Acetonitrile (%) |
|---|---|---|---|
| 1 | 0.00 | 60 | 40 |
| 2 | 8 | 40 | 60 |

TABLE 2-continued

Gradient profile of HPLC method for detection of prednisolone

| Step. No. | Time (min) | Water (%) | Acetonitrile (%) |
|---|---|---|---|
| 3 | 12 | 40 | 60 |
| 4 | 12.01 | 60 | 40 |
| 5 | 14 | 60 | 40 |

2.5 Experiment 2D—Tablet Design and Printing Process

Blank and drug-loaded PVA tablets were designed in an ellipse shape using Autodesk® 3ds Max® Design 2012 software version 14.0 (Autodesk, Inc., USA) and saved in STL format (FIG. 8).

FIG. 8A, FIG. 8B and FIG. 8C, respectively, show schematic top projection, side, and plan views of the tablet design.

The design was imported to the 3D printer's software, MakerWare Version 2.4.0.17 (Makerbot Industries, LLC., USA). A series of tablets with different volumes were printed by modifying the dimensions of the design: length× width×heights (L, H, W) without altering the ratios between these dimensions.

The promising results enabled to printing of tablets with target drug doses of 2 mg; 3 mg; 4 mg; 5 mg; 7.5 mg; and 10 mg. Volumes and dimensions were calculated and are shown in 3. Measured tablet mass was similar to theoretical mass of product.

TABLE 3

The mass, theoretical and measured dose of prednisolone loaded PVA tablets

| Tablet target dose (mg) | Filament loading (%) | Dimensions (L × W × H) (mm) | Tablet theoretical volume (mm³) | Tablet theoretical mass (mg) | Tablet measured mass (mg) ± SD |
|---|---|---|---|---|---|
| 2 | 1.97 | 8.39 × 3.36 × 3.36 | 74.23 | 101.52 | 102 ± 1.73 |
| 3 | 1.89 | 10.11 × 4.04 × 4.04 | 129.66 | 158.73 | 168.30 ± 1.43 |
| 4 | 1.89 | 11.29 × 4.52 × 4.52 | 180.92 | 211.64 | 216.18 ± 1.01 |
| 5 | 1.86 | 12.34 × 4.94 × 4.94 | 236.31 | 268.82 | 283.44 ± 5.03 |
| 7.5 | 1.97 | 14.00 × 5.60 × 5.60 | 344.71 | 380.71 | 396.67 ± 4.93 |
| 10 | 1.97 | 15.50 × 6.20 × 6.20 | 467.66 | 507.61 | 498.67 ± 5.69 |

FIG. 9 shows a top projection view of several tablets, with the top row showing prednisolone-loaded PVA tablets at respective prednisolone doses of 2 mg, 3 mg, 4 mg, 5 mg, 7.5 mg and 10 mg; and the bottom row showing blank PVA-only tablets of the same size as the tablets corresponding to the 2 mg, 3 mg, 4 mg, 5 mg, 7.5 mg and 10 mg doses in the top row. Quality of prednisolone loaded tablets is similar to blank due to modifications implemented to the printing process.

Figure 10:
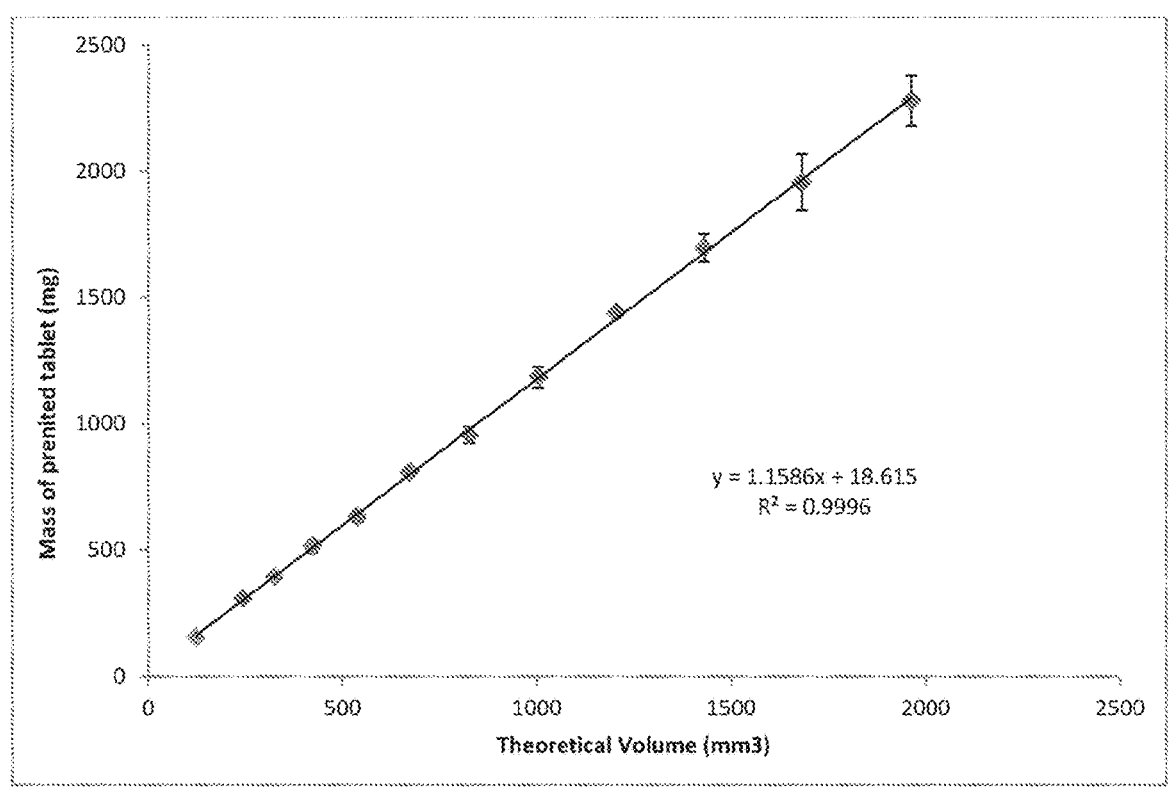
FIG. 10 shows a graph illustrating a linear correlation between theoretical volume and the mass of a printed default (drug free) PVA tablet.

FIG. 10 shows a graph illustrating a linear correlation between theoretical volume and the mass of a printed default (drug free) PVA tablet.

Figure 11:
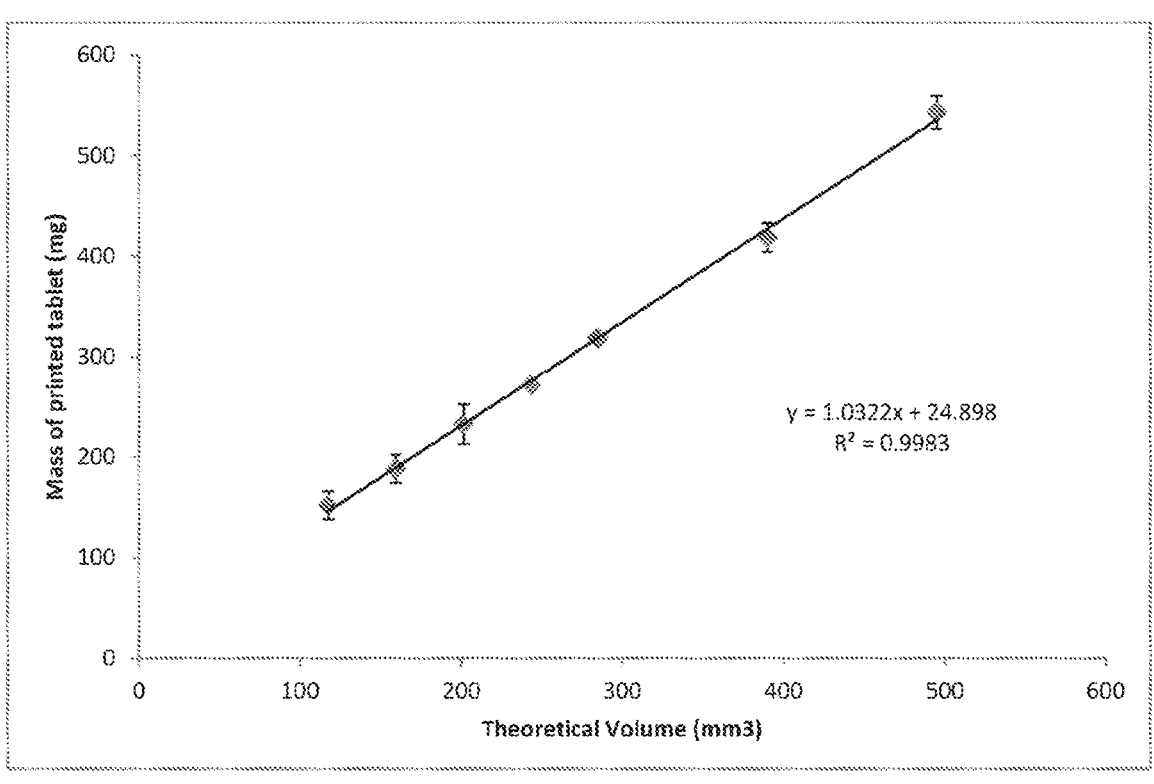
FIG. 11 shows a graph illustrating a linear correlation between theoretical volume and the mass of printed prednisolone-loaded PVA tablets.

FIG. 11 shows a graph illustrating a linear correlation between theoretical volume and the mass of printed prednisolone-loaded PVA tablets.

In order to correlate between the volume of the design and the mass of the printed tablet, a series of tablets of increased weight were printed (FIG. 9 bottom row). A good correlation was established and the "coefficient of determination" was calculated as R 2=0.9996, as shown in FIG. 10. This indicated the ability of this volume modelling to control the printed mass. When a similar series of tablets (shown in FIG. 9 top row) were printed with prednisolone loaded tablet (modified), the same correlation was maintained (R 2=0.9983), as shown in FIG. 11. Hence, it was possible to utilize the equation to design drug with suitable tablet weight that reached the target dose.

Theoretical and measured dose of prednisolone were compared (shown on Table 4).

TABLE 4

| | | | | | |
|---|---|---|---|---|---|
| The mass, theoretical and measured dose of prednisolone loaded PVA tablets | | | | | |
| Tablet target dose (mg) | Filament loading (%) | Theoretical dose (mg) ± SD | Measured dose (mg) ± SD | Dose accuracy (%) ± SD | CV (%) |
| 2 | 1.97 | 2.01 ± 0.03 | 1.98 ± 0.10 | 98.67 ± 3.43 | 3.48 |
| 3 | 1.89 | 3.18 ± 0.03 | 3.43 ± 0.34 | 107.71 ± 9.96 | 9.25 |
| 4 | 1.89 | 4.09 ± 0.02 | 4.37 ± 0.11 | 107.06 ± 2.98 | 2.79 |
| 5 | 1.86 | 5.27 ± 0.09 | 5.27 ± 0.22 | 99.95 ± 2.51 | 2.51 |
| 7.5 | 1.97 | 7.81 ± 0.10 | 6.99 ± 0.22 | 89.49 ± 2.37 | 2.65 |
| 10 | 1.97 | 9.82 ± 0.11 | 8.71 ± 0.17 | 88.70 ± 0.79 | 0.89 |

Figure 12:
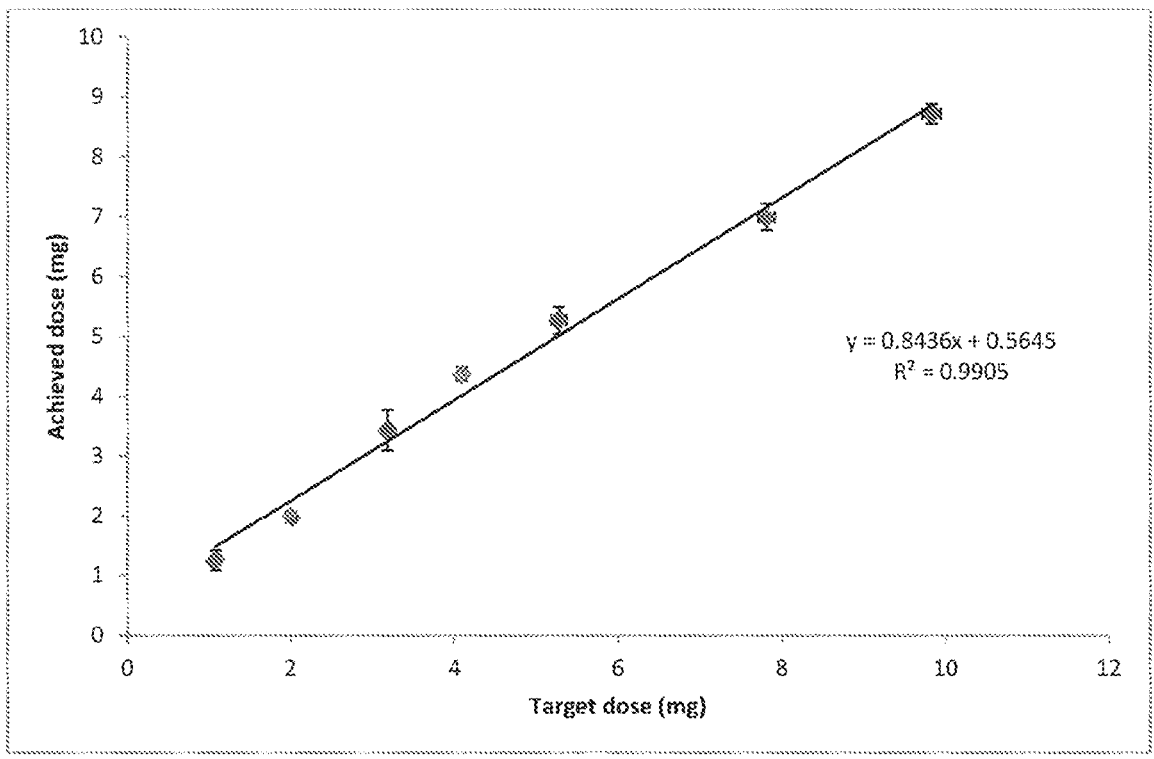
FIG. 12 shows a graph illustrating the relationship between target and achieved doses of prednisolone loaded tablets.

FIG. 12 shows a graph illustrating the relationship between target and achieved doses of prednisolone loaded tablets.

The dose accuracy tested here ranged between 88.70±0.79 for 10 mg tablet and 107.71±9.96 for 3 mg tablet. The relationship between the target and achieved dose of drug is shown in FIG. 12.

The value for the coefficient of determination (R 2=0.9905), as shown in FIG. 12, shows that it is possible to fabricate tablets with the desired dose of prednisolone.

2.6 Experiment 2E—Surface Morphology Analysis of Filaments, Printer Extrudes, and Tablets Surface morphologies of the original PVA filament, extrudes of 3D printer, and the printed tablets, were assessed using a Quanta-200 SEM microscope at 20 kV. Samples were placed on metallic stubs and gold coated under vacuum for 2 min using JFC-1200 Fine Coater (Jeol, Tokyo, Japan).

FIG. 13A, FIG. 13B, FIG. 13C and FIG. 13D show SEM images of: A) a surface view, and B) a cross-sectional view of a default PVA filament (PVA only); and C) a surface view, and D) a cross-sectional view of a prednisolone-loaded PVA filament.

FIG. 14A and FIG. 14B show SEM images of PVA after extrusion from nozzle of fused deposition modelling 3D printer at A) 1000 μm magnification; and B) 50 μm magnification.

FIG. 15A, FIG. 15B and FIG. 15C show SEM images of the side surface of prednisolone-loaded PVA tablets at different magnifications: A) at 2000 μm; B) at 200 μm; C) at 20 μm.

FIG. 16A and FIG. 16B show SEM images of the top surface of prednisolone-loaded PVA tablets at different magnifications: A) at 1000 μm; and B) at 100 μm.

FIG. 17A, FIG. 17B and FIG. 17C show SEM images of a cross section of prednisolone-loaded PVA tablets: A) general view; B) magnification of peripheral domain; and C) magnification of central domain.

SEM images of the original and prednisolone-loaded PVA filaments (1.75 mm) indicated the smooth nature of the surface of the filament. However, upon extrusion through the 3D printer nozzle, at 250° C., the surface of the extruded filament (200 μm) appeared to be generally rough with irregular pores and void between layers, this might be due to rapid humidity evaporation and other solvent evaporation upon rapid exposure to high temperature.

SEM images of Surface of prednisolone loaded PVA indicated an irregular and rough surface with partially fused filament. Whilst the side of the tablet illustrate the overlaid layers of filament with approximate height of 200 μm. this indicate that minimum compression takes place upon printing. When inner section of a 50% printed layer was assessed, the direction of fused filament was distinct between the peripheral and central domains.

2.7 Experiment 2F—Assessing Crystallinity of Prednisolone in the Drug-Loaded Tablets The powder X-ray diffractometer, D2 Phaser with Lynx-eye (Bruker, Germany) was used to assess the crystallinity of prednisolone in the drug loaded tablets. Samples were scanned from 2 Theta=5° to 50° with a scan type coupled two theta/theta using scintillation counter over 30 min.

Figure 18:
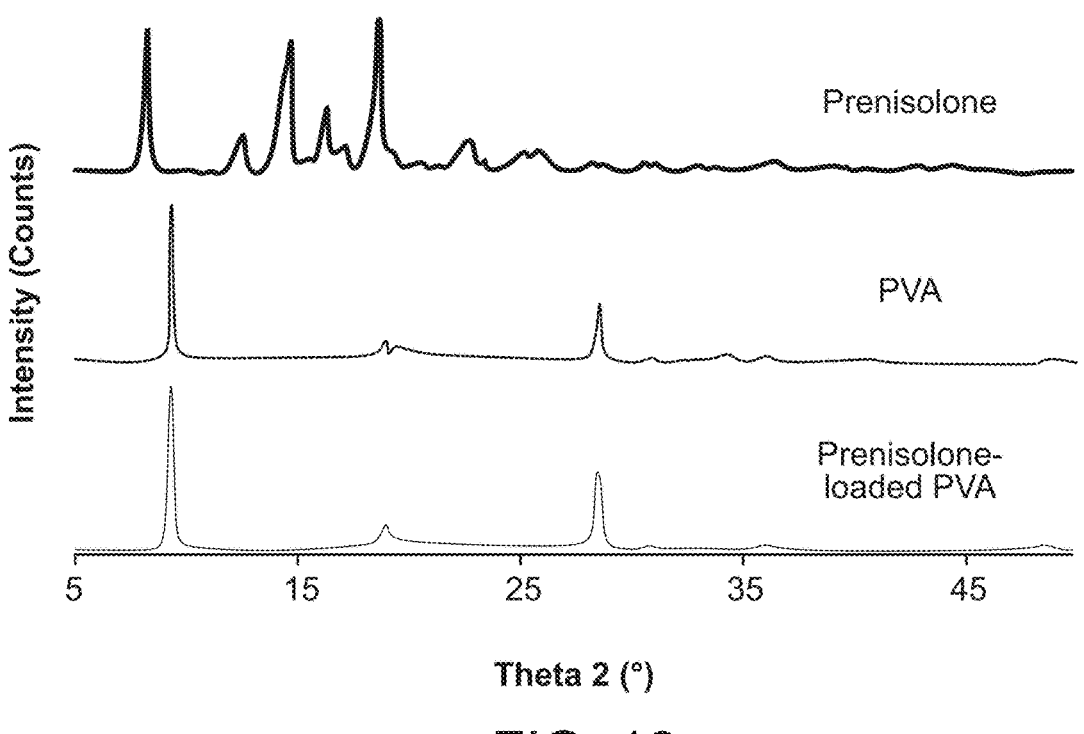
FIG. 18 shows spectra obtained from a powder X-ray diffractometer of default prednisolone (top spectrum), PVA filament (middle spectrum) and prednisolone loaded PVA filament and tablet (bottom spectrum).

FIG. 18 shows spectra obtained from a powder X-ray diffractometer of default prednisolone (top spectrum), PVA filament (middle spectrum) and prednisolone loaded PVA filament and tablet (bottom spectrum).

Prednisolone showed peaks at 2Theta=8, 14 and 18.6. The absence of such peaks suggests the majority of prednisolone exists in amorphous form.

2.7 Experiment 2G—Thermal Analysis by Differential Scanning Calorimetry (DSC)

Mettler Toledo DSC823e DSC (Mettler, Switzerland) was utilized to perform thermal analysis. In each case, approximately a 5 mg sample was accurately weighed and placed in a 40 µL standard aluminium pan used for DSC analysis. Analysis was carried on under a nitrogen environment (50 mL/min). In order to rule out the effect of humidity, samples were heated to 100° C. for 5 min then cooled to −20 at 10° C./min. This was followed by a heat scan from −20 to 300° C. at 10° C./min. All samples were tested in triplicate. This method is suitably applied inter alia to measurements of glass transition temperatures.

Figure 19:
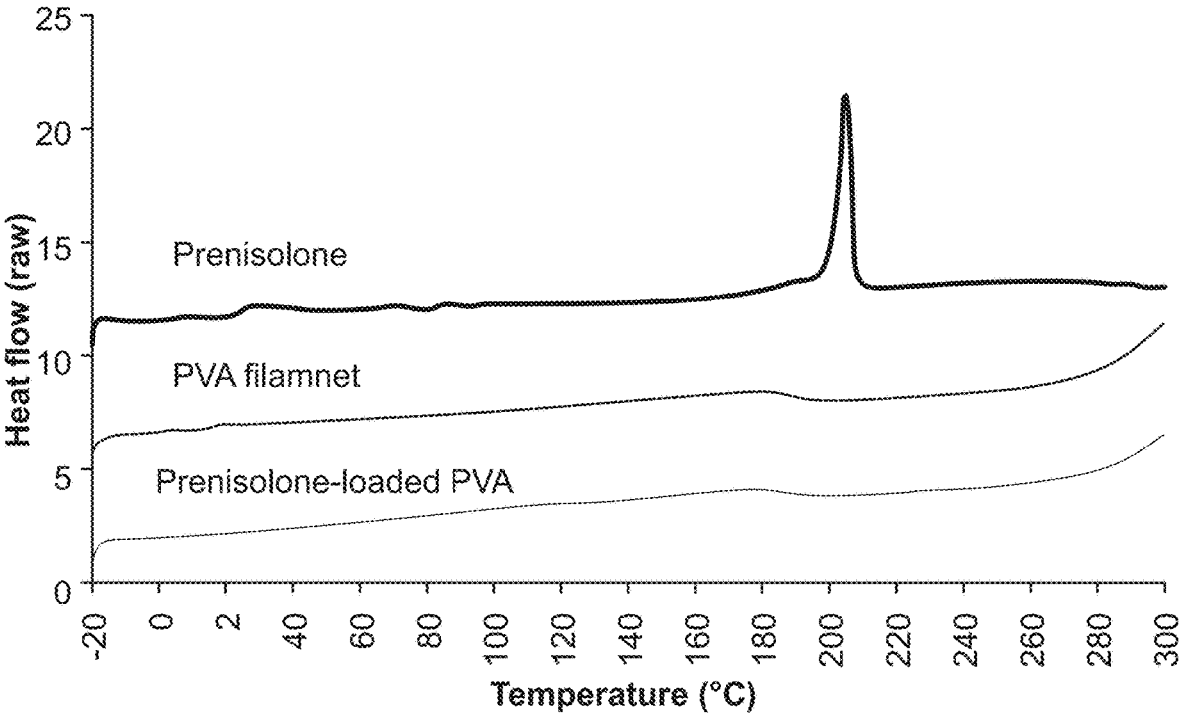
FIG. 19 shows a DSC thermograph of prednisolone (top spectrum), default PVA filament (middle spectrum) and prednisolone-loaded PVA tablets (bottom spectrum).

FIG. 19 shows a DSC thermograph of prednisolone (top spectrum), default PVA filament (middle spectrum) and prednisolone-loaded PVA tablets (bottom spectrum).

2.8 Experiment 2H—Drug Release Studies Using Flow-Through Dissolution

The flow-through cell (Sotax, Switzerland) dissolution apparatus utilized in this study was an open loop system through which fresh solvent (maintained at 37±0.5° C.) was continuously passed through the cell from the reservoir. This was connected to piston pumps and a fraction collector (Sotax, Switzerland). Cells of 12 mm diameter containing 5 mm glass beads were utilized during the study. Filtration was conducted using 25 mm glass microfibre filter discs (FG/B) (Whatman, US) which were placed above the cells. The prednisolone-loaded tablets were analysed using dissolution media of a pH 1.2 (HCl 0.1M) for 2 hours followed by phosphate buffer pH 6.8 for additional 22 hours. The flow rate was with flow rates of 8 ml/min and samples were collected to Sotax fraction collector at time intervals 0, 0.5, 1, 1.5, 2, 2.5, 3, 3.5, 4, 6, 8, 10, 12, 15, 18, 21 and 24 hours. Samples were further filtered 0.22 µm Millex-GP syringe filter (Merck Millipore, USA) for HPLC analysis (section 2.5). Each tablet strength was assessed in triplicate.

Figure 20:
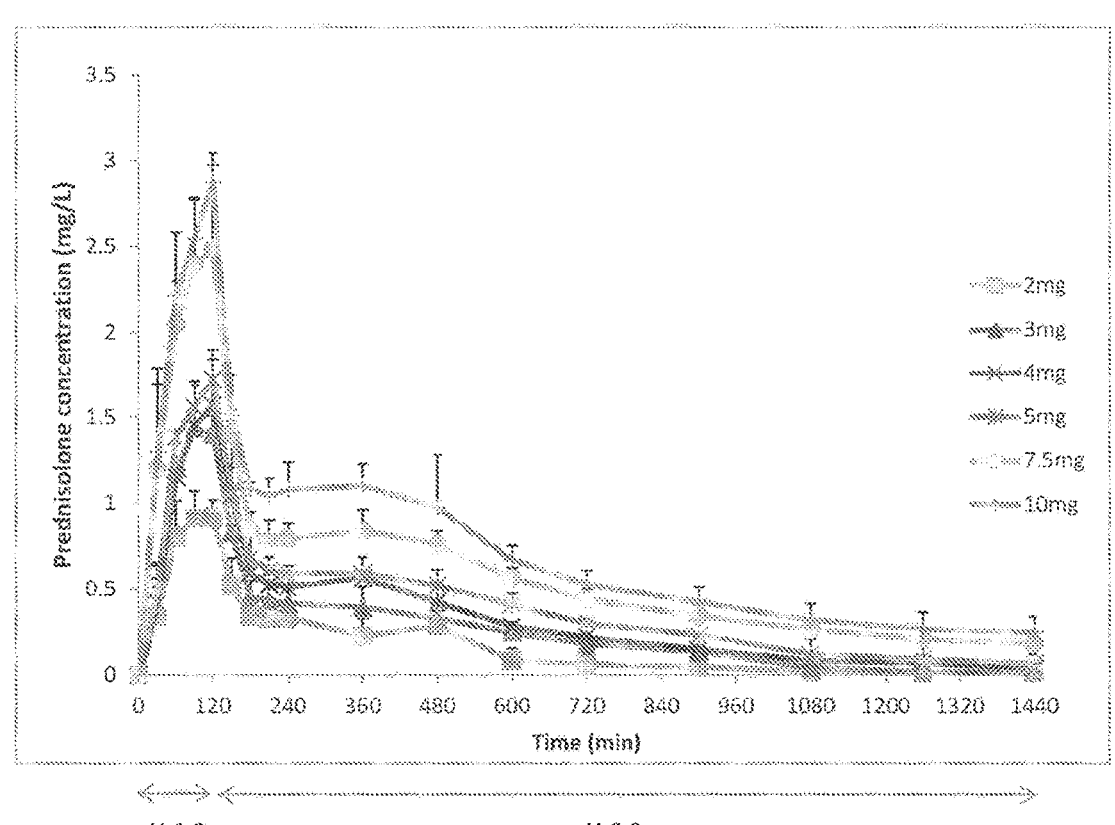
FIG. 20 is a graph showing time versus prednisolone concentration of 3D printed PVA tablets during a pH change flow-through dissolution test.

FIG. 20 is a graph showing time versus prednisolone concentration of 3D printed PVA tablets during a pH change flow-through dissolution test.

Figure 21:
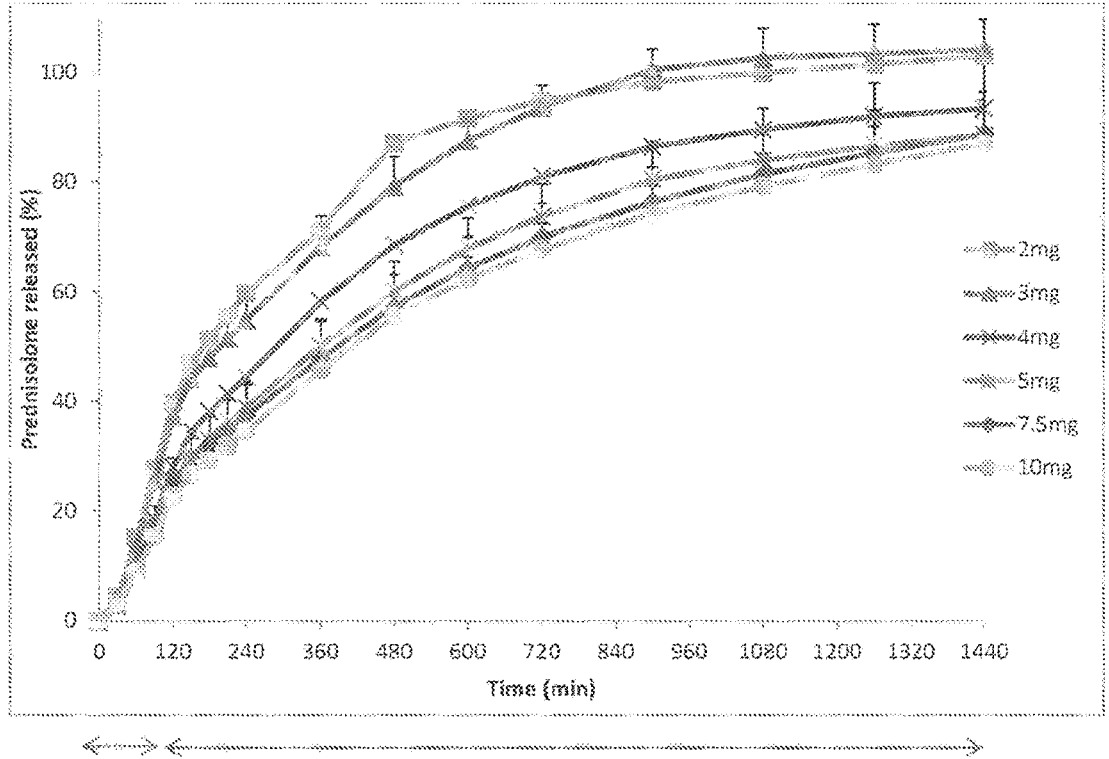
FIG. 21 is a graph showing an in vitro release pattern of prednisolone from 3D printed PVA tablets using a pH change flow-through dissolution system.
Figures 22, 23, 24, 25, 26, 27, 28, 29, 30, 31, 32A, 32B, 33A, 33B, 34A, 34B, 35, 36:
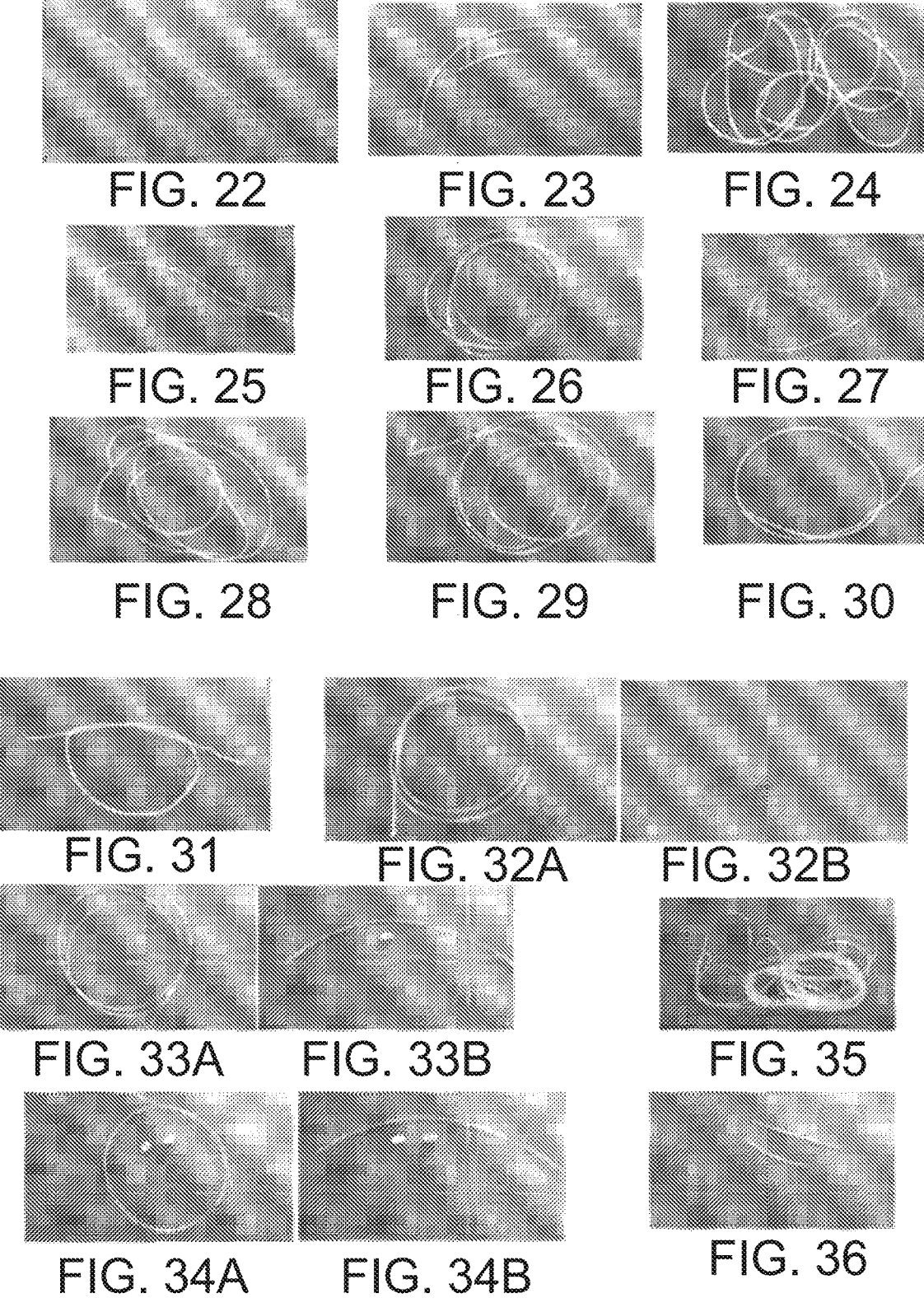
FIG. 22, FIG. 23, FIG. 24, FIG. 25, FIG. 26, FIG. 27, FIG. 28, FIG. 29, FIG. 30, FIG. 31, FIG. 32A, FIG. 32B, FIG. 33A, FIG. 33B, FIG. 34A, FIG. 34B, FIG. 35, FIG. 36, FIG. 37, FIG. 38, FIG. 39A, FIG. 39B, FIG. 40, FIG. 41, FIG. 42A, FIG. 42B, FIG. 43A, FIG. 43B, and FIG. 44 are illustrations of filaments and/or solid dosage forms produced in Examples 3.1 to 3.28 depicted in Table 5.
Figures 37, 38, 39A, 39B, 40, 41, 42A, 42B, 43A, 43B, 44:
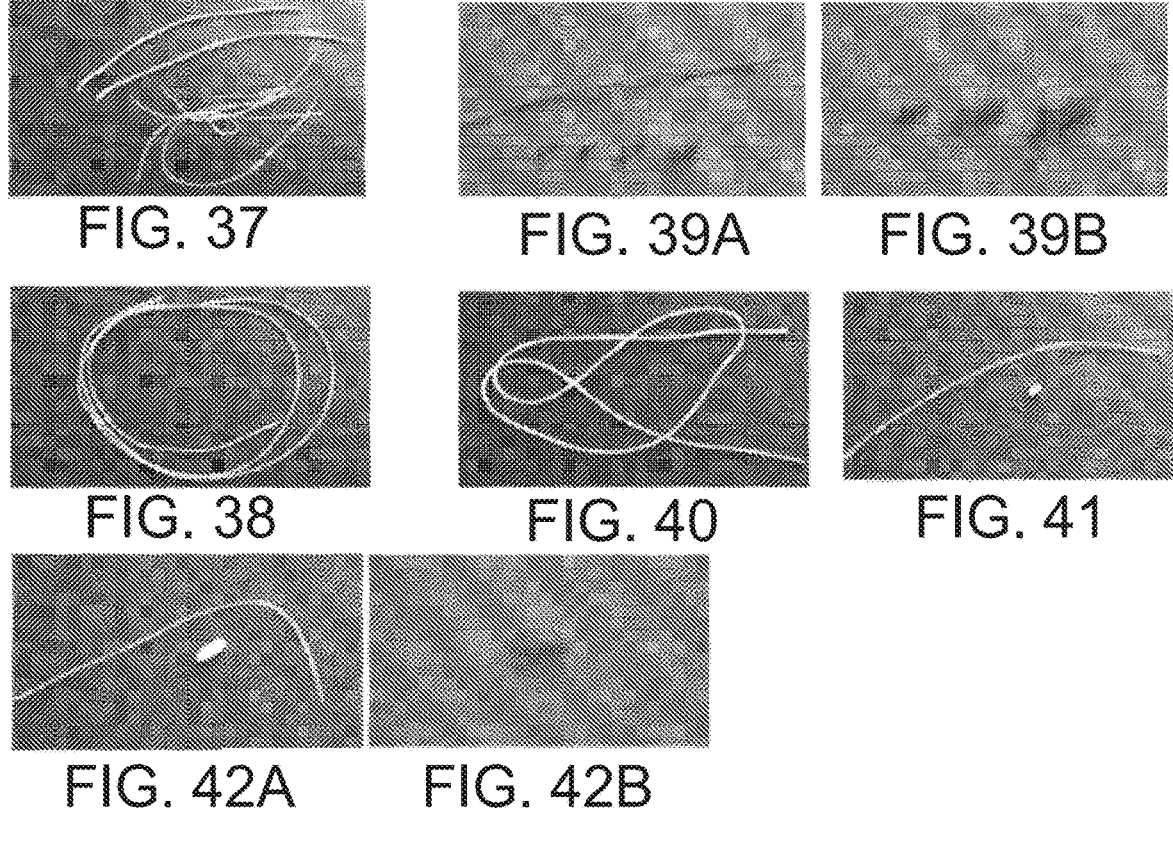

FIG. 21 is a graph showing an in vitro release pattern of prednisolone from 3D printed PVA tablets using a pH change flow-through dissolution system.

Prednisolone was chosen as a model drug due to its high thermal stability, neutral nature and wide range of dose. All investigated prednisolone tablets exhibited a similar release profile (FIGS. 20 and 21). Interestingly, the first two hours showed a faster rate of drug release compared to intestinal phase (pH 6.8). The majority of drug release (>80%) took place after 12 hours for 2 and 3 mg tablets and over 18 hours for tablets with dose 4, 5, 7.5 and 10 mg. Approximately 100% of prednisolone release was reached during 16 h for tablets with 2 and 3 mg drug loading. Whilst after 24 h test nearly 85% of initial amount of prednisolone was released for 4 mg; 5 mg; 7.5 mg; 10 mg tablets and 100% for 2 mg and 3 mg. This might be related to the smaller surface area/mass of the larger tablet which increase diffusion and delay erosion of the tablets.

2.9 Conclusions from Example 2

It is possible to control the mass of printed tablet through controlling the volume of the design.

Through the control of weight of the printed design it was possible to control the final dose.

The precision range for dose control was between 88.7%-107%.

It is likely that prednisolone existed in amorphous within the tablets based on DSC and XRPD analysis.

An extended drug release pattern from tablets suggests drug release though combined erosion and diffusion mechanism.

Controlling drug release though controlling the volume of the design has therefor been credibly verified.

Example 3—Development of Pharmaceutical Grade Filament for 3D Printing

A wide variety of experiments were performed in the development and optimization of pharmaceutical grade filaments. The following experiments elucidated some of the principal considerations in the preparation of pharmaceutical grade filaments and solid dosage forms printed therefrom. The elucidation of these principal considerations contributes a wealth of knowledge which the skilled person may use to develop a wide range of pharmaceutical formulations with various drugs, excipients, and release profiles. For instance, the ensuing experiments enable the preparation of solid dosage forms with immediate, extended and delayed release properties.

3.1 Experiment 3A—Preparation of Filaments

Active ingredient-containing printing filaments (those which do contain an active, which in these examples is generally a drug) and further printing filaments (which do not necessarily contain an active), were prepared via a hotmelt extrusion process. This process generally involved first mixing the relevant ingredients (e.g. drug, carrier(s), and optional plasticizer) within a hotmelt extruder at an appropriate temperature ($T_1$—mixing temperature) to suit the mixture in question (i.e. to allow for fluid mixing) to give a substantially uniform mixture, before the mixture was then extruded through a heated filament-forming nozzle (having the desired size/diameter, $N_1$) at an appropriate temperature ($T_2$— processing temperature) to suit the mixture and to achieve a desirable torque. Filaments were extruded from the filament-forming nozzle using counter-flow extruders which rotate at an appropriate speed to yield filaments having the desired properties. Filaments were typically dispensed onto a Teflon™ coated surface and stored in a plastic back prior to their use in 3D printing.

Generally about 7 g (total preparation mass) of the preparation was accurately weighed—for instance to achieve 80:20 polymer drug ratio 5.6 g of polymer and 1.4 g of drug were weighed. The resulting weighed preparation was manually loaded to a HAAKE MiniCTW hotmelt extruder, wherein the preparation was allowed to mix at an appropriate mixing temperature ($T_1$—typically 110-130° C.) to suit the mixture and allow for substantial homogenisation for at least 5 minutes prior to extrusion. The counter flow extruders rotation speed was set at 100 rpm. Once properly mixed, the mixture was extruded from a heated filament-forming nozzle at an extrusion temperature ($T_2$—typically 90-110° C.) suitable to achieve a torque of approximately 0.6 Nm/screw (extrusion temperature $T_2$ is typically 20-30 lower than preparation temperature, $T_1$—i.e. $T_1$-$T_2$=between 20 and 30). Extrusions were carried out using different nozzle sizes (0.5-2.0 mm) using torque control of 0.6 Nm/screw. The extrudes were received on Teflon coated conveying belt and stored in plastic bag until it is used as a filament for 3D printing.

Where a drug is present, the resulting filaments general display a substantially uniform distribution of the drug within the carrier/polymer matrix. Drug-loadings within the filament were generally 10 wt % and above, and generally 60 wt % and below.

The target diameter of the filaments (i.e. their thickness) was approximately 1.75 mm, since this diameter is most compatible with the 3D printer being used.

After hot extruding the polymer into a filament, they were used as a filament (ink) for 3D printing of tablets.

Specific examples and results relating to both filaments and printed dosage forms are presented below. However, the following ingredients were employed in the formation of the aforesaid filaments:

Active Ingredient:

In filaments having a drug incorporated therein, the drugs used were Drug A: dipyridamole (mp 163° C.; water sol. 9.22e-01 g/l; 25-75 mg tablets); or Drug B: theophylline (mp 273° C.; water sol. 7360 mg/L at 25° C.; 100-300 mg immediate release or sustained release tablets). These drugs represent a good spectrum for these studies.

Active Ingredient Carrier(s):

Different carriers were tested to assess the viability of various different drug release patterns:

Immediate Release: Eudragit® E, Eudragit® NE, HPC SSL

Extended Release: Eudragit® RS, Eudragit® RL, HPC SL, HPC M and HPC H

Delayed release (i.e. enteric formulations): Eudragit® L100-55, Eudragit® L100, Eudragit®S100, and Aqoat LG,MG,HG (also called AS-LG, AS-MG, and AS-HG).

All carriers are commercially available. Eudragit® carriers are acrylate-based polymers having different properties. HPC carriers are hydroxypropyl cellulose (HPC) polymers having different properties. Aqoat carriers are hydroxypropyl methyl cellulose acetate-succinate (HPMCAS) polymers having varying properties.

Plasticizer:

In some cases, plasticizers were used for optimizing the filament melting and glass transition temperature. In the ensuing experiments, plasticizers used include glycerol, TEC, triacetin, and PEG400.

Plasticizers are used, where necessary, to optimize the physical form of the filament. Filaments with glass transition temperature Tg that is too high will be too brittle and break upon handling. On the other hand, if the Tg of the filament is too low, the filament will be too flexible for loading through the nozzle of the 3D printer. Moreover, using filament with low Tg can lead to melted extrudes out of the nozzle of the 3D printer. This can lead to poor shape of the final product. The skilled person is well able to assess, in view of the guidance provided in the present application, the skilled person is readily able to assess whether or not, how much, and what type of plasticizer may be used to improve the quality and properties of the filaments. In general, a filament will desirable have a Tg high enough to avoid the above mentioned pitfalls and low enough to permit formation of and printing with the filaments at temperatures which minimize any degradation of the ingredients, especially the active ingredient. Simple stability studies can be used to assess this.

Other Excipients:

Talc is sometimes used to improve the flow properties and the shape of a printed tablet. It is thought that this may be due to the lubricant effect provided by talc, which may reduce friction between the filament and the printing nozzle. It also provides non-melting particles at the relevant processing temperature, which can be highly advantageous.

Fillers, such as lactose, may be used for immediate release formulations due to its high water solubility. It can increase the size of the tablet and can also provide non-melting particles within the filament at the processing temperature.

3.2 Experiment 38—Printing 3D Tablets with Filaments

Blank and drug-loaded tablets were designed in an ellipse shape, as per the previous section, using Autodesk® 3ds Max® Design 2012 software version 14.0 (Autodesk, Inc., USA) and saved in STL format (FIG. 8A, FIG. 8B and FIG. 8C). The design was imported to the 3D printer's software, MakerWare Version 2.4.0.17 (Makerbot Industries, LLC., USA). A series of tablets with different volume were printed by modifying the dimensions of the design: length×width× heights (L, H, W) without altering the ratios between these dimensions. The 3D printer was modified as described in the previous section (2.2) to print the filaments. Other variations in the 3D print or its operation are explained in the Examples below. For instance, printing temperatures ($T_3$) were varied depending on the composition of the filament in question, as were mixing temperatures ($T_1$) and processing temperatures ($T_2$) during the formation of the relevant filament. Generally, printing temperatures ($T_3$) are 50-70° C. higher than the processing temperatures ($T_2$). The printing/extrusion nozzle generally has a diameter/size ($N_2$) of around 200 μm.

3.3 Experiment 3C—Variety of Examples Based on Sections 3.1 and 3.2

Table 5 (below) provides details of multiple experiments relating to the formation of (and in some case the printing with) filaments. The weight percentage values relating to particular ingredients are wt % based on the total weight of the relevant filament. Any ratios (e.g. if multiple carriers are given) are suitably weight ratios.

The main difference in the drug-loading examples of this section compared to those of the previous two sections is that the drugs (or active ingredient) are present from the start (i.e. during the formation of the filaments), rather than being infused into a filament after the filament has been formed. This enables much higher drug loadings.

TABLE 5

| | | | | | | | | | | | | | |
|---|---|---|---|---|---|---|---|---|---|---|---|---|---|
| | Example Filaments and Solid Dosage Forms Producted by Methods 3.1 and 3.2 | | | | | | | | | | | | |
| Ex. | Carrier(s) (wt. ratio) | Wt % | Plasti- cizer | Wt % | Drug | Wt % | $T_1$ (° C.) | $T_2$ (° C.) | $T_3$ (° C.) | $N_1$ (mm) | $N_2$ (mm) | Comment Filament | Comment Tablet | FIG. |
| 3.1 | AS-LG/HPC-SSL (1:1) | 80 | — | — | A | 20 | 130 | 130 | | | | Too brittle. Add plasticizer or ↑ ratio of drug (which should act as plasticizer) | Cannot print - extrusion temp causes burning. | 22 |
| 3.2 | AS-LG/HPC-SSL (1:1) | 60 | | | A | 40 | 140 | 140 | | | | Much more flexibile with higher drug loading | Cannot print - extrusion temp causes burning | 23 |

TABLE 5-continued

Example Filaments and Solid Dosage Forms Producted by Methods 3.1 and 3.2

| Ex. | Carrier(s) (wt. ratio) | Wt % | Plasti-cizer | Wt % | Drug | Wt % | T$_1$ (° C.) | T$_2$ (° C.) | T$_3$ (° C.) | N$_1$ (mm) | N$_2$ (mm) | Comment Filament | Comment Tablet | FIG. |
|---|---|---|---|---|---|---|---|---|---|---|---|---|---|---|
| 3.3 | HPC-SSL | 60 | Glycerol | 40 | | | 40 | 40 | | | | Too greasy and soft | | |
| 3.4 | HPC-SSL | 80 | Glycerol | 20 | | | 75 | 65 | | | | Using lower extrusion temp (T$_2$) improves rheological properties of filament, but filament is still too soft, ↑ plasticizer ↓ T$_2$ | Too soft to print. | 24 |
| 3.5 | HPC-SSL | 90 | Glycerol | 10 | | | 130 | 90 | 180 | | | Too soft - foams out of nozzle during formation | Too soft to print. Metls in print. | 25 |
| 3.6 | HPC-SSL | 92.5 | Glycerol | 7.5 | | | 150 | 110 | 140-160 | | | Filament does form. ↓ plasticizer ↑ T$_2$ | Impossible to extrude/print | |
| 3.7 | HPC-SSL | 95 | Glycerol | 5 | | | 170 | 120 | | | | T$_1$ so high that polymer visibly degrades | | 26 |
| 3.8 | HPC-SSL | 90 | TEC | 10 | | | 130 | 90 | 185 | 1.5 | | Thin filament produced. Filament needs to be thicker (try 2 mm nozzle) for better loading to printer. | Printing possible but printed filament non-uniform. Nozzle blocks with slow flow. Higher temp better flow but polymer degrades. | 27 |
| 3.9 | HPC-SSL | 87.5 | TEC | 12.5 | | | 120 | 85 | | 2.0 | | Filament produced ↑ plasticizer ↓ T$_1$/T$_2$, and avoids polymer degradation | | |
| 3.10 | HPC-SSL | 85 | TEC | 15 | | | 110 | 80 | 185 | | | | Printing is possible. TEC is a good plasticizer in 3D printing | 28 |
| 3.11 | HPC-SSL | 90 | PEG400 | 10 | | | 135 | 100 | | | | Structure much worse than with TEC as plasticizer | | 29 |
| 3.12 | HPC-SL | 90 | TEC | 10 | | | 125 | 105 | 185 & 220 | 2.0 | | Thick filament forms. 2.0 mm nozzle N$_1$ too big as polymer expands with temp. | Flow at beginning, but then 3D printer stops extruding. At higher temp polymer degrades. Higher grade HPC is no better for 3D printing. | 30 |
| 3.13 | HPC-M | 90 | TEC | 10 | | | 135 | 125 | | | | T$_1$/T$_2$ higher for this HPC and filament has irregular surface. | Printing inpossible due to irregular structure of filament | 31 |
| 3.14 | AS-LG | 80 | TEC | 20 | | | 125 | 100 | 185 | 1.5 | | Filament doesn't expand much with temp, and has smooth surface | Very printable | 32 |
| 3.15 | AS-MG | 80 | TEC | 20 | | | 130 | 110 | 185 | 1.0 | | Filament expands with temperature but smooth surface | Very printable | 33 |
| 3.16 | AS-HG | 80 | TEC | 20 | | | 125 | 100 | 185 | | | Filament expands with temperature but smooth surface | Very printable | 34 |
| 3.17 | AS-LG/HPC-SSL (1:1) | 80 | TEC | 20 | | | 125 | 105 | | 1.0 | | Filament expands with temperature. Irregular surface. High flexibility. | Printing impossible | 35 |
| 3.18 | Eudragit ® E PO | 50 | | | B | 50 | 130 | 125 | 180 | 1.5 | | Filament doesn't expand, has a smooth surface, but is too brittle. | Printing possible | 36 |
| 3.19 | Eudragit ® E PO | 30 | TEC | 20 | B | 50 | 70 | 45 | 185 | | | Filament is not viscous enough | Printing possible | |
| 3.20 | Eudragit ® E PO | 40 | TEC | 10 | B | 50 | 95 | 85 | 185 | | | Smooth surface, not too flexible | Printing possible | |
| 3.21 | Eudragit ® E PO | 45 | TEC | 5 | B | 50 | 95 | 85 | 185 | | | | Printing possible | 37 |

TABLE 5-continued

Example Filaments and Solid Dosage Forms Producted by Methods 3.1 and 3.2

| Ex. | Carrier(s) (wt. ratio) | Wt % | Plasti-cizer | Wt % | Drug | Wt % | $T_1$ (° C.) | $T_2$ (° C.) | $T_3$ (° C.) | $N_1$ (mm) | $N_2$ (mm) | Comment Filament | Comment Tablet | FIG. |
|---|---|---|---|---|---|---|---|---|---|---|---|---|---|---|
| 3.22 | Eudragit ® E PO | 47.5 | TEC | 2.5 | B | 50 | 95 | 85 | 185 | | | | Printing good for tablets | 38 |
| 3.23 | Eudragit ® RL100 | 45 | TEC | 5 | B | 50 | 130 | 120 | 180 | | | Excellent filament | Readily printable as tablets in high res detail | 39 |
| 3.24 | Eudragit ® NE | 50 | | | B | 50 | 120 | 110 | | | | Too flexible + expands with temp | | 40 |
| 3.25 | Eudragit ® L100-55 | 80 | TEC | 20 | | | 120 | 110 | 185 | | 1.0 | Expands during formation | Printing possible | 41 |
| 3.26 | Eudragit ® S100 | 60 | TEC | 40 | | | 120 | 110 | 185 | | 1.0 | Expands during formation | Printing possible. Can be used to form shell of tablets | 42 |
| 3.27 | Eudragit ® S100/talc (2.5:1) | 70 | TEC | 30 | | | 130 | 120 | | | | Talc prevents expansion of filament with temperature | Printing is very good - ideal for core-shell tablets (see figure) | 43 |
| 3.28 | Eudragit ® NE/lactose (1.5:1) | 50 | | | B | 50 | 120 | 110 | | | | Lactose prevents expansion of filament with temperature. | Printing not possible | 44 |

3.4 Conclusions from Example 3

Printing appears to be more successful, in terms of the final shape of the solid dosage form, when the filaments contain a reasonable amount of particles of high melting point (i.e. higher than the printing nozzle temperature, $T_3$). These particles may simply be drug particles or filler particles (e.g. lactose or talc). Interestingly, the presence of such particles during print appears to produce a final solid dosage form that is a much better, in terms of shape and integrity, than the default filament from the 3D printer maker. The absence of these particles often leads to nozzle blockage, formation of bubbles of during printing, or the degradation of the polymer matrix.

The glass transition temperature appears to be important for successful filaments, since optimal glass transition temperatures can yield optimal processing/printing temperatures, which may minimise problems with the filaments and final dosage forms formed therefrom.

In general the 3D printing temperature ($T_3$) appears to be 50-70° C. higher than the ideal temperature of filament preparation ($T_2$). The 3D printer may require higher temperatures for printing than the hotmelt extruder does in filament formation because the filament spends a shorter time in contact with the nozzle in the 3D printer.

The most suitable plasticizer for Eudragit® polymers appears to be TEC (triethyl acetate) (0.5-30%), and triacetin appears to be optimal for cellulose based polymers (0.5-10%).

In case of dual printing (2 colours or core-shell structures), a lower Tg polymer is most appropriate as the filament is likely to stay longer in the nozzle under high temperature (i.e. there is downtime when one filament is being printed whilst the other is not).

Adding high percentage of talc (>15%) might make the printed project detach easily from the base during printing process. Therefore, there is likely to be an optimal amount.

Example 4—Model Studies with Theophylline (Model Drug) and Eudragit® RL (Model Carrier Polymer)

A variety of model studies were performed to explore variables and parameters in the production of solid dosage forms from pharmaceutical grade filaments. The following experiments elucidated further considerations in the preparation of pharmaceutical grade filaments and solid dosage forms printed therefrom. The elucidation of these considerations contributes a wealth of knowledge which the skilled person may use to develop a wide range of pharmaceutical formulations with various drugs, excipients, and release profiles. For instance, the ensuing experiments enable the preparation of solid dosage forms with immediate, extended and delayed release properties.

4.1 Experiment 4A—Preparation of Filaments

Theophylline was purchased from Arcos (UK). Eudragit® RL100 (Glass Transition temperature (Tg): 63° C. +/−5° C.) and Eudragit® RS100 formulation (Glass Transition temperature (Tg): 65° C.) were generously donated by Evonik Industries (Darmstadt, Germany). Hydroxypropyl cellulose SSL grade was donated by Nisson. Triethyl citrate (TEC) and triacetin were supplied by Sigma-Aldrich (UK). Scotch blue painter's tape 50 mm was supplied by 3M (Bracknell, UK).

MakerBot Replicator® 2X Experimental 3D Printer (MakerBot Industries, LLC, New York, USA) was utilized to print theophylline tablets. In order to obtain the new formulation hot melt extrusion method was implemented using Thermo Scientific HAAKE MiniCTW (Thermo Fisher Scientific, Karlsruhe, Germany).

The composition and ratio of drug, polymer plasticizer mixture is shown in Table 6 below. About 6 g of total blend were carefully weighed and added gradually to counter flow twin screw extruder. The molten mass was allowed to mix for at least 5 min to allow homogeneous distribution of drug and polymer within the matrix. The molten mass was then extruded through a die nozzle with cylindrical shape with appropriate diameters. Sample was fed manually using a funnel into the inlet of the extruder setting the feeding temperature as specified in Table 6 and speed of 80 rpm. Mixing temperature was set at 120° C. and speed of 50 rpm. Filament was extruded at 120° C. using control torque of 0.6 Nm.

Filaments were stored in sealed plastic bags at room temperature before extrusion.

4.2 Experiment 48—Tablet Design and Printing

Blank and drug loaded Eudragit® RLwere designed in a typical capsule-like shape using Autodesk® 3ds Max® Design 2012 software version 14.0 (Autodesk, Inc., USA) and saved in STL format. The design was imported to the 3D printer's software, MakerWare Version 2.4.0.17 (Makerbot Industries, LLC., USA). A series of tablets with increasing volumes were printed by modifying the dimensions of the design: length×width×heights (L, H, W) without altering the ratios between these dimensions.

TABLE 6

| | | | | 3D Printing process | |
|---|---|---|---|---|---|
| | | HME process | | Extruding | Platform |
| Example | Formulation (Weight ratio) | Initial temperature, $T_1$ (° C.) | Extruding temperature, $T_2$ (° C.) | temperature, $T_3$ (° C.) | temperature, $T_4$ (° C.) |
| 4.1 | Eudragit ® RL/Theophylline/ TEC (45/50/5) | 130 | 120 | 170 | 90 |
| 4.2 | Eudragit ® RS/ Theophylline/TEC (42.5/50/7.5) | 130 | 110 | 150 | 60 |
| 4.3 | Eudragit ® E/ Theophylline/TEC (46.5/50/3.5) | 130 | 110 | 140 | 60 |
| 4.4 | Eudragit ® RL/Eudragit ® E/ Theophylline/TEC (22.5/22.5/50/5) | 130 | 115 | 140 | 90 |
| 4.5 | Eudragit ® RL/Eudragit ® RS/ Theophylline/TEC (22.5/22.5/50/5) | 130 | 120 | 150 | 90 |
| 4.6 | HPC SSL/ Theophylline/ Triacetin (46/50/4) | 125 | 110 | 160 | 20 |

A MakerBot Replicator® 2X Experimental 3D Printer (MakerBot Industries, New York, USA) was utilized to print Eudragit® HPC SSL based tablets. Tablets were printed using default settings of the software for produced filament as follows: type of printer: Replicator 2X; type of filament: PLA; resolution: standard; temperature of nozzle: 230° C.; temperature of building plate: 20° C.; speed of extruder 90 mm/s while extruding and 150 mm/s while traveling; infill: 100%; height of the layer: 200 µm. No supports or rafts were utilized in the printed model.

In order to be able to print prednisolone loaded PVA tablets, the following modifications were implemented:

i) Kapton tape layer (default) provided poor adhesion of the designs to the built plate. Blue Scotch painter's tape was applied to the surface of the printing board to improve adhesion to the surface layer.

j) Changing extruder temperature during printing as specified in Table 6 was essential to maintain constant flow of Theophylline loaded filaments.

4.3 Experiment 4C—Protocols for Analysis of Filaments and 3D-Printed Tablets 4.3.1 Determination of Drug Content In order to assess theophylline content in the printed tablets each tablet was weighed and transferred to 1000 ml volumetric flask. Tablets were sonicated for 4 h with completing the volume to 1000 ml with 0.1 M HCl, left overnight and subsequent sonication additional 4 hours next day.

After cooling to room temperature, theophylline drug content was determined in the obtained solution by spectrophotometry (Jenway, Japan). The absorbance was measured at 272 nm. For higher concentrations, 10 mL of the obtained solution were diluted to a final volume of 20 mL with 0.1 M HCl.

4.3.2 Scanning Electron Microscopy

The surface morphology of the produced filament, extruded filament from the nozzle of the 3D printer as well as the printed tablet was assessed using a Quanta-200 SEM microscope at 20 kV. Samples were placed on metallic stubs and gold coated under vacuum for 2 min using JFC-1200 Fine Coater (Jeol, Tokyo, Japan), prior to imaging.

4.3.3 X-Ray Powder Diffraction

A powder X-ray diffractometer, D2 Phaser with Lynxeye (Bruker, Germany) was used to assess the crystallinity of theophylline in the drug loaded tablets. Samples were scanned from 2Theta (2θ)=5° to 50° using 0.01° step width and a 1 second time count. The divergence slit was 1 mm and the scatter slit 0.6 mm. The wavelength of the X-ray was 0.154 nm using Cu source. The voltage used was 30 KV. Filament emission was 10 mA using a scan type coupled with a two theta/theta scintillation counter over 60 min. Samples from the extruded filaments and printed tablets were immersed in liquid nitrogen to assist the grinding process.

4.3.4 Differential Scanning Calorimetry

A differential scanning calorimeter DSC Q2000 (TA Instruments, Elstree, Hertfordshire, UK) was utilized to perform thermal analysis. Samples of approximately 5 mg were accurately weighed and placed in a 40 μL standard aluminium pan DSC analysis. Analysis was carried on under a nitrogen environment (50 mL/min). In order to exclude the effect of humidity and to get a clearer Tg, samples were cooled to −10° C., then heated to 100° C. The temperature was kept isothermal for 5 min then cooled to −20° C. and left for 2 minutes. The heating and cooling of the samples were performed at of 10° C./min. This was followed by a heat scan from −20° C. to 300° C. at the same rate. All measurements were carried out in triplicates. The data was analyzed using TA 2000 analysis software.

All the samples were subjected to a cycle of heat/cool/heat in order to ensure accurate reading and drying of the polymeric matrices. The samples were cooled to −20° C., and kept isothermal for 2 minutes, then heating sequence was followed to bring the samples to 100° C. Samples were kept isothermal at 100° C. for 5 minutes. This was followed by cooling step to −20° C. again. Temperature was left isothermal for 2 minutes. Finally a heating step to 300° C. was followed to measure the endothermic peak of theophylline if existed. All the heating and cooling sequences were carried out at a rate of 10° C./min.

4.3.5 Thermo-Gravimetric Analysis (TGA)

A thermo-gravimetric analysis TGA Q5000 (TA Instruments, Elstree, Hertfordshire, UK) was used to measure the thermal decomposition profiles of the extruded filaments and printed tablets, in addition to the raw materials.

Samples of approximately 5-7 mg were added to the tared aluminum pan in the TGA. Samples were heated between 25° C. and 600° C. with a heating rate of 10° C./min. The data was analyzed using TA 2000 analysis software.

4.3.6 In Vitro Drug Release Study Via pH Change USP II Dissolution Test

In vitro drug release studies for all gastro-resistant coating formulations used in this study were conducted in dissolution USP II apparatus (AT 7 Smart, SOTAX, Switzerland). Each experiment was carried out in triplicate in dissolution medium at 37±0.5° C. with paddle speed of 50 rpm. The tablets were tested in 750 mL of a stimulated gastric fluid (0.1M HCl, pH 1.2) for 2 h, followed by 16-hour exposure to pH 6.8 phosphate buffer. Within all the experiment the amount of released theophylline was determined at 5 min intervals by UV/VIS spectrophotometer (PG Instruments Limited, UK) at the wavelength of 272 nm and path length of 1 mm. Data was analysed using IDISis software (Automated Lab, 2012).

4.4 Experiment 4D—Analytical Results and Discussion 4.4.1 Stage I: Control of Dose of Theophylline from Eudragit® RL Based 3D Printed Tablet Using Eudragit® RL tablets it with increasing volume, it was possible to print tablet with increasing weight and establish a linear relation between volume and tablet weight as shown in Table 7 and FIG. 46.

Figure 46:
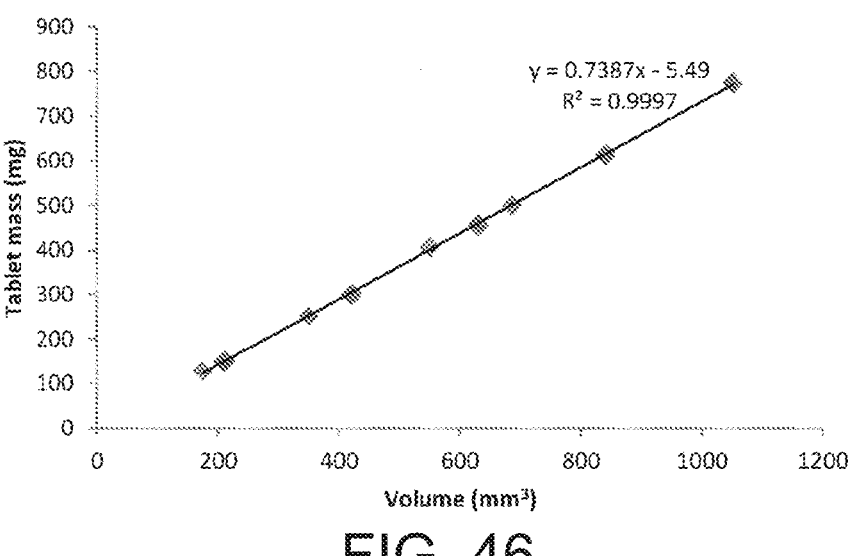
FIG. 46 is a graph showing the linear relationships between theoretical printed volume and retrieved mass.

FIG. 46 is a graph showing the linear relationships between theoretical printed volume and retrieved mass.

TABLE 7

| Target and actual tablet mass, volume and dimensions. | | | | | |
|---|---|---|---|---|---|
| Expected tablet mass (mg) | Volume (mm³) | Dimensions (mm) X × Y × Z | Average tablet mass ± SD (mg) | CV (%) | Weight accuracy ± SD (%) |
| 150 | 210.14 | 11.34 × 4.13 × 4.49 | 149.77 ± 3.15 | 99.84 | 99.84 ± 2.10 |
| 300 | 420.27 | 14.29 × 5.20 × 5.66 | 300.53 ± 4.23 | 100.18 | 100.18 ± 1.41 |
| 450 | 630.42 | 16.35 × 5.95 × 6.48 | 455.17 ± 1.84 | 101.15 | 101.15 ± 0.41 |
| 600 | 840.55 | 18.00 × 6.55 × 7.13 | 613.43 ± 4.69 | 102.24 | 102.24 ± 0.78 |
| 750 | 1050.69 | 19.39 × 7.06 × 7.68 | 774.43 ± 8.71 | 103.26 | 103.26 ± 1.16 |

It was decided to use the equation to print different tablets with therapeutic dose of theophylline: 60, 124, 200, 250 and 300 mg as shown in Table 8.

Figure 47:
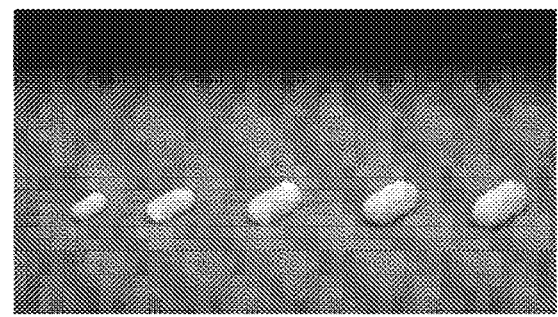
FIG. 47 shows an array of Theophylline 3D printed tablets of increasing size and strength.

The printed tablet showed a good morphology with comparable aesthetic quality to commercially available tables as shown in FIG. 47.

Figure 48:
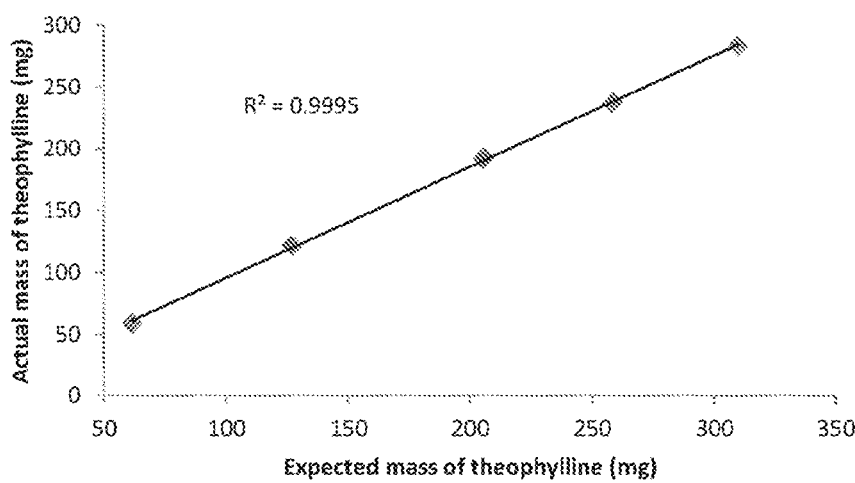
FIG. 48 is a graph showing the linear relationship between achieved and expected dose of theophylline tablets.

When drug contents of the tablets were analysed, there was a linear relationship with the target dose (Table 8 and FIG. 48).

Figure 49:
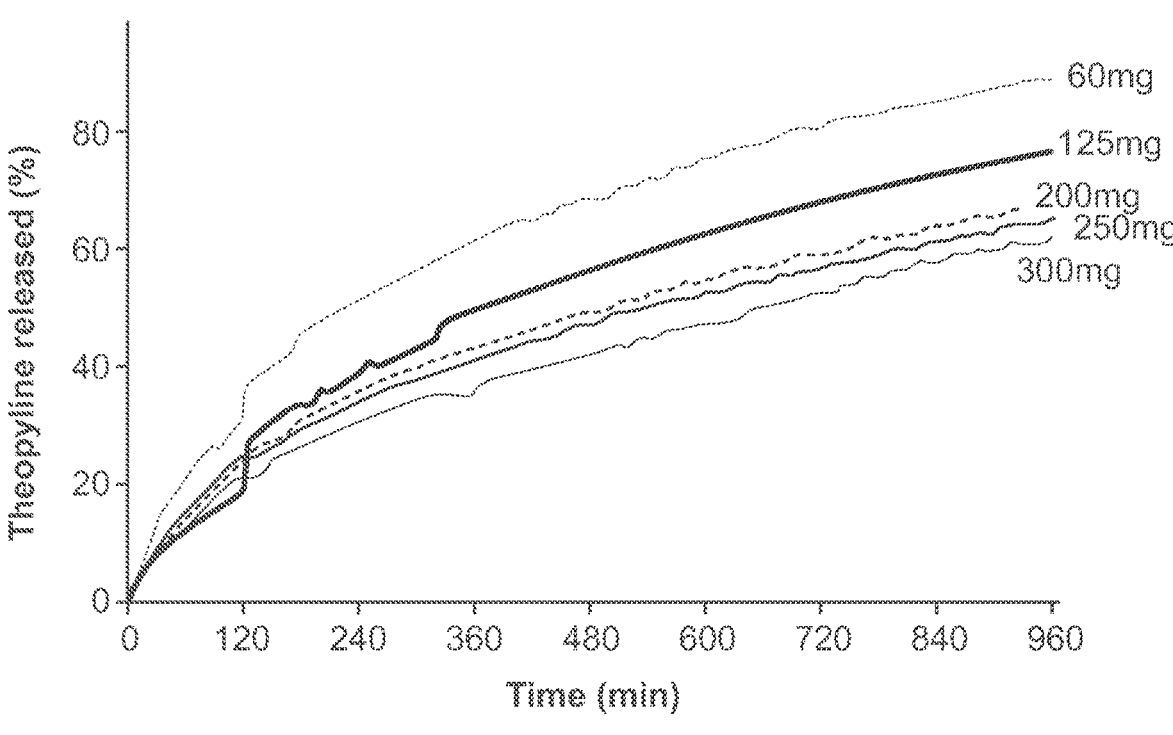
FIG. 49 is a graph showing the in vitro release profile of theophylline from 3D tablets with different strength.

When the release profile was studied, a slower release was noted with larger size tablets due to increase in surface area (FIG. 49)

FIG. 47 shows an array of theophylline 3D printed tablets of increasing size and strength.

FIG. 48 is a graph showing the linear relationship between achieved and expected dose of theophylline tablets.

FIG. 49 is a graph showing the in vitro release profile of theophylline from 3D tablets with different strength.

TABLE 8

Target and actual theophylline dose in 3D printed Eudragit RL based tablets.

| Target dose (mg) | Tablet mass ± SD (mg) | Theoretical dose ± SD (mg) | Achieved dose ± SD (mg) | Dose accuracy ± SD (%) | CV (%) |
|---|---|---|---|---|---|
| 60 | 123.0 ± 1.1 | 61.5 ± 0.57 | 58.8 ± 0.8 | 95.56± | 2.03 |
| 125 | 253.7 ± 4.5 | 126.9 ± 2.26 | 121.7 ± 2.3 | 95.92± | 0.80 |
| 200 | 411.2 ± 5.9 | 205.6 ± 2.97 | 192.4 ± 4.0 | 93.62± | 3.39 |
| 250 | 516.6 ± 10.7 | 258.3 ± 5.35 | 237.1 ± 1.3 | 91.83± | 2.63 |
| 300 | 618.9 ± 6.3 | 309.5 ± 3.13 | 282.6 ± 3.0 | 91.34± | 2.01 |

4.4.2 Stage 2: Effect of Printing Resolution (Printing Speed)

Theophylline 3D printed tablets were fabricated at 3 different speeds: low resolution, standard resolution and high resolution.

Figure 53:
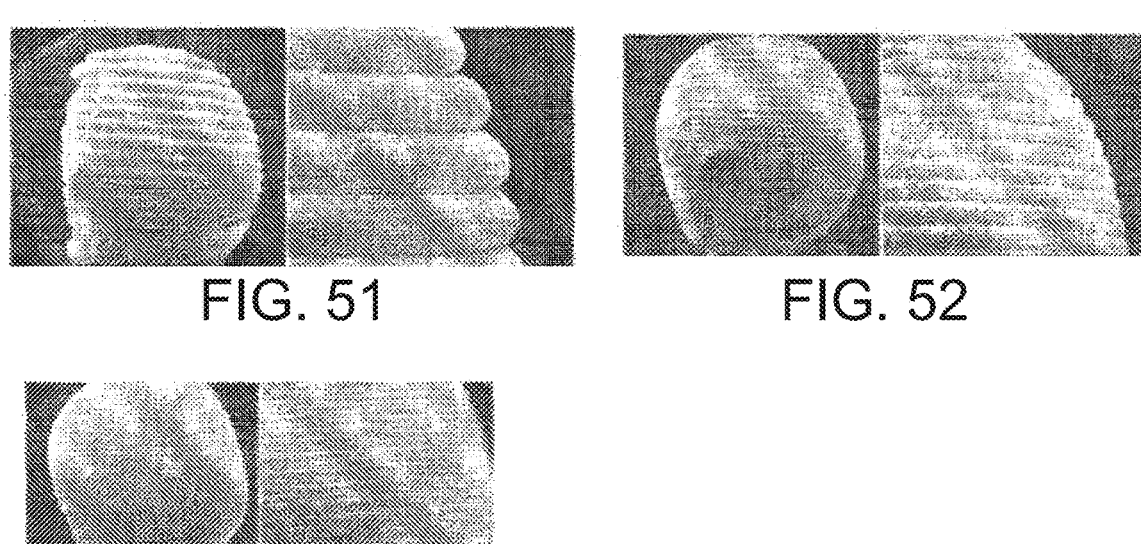
FIG. 53 shows SEM images of Theophylline Eudragit® RL 3D printed tablet at high resolution.

Table 9 provides details of their weights and printing time. Apparently the larger the tablet the longer the printing time required. Low and standard resolution appear to have similar printing time, whilst high resolution takes almost twice as long. The mass of printed tablet and variation reflected in SD appeared to be similar in all three formulations. FIGS. 51-53 provide SEM images of the printed tablets. The number of layers per height increase significantly when higher resolution is applied.

Figure 50:
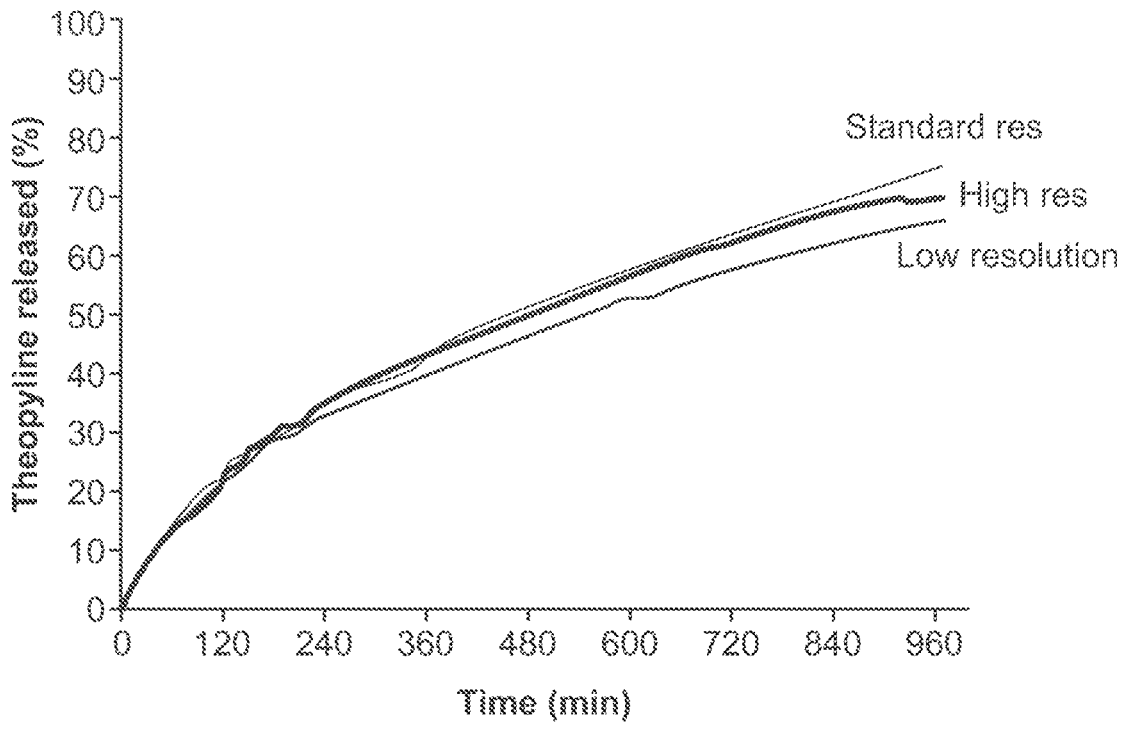
FIG. 50 is a graph showing the effect of resolution of 3D printing resolution on drug release pattern.

The resolution setting appeared to have little influence on the pattern of drug release from the tablet (FIG. 50).

FIG. 50 is a graph showing the effect of resolution of 3D printing resolution on drug release pattern.

FIG. 51 shows SEM images of Theophylline Eudragit® RL 3D printed tablet at low resolution.

FIG. 52 shows SEM images of Theophylline Eudragit® RL 3D printed tablet at standard resolution.

FIG. 53 shows SEM images of Theophylline Eudragit® RL 3D printed tablet at high resolution.

TABLE 9

Mass and 3D printing time using low, standard or high resolution of Eudragit RL based tablets

| Target tablet mass (mg) | Low resolution | | Standard resolution | | High resolution | |
|---|---|---|---|---|---|---|
| | Tablet weight ± SD (mg) | Printing time (min) | Tablet weight ± SD (mg) | Printing time (min) | Tablet weight ± SD (mg) | Printing time (min) |
| 120 | 119.3 ± 0.2 | 2 | 120.5 ± 2.5 | 3 | 121.0 ± 1.4 | 5 |
| 300 | 311.9 ± 2.7 | 4 | 300.5 ± 4.2 | 4 | 308.4 ± 1.4 | 7 |
| 400 | 404.1 ± 3.5 | 5 | 404.2 ± 1.4 | 5 | 407.3 ± 6.4 | 8 |
| 600 | 632.4 ± 14.8 | 5 | 611.9 ± 4.7 | 5 | 646.8 ± 13.1 | 10 |

4.4.3 Stage 3: Tailoring Drug Release Using Other Methacrylate and Cellulose Based Polymers In order to test the applicability of this method to tailor drug release from 3D printed tablets, different polymer or a mixture of polymers were used in replacement of Eudragit® RL. The details of the formulation and preparation method are available in Table 6. Two immediate release polymers HPC SSL and Eudragit® E were applied. For extended release formulation Eudragit® RS was used. To test the possibility of controlling drug release mixtures of Eudragit® RL with Eudragit® RS or Eudragit® E were also investigated.

a. Immediate Release Systems

Figure 54:
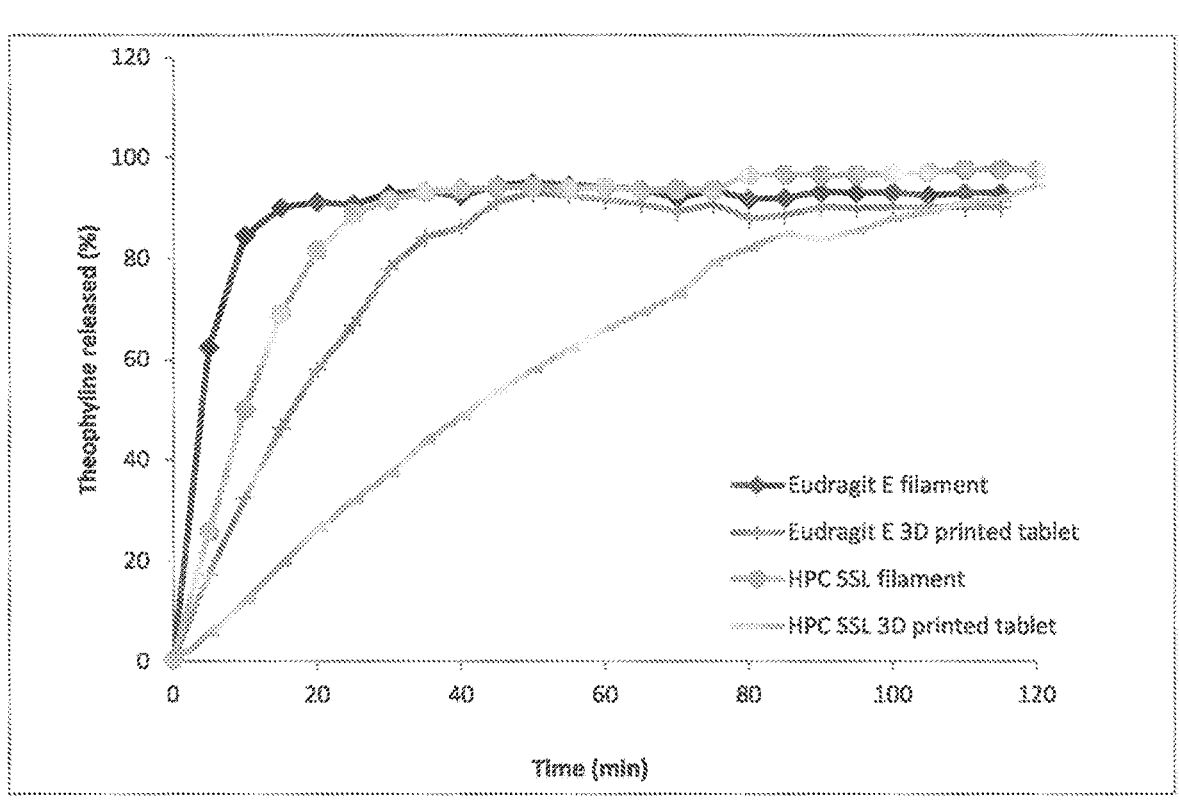
FIG. 54 is a graph showing the drug release profile of Eudragit® E filaments (hollow diamonds), Eudragit® E 3D printed tablet (solid diamond), HPC SSL filament (hollow circle), and HPC SSL 3D-printed tablet (solid circle).

Immediate release effects with theophylline 3D printed tablets were achieved with Eudragit® E (FIG. 54). However, a slower pattern of drug release was noted with SSL HPC tablets. It is obvious in both examples that drug release was slowed down after 3D printing (compared to non-printed filament). This might be attributed to the loss of surface area upon printing. It is also possible that further thermal treatment of drug polymer filament during printing, increased the drug-polymer interaction within polymeric matric and reduce chances of water imbibition upon introduction to dissolution medium.

FIG. 54 is a graph showing the drug release profile of Eudragit® E filaments (hollow diamonds), Eudragit® E 3D printed tablet (solid diamond), HPC SSL filament (hollow circle), and HPC SSL 3D-printed tablet (solid circle).

b. Extended Release Systems

Figure 55A:
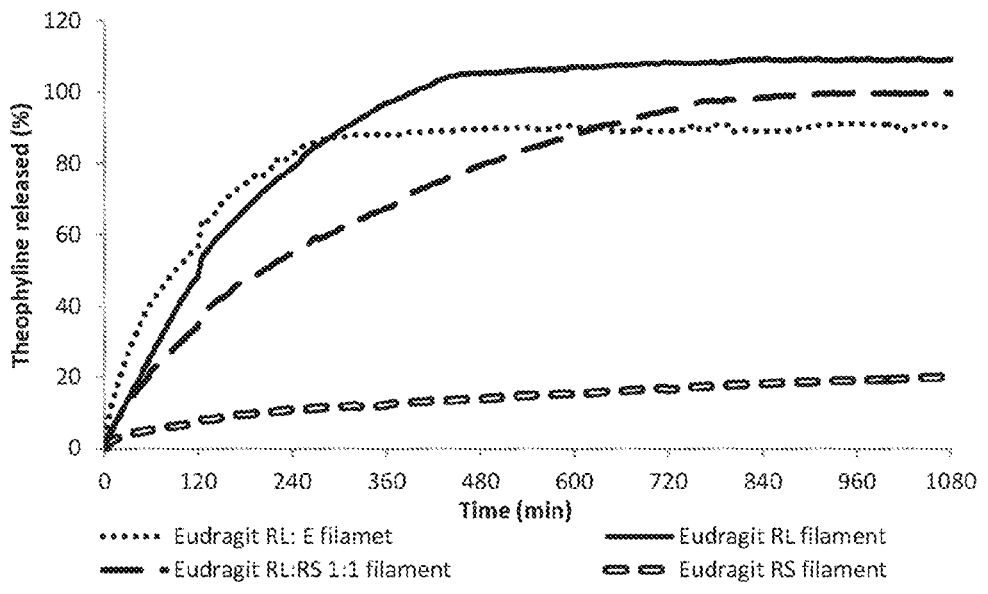
FIG. 55A and FIG. 55B show graphs illustrating the drug release profile from FIG. 55A filaments of Eudrafit RL:E (hollow squares), Eudragit® RL:RS 1:1 (hollow diamonds), Eudragit® RL (hollow triangle), Eudragit® RS (hollow circle)
Figure 55B:
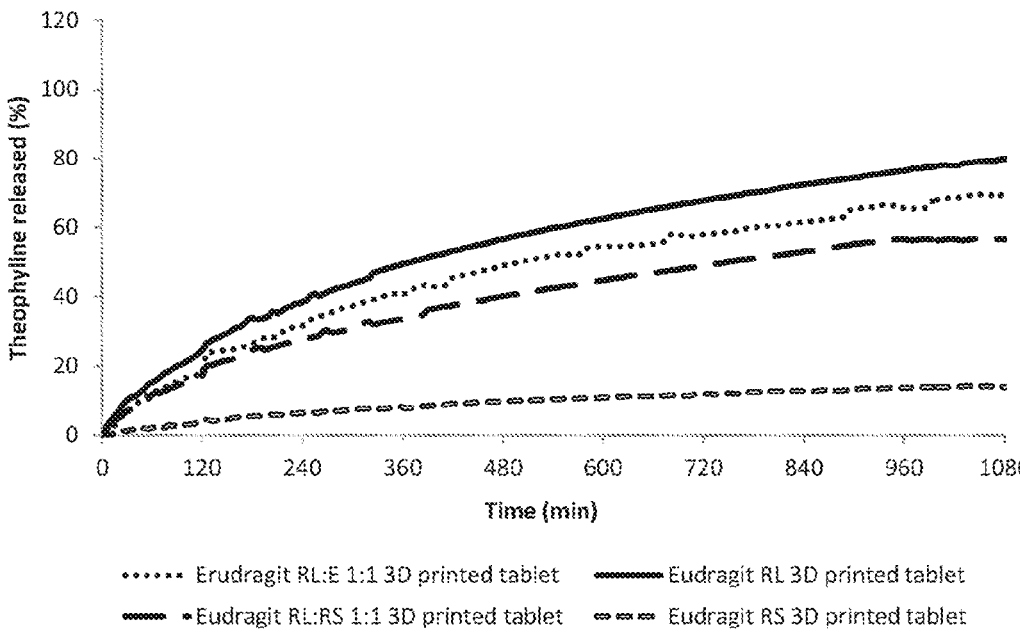

FIG. 55A shows a graph illustrating the drug release profile from filaments of Eudrafit RL:E (hollow squares), Eudragit® RL:RS 1:1 (hollow diamonds), Eudragit® RL (hollow triangle), Eudragit® RS (hollow circle); and FIG. 55B shows a graph illustrating the drug release profile from 3D printed tablets of drugs formulated with Eudrafit RL:E (solid squares), Eudragit® RL:RS 1:1 (solid diamonds), Eudragit® RL (solid triangle), Eudragit® RS (solid circle).

4.4.4 Stage 4: Impact of Infill Percentage

The effect of infill percentage on the pattern of drug release was investigated with SSL HPC tablets. Increasing the filling percentage allows the printing of tablets with the same size but with increased weight (100% to 141.4% when infill percentage increases from 10% to 100%).

Figure 56:
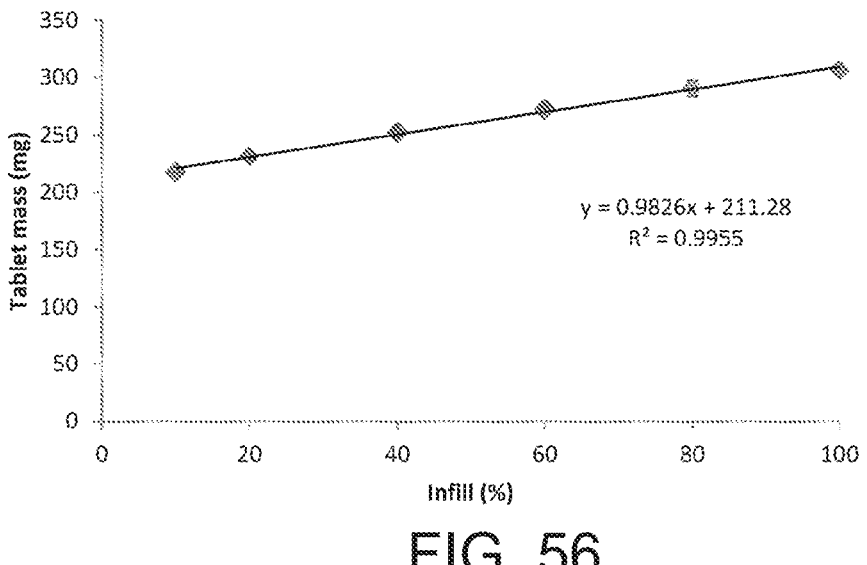
FIG. 56 is a graph showing the Influence of infill setting on the mass of the 3D printed tablet.

The reduced infill percentage allows the design of hollow tablets which is not possible with regular tableting technology. It also allows the design of low density systems that can float in the stomach and show gastric-retentive properties (FIG. 56). Drug release appeared to have slight increased with low infill tablets due to the increase in the contact surface with the dissolution media (FIG. 57).

FIG. 56 is a graph showing the Influence of infill setting on the mass of the 3D printed tablet.

Figure 57:
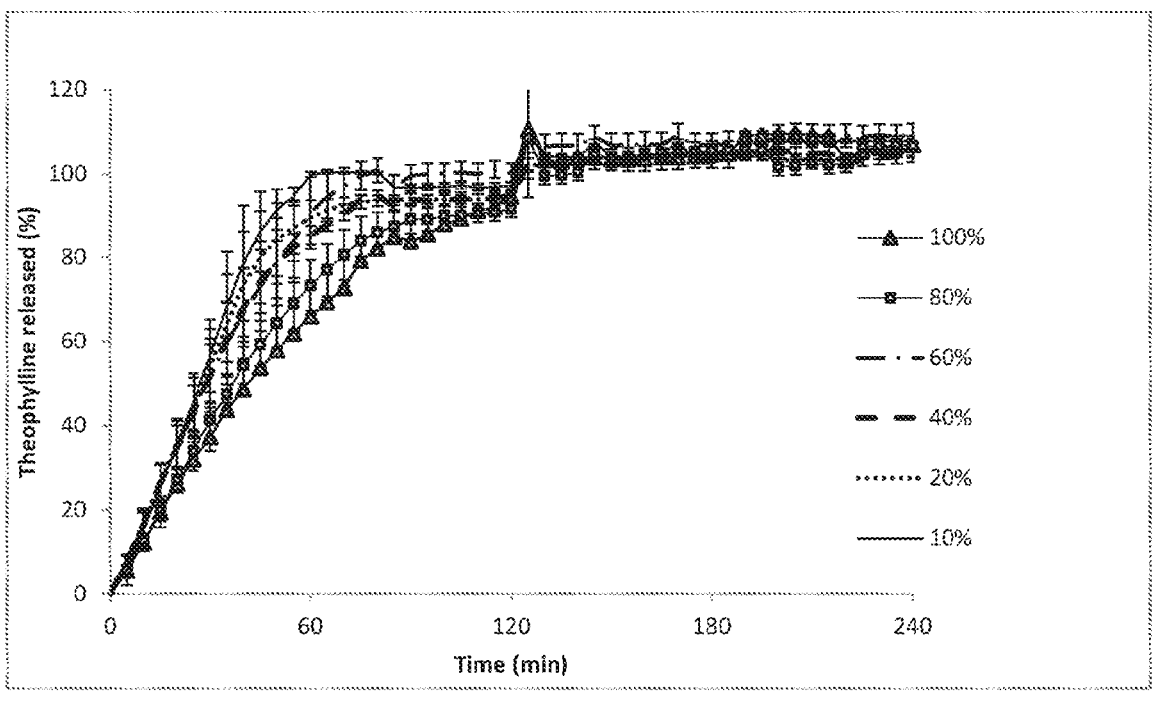
FIG. 57 is a graph showing the Influence of infill setting on theophylline release from 3D printed Eudragit® RL tablet.

FIG. 57 is a graph showing the Influence of infill setting on theophylline release from 3D printed HPC SSL tablets.

4.4.5 Stage 5: Thermal and X-Ray Analysis of the 3D Printed Tablets

Eudragit® RL Tablets Containing Theophylline

TGA Analysis:

The printed tablets were analysed using thermo-gravimetric analysis in order to compare the thermal decomposition pattern of the printed tablet to that of the extruded filaments and raw materials.

Figure 58:
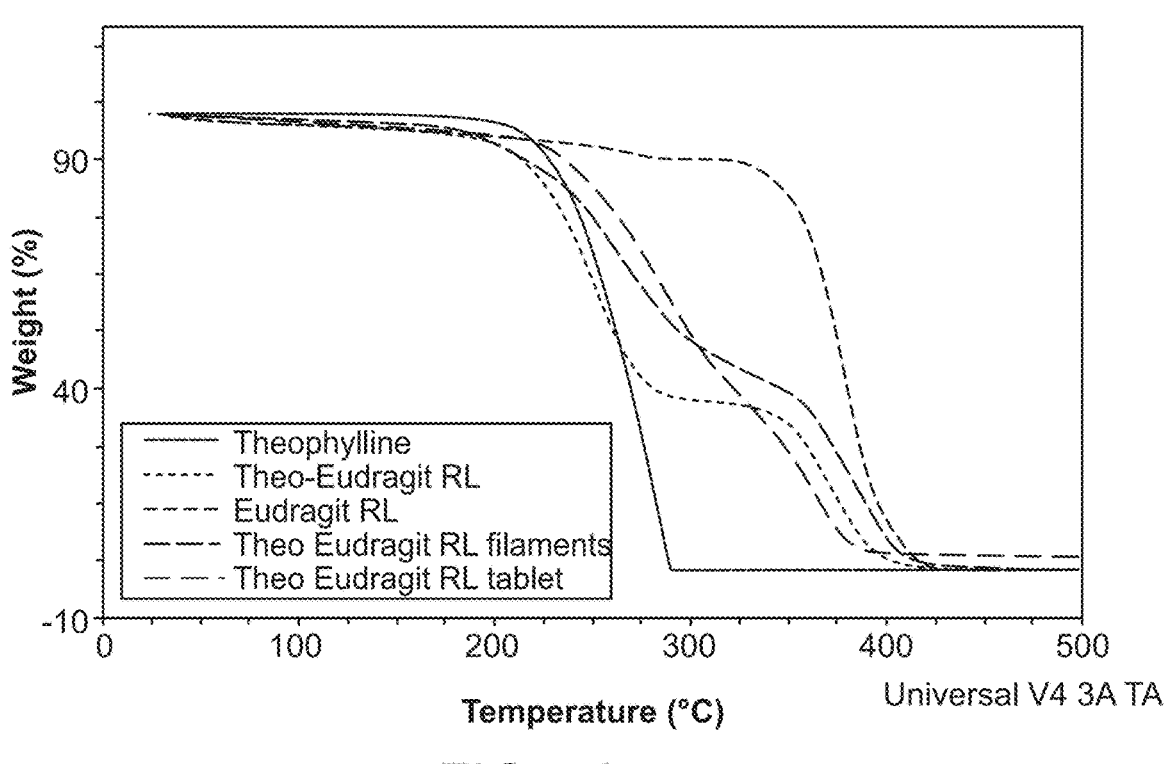
FIG. 58 is a graph showing the thermal degradation profile of Theophylline, Eudragit® RL, physical mixture of Theophylline and Eudragit® RL, Extruded filaments of Theophylline and Eudragit® RL, Tablet of Theophylline and Eudragit® RL.

It was noticed that the pure polymer lost around 3% of its weight up to 110° C. which is believed to be the moisture content of the polymer (FIG. 58).

The degradation pattern of the physical mixture revealed two degradation steps. The first degradation step that starts around 200° C. represents the degradation of theophylline which represents around 60% of the sample. The second degradation step on the other hand starts around 340° C. which represent the degradation of the Eudragit® RL. It can be noticed that the degradation of the theophylline in the physical mixture is steeper than that of the filament or the tablet which can be related to the distribution and interaction of theophylline particles with the polymeric matrix.

FIG. 58 is a graph showing the thermal degradation profile of theophylline, Eudragit® RL, physical mixture of Theophylline and Eudragit® RL, Extruded filaments of Theophylline and Eudragit® RL, Tablet of Theophylline and Eudragit® RL.

DSC Analysis:

Printed tablets revealed that the Tg of Eudragit® has shifted from about 70° C. for the pure polymer into about 46° C. for the extruded filaments and the printed tablet. The difference between the Tg of the polymer for the printed tablet and the extruded filament is minimal and not worth mentioning (FIG. 59).

Figure 59:
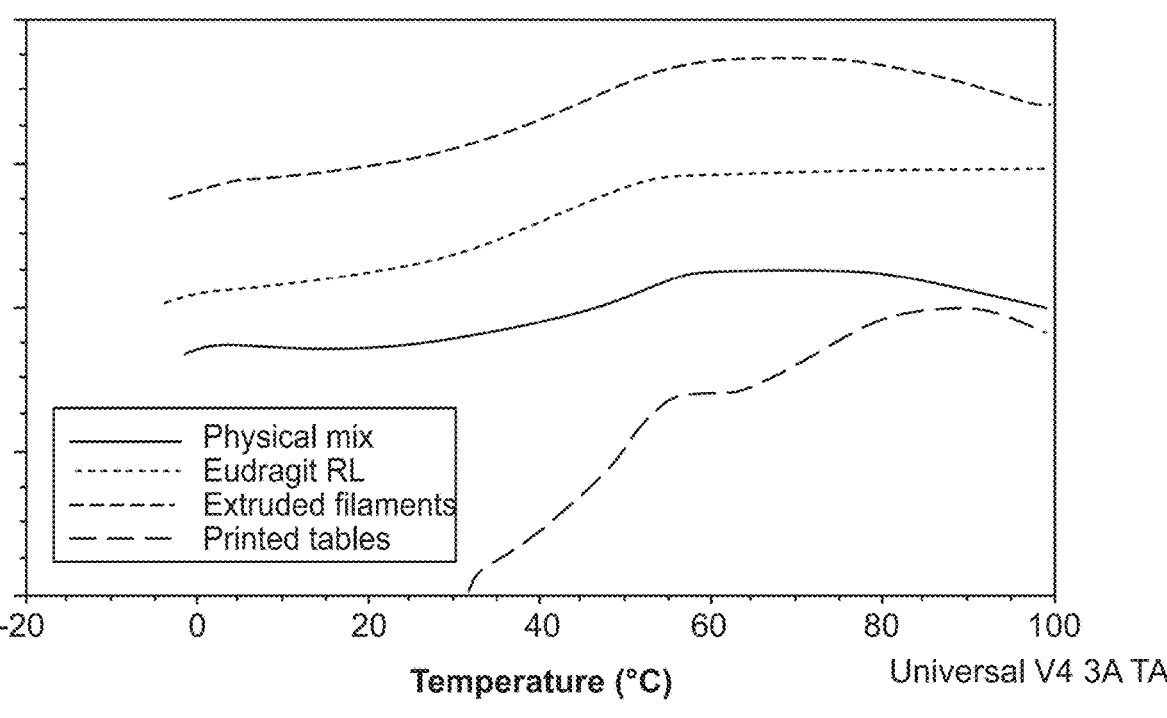
FIG. 59 Glass transition temperature in the first heating step for Eudragit® in: pure polymer, physical mixture with theophylline, extruded filaments, and printed tablets.

FIG. 59 shows glass transition temperature in the first heating step for Eudragit® in: pure polymer, physical mixture with theophylline, extruded filaments, and printed tablets.

The first heating step revealed that the glass transition temperature of Eudragit® did not change much between the pure polymer CA 50° C. and the extruded filaments or the printed tablets although there was a noticeable widening in the Tg range.

On the other hand, the third heating sequence revealed the existence of theophylline endothermic peak around 259° C. in the sample of printed tablet and 254° C. with the extruded filaments.

These peaks are expected to be for theophylline crystals as the melting point of pure theophylline can be noticed at 272° C. However, the impurity effect of the polymer caused this slight shift in the melting endotherm.

Figure 60:
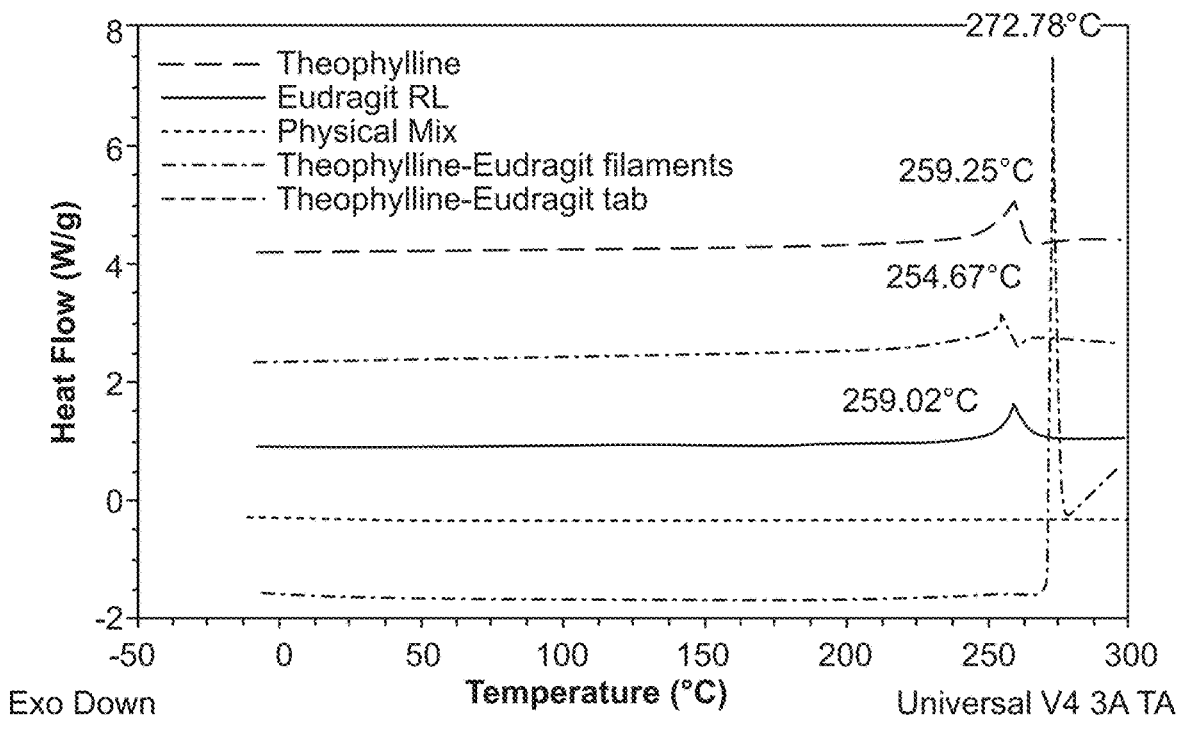
FIG. 60 shows a DSC scan of theophylline, physical mixture of theophylline and Eudragit®, extruded filaments, and printed tablets of theophylline and Eudragit® RL.

FIG. 60 shows a DSC scan of theophylline, physical mixture of theophylline and Eudragit®, extruded filaments, and printed tablets of theophylline and Eudragit® RL.

Powder X Ray Diffraction:

The diffraction pattern of tablets containing theophylline revealed diffraction peaks at 7 A°, 12 A°, 14 A° and 24 A° (Rasanen, E., et al., Novel identification of pseudopolymorphic changes of theophylline during wet granulation using near infrared spectroscopy. Journal of Pharmaceutical Sciences, 2001. 90 (3): p. 389-396) that match the diffraction pattern of theophylline. The same diffraction pattern appeared with the extruded filaments from the hot melt extrusion process and in the physical mixture as well as it can be noticed in FIG. 61. The reduced intensity of the peak suggest that more theophylline is dissolved in the Eudragit® RL polymeric matrix.

Figure 61:
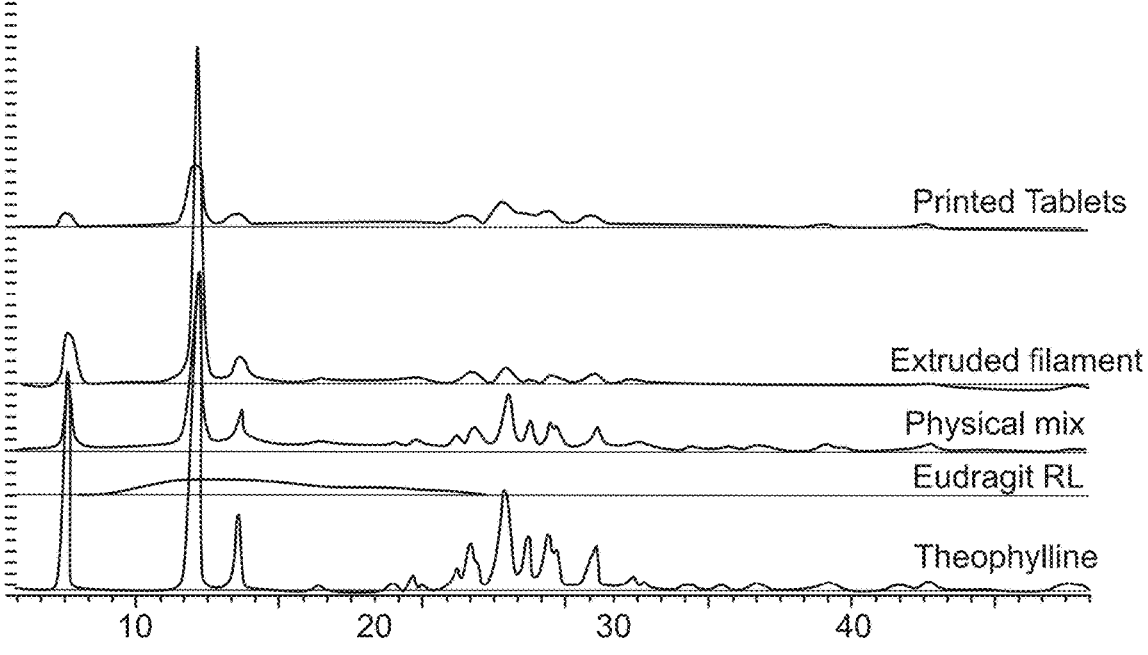
FIG. 61 shows an X-ray diffraction pattern of: pure theophylline, pure Eudragit® RL, physical mixture of both, extruded filaments, and printed tablets.

FIG. 61 shows an X-ray diffraction pattern of: pure theophylline, pure Eudragit® RL, physical mixture of both, extruded filaments, and printed tablets.

Printed Tablets of HPC SSL and Theophylline

TGA Analysis:

Thermal degradation profiles of tablets of HPC SSL containing theophylline revealed two steps degradation in addition to a weight loss of about 3% around 110° C. which is expected to be the due to evaporation of the moisture content of the polymer. The first thermal decomposition starts around 210° C. which is related to the thermal degradation of theophylline. This step causes a loss of about 60% of the total weight which match the formulation concentration of the drug in the extruded filaments or tablets.

The second step starts around 330° C. which is related to the thermal degradation of the polymer. This degradation is related to the thermal degradation of HPC SSL as it can be noticed in FIG. 62.

Figure 62:
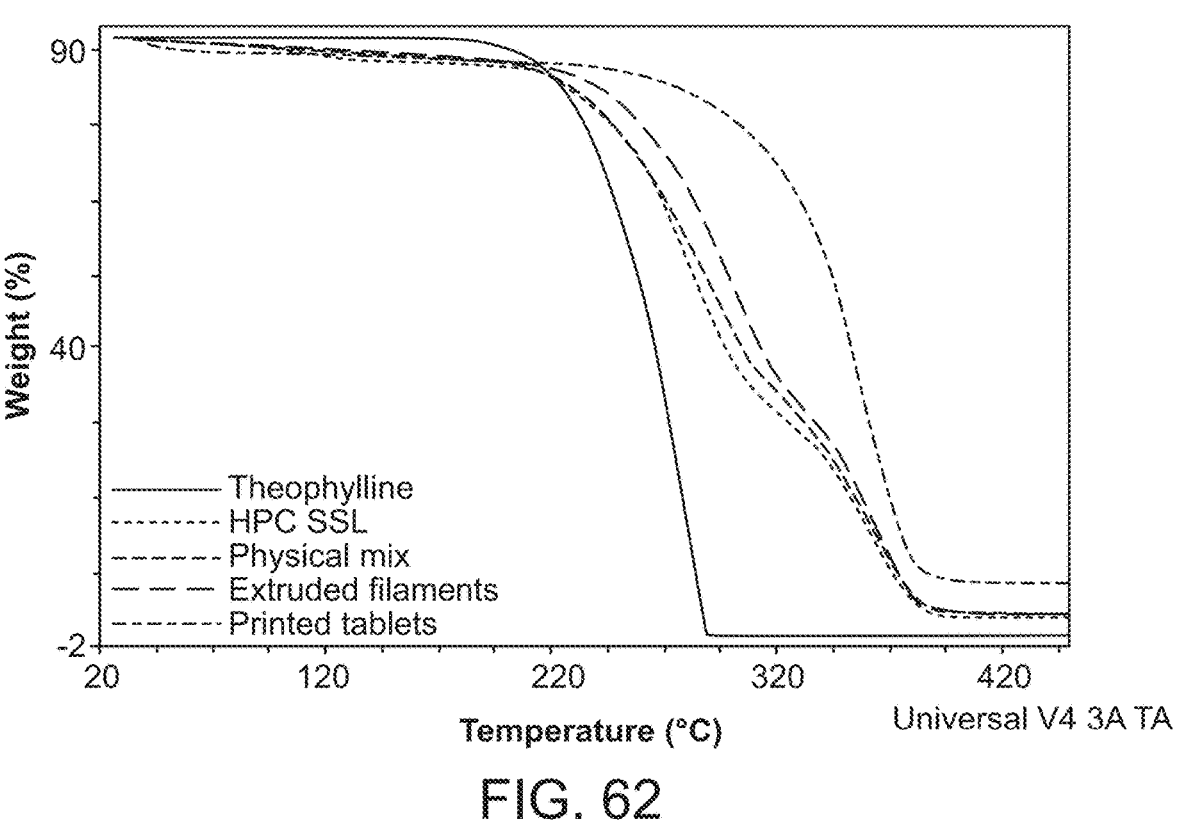
FIG. 62 shows the thermal degradation profiles of: pure theophylline, pure HPC SSL, physical mix, extruded filaments, and printed tablets.

FIG. 62 shows the thermal degradation profiles of: pure theophylline, pure HPC SSL, physical mix, extruded filaments, and printed tablets.

Figure 63:
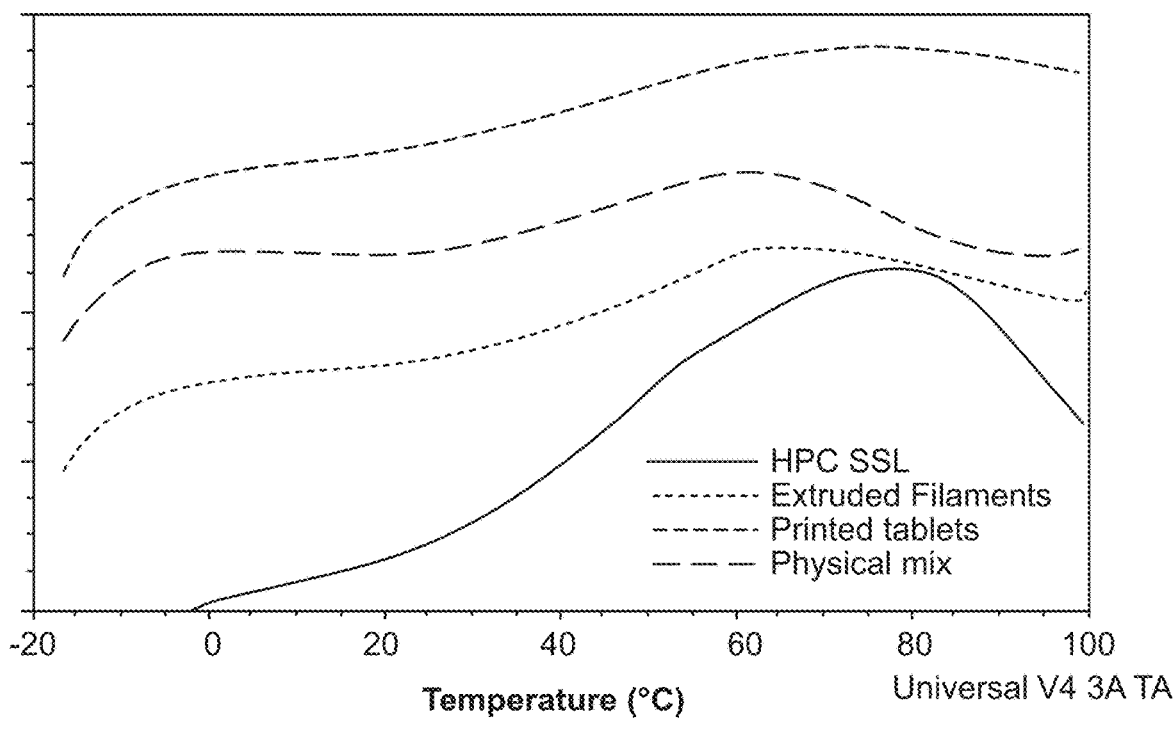
FIG. 63 shows a DSC scan showing the glass transition temperature of pure HPC SSL, physical mixture of theophylline and HPC SSL, extruded filaments, and printed tablet.

DSC Analysis:

The thermal profiles of SSL tablets revealed a slight change in the Tg of the polymer from 63° C. for the pure HPC SSL to 46° C. and 56° C. for the extruded filaments and the printed tablets respectively (FIG. 63).

FIG. 63 shows a DSC scan showing the glass transition temperature of pure HPC SSL, physical mixture of theophylline and HPC SSL, extruded filaments, and printed tablet.

The final heating run revealed the presence of an endothermic peak around 262° C. which is the endothermic melting of theophylline. The change in theophylline melting endotherm could be due to the impurity effect of HPC on theophylline. It can be noticed that there is a minimal difference between the melting endotherm of the extruded filaments and the printed tablets. However, the difference is negligible (FIG. 64).

Figures 64, 65:
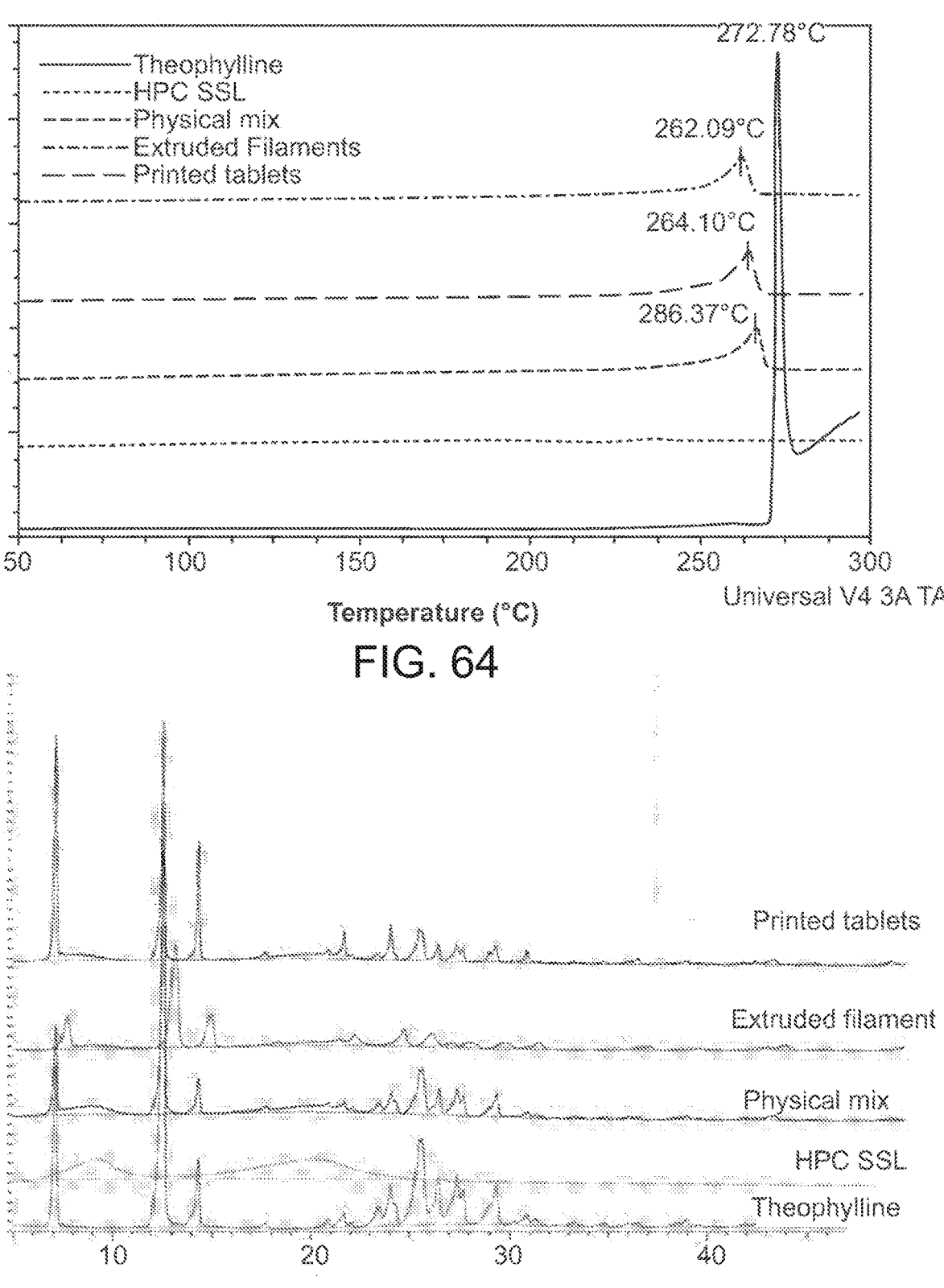
FIG. 64 shows a DSC scan showing the melting endotherm of pure theophylline, HPC SSL, physical mix, extruded filaments, and printed tablets.
FIG. 65 shows an X ray diffraction pattern of: pure theophylline, HPC SSL, physical mixture, extruded filaments, and printed tablets.

FIG. 64 shows a DSC scan showing the melting endotherm of pure theophylline, HPC SSL, physical mix, extruded filaments, and printed tablets.

The powder x-ray diffraction obtained from the printed tablets and the extruded filaments revealed the three distinguished peaks of theophylline at 7 A°, 12 A°, 14 A° and 24 A° (Rasanen, E., et al., *Novel identification of pseudopolymorphic changes of theophylline during wet granulation using near infrared spectroscopy*. Journal of Pharmaceutical Sciences, 2001. 90 (3): p. 389-396) (FIG. 65). Hence, it can be confirmed from both X-ray diffraction data and the DSC analysis that all or part of theophylline still exists as crystalline particles.

FIG. 65 shows an X ray diffraction pattern of: pure theophylline, HPC SSL, physical mixture, extruded filaments, and printed tablets.

4.5 Conclusions

The 3D printing process proved to be universal with respect to different methacrylic polymers such as Eudragit® RL, Eudragit® RS and Eudragit® E. It was also possible to print tablets using HPC SSL polymer. The use of our in-house pharmaceutical filament preserved the linear relationship between the mass and printed volume and was utilized to effectively control the dose (R 2=0.9995) and dose accuracy (91-95%). High resolution doubles the printing time but have little effect on release pattern and weight accuracy. Manipulating the infill percentage allowed the manipulating of dose (40+% range) and enabled the formation of hollow tablets. Thermal analysis indicated that a potential amount of theophylline remained in crystal form in the 3D printed tablet with possible reduction in the crystallinity percentage compared to non-printed filament.

Example 5—Disposable Filament Cartridges with Integrated or Associated Nozzle

This Example employs an alternative 3D printer which, instead of having its own integral nozzle (which may be prone to blockages under certain circumstances), is configured to receive and operate a disposable filament cartridge which has its own nozzle. In the present example, the nozzle is integral to the cartridge, though in other examples a nozzle may be releasably fixed (or releasably fixable) to the filament cartridge to allow the nozzle to be replaced (e.g. if it becomes blocked) without having to replace the entire cartridge.

Such nozzle-bearing filament cartridges may be used in circumstances where printer nozzle blockages would otherwise become a problem that is expensive and/or laborious to replace, fix, or clean (e.g. integral 3D printer nozzles can be expensive and difficult to replace and/or clean). Instead, a cheap disposable nozzle that is part of the cartridge may be preferentially sacrificed.

The 3D printer itself may either be purpose built for releasably receiving and operating the nozzle-bearing cartridges or else be a conventional 3D printer that has been judiciously adapted to releasable receive and operate such cartridges. Such adapted 3D printers may need to be modified in such a manner that the nozzle of the cartridge is substantially located in the same position as the now-replaced printer nozzle. The person skilled in the art can, in light of the present disclosure, readily adapt conventional 3D printers using routine workshop practice to achieve this end.

Figure 66:
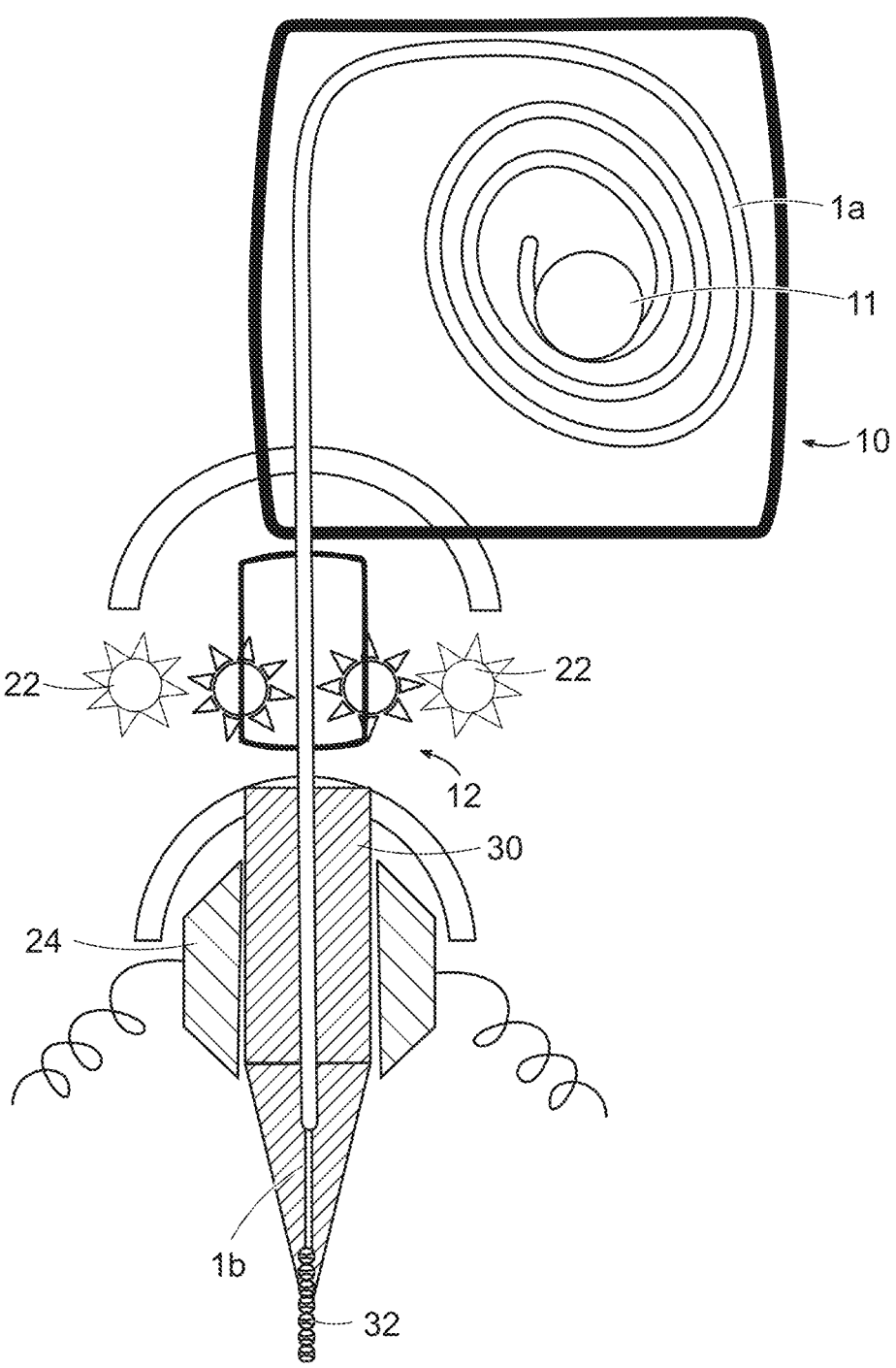
FIG. 66 shows a nozzle-bearing filament cartridge releasably affixed within a 3D printer.
Figure 67A:
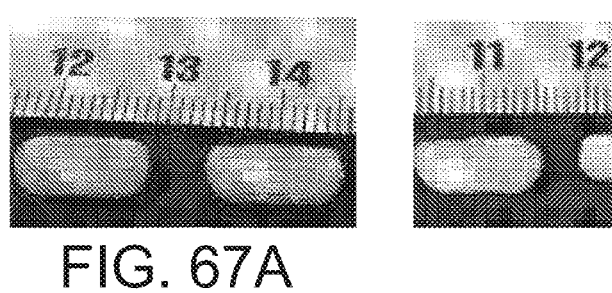
FIG. 67A, FIG. 67B, FIG. 67C and FIG. 67D show photographs of filaments formed with spray-dried lactose fillers.
Figure 67B:
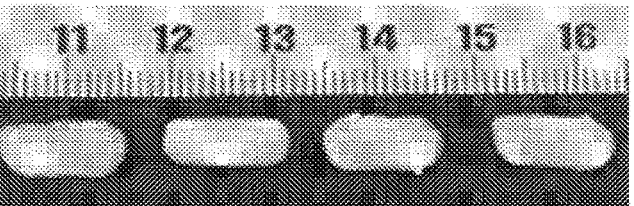
Figure 67C:
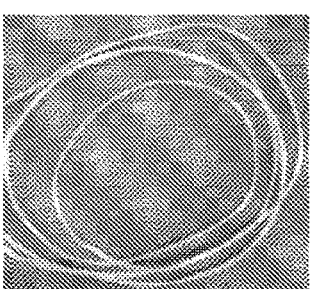
Figure 67D:
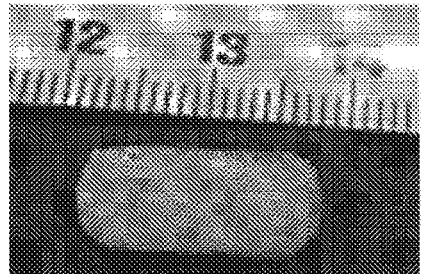
Figure 68A:
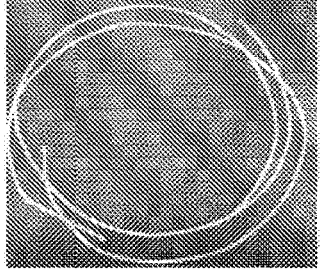
FIG. 68A, FIG. 68B, FIG. 68C and FIG. 68D show photographs of filaments formed with compressible lactose fillers.
Figure 68B:
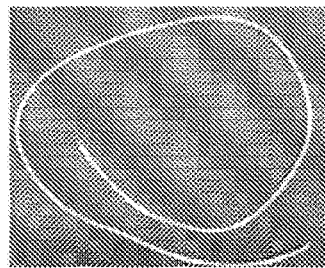
Figure 68C:
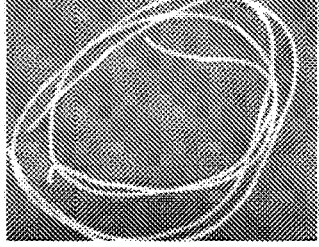
Figure 68D:
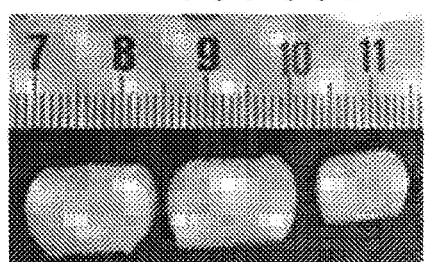

FIG. 66 shows a nozzle-bearing filament cartridge releasably affixed within a 3D printer.

The nozzle-bearing filament cartridge contains within its body (which may be fabricated from standard plastics material and/or suitable metallic or alloy materials) a pharmaceutical filament 1*a* coiled around a rotatable spool 11. In the present example, the cartridge also has a humidity-controlled, sealed case 10 through which the pharmaceutical filament 1*a* may be conveyed from its spool. The case 10 itself encloses a conveyor mechanism 12 (which in this example includes built-in-gears within the cartridge to allow driving the filament to the nozzle without exposing the filament to the external environment) which can be externally engaged and operated (e.g. via appropriate mechanical contact and gearing), for instance, via a mechanical drive/gear mechanism 22 associated the printer itself, to drive the pharmaceutical filament 1*a* through the case towards and through a nozzle 30 without the filament being exposed to an external environment or making contact with internal components within the printer itself. The nozzle 30 itself is made of a thermo-conductive material, such as steel. In this manner, a heating mechanism 24 within the 3D printer may heat the nozzle (including the filament contained therein) to enable facile extrusion of the pharmaceutical filament 1*a* through and from the nozzle 30. Whilst the nozzle 30 is not being used, it may be protected with a plug 32 which can be inserted into the end of the nozzle 30 in order to seal and lubricate the nozzle head.

The conveyor mechanism 12, which drives the filament to the nozzle, is suitably configured and/or positioned to allow the mechanical drive/gear mechanism 22 to engage and (efficiently and consistently) operate the conveyor mechanism 12. In this particular example, the gears 22 of the 3D printer surround and engage with the gears of the conveyor mechanism 12.

The nozzle 30 of the cartridge is suitably configured and/or positioned to allow the heating mechanism 24 within the 3D printer to (efficiently and consistently) heat the nozzle 30 to a predesignated temperature.

In use, the relevant cartridge is installed within the 3D printer (suitably within a predesignated docking position/station that configures the cartridge relative to printer components to enable all relevant components to be appropriately mutually engaged) and the 3D printer is operated so as to heat the nozzle 30 via the printer's own heating mechanism 24 and, once the nozzle is at the correct temperature (suitably verifiable with appropriate sensor/detection features as described hereinbefore) the 3D printer may be operated pursuant to a pre-programmed or manually operated printing cycle. Under operation, the mechanical drive/gear mechanism 22 of the printer is operated to engageably drive the conveyor mechanism 12 within the cartridge, which in turn conveys the filament 1a form its spool, via the conveyor mechanism 12, to the nozzle 30. When the nozzle is at the appropriate temperature the filament will transform into a printable form (e.g. through softening and/or melting) before being "printed". The filament is conveyed and "printed" through the nozzle 30 until 3D printing is complete. After printing, the cartridge may be either left in place for a future round of printing (suitably with the plug 32 inserted into the nozzle 30 to seal and lubricate the nozzle head) or otherwise removed and optionally either stored or disposed of. A new cartridge (optionally containing a filament comprising a new drug substance or new pharmaceutical formulation) may be inserted and another print cycle be performed using the new cartridge/filament. The 3D printer may optionally have capacity (e.g. docking stations) for multiple cartridges to enable individual cartridges to be selected for use.

Such a disposable nozzle arrangement alleviates blockages during the printing process whilst also alleviating cross-contamination (within the nozzle) that may otherwise arise where an integral 3D printer nozzle is used to extrude different pharmaceutical filaments (which may contain different drug substances).

Additionally, the cartridge can be adapted to preserve the quality of the filament contained therein during the shelf-life of the cartridge. The humidity-controlled case 10, which is ideally a sealed case, suitably secures the stability of the filament and prevents the uptake of moisture which may otherwise affect the quality of the printed tablets.

The cartridge may also allow for a consistent flow of the filament to ensure highly accurate dosing of the 3D tablets being produced.

Such a cartridge may also be easily installed within a 3D printer, especially a 3D printer which is specifically adapted to receive such cartridges.

Such a cartridge configuration may also enable increased control over the number of printed tablets, for instance, by suitably tailoring the length of the filament contained therein.

The independent cartridge arrangement, especially those with an integrated conveyor mechanism, can help prevent or at least alleviate cross-contamination problems, which may otherwise be inevitable where non-disposable components of the 3D printer come into contact with two or more different filaments (e.g. containing different drug substances). Moreover, such cartridges can relieve a 3D printer (or certain components thereof) of certain mechanical burdens which would otherwise inevitably lead to wear and tear of the 3D printer components, that may in turn cause operational inconsistencies which could lead to batch variations in the printed tablets. For instance, where the entire conveyance mechanism is incorporated within the 3D printer itself (including all gearing), the gears may be vulnerable to wear and tear which can lead to inconsistent gripping of the filament, which may lead to inconsistent filament flows during printing. This will compromise dosing accuracy. The aforementioned cartridges address this by rendering some of the vulnerable components disposable and therefore replaceable for each new filament run.

Example 6—Model Studies for Immediate Release Formulations

For immediate release tablets that contains a limited concentration of potent drug (typical dose of 0.01-40 mg), it is necessary to include a solid diluent to reach a minimal mass that the patient can handle easily (Traditionally a minimal of 150 mg in most commercially available tablets). Our previous results suggest that printing of immediate release tablets is more consistent when using one or more non-melting components in conjunction with Eudragit® E100 and a plasticizer.

The following analytical tests and techniques were used during the course of these model studies:

Determination of Drug Loading in 3D Tablets

To ensure drug contents in 3D printed tablets, the accurately weighed tablets were sonicated in 1000 ml volumetric flask for 2 hours in 950 ml of 0.1M HCl. The flasks were kept afterwards at room temperature. The volume after cooling was increased by adding 0.1 M HCl to 1000 ml. Drug content in each tablet was then determined by using spectrophotometry (Jenway, Japan) at specific absorbance Amax of 230, 232, 272, 278, 204 for Aspirin, 5-ASA, theophylline, hydrochlorothiazide and captopril respectively. The solution was diluted further as suitable, with 0.1 M HCl.

Differential Scanning Calorimetry (DSC)

A differential scanning calorimeter DSC Q2000 (TA Instruments, Elstree, Hertfordshire, UK) was utilized to carry out thermal analysis. Samples were accurately weighed to around 5 mg and placed in a 40 μL TA standard aluminum pan for DSC analysis. The analysis was carried out under Nitrogen environment. To get a more accurate $T_g$, samples were cooled to −50° C. The heating and cooling of samples were performed at 10° C./min. The heat scan was performed from −50° C. to 280° C. for all of samples other than theophylline. The data was then analysed using a TA 2000 analysis software. All the measurements were carried out in triplicates.

ThermoGravimetric Analysis (TGA)

TGA of the raw materials as well as extruded filaments was measured using METTLER TGA/sDTA851e ThermoGravimetric Analyzer. Samples of approximately 10 mg were added to an aluminium pan and were heated from 25° C. to 500° C. at a heating rate of 10° C./min. The data retrieved after experiment was analysed using Microsoft Excel.

Scanning Electron Microscopy

The surface morphology of the printed tablets was assessed after coating with gold by placing on metallic stubs under vacuum for two minutes in JFC-1200 Fine Coater (Jeol, Tokyo, Japan). The coated tablets were then placed in Quanta-200 SEM microscope at 20 KV for imaging.

In Vitro Drug Release Study Dissolution Test:

The tablets for immediate releasing drugs were studied by using ERWIKA® manual dissolution apparatus. The time of experiment was set to one hour at 50 rpm paddle speed. The temperature was kept constant at 37±5° C. The samples were taken out manually after every 5, 10, 15, 20, 25, 30, 40, 50 and 60 minutes. The drug release was studied by measuring absorbance using spectrophotometry (Jenway, Japan) at specific absorbance λmax of 230, 232, 272, 278, 204 for aspirin, 5 ASA, theophylline, hydrochlorothiazide and captopril respectively. The samples were diluted as required. Experiments for each drug were carried out in triplicates.

81

Disintegration Tests

The disintegration test was performed to determine whether tablets disintegrate in a prescribed period of time. The examination was conducted in accordance with British Pharmacopeia. Disintegration test for tablets was carried out in a basket rack assembly having 6 cylinders inside. A volume of 750 ml 0.1 M HCl was taken in each cylinder. The time and temperature were set to 37 t and 15 minutes respectively. The tablets prior to test were weighed accurately. The exact time was noted for the tablets at which they were disintegrated. Disintegration test for drugs was carried out with six tablets each.

Hardness Tests

The hardness of 6 tablets with each drug and blank was tested with Erwika hardness tester in Newton (N).

Friability

Friability of 20 tablets was tested. The tablets were weighed accurately before and after the test and percentage of weight loss was calculated.

6.1—Developing Standard Filler-Containing Formulations 6.1A—Formulations with Spray-Dried Lactose In this formulation, widely used diluent (spray-dried lactose) was included in the filament at different ratios, as shown in Table 10:

TABLE 10

| Filament formulations (wt % ingredients) with spray dried lactose filler | | | | |
|---|---|---|---|---|
| Lactose (spray dried) | Eudragit ® EPO | Tec | Comments | FIG. |
| 50% | 47.5% | 2.5% | Dark coloured, (1.5 mm) | 67A |

82

TABLE 10-continued

| Filament formulations (wt % ingredients) with spray dried lactose filler | | | | |
|---|---|---|---|---|
| Lactose (spray dried) | Eudragit ® EPO | Tec | Comments | FIG. |
| 50% | 45% | 5% | Dark coloured (1.5 mm) | 67B |
| 65% | 30% | 5% | Too flexible, dark and rough (1.5 mm) | 67C |
| 65% | 31.5% | 3.5% | Not sticking to plate (less darker than last one because of decreasing tec. ratio) (1.5 mm) | 67D |

As per the comments and referenced figures of Table 10, dark and rough filaments were produced by HME, with colour intensity increasing after 3d printing. This is likely to be a consequence of the interaction between plasticizer, polymer, and the sugar. The increasing brown colour suggests possible degradation (e.g. caramelization) of lactose under elevated temperature.

6.18—Formulations with Directly-Compressible Lactose (Includes Binder)

Filaments were also formulated with directly compressible lactose (Ludipress™), where the lactose has larger particles by virtue of an incorporated binder (96.5% lactose monohydrate and 3.5% povidone). Such lactose (with binder) was incorporated at different ratios, as described in Table 11 below:

TABLE 11

| Filament formulations (wt % ingredients) with compressible lactose filler | | | | |
|---|---|---|---|---|
| Lactose (directly compressible) | Eudragit ® EPO | Tec | Comments | FIG. |
| 65% | 31.5% | 3.5% | White, but couldn't stick to itself (1.5 mm) | 68A |
| 40% | 54% | 6% | White, thick, flexible, couldn't print because it blocks nozzle while trying. Although it comes out in the beginning well. (1.5 mm) | 68B |
| 55% | 40.5% | 4.5% | Not sticking to itself and neither coming out of printer. Was thick with 1.5 mm and a bit flexible but not much. | 68C |
| 75% | 22.5% | 2.5% | Quite brittle, not flexible at all, thick with 1.5, | 68D |

As per the comments and referenced figures of Table 11, inclusion of larger sized lactose particles precipitated a lighter coloured filament but no significant improvement in the filament printing colours.

6.1C—Formulations with Calcium Tribasic Phosphate

Calcium tribasic phosphate is widely used as a water-insoluble diluent in tablets. In view of previous studies around the present invention, the high melting point (1391° C.) of calcium tribasic phosphate was thought to be a good candidate as a filler which may yield more filaments than corresponding lactose-based filaments (given lactose has an mp of about 202° C.). Calcium tribasic phosphate will not melt under the prevailing 3D printing conditions. As shown in Table 12 below, various ratios of melting ingredients: non-melting ingredients were tested. However, the ratio between TEC and Eudragit® E was kept the same in most examples.

TABLE 12

Filament formulations (wt % ingredients) with calcium tribasic phosphate

| Tri. Ca. Phosphate | Eudragit ® EPO | TEC | Comments | FIG. |
|---|---|---|---|---|
| 50% | 47% | 3% | Printed tablets were a bit darker and sticky to the plate, made good tablets. (1 mm) | 69A |
| 65% | 31.5% | 3.5% | Filament is too thin with 1 mm. | |
| 35% | 60.8% | 4.2% | 1.25 mm nozzle orifice | 69B |
| 40% | 56.1% | 3.9% | 1.25 mm nozzle orifice | 69C |
| 45% | 51.43% | 3.6% | 1.25 mm nozzle orifice | 69D |
| 55$ | 42.08 | 2.93 | 1.25 mm nozzle orifice | |
| 60% | 37.4% | 2.6% | 1.5 | Too thick to be fed in the extruder as its diameter was more than the size of the nozzle. |

Incorporation of calcium tribasic phosphate allowed the preparation of easy-to-print and consistent filament. Filaments having a concentration of calcium tribasic phosphate from 35% to 55% appeared to be compatible with the 3d printing process. However, increasing calcium tribasic phosphate concentrations to 60% and beyond led to thick and brittle filaments that are less practical in 3D printing, especially with spool feeding.

As illustrated in FIG. 70, thermal analysis of these filaments indicates that all of the filaments of Table 12 appear to have a $T_g$ in the range of 31-33° C.

6.1.1—Studies of Dissolution Rates of Tablets

Dissolution patterns of the aforementioned drug free tablets (based on formulations 6.1A, 6.1B, and 6.1C) were observed using USP II dissolution apparatus with 750 ml HCl and at rotation speed of 50 rpm. Dissolution times were recorded based on when complete drug dissolution was visually observed. Increasing Ca Tri Phosphate percentages led to a reduction in the dissolution time, albeit with dissolution times still exceeding that required by law for an "immediate release tablet". (More than 85% of drug dissolution is required to take place in 30 min according to British and US Pharmacopeia). Tables 13 and 14 respectively show the dissolution and disintegration rates for model 3D-printed solid form formulations containing various concentrations of calcium tribasic phosphate (CAP). The % CAP was varied relative to the other Eudragit® E PO/TEC components, where the ratio of Eudragit® E PO/TEC was kept constant.

TABLE 13

Dissolution rates for various formulations

| No. | % CAP | Weight | Time |
|---|---|---|---|
| 1 | 35% | 1: 176.26 mg | 52:28 min |
| | | 2: 220.04 mg | 1:02:51 |
| | | 3: 203.74 mg | 57:55 |
| 2 | 40% | 1: 272.5 mg | 58.5 min |
| | | 2: 238.5 mg | 59.53 min |

TABLE 13-continued

Dissolution rates for various formulations

| No. | % CAP | Weight | Time |
|---|---|---|---|
| | | 3: 249.57 mg | 1:00:02 |
| 3 | 45% | 1: 224.48 mg | 56.20 min |
| | | 2: 236.62 mg | 58:23 min |
| | | 3: 185.16 mg | 1:02:00 |
| 4 | 50% | 1: 260.56 mg | 59.53 min |
| | | 2: 224.56 mg | 52.42 min |
| | | 3: 212.18 mg | 47.03 in |

6.1.2—Studies of Disintegration Rates of Tablets

TABLE 14

Disintegration rates for various formulations

| No. | % CAP | Weight | Time |
|---|---|---|---|
| 1 | 35% | 1: 216.08 mg | 21.50 min |
| | | 2: 214.12 mg | 19.29 min |
| | | 3: 220.76 mg | 21.00 min |
| 2 | 40% | 1: 199.44 mg | 18:33 min |
| | | 2: 276.51 mg | 22:51 min |
| | | 3: 250.50 mg | 21:11 min |
| 3 | 45% | 1: 216.95 mg | 19.44 min |
| | | 2: 244.38 mg | 21:23 min |
| | | 3: 249.74 mg | 19:54 min |
| 4 | 50% | 1: 255.68 mg | 18:07 min |
| | | 2: 230.62 mg | 16:51 min |
| | | 3: 221.30 mg | 13:42 min |
| 5 | 65% | | 3.05 min |
| | | | 4:42 min |
| | | | 5:27 min |
| | | | 5:12 min |

Increasing calcium tribasic phosphate percentage led to a faster disintegration of tablets. However, the structure of both tablets and filaments became more brittle with increasing calcium tribasic phosphate.

6.1.3—Studies into Plasticizer Concentrations

The effects of plasticizer (in this study TEC was used) concentrations were examined at plasticizer concentrations between 2.5 and 5 wt %, whilst keeping the concentration of the non-melting (filler) component the same at 50 wt %.

TABLE 15

| | | | | Observations of the effect of plasticizer concentration | |
| --- | --- | --- | --- | --- | --- |
| Date | Tri. Ca. Phosphate | Eudragit ® EPO | Tec | Comments | FIG. |
| 5th Mar 15 | 50% | 45% | 5% | Flexible, unable to feed in printer, thicker with 1.5 mm). (1 mm) | 71A |
| 5th Mar 15 | 50% | 47.5% | 2.5% | Was good, making tablets at even 110 C., (unable to reproduce the same characteristics) (1 mm) | 71B |
| 6th Mar | 50% | 47.5% | 2.5% | Was brittle, couldn't print a single tablet. | 71C |

TABLE 15-continued

| | | | | Observations of the effect of plasticizer concentration | |
| --- | --- | --- | --- | --- | --- |
| Date | Tri. Ca. Phosphate | Eudragit ® EPO | Tec | Comments | FIG. |
| 9th Mar 15 | 50% | 46.75% | 3.25% | (1 mm) Was good, acceptably flexible, could make good tablets and brighter at lower temperature. (1 mm) | 71D |
| 9th Mar 15 | 50% | 47% | 3% | Printed tablets were a bit darker and sticky to the plate, made good tablets. (1 mm) | 71E |

FIG. 72 shows a DSC Thermograph of filaments with various concentrations of TEC.

The ratio Eudragit® E:TEC 46.75:3.25 appeared to have the most suitable filament for 3D printing. Thermal analysis indicated that the optimal $T_g$ of 34° C. of the filament for 3D printing.

6.2—Developing Filler-Containing Formulations with Lubricant

To study filament flow in the nozzle of the 3d printer, talc was included as an additional component or as a replacement for the calcium tribasic phosphate.

TABLE 16

| | | | | Observations of the effect of plasticizer concentration | |
| --- | --- | --- | --- | --- | --- |
| Tri. Ca. Phosphate | Tec | Eudragit ® EPO | Talc | Comment | FIG. |
| 0% | 3.25% | 46.75% | 50% | Was easy to make tablets, filament was quite thick and brittle but was making good tablets, though dark in colour (1 mm). | 73A |
| 45% | 3.25% | 46.75% | 5% | Filament was good and flexible a bit. (1 mm). | 73B |
| 40% | 3.25% | 46.75% | 10% | Filament was a bit flexible. (1 mm) | 73C |

Viable filaments and printed tablets were achievable when using either talc without calcium tribasic phosphate or talc with calcium tribasic phosphate. However, addition of talc resulted in darker coloured filaments and tablets.

FIG. 74 shows a TGA graph of different filler combinations used with Eudragit® E.

FIG. 75 shows DSC thermographs of different fillers combinations used with Eudragit® E. Thermal analysis indicated that both lactose and MCC tend to start to degrade post 140° C., whereas both talc and calcium tribasic phosphate remained stable above 240° C.

6.3—Developing Filler-Containing Formulations with Disintegrants

The use of FDM and HME processes for production of tablets usually requires the incorporation of a thermoplastic polymer e.g. Eudragit® E. Despite the high solubility of this polymer in gastric medium, the overall dissolution rate of the 3D printed tablets tend to be slower than conventional tablets.

Clearly the size of the tablet will, at least to some extent, dictate the dissolution rate. Including a disintegrant (filler which expand upon introduction of aqueous media) is a common technique in traditional tablet formulation to accelerate dissolution rates. In this work, a various disintegrants were tested, for example: Ac Di Sol, Primojel and Primellose.

TABLE 17

| | | | | Observations of the effect of additional disintegrants | |
|---|---|---|---|---|---|
| Tri. Ca. Phosphate | TEC | Eudragit® EPO® | Ac Di Sol | Comment | FIG. |
| 40% | 3.25% | 46.75% | 10% | Was less sticky and rough to plate. (1 mm) | 76A |
| 47.5% | 3.25% | 46.75% | 2.5% | Good filament, not very flexible and neither was brittle. (1 mm) | 76B |
| Tri. Ca. Phosphate | TEC | Eudragit® EPO | Primojel | Comments | |
| 47.5% | 3.25% | 46.75% | 2.5% | Bright filaments and tablets, was not blocking nozzle more often. (1 mm) | 76C |
| Tri. Ca. Phosphate | TEC | Eudragit® EPO | Primellose | Comments | |
| 47.5% | 3.25% | 46.75% | 2.5% | Good filament, but couldn't print even a single tablet. (1 mm) | 76D and 76E |
| Tri. Ca. Phosphate | TEC | Eudragit® EPO | Polyplasdone | Comments | |
| 31% | 3.25% | 46.75% | 4% | Good filament prints excellent tablets | No significant different on tablet dissolution |
| 35% | 3.25% | 42.75% | 4% | Good filament prints excellent tablets | No significant different on tablet dissolution |
| 27.5% | 3.25% | 46.75% | 10% | Good filament prints excellent tablets | No significant different on tablet dissolution |

Figure 77:
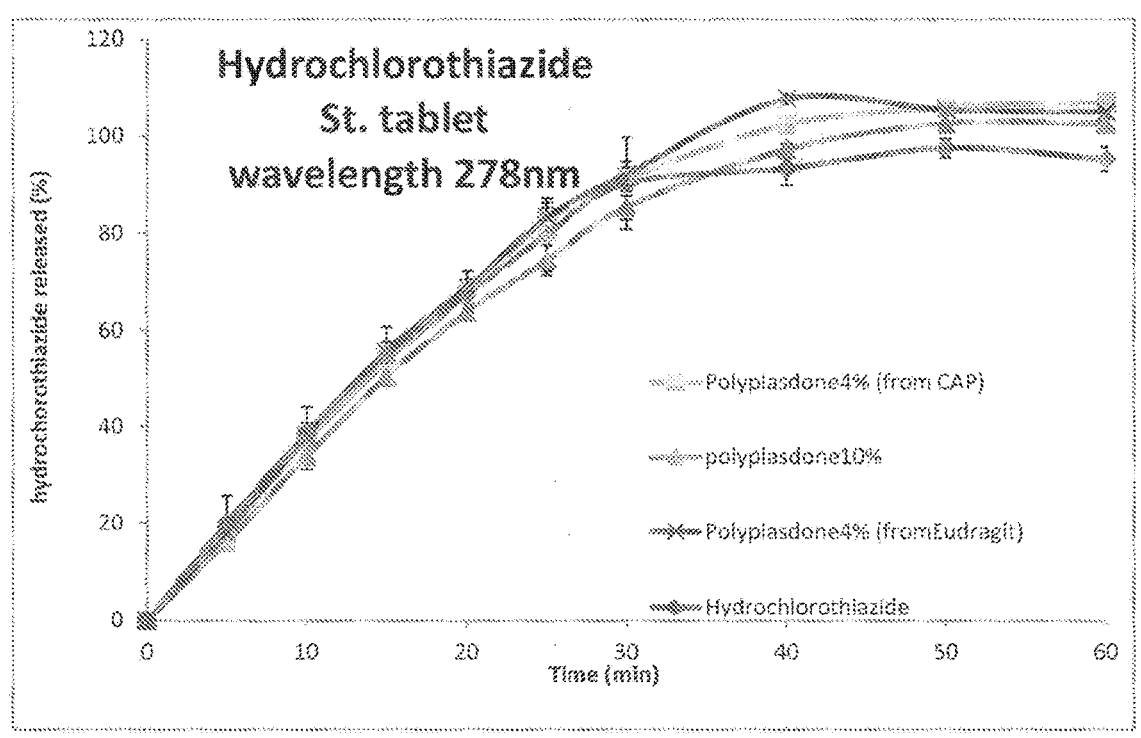
FIG. 77 shows a graph illustrating drug release profiles for tablets containing various amounts of polyplasdone.

FIG. 77 shows a graph illustrating drug release profiles for tablets containing various amounts of polyplasdone (as per Table 17 above). These model studies utilized hydrochloro-thiazide as a test drug.

TABLE 18

Disintegration times for various tablet
formulations with and without disintegrants

| No. | Ratio/ingredients | Time taken for disintegration |
|---|---|---|
| 1 | Cap:EPO:TEC (50:46.75:3.25) Control | 10:10 min |
| 2 | Cap:EPO:TEC (50:47.5:2.5) | 7:45 min |
| 3 | Cap:Pjel:EPO:TEC (47.5:2.5:46.75:3.25) | 9.40 min |
| 4 | Cap:Ac.disol:EPO:TEC (47.5:2.5:46.75:3.25) | 15:18 min |
| 5 | Cap:Ac.disol:EPO:TEC (30:10:46.75:3.25) | 16:10 min |

TABLE 19

Disintegration times for different filaments
with an without disintegrants

| No. | Cap:epo:tec (50:46.75:3.25) Filaments | Cap:epo:tec (65:46.75:3.25) |
|---|---|---|
| 1 | 6:22 min | 5:34 min |
| 2 | 6:59 min | 5.53 min |

6.4—Developing Drug-Loaded Filaments

Calcium tribasic phosphate was chosen as a non-melting filler along with Eudragit® E and TEC in the following drug-loaded filaments. In these particular studies, the amount of drug incorporated within the formulation directly replaced said amount of calcium tribasic phosphate to produce compositions corresponding with those in Table 20 below:

TABLE 20

General drug-containing filament formulations

| Drug | Ca. Tri. Phosphate | EPO | TEC | Diameter |
|---|---|---|---|---|
| X % | (50-X) % | 46.75% | 3.25% | 1.25 mm (initially) |

It was expected that the addition of the drug might lead to a change in the glass transition temperature of the mixture/filament. However, the present invention enables optimization of the Tg of a drug-loaded filament by adapting the plasticizer (e.g. TEC) concentration to compensate.

6.4.1—Production of Drug-Loaded Filaments Via Hot-Melt Extrusion (HME)

For Eudragit® EPO, the operating temperature in HME remained between 95° to 115° C. (105° in most cases). For printing however the temperature that worked well was between 135°-145° C. (other than lactose preparations which were more than 165° C.).

In order to optimize the feasibility of printing dosage forms, blank filaments (without drugs) were first prepared using Thermo Scientific HAAKE MiniCTW (Karlsruhe, Germany).

A specific ratio of polymer, plasticizer and filler were weighed accurately. They were fed into hot melt extrusion in a counter flow twin-screw extruders at 90 rpm for melting, mixing and then extrusion. The temperature for melting and mixing was kept constant and the temperature for extrusion was 10° C. less than feeding. The components were allowed to mix while feeding to ensure the uniform distribution of drug and other components uniformly. The temperature was decreased to start extrusion through a die nozzle with cylindrical shape having a diameter of 1.25 mm (varies according to formulation) at torque control of 0.8 Nm.

The extruded filaments were then placed in sealed plastic bags to be used in 3D printer. Once the working ratio was optimized, the drug was incorporated in the filament by using same HAAKE hot melt extruder.

6.5—Printing of Drug-Loaded Tablets 6.5.1—Tablet Design

Blank and drug loaded tablets were designed in typical capsule shape using the techniques described in Section 3.2 above. A series of tablets containing hydrochlorothiazide with increasing volumes were printed by modifying the dimensions of the design: Length×width×heights (L, W, H) without altering the ratios between these dimensions (W=0.3636 L, H=0.396 L). In drug loaded examples all tablets were 12 mm in length.

6.6—Incorporation of Model Drugs into Standard Formulations

In order to verify the suitability of this model for different drug candidates, five different drug molecules were incorporated into the tested formulations at a concentration of 12.5% w/w. the drugs were considered as non-melting components and were thus included within the formulation by directly replacing a portion of the calcium tribasic phosphate to yield formulations as per Table 21 below:

TABLE 21

General composition of drug-loaded formulations to be tested

| Drug | Ca. Tri. Phosphate | EPO | TEC | Diameter |
|---|---|---|---|---|
| Model drug 12.5% | 37.5 | 46.75 | 3.25 | 1.25 |

For Eudragit® EPO, the operating temperature in HME remained between 95° C. to 115° C. (105° in most cases). For printing however the temperature that worked well was between 135° C.-145° C. (other than lactose preparations which was more than 165 t).

Figure 78:
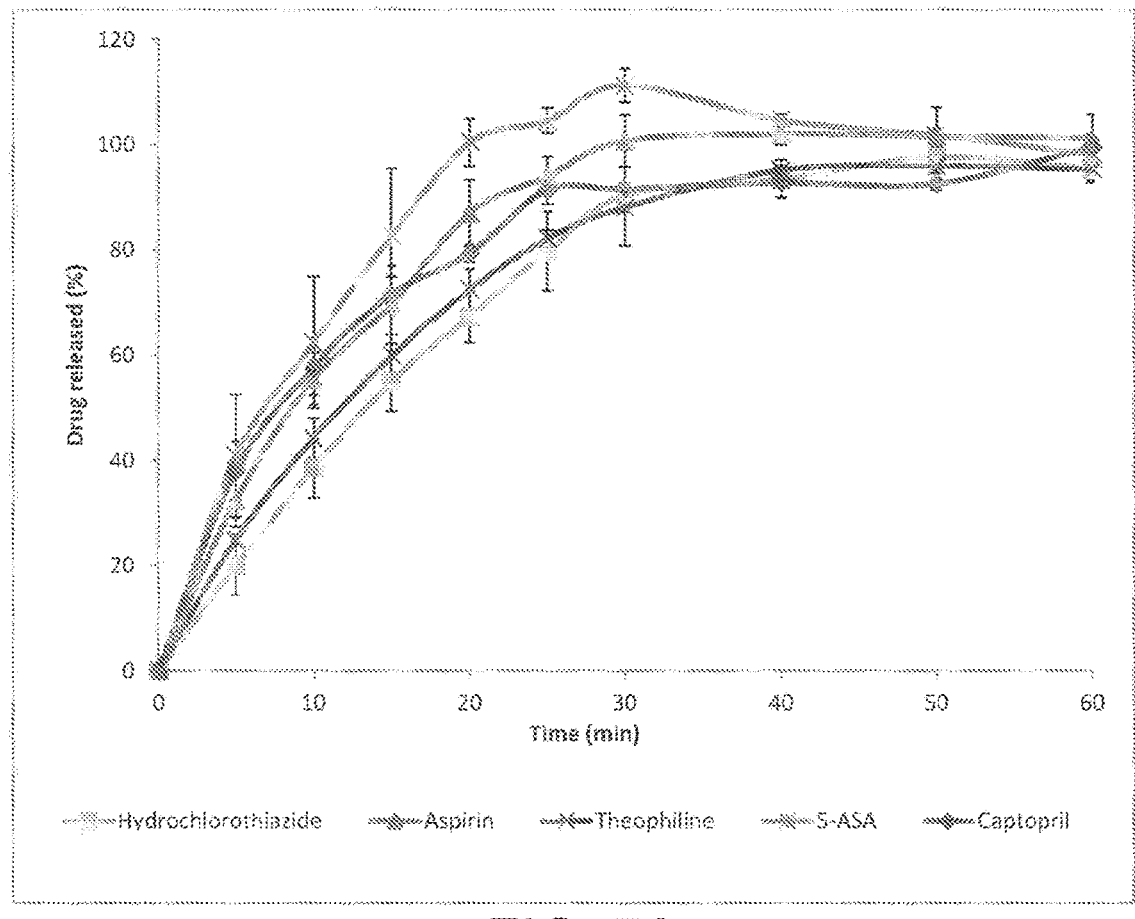
FIG. 78 is a graph showing in vitro drug release profiles for drug formulations of Table 21.

The standard ratio for the drug to incorporate into the filament was chosen to be 12.5:37.5 (drug:Cap). Different drugs were tested with the filament for printing, e.g. Aspirin, SASA, Captopril, Theophylline and hydrochlorothiazide. Once the tablets were printed with each drug, those were then subjected to different pharmacopeial tests to ensure if they meet all standards of pharmaceutical products. FIG. 78 shows relevant in vitro drug release profiles for each drug formulation of Table 21.

Table 22 shows further data for each of the relevant drug formulations, including average values (Av) and standard deviations (SD).

TABLE 22

Disintegration times, crushing strengths, weight uniformity and
friability of each of the drug loaded tablets being tested

| | Disintegration time | | Crushing strength (N) | | Weight (mg) | | | Fria- bility |
|---|---|---|---|---|---|---|---|---|
| Drug | Av | SD | Av | SD | Av | SD | SD % | (%) |
| Theophylline | 9.2 | 0.2 | 143.4 | 29.7 | 194.8 | 10.8 | 5.6 | 0 |
| Hydrochlorothiazide | 10.3 | 0.6 | 140.3 | 19.8 | 193.9 | 12.3 | 6.3 | 0 |
| Aspirin | 10.3 | 0.9 | 46.1 | 80.4 | 213.7 | 17.8 | 7.6 | 0.65% |
| 5-ASA | 11.4 | 2.8 | 347.3 | 321.3 | 203.6 | 16.9 | 8.3 | 0 |
| Captopril | 11.6 | 2.9 | | | 206.6 | 25.8 | 12.5 | 0 |

Table 23 details the drug content (by way of % drug contents) by way of average and standard deviation values. The results here indicate that the expected dose from the tablet weight was close to detected amount of drug by UV absorbance. This is a good indication that no major drug losses were suffered during HME and the FDM printing process.

TABLE 23

Drug content for each relevant drug formulation

| Drug | Encapsulation efficiency (%) | |
| --- | --- | --- |
| | Av | SD |
| Theophylline | 99.04 | 3.94 |
| Hydrochlorothiazide | 94.79 | 0.78 |
| Aspirin | 98.47 | 2.58 |
| 5-ASA | 103.30 | 1.46 |
| Captopril | | |

The standard formulation, developed following the afore-described model studies, works well with all 5 drug compounds hereby tested, despite the variation in physiological properties of each drug. Dissolution rates, disintegration rates, and friabilities fulfilled the standard pharmacopeial criteria, whilst drug contents were in the range of 0.78-4% of the expected dose based on weight, which is a reasonable error margin.

Example 7—Further Model Studies into Alternative Active Ingredient Carriers (PVP and PEG)

7.1—Model Studies Using PVP K29-32 (Crospovidone) in FDM 3D Printing

PVP (K 29-32, MW 40000-58000 also known as crospovidone) is widely used in pharmaceutical industry as a disintegrant, dissolution agent and solubility enhancer for poorly soluble drugs. Such polymers have also been shown to prevent or inhibit precipitation of poorly soluble drugs in relevant dissolution media. The following model studies assess the viability of incorporating such polymers as active ingredient carriers, and such like, in the 3D printing methods of the invention.

7.1.1—Screening of Various PVP-Based Filament Formulations

Table 24 gives details of a formulation screen upon a particular formulation model which incorporated theophylline as a model poorly-soluble drug. This formulation screen elucidated a greater understanding of the factors and parameters involved in the 3D printing of filaments containing PVP polymers.

TABLE 24

Formulation screen and observations for PVP-based systems

| Formulation composition and processing temperature | Compatibility with printing |
| --- | --- |
| Mixture:<br>PVP:Tec:Theophylline (Theo)<br>50%:25%:25%<br>Processing temperature:<br>Feeding = 100° C.<br>Extrusion = 90° C. | Printing was not possible |

TABLE 24-continued

Formulation screen and observations for PVP-based systems

| Formulation composition and processing temperature | Compatibility with printing |
| --- | --- |
| Extruded filament was too flexible, will load be able to load into the 3D printer | |
| Mixture:<br>PVP:Theo<br>50%:50%<br>Feeding = 175° C.<br>Extrusion = 165° C. | Printing was impossible |
| Extruded filament was very brittle | |
| Mixture<br>PVP:TEC:Theo<br>50%:10%:40%<br>Feeding = 110° C.<br>Extrusion = 100° C. | Unable to load. Printing was not possible |
| Filament was very fragile | |
| Mixture<br>PVP:TEC:Theo<br>50%:15%:35%<br>Feeding = 110° C.<br>Extrusion = 90° C. | Printing temp.<br>Extruder 130° C.<br>Plate 80° C.<br>Extrusion and printing was efficient<br>Tablet size 12 mm |
| Filament was flexible but strong enough | |
| Mixture<br>PVP:TEC<br>3.333:1<br>Feeding = 100° C.<br>Extrusion = 85° C. | Filament was too brittle and crushed by 3D printer, extrudes at 150° C. |
| Filament was hard | |
| Mixture<br>PVP:TEC:Ca phosphate<br>50%:15%:35%<br>Feeding 110° C.<br>Extrusion 95° C. | Printed at<br>Extruder 130° C.<br>Plate 50° C.<br>Unable to completely print a tablet. Blocks |
| Filament looks good but sticky!<br>PVP:TEC:Talc<br>50%:15%:35%<br>Feeding 100° C.<br>Extrusion 90° C. | Printing temp.<br>Extruder 115° C.<br>Plate 60° C.<br>The extruder blocks after few tabs |
| Filament was flexible and white<br>PVP:TEC:Ca Pho:talc<br>50%:15%:28%:7%<br>Feeding 100° C.<br>Extrusion 90° C. | Extrude 105° C.<br>Plate 60° C.<br>Prints very deformed tablets |
| PVP:Tec:Ca ph:Talc<br>50%:15%:17.5%:17.5<br>Feeding 100° C.<br>Extrusion 90° C. | Prints temp<br>Extruder 120° C.<br>Plate 60° C.<br>Nozzle blocks after few tabs |
| PVP:Tec:Talc:Theo<br>50%:15%:25%:10%<br>Feeding 100° C.<br>Extrusion 90° C. | Not possible to print |
| Filament was too flexible | |

The highlighted formulation (PVP:TEC:Theo 50%:15%:35%) appeared to be the most viable for producing filaments compatible with the 3D printing process. The next aim was to incorporate different model drugs at 10% concentration. These drugs are aspirin, diclofenac, prednisolone, and theophylline.

TABLE 25

| Date | Formulation composition and processing temperature | Compatibility with printing |
|---|---|---|
| | PVP:Tec:Talc:Prednisolone 50%:15%:25%:10% Feeding 100° C. Extrusion 90° C. Filament was too flexible | Not possible to print It is possible that prednisolone has a plasticizing effect. |
| 11.05.2015 | PVP:Tec:Talc:Diclofenac 50%:15%:25%:10% Feeding 100° C. Extrusion 90° C. | Printing temp Extruder 115° C. Plate 80° C. Was able to print although the filament was very brittle |
| | PVP:Tec:Talc:Aspirin 50%:15%:25%:10% Feeding 100° C. Extrusion 90° C. | Extrusion was hard Printing of deformed tablets. Printing temp Extruder 110° C. Plate 80° C. |
| 19.05.2015 | PVP k29-32:Tec:Talc:Aspirin 50%:10%:30%:10% Feeding 100° C. Extrusion 90° C. Filament seems good | Printing was successful Printing temp Extruder 115° C. Plate 80° C. |
| 20.05.2015 | PVP k29-32:Tec:Talc:theophylline 50%:10%:30%:10% Feeding 110° C. Extrusion 80° C. Filament seems good | Crushed by the gears of the extruder. Printing not successful. |
| | PVP k29-32:Tec:Talc:Diclofenac 50%:10%:30%:10% Feeding 100° C. Extrusion 90° C. Filament seems good | Crushed by the gears of the extruder |
| | PVP k29-32:Tec:Talc:Prednisolone 50%:10%:30%:10% Feeding 105° C. Extrusion 95° C. Filament seems good | Crushed by the gears of the extruder |
| 21.05.15 | PVP 40,000:Tec:Talc:Theophylline 50%:12.5%:27.5%:10% Feeding 100° C. Extrusion 95° C. Filament was strong enough and flexible | Printing was successful Printing temp Extruder 115° C. Plate 70° C. Tablets had issues sticking to the building plate |
| | PVP 40,000:Tec:Talc:Diclofenac 50%:12.5%:27.5%:10% Feeding 110° C. Extrusion 95° C. Filament was strong enough and flexible | |
| | PVP 40,000:Tec:Talc:Theophylline 50%:15%:25%:10% Feeding 100° C. Extrusion 95° C. Filament was too flexible and hard to feed as they stick to the gears. Dissolution test for Aspirin tablets (PVP k29-32:Tec:Talc:Aspirin 50%:10%:30%:10%) | Extrudes at 100° C. Plate 60° C. Printing deformed tablets probably due to low Tg. Same problem at 90° C. Extrusion stops below this temperature |
| 28.05.2015 | PVP 40,000:Tec:Diclofenac 66.7%:20%:13.3% Feeding 105° C. Extrusion 95° C. Filament was brown and transparent. It was too big to load into the printer | |
| | PVP 40,000:Tec:Aspirin 71.43%:14.29%:14.29% Feeding 105° C. Extrusion 95° C. Filament was clear and transparent, very flexible. Filament was bigger in some regions | Printing was not successful |
| | PVP 40,000:Tec:theophylline 68.97%:17.24%:13.79% Feeding 105° C. Extrusion 95° C. Cream coloured brittle filament. Crushed by the gears | Printing was not successful |
| 2.06.15 | PVP 40,000:Tec:Talc:Aspirin 50%:12.5%:27.5%:10% | Printing temp Extruder 110° C. |

TABLE 25-continued

| | | |
|---|---|---|
| Date | Formulation composition and processing temperature | Compatibility with printing |
| | Feeding 100° C.<br>Extrusion 90° C.<br>Filament was a little sticky, very flexible and white | Plate 70° C.<br>Printing was successful |
| | PVP 40,000:Tec:Talc:Prednisolone 50%:12.5%:27.5%:10%<br>Feeding 100° C.<br>Extrusion 90° C.<br>Filament was white and very flexible. It was compressed gears and was sticky. | Not successful |
| 25.06.2015 | They filament that was printed successfully were manufactured and the time for mixing reduced to 5 mins as temperature seem to have an effect on the polymers during HME | |
| 30.06.2015 | Formulation for diclofenac was changed as the previous (15% TEC) was giving problems.<br>PVP 40,000:Tec:Talc:Diclofenac 50%:17.5%:22.5%:10% | Printing successful<br>Printing temp<br>Extruder 115° C.<br>Plate 40° C.<br>Prints easily with few cases of blocking. Sometimes compressed by the gear |
| 07.07.2015 | Dissolution test for diclofenac tablets using manual dissolution in a phosphate buffer (7.4) | |

7.1.2—Preparation of PVP-Based Filaments for Making Immediate Release Dosage Forms The sample (10 g: 50% PVP40, 15% TEC, 25% Talc, 10% Theophylline) was prepared by weighing components in the required proportion and mixing them using mortar and pestle. The feeding temperature was set to 100° C. When the temperature was reached, the screw speed was set to 80 rpm and the mixture was manually fed into the running extruder. The sample was mixed for 5 minutes and extruded at 95° C. The torque was set at 0.4 Nm.

TABLE 26

Formulations and NME parameters

| | Drug | | |
|---|---|---|---|
| | Theophylline | Aspirin | Diclofenac sodium |
| Formulation | PVP 40: 50%<br>TEC: 12.5%<br>Talc: 27.5%<br>Theo: 10% | PVP 40: 50%<br>TEC: 12.5%/10%<br>Talc: 27.5%/30%<br>Asp: 10% | PVP 40: 50%<br>TEC: 17.5%<br>Talc: 22.5%<br>Diclo: 10% |
| Feeding temperature | 100° C. | 100° C. | 100° C. |
| Extrusion temperature | 90° C. | 90° C. | 90° C. |
| Screw speed | 80 rpm | 80 rpm | 80 rpm |
| Residence time | 5 min | 5 min | 5 min |
| Torque | 0.4 Nm | 0.4 Nm | 0.4 Nm |
| Die diameter | 1.25 mm | 1.25 mm | 1.25 mm |

Figure 79:
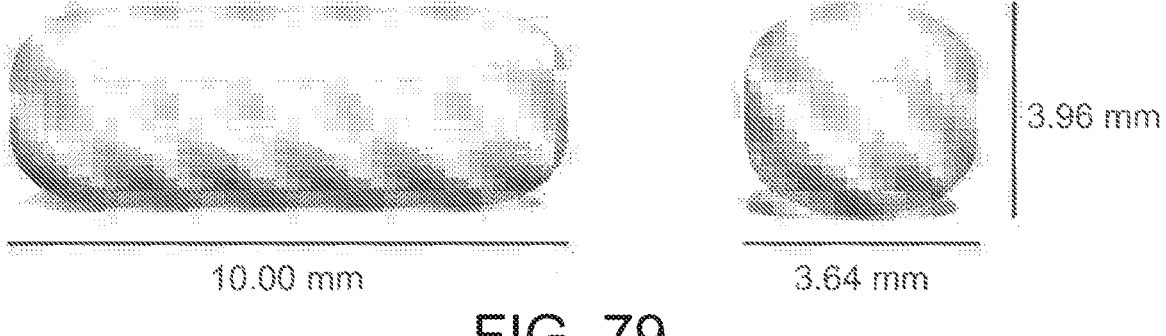
FIG. 79 is a diagram of the tablet structure designed and imported into MakerBot Desktop Software.

For this study the oblong-shaped tablet design was created. As shown in FIG. 79 tablet structure was set to have dimensions of 10.00×3.96×3.64 mm (X, Y, Z). STL model was imported into MakerBot Desktop Software. The .stl (StereoLithography) is popular 3D printing file format and contains information about the printed object.

Tablets were printed by MakerBot Replicator® 2X Experimental 3D Printer (MakerBot Industries, LLC, New York, USA). The process was controlled with MakerBot Desktop Software (FIG. 5). Settings used for the print process are listed in Table 27 below.

Tablet model was imported into software by adding the .stl file. It showed up at the centre of the build plate. With the scale function selected the required dimensions were set (10.00×3.96×3.64 mm (X, Y, Z)).

Once the extruder reached the temperature of 110° C. the filament was loaded into the extruder. After loading the filament the following settings were selected within MakerBot Desktop Software: resolution: standard, infill: 100%, layer height: 0.2 mm, extruder temperature: 110° C., plate temperature: 40° C. Tablets were printed and packed into airtight plastic bags.

TABLE 27

Settings used during the 3D printing process

| | Drug | | |
|---|---|---|---|
| | Theophylline | Aspirin | Diclofenac sodium |
| Resolution | | Standard | |
| Layer height | | 0.2 mm | |
| Infill | | 100% | |
| Extruder temperature | 110° C. | 100° C. | 115° C. |
| Plate temperature | 40° C. | 90° C. | 40° C. |
| 3D Printer Nozzle | | 0.4 mm | |

In order to obtain the highest quality of the printed tablets few modifications were made. A Blue Scotch Blue painter's tape was added to build plate to aid adhesion. It prevented objects from shaking and kept them firmly placed on the building plate during the printing process. Additionally, blue tape didn't need changing between processes and it was easy to peal tablets off the tape.

In case of theophylline for example, the extruder temperature was set to 110° C. It was 15° C. higher than extrusion temperature during producing filaments (Table 1). It was high enough to assure smooth filament extrusion through the nozzle and low enough to prevent the decomposition of the theophylline.

The building plate temperature was set to 40° C. This temperature did not give enough heat to melt tablets as it was observed with higher temperatures of the building plate. 40° C. provided enough adhesion to the build plate.

Since the polyvinylpyrrolidone is hygroscopic, filaments and tablets were stored in airtight plastic bags in a cool, dry place.

7.1.6—Characterisation of Tablets

The physical parameters of the printed tablets were evaluated. Uniformity of mass, uniformity of content, hardness, friability, and dissolution rate and disintegration time were evaluated according to the European Pharmacopeia (Ph. Eur.).

Tablet Shape and Size

Figure 80:
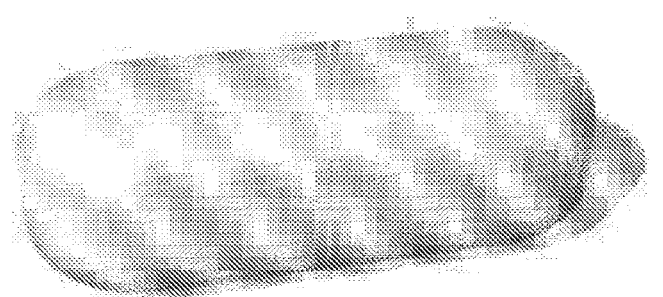
FIG. 80 is a diagrammatic representation of the geometry of 3D printed tablets.

The dimensions of the 3D printed tablets were determined by using Electronic Digital Micrometer (Marathon Management Company, Fisher Scientific). Ten tablets were randomly selected, measured individually and then compared to the design. The tablet geometry is depicted in FIG. 80.

Uniformity of Mass

The weights were determined by using Kern Analytical balance. Twenty tablets were randomly selected and weighed individually.

Uniformity of Content

Ten printed tablets were randomly selected and weighed individually. In order to assess theophylline content in the printed tablets, each tablet was sonicated in 500 ml volumetric flask containing 0.1 M HCl for 2 hours in an ultrasonic water bath (VWR Ultrasonic Cleaner). After sonication the samples were cooled to room temperature. The absorbance was measured at 272 nm in a spectrophotometer (Jenway) with 0.1 M HCl as a reference.

Drug Dissolution

The dissolution test was performed in 900 ml of 0.1M HCl at 50 rpm and 37±0.5° C. using Erweka DT 600 Dissolution Tester (Paddle apparatus). Manual sampling was performed. Six tablets were dropped into each of the vessels. 4 ml of dissolution sample was withdrawn at pre-determined time intervals (5, 10, 15, 20, 25, 30, 40, 50, 60 and 70 min) using 5 ml Luer-Lok syringes. Samples were filtered through a Millex-HA 0.45-μm filter. 4 ml of 0.1M HCl were replaced after sampling. The absorbance of samples was measured at 272 nm in a spectrophotometer (Jenway) with 0.1 M HCl as a reference.

Disintegration

The disintegration test was determined by Erweka ZT ×20 Disintegration Tester. Six tablets were placed in each of six tubes of the basket and the discs were added. The test was carried out in 750 ml of 0.1M hydrochloric acid at 37±0.5° C. At the end of 15 minutes, the basket was lifted from the medium.

Friability

The friability of the tablets was determined by Erweka Friability Tester. For this test, the sample of twenty tablets were weighed and placed in the drum. The drum was rotated 100 times at a speed 25 rpm. The tablets were removed from drum and then dusted and reweighed. The test was run once. Ideally, the weight loss should not be more than 1.

Hardness

The hardness of each tablet was determined by Erweka Tablet Hardness Tester. Each tablet was placed between the jaws of the apparatus and the measurement was carried out on 10 tablets. An average of ten readings was taken to determine the final hardness.

7.1.7—Testing

Figure 81:
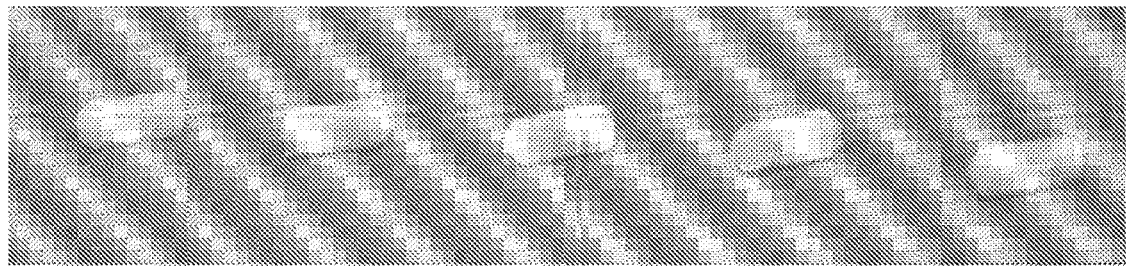
FIG. 81 shows images of successfully-printed PVP-based tablets, all with a uniform design.

FIG. 81 shows images of successfully-printed PVP-based tablets, all with a uniform design. This illustrates the viability and consistency of 3D printing with filaments in the production of tablets.

Figure 82:
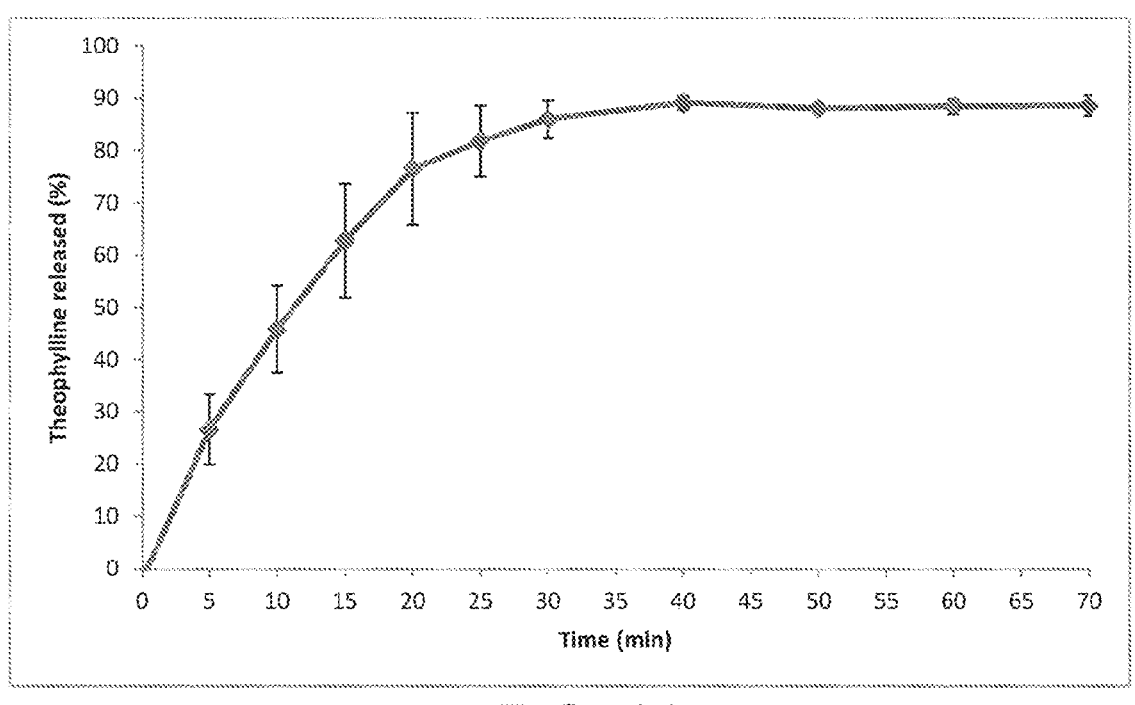
FIG. 82 shows a drug release profile for theophylline-loaded PVP-based tablets.

FIG. 82 shows a drug release profile for theophylline-loaded PVP-based tablets. This release profile suggests that the PVP carrier facilitates more rapid and more thorough release (cf. FIGS. 49-50).

Table 28 shows the weights of a statistical ensemble of 3D printed theophylline-loaded PVP-based tablets, and illustrates a very high degree of weight uniformity.

TABLE 28

Individual weights of a representative statistical ensemble (20 tablets in all) theophylline-loaded PVP-based tablets showing a high degree of weight uniformity

| Tablet number | Tablet weight |
|---|---|
| 1 | 103.39 |
| 2 | 103.57 |
| 3 | 104.96 |
| 4 | 105.3 |
| 5 | 105.8 |
| 6 | 106.45 |
| 7 | 107.6 |
| 8 | 107.71 |
| 9 | 110.48 |
| 10 | 110.73 |
| 11 | 110.93 |
| 12 | 112.47 |
| 13 | 112.72 |
| 14 | 113.21 |
| 15 | 114.53 |
| 16 | 115.99 |
| 17 | 116.99 |
| 18 | 118.43 |
| 19 | 118.56 |
| 20 | 120.28 |
| Mean | 111.005 |
| STDEV | 5.30 |
| % STDEV | 4.78 |

Disintegration rates were measured for a statistical ensemble of 3D printed theophylline-loaded PVP-based tablets (6 in total), all of which disintegrated in approximately 13 minutes.

Table 29 shows the total weight of 20 3D printed theophylline-loaded PVP-based tablets before and after completion of a friability test. The result shows that the tablets have statistically the same weight and are thus non-friable.

TABLE 29

Weight of 20 tablets before and after friability test for theophylline-loaded PVP-based tablets

| 25 rev/min | Tablet weight |
|---|---|
| 0 | 2198.4 mg |
| 100 | 2204.9 mg |

TABLE 30

Hardness measurements for theophylline-loaded PVP-based tablets Hardness test (11 tablets)

| Tablet number | Force (N) |
|---|---|
| 1 | 333 |
| 2 | 349 |
| 3 | 377 |

TABLE 30-continued

Hardness measurements for theophylline-loaded PVP-based tablets
Hardness test (11 tablets)

| Tablet number | Force (N) |
|---|---|
| 4 | 420 |
| 5 | 409 |
| 6 | 362 |
| 7 | 349 |
| 8 | 415 |
| 9 | 372 |
| 10 | 388 |
| 11 | 397 |
| Mean | 379 |
| STDEV | 29 |

Table 30 shows the results of hardness tests upon a statistical ensemble (11 tablets in all) of 3D printed theophylline-loaded PVP-based tablets. These results illustrate a substantially consistent hardness for all tablets.

Figure 83:
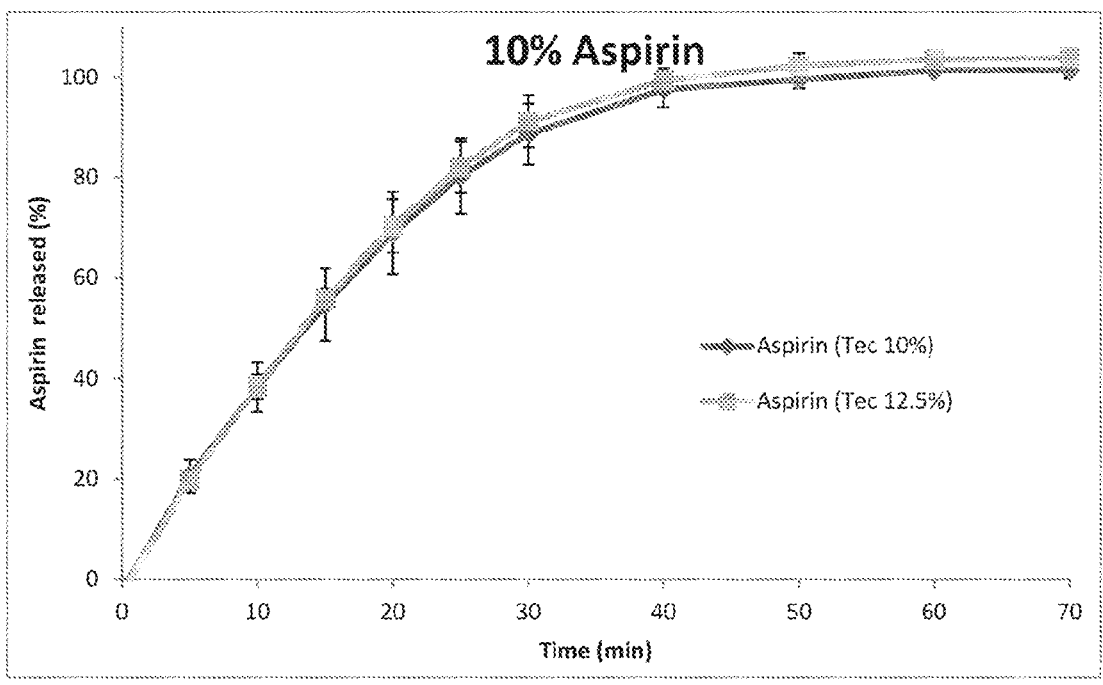
FIG. 83 shows a drug release profile for aspirin-loaded PVP-based tablets.

FIG. 83 shows a drug release profile for aspirin-loaded PVP-based tablets.

Table 31 shows the weights of a statistical ensemble of 3D printed aspirin-loaded PVP-based tablets, and illustrates a very high degree of weight uniformity.

TABLE 31

Individual weights of a representative statistical ensemble (20 tablets in all) aspirin-loaded PVP-based tablets showing a high degree of weight uniformity

| Tablet number | Tablet weight |
|---|---|
| 1 | 103.39 |
| 2 | 106.09 |
| 3 | 106.47 |
| 4 | 106.63 |
| 5 | 106.85 |
| 6 | 109.56 |
| 7 | 110.51 |
| 8 | 110.79 |
| 9 | 111.28 |
| 10 | 112.47 |
| 11 | 112.55 |
| 12 | 113.15 |
| 13 | 114.33 |
| 14 | 114.36 |
| 15 | 114.39 |
| 16 | 114.82 |
| 17 | 116.4 |
| 18 | 118.53 |
| 19 | 118.86 |
| 20 | 119.63 |
| Mean | 112.053 |
| STDEV | 4.58 |
| % STDEV | 4.09 |

Disintegration rates were measured for a statistical ensemble of 3D printed aspirin-loaded PVP-based tablets (6 in total), all of which disintegrated in approximately 8 minutes.

Table 32 shows the total weight of 20 3D printed aspirin-loaded PVP-based tablets before and after completion of a friability test. The result shows that the tablets have statistically the same weight and are thus non-friable.

TABLE 32

Weight of 20 aspirin tablets before and after friability test for aspirin-loaded tablets

| 25 rev/min | Tablet weight |
|---|---|
| 0 | 2218.63 mg |
| 100 | 2220.36 mg |

TABLE 33

Hardness measurements for aspirin-loaded PVP-based tablets

| Tablet number | Force (N) |
|---|---|
| 1 | 411 |
| 2 | 397 |
| 3 | 426 |
| 4 | 445 |
| 5 | 423 |
| 6 | 397 |
| 7 | 415 |
| 8 | 372 |
| 9 | 388 |
| 10 | 397 |
| Mean | 407.1 |
| STDEV | 21.15 |

Table 33 shows the results of hardness tests upon a statistical ensemble (10 tablets in all) of 3D printed aspirin-loaded PVP-based tablets. These results illustrate a substantially consistent hardness for all tablets.

Figure 84:
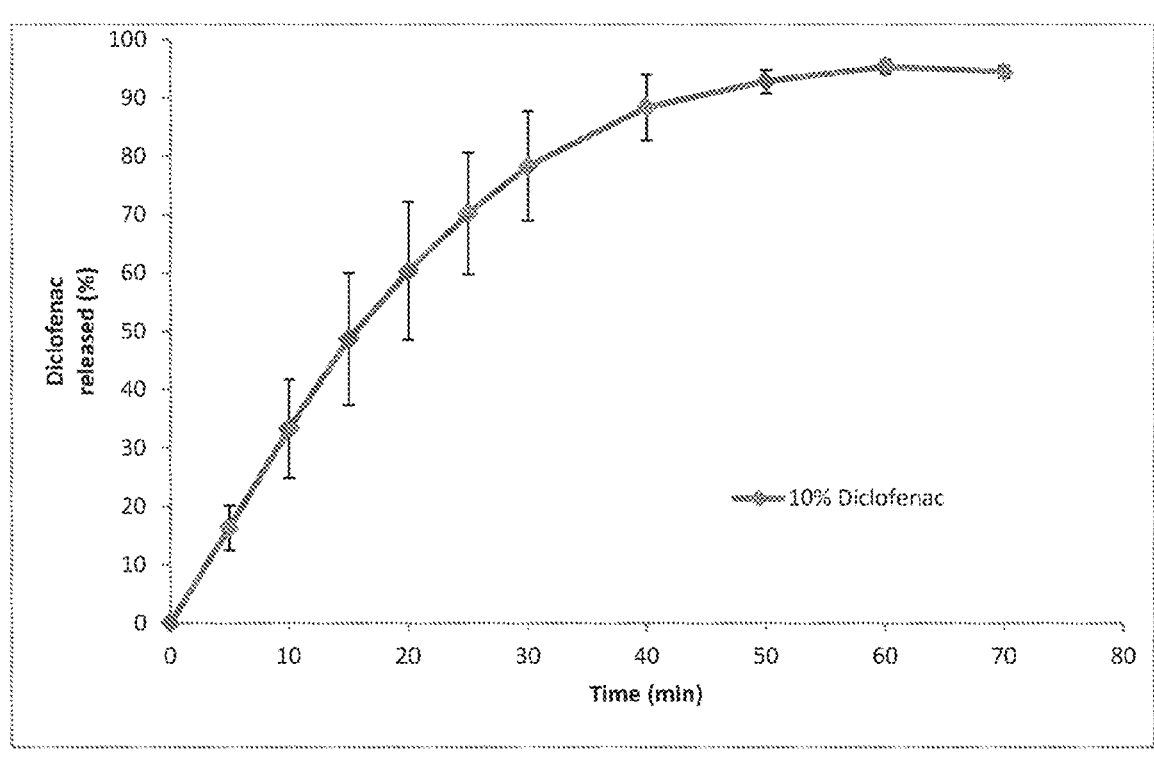
FIG. 84 shows a drug release profile for diclofenac-loaded PVP-based tablets.

FIG. 84 shows a drug release profile for diclofenac-loaded PVP-based tablets.

Table 34 shows the weights of a statistical ensemble of 3D printed diclofenac-loaded PVP-based tablets, and illustrates a very high degree of weight uniformity.

TABLE 34

Individual weights of a representative statistical ensemble (20 tablets in all) diclofenac-loaded PVP-based tablets showing a high degree of weight uniformity

| Tablet number | Tablet weight (mg) |
|---|---|
| 1 | 141.11 |
| 2 | 129.49 |
| 3 | 124.22 |
| 4 | 134.33 |
| 5 | 123.97 |
| 6 | 124.00 |
| 7 | 129.26 |
| 8 | 127.48 |
| 9 | 104.40 |
| 10 | 145.42 |
| 11 | 125.63 |
| 12 | 127.77 |
| 13 | 104.65 |
| 14 | 124.75 |
| 15 | 130.92 |
| 16 | 122.20 |
| 17 | 122.05 |
| 18 | 136.56 |
| 19 | 128.89 |
| 20 | 114.77 |
| Mean | 126.0935 |
| STDEV | 10.10 |
| % STDEV | 8.01 |

Disintegration rates were measured for a statistical ensemble of 3D printed diclofenac-loaded PVP-based tablets (6 in total), all of which disintegrated in approximately 22 minutes.

Table 32 shows the total weight of 20 3D printed aspirin-loaded PVP-based tablets before and after completion of a friability test. The result shows that the tablets have statistically the same weight and are thus non-friable.

TABLE 35

Weight of 20 aspirin tablets before and after friability test for diclofenac-loaded tablets

| 25 rev/min | Tablet weight |
| --- | --- |
| 0 | 2508.83 mg |
| 100 | 2512.02 mg |

TABLE 36

Hardness measurements for diclofenac-loaded PVP-based tablets

| Tablet number | Force (N) |
| --- | --- |
| 1 | 406 |
| 2 | 383 |
| 3 | 414 |
| 4 | 428 |
| 5 | 445 |
| Mean | 415 |
| STDEV | 23 |

Table 36 shows the results of hardness tests upon a statistical ensemble (5 tablets in all) of 3D printed diclofenac-loaded PVP-based tablets. These results illustrate a substantially consistent hardness for all tablets.

It was possible to fabricate immediate release tablets using a combination of PVP-TEC as a melting component and talc as a non-melting component. It was important to change the concentration of TEC to achieve a suitable flexibility of the filament for the 3D printing process. Calcium tribasic phosphate was less suitable for 3D printing process due to the stickiness of the filament which tend to adhere to itself or to the printer gears. Theophylline and aspirin tablets were possible to 3D print and comply with most pharmacopeial criteria. The tablets enjoyed a high crushing strength and negligible friability.

7.2—Model Studies Using Various PEG Polymeric Drug Carriers in FDM 3D Printing

Polyethylene Glycol is one of the most used polymers in pharmaceutical and medical applications. Many oral, parental, dermal, ocular and rectal formulations contain PEG as an ingredient. In many formulations PEG is used as coating agent; ointment base; plasticizing agent; solvent; suppository base; tablet and capsule diluent; tablet and capsule lubricant. It is generally regarded as safe and is classified as GRAS by FDA. It is of vital importance to incorporate such an important polymer in the 3d printing process. The aim of this work is to explore the feasibility of printing tablets based on PEG as a melting component in combination with talc as a non-melting component. PEG with different molecular weight will be included in this screening.

Table 37 shows details of a formulation screen carried out to better understand the factors and parameters involved in 3D printing of filaments containing PEG polymers. Various different molecular weights of PEG were employed, including $M_w$ of 0.4k, 10k, 20k, 100k, 200k, 300k, 400k, and sometimes mixtures thereof (e.g. 200k with 0.4k). Ratios of PEG to non-melting component (e.g. talc) were also varied and, in some examples, PEG was co-mixed with other carrier polymers, such as Eudragit® and PVP-based polymers. In some examples, a model drug compound (Theophylline was present)

TABLE 37

Formulation screen and observations for various PEG-based systems

| | |
| --- | --- |
| PEG 10,000:Talc 50%:50% Feeding 62° C. Extrusion 50° C. Filament was very fragile | Crushed by the gears of the extruder |
| PEG 20,000:talc 50%:50% Feeding 62° C. Extrusion 50° C. Filament was very fragile | Crushed by the gears of the extruder |
| PEG 20,000:PEG 400:talc 45%:5%:50% Feeding 62° C. Extrusion 47° C. Filament was very fragile and brittle | Impossible to print: fragile filament |
| PEG 20,000:ca phosphate 50%:50% Feeding 62° C. Extrusion 41° C. | Impossible to print |
| PEG 20,000:Talc 40%:60% Feeding 64° C. Extrusion 54° C. | Impossible to print |
| PEG 20,000:Talc 30%:70% Feeding 69° C. Extrusion 59° C. | Impossible to print |
| PEG 20,000:Talc 35%:65% Feeding 68° C. Extrusion 58° C. Filament breaks during extrusion. Very fragile and brittle | Impossible to print |

TABLE 37-continued

| Formulation screen and observations for various PEG-based systems | |
| --- | --- |
| PEG 20,000:Talc<br>45%:55%<br>Feeding 65° C.<br>Extrusion 53° C. | Impossible to print: fragile<br>filament |
| PEG 20,000:Talc:Eudragit ® E<br>30%:60%:10%<br>Feeding 100° C.<br>Extrusion 90° C.<br>Filament was very fragile | Impossible to print |
| PEG 20,000:Talc:Eudragit ® E<br>30%:50%:20%<br>Feeding 100° C.<br>Extrusion 90° C.<br>Filament dark and fragile | Impossible to print |
| PEG 20,000:Talc:PVP K29-32<br>30%:50%:20%<br>Feeding 105° C.<br>Extrusion 95° C.<br>Filaments were fragile | |
| PEG 600,000:Talc<br>50%:50%<br>Feeding 140° C.<br>Extrusion 140° C.<br>Filament was very strong and dark | Impossible to print |
| PEG 200,000<br>Feeding 80° C.<br>Extrusion 75° C.<br>5 min mixing time<br>Filament was very strong and flexible. Powder was<br>very compactible, therefore very short filament was<br>produced | Impossible to print but looks<br>promising as the printer draws<br>initial priming lines |
| PEG 100,000<br>Feeding 80° C.<br>Extrusion 75° C.<br>Filament was flexible and strong | Printing shows some<br>potentials. Draws the initial<br>priming line but unable to build<br>the layers |
| PEG 100,000:Talc<br>Feeding 75° C.<br>Extrusion 70° C.<br>5 min mixing time<br>Filament was strong and flexible | Extrusion was very slow even<br>at very high temperature.<br>Unable to print. |
| PEG 200,000:Talc<br>50%:50%<br>Feeding 80° C.<br>Extrusion 75° C.<br>5 min mixing time | Filament is being crushed by<br>the gears. |
| PEG 300,000:Talc<br>50%:50%<br>Feeding 90° C.<br>Extrusion 85° C.<br>5 min mixing time | Not able to print |
| PEG 400,000:Talc<br>50%:50%<br>Feeding 100° C.<br>Extrusion 95° C.<br>5 min mixing time | Not able to print |
| PEG 200,000:Talc<br>70%:30%<br>Feeding 80° C.<br>Extrusion 75° C.<br>5 min mixing time<br>Filament was strong and flexible | Printing temp<br>Extruder 145° C.<br>Plate 30° C.<br>Tablets were deformed but<br>became better when the size<br>was increased from 10 mm to<br>15 mm. printing parameter was<br>modified for slow printing |
| PEG 300,000:Talc<br>70%:30%<br>Feeding 90° C.<br>Extrusion 85° C.<br>5 min mixing time<br>Filament was strong and flexible | Similar problem with PEG<br>200,000 |
| PEG 200,000:Talc<br>65%:35%<br>Feeding 80° C.<br>Extrusion 75° C.<br>5 min mixing time<br>Filament was strong and flexible | Printing was not successful but<br>extrusion was better when the<br>head movement was slow<br>Extruder 200° C.<br>Plate 30° C. |
| PEG 200,000:Talc<br>70%:30%<br>Feeding 80° C. | |

TABLE 37-continued

| Formulation screen and observations for various PEG-based systems |
| --- |

| | |
| --- | --- |
| Extrusion 75° C. | |
| 5 min mixing time | |
| Filament was strong and flexible. | |
| The polymer and its ratio to talc was chosen as it | |
| showed more 3D printing potentials. | |
| PEG 300,000:Talc | Printing was attempted using |
| 70%:30% | MakerGear. 0.35 mm nozzles |
| Feeding 90° C. | keeps blocking but this |
| Extrusion 85° C. | reduced when it was changed |
| 5 min mixing time | to 0.75 mm. Extrusion from the |
| | nozzles were very slow which |
| | was not efficient enough for |
| | printing. Also, extrusion can |
| | only be carried out from 170° C. |
| | using the MakerGear. |
| PEG 200,000:Talc | Printing was not successful |
| 90%:10% | |
| Feeding 80° C. | |
| Extrusion 75° C. | |
| 5 min mixing time | |
| This ratio was used to know if that improves | |
| melting and probably improve extrusion. | |
| PEG 200,000:Talc | Printing was successful. |
| 70%:30% | Makerbot printing parameters |
| Feeding 80° C. | were modified. Printing was |
| Extrusion 75° C. | slower and a fan was also |
| 5 min mixing time | used to speed up solidification. |
| | Had issues of not sticking to |
| | the plate. |
| | Printing temp: extruder 145° C., |
| | plate 40° C. |
| | Travel speed - 25 |
| | Z-axis travel speed - 23 |
| | First layer speed - 5 |
| | Infill speed - 10 |
| | Insert speed - 10 |
| | Outline speed - 5 |
| | Infill pattern - linear |
| | Layer height - 0.3 mm |
| | Infill layer height - 0.3 mm |
| PEG 200,000:Talc:Theo | Printing was successful |
| 70%:20%:10% | Sticking to the building plate |
| Feeding 80° C. | was not a problem but the |
| Extrusion 70° C. | Filament tangles with the gear |
| 5 min mixing time | during printing. |
| Nozzle 1.25 mm | |
| Dissolution test for PEG 200,000:Talc:Theo | Extended release kinetics was |
| 70%:20%:10% | obtained. |

Figure 85:
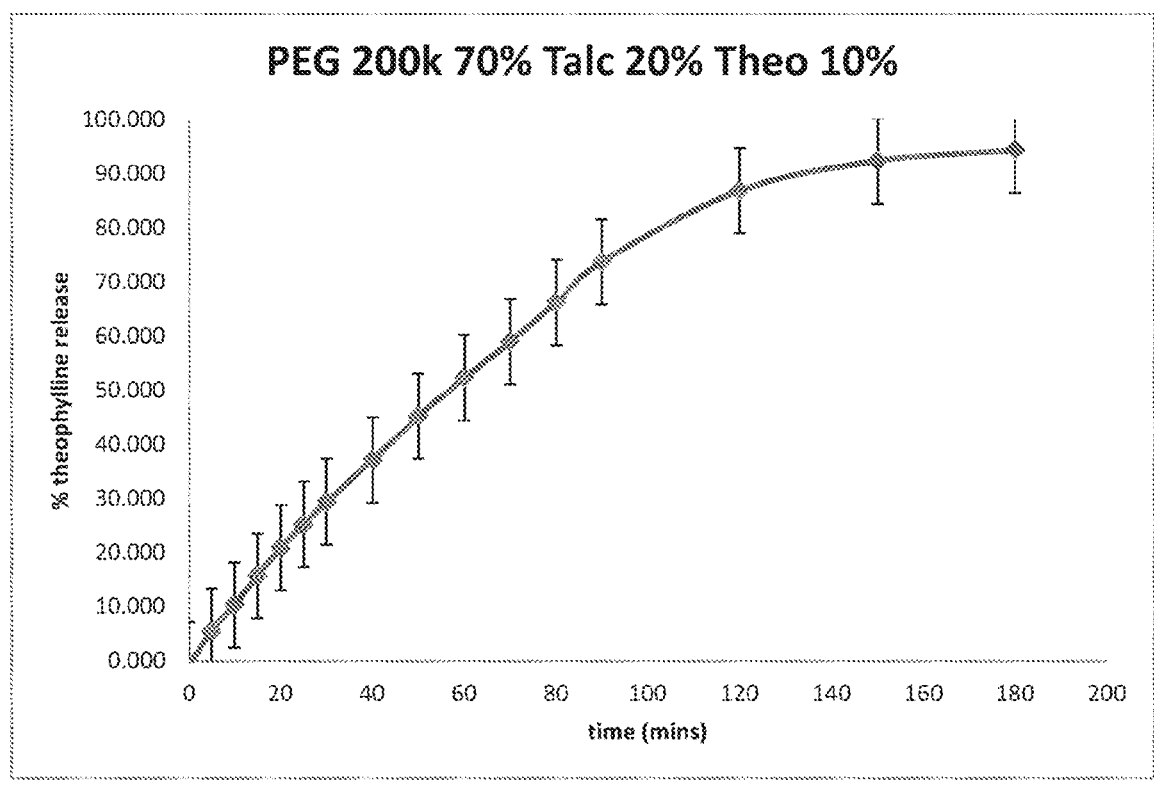
FIG. 85 shows the theophylline release profile for the successfully-printed filament composition of Table 37 containing PEG 200,000:Talc:Theo in a ratio of 70%:20%:10%.

FIG. 85 shows the theophylline release profile for the successfully-printed filament composition of Table 37 containing PEG 200,000:Talc:Theo in a ratio of 70%:20%:10%.

Figure 86:
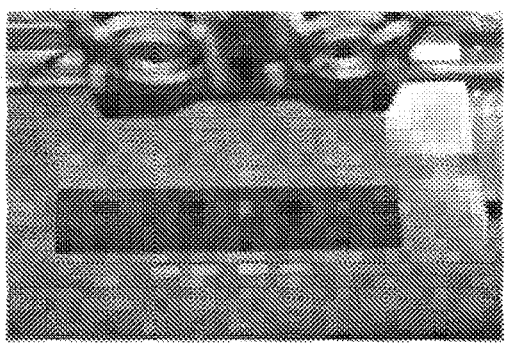
FIGS. 86 and 87 are photographic images of the successfully-printed PEG 200,000-based tablets.
Figure 87:
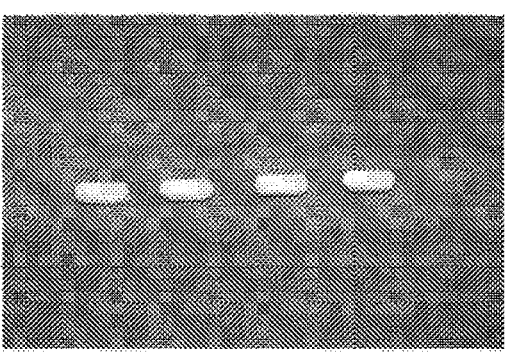

FIG. 86 and FIG. 87 are photographic images of the successfully-printed PEG 200,000-based tablets.

In the context of these model studies, low molecular weight PEG grades (e.g. <100,000) appeared to produce fragile and easy-to-break filaments when combined with talc.

Increasing the molecular weight of PEG led to the formation of increasingly strong filaments. PEG 200,000-300,000 appeared to produce the most suitable filament for 3D FDM printing process.

It is envisaged that higher $M_w$ PEGs contribute to the structural integrity of the filaments (and corresponding 3D-printed tablets), whereas low $M_w$ PEGs are likely to be more useful as a plasticizer (e.g. which could replace other plasticizers). As such, mixtures of PEGs of different molecular weights may be appropriate.

Example 8—Studies into Glass Transition Temperatures in 3D Printing

The inventors studied glass transition temperatures ($T_g$) for various HME-produced filaments deemed to be compatible with FDM 3D-printing. Glass transition temperatures of the filaments per se are considered potentially important when developing filament formulations, especially those specific to a particular drug substance where keeping nozzle temperatures low may be preferable to minimize any degradation.

Calculations of glass transition temperatures were based on a simplified version of the Gordon-Taylor equation, and we carried out based on the following assumptions:

1. The addition of drug had a negligible effect on the Tg of polymeric matrix.
2. The addition non-melting component such as talc and Ca tribasic phosphate had negligible effect on the Tg of polymeric matrix.
3. The density of different component in the matrix is equal.

Table 38 shows details of the glass transition temperature studies, including the relevant formulations.

TABLE 38

Details of glass transition temperature studies and calculations

| Filament formulation | Component % | Polymer | Tg (° C.) | Plasticiser | Tg (K) plasticiser | % | Calculated Tg of Filament (° C.) |
|---|---|---|---|---|---|---|---|
| Eudragit ® S100:Tec:Talc | 50:21.42:28.57 | S100 | 145 | TEC | 203.55 | 42.8 | 44.5 |
| Eudragit ® L100-55:Tec:Ca—P (Talc) | 50:16.67:33.33 | L55 | 110 | TEC | 203.55 | 33 | 41.1 |
| Eudragit ® E:Theo:TEC | 46.5/50/3.5 | E100 | 48 | TEC | 203.55 | 7.5 | 35.5 |
| Eudragit ® RL:Theo:TEC | 45:50:5 | RL | 70 | TEC | 203.55 | 11.1 | 48.0 |
| Eudragit ® RS:Theo:TEC | 42.5/50/7.5 | RS | 65 | TEC | 203.55 | 17 | 35.3 |
| HPC SSL:Theo:Triacetin | 46:50:4 | HPC SSL | 75 | Triacitin | 193.7 | 8.6 | 54.2 |
| PVP 29-32:Tec:Talc:Diclo | 50:15:25:10 | PVP 29-32 | 164 | TEC | 203.55 | 30 | 72.4* |
| PVP 29-32:Tec:Talc:Theo | 50:12.5:27.5:10 | PVP 29-32 | 164 | TEC | 203.55 | 25 | 82.3* |
| PVP 29-32:Tec:Talc:Asp | 50:10:30:10 | PVP 29-32 | 164 | TEC | 203.55 | 20 | 93.8* |

*The measured values are likely to be significantly lower based on the interference of adding drug molecule with the required concentration of TEC for successful printing.

There seems to be a preferred range of Tg for the melting component in the range of 30-95° C. More specifically the range is likely to be in the range of 31-60° C. we expect that any melting component of this range to be compatible with 3D printing provided that is thermally stable.

Example 9—Studies into Design and Fabrication of Enteric-Coated Tablets

Enterically-coated tablets are usually designed to protect the stomach from the drug or to protect an acid- or enzyme-labile drug from the stomach. Fabrication of such solid dosage forms pose a significant challenge given that the dose of this enteric preparation requires partition. Breaking enterically-coated tablets will inevitably damage the integrity of the enteric coating and compromise its gastric resistance function. Hence 3D printing of enteric-coated tablets should allow for tailoring of the dose for a particular patient without compromising the integrity of the dosage form.

In these model studies, the 3D printing of enteric-coated tablets was carried out via dual nozzle FDM 3D printer. Nozzle head one was loaded with the enteric polymer (e.g. Eudragit® L55-100) and the other nozzle is loaded with drug (PVP filament loaded with theophylline as a model drug).

Figure 88:
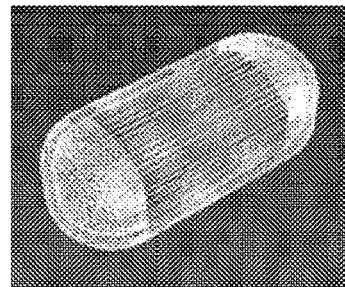
FIGS. 88, 89, and 90 illustrate an array of designs using 3D max software to represent the core (dark) and shell (light).
Figure 89:
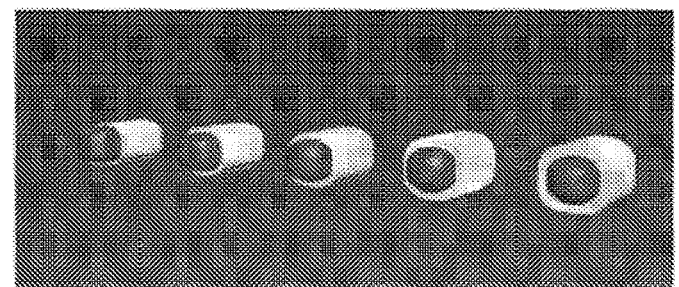
Figure 90:
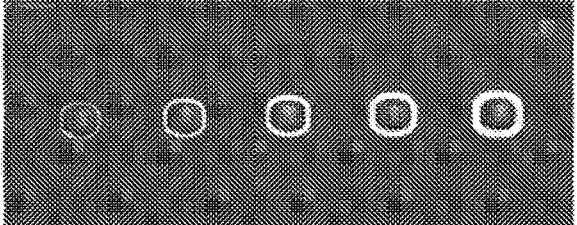

Five different designs are implemented, all designs share the same core (theophylline) while they have different shell thicknesses of 0.3, 0.6, 0.9, 1.2 and 1.5 mm. FIG. 88, FIG. 89, and FIG. 90 illustrate this array of designs using 3D max software to represent the core (dark) and shell (light).

One major challenge when printing these shell-core tablets is the co-ordination between the two nozzles during the printing process. As one nozzle is printing the other nozzle will remain at elevated temperatures, which can lead to degradation of material where a filament remains in contact with the temporarily unused nozzle. Many attempted solutions have involved retracting the filament from the 'standby nozzle head'. However, significant degradation can still take place in such scenarios.

In these experiments the inventors found that the use of olive oil BP, oleic acid, arachidonic acid and glycerol helps co-ordination between the two-nozzle and to evade drug-polymer filament degradation. Using such components to coat a filament is thought to provide a protective layer on the surface of the filament. Such components also have relatively high melting points and do not degrade at the processing temperature of the 3D nozzle.

It is envisaged that such protective filament coatings could be applied to any or all filaments, regardless of whether single-head or multi-head (e.g. dual-head) printing is used.

Example 9.1—Fabrication of Shell and Core Filaments

Shell

Eudragit® L100-55, TEC and Talc was mixed using a pestle and mortar in the ratio 50%:16.66%:33.33% respectively. The feeding temperature into the HME was 135° C. and the filament was extruded at 125° C. with 5 min mixing time (HME nozzle 1 mm).

Core

PVP, TEC, Talc and Theophylline were mixed using pestle and mortar in the 50%:9.5%: 0.5%:10% respectively. The feeding temperature in the HME was 100° C. and the filament was extruded at 90° C. after 5 mins mixing time (HME nozzle 1.25 mm).

Example 9.2-3D Printing of Core-Shell Tablets

Tablets were printed by MakerBot Replicator® 2X Experimental 3D Printer (MakerBot Industries, LLC, New York, USA). The process was controlled with MakerBot Desktop Software. Settings used for the print process are listed in Table 39 below.

Tablet model was imported into software by adding 2 different .stl files for shell and core. Left nozzle was assigned to print the core and the right nozzle to print the shell. It showed up at the centre of the build plate. With the scale function selected the required dimensions of the core (10.00×3.96×3.64 mm (X, Y, Z)).

Once the extruder reached the temperature of 110° C. the filament was loaded into the extruder. After loading the filament the following settings were selected within MakerBot Desktop Software: resolution: standard, infill: 100%, layer height: 0.2 mm, extruder temperature: 110° C., plate temperature: 40° C. Tablets were printed and packed into airtight plastic bags. Table 40 illustrates the dimensions and X, Y, Z coordinates for the core-shell tablets.

TABLE 39

Setting used during 3D printing of core-shell tablets

| | Drug | |
|---|---|---|
| | Shell | Core |
| Resolution | standard | standard |
| Layer height | 0.3 mm | 0.3 mm |
| Infill | 100% | 100% |

TABLE 39-continued

| Setting used during 3D printing of core-shell tablets | | |
|---|---|---|
| | Drug | |
| | Shell | Core |
| Extruder temperature | 180° C. | 115° C. |
| Plate temperature | 70° C. | |
| 3D Printer Nozzle | 0.4 mm | 0.4 mm |

TABLE 40

| Dimensions and X, Y, Z co-ordinates for core-shell structures | | | |
|---|---|---|---|
| | X (mm) | Y (mm) | Z (mm) |
| Core (0 mm shell) | 17.19 | 6.81 | 6.25 |
| 0.3 mm shell | 17.79 | 7.40 | 6.85 |
| 0.6 mm shell | 18.38 | 8.00 | 7.45 |
| 0.9 mm shell | 18.99 | 8.61 | 8.05 |
| 1.2 mm shell | 19.59 | 9.20 | 8.65 |
| 1.5 mm shell | 20.19 | 9.81 | 9.25 |

9.3—pH Change Dissolution Test

In vitro drug release studies for all gastro-resistant coating formulations used in this study were conducted in dissolution USP II apparatus (AT 7 Smart, SOTAX, Switzerland). Each experiment was carried out in triplicate in a dissolution medium at 37±0.5° C. with paddle speed of 50 rpm. The tablets were tested in 750 mL of a stimulated gastric fluid (0.1M HCl, pH 1.2) for 2 hours, followed by 4-hour exposure to pH 6.8 phosphate.

Within all the experiment the amount of released theophylline was determined at 5 min intervals by UV/VIS spectrophotometer (PG Instruments Limited, UK) at the wavelength of 272 nm and path length of 1 mm. Data was analysed using IDISis software (Automated Lab, 2012).

Figure 91:
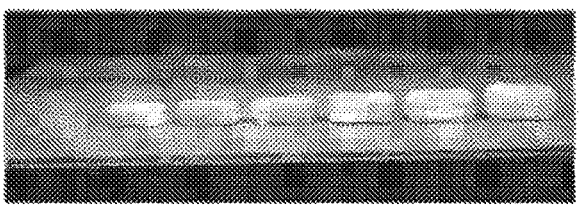
FIG. 91 shows a photograph of 3D printed theophylline PVA based core (left) and shell-core structure with increasing shell thickness of 0.3, 0.6, 0.9, 1.2 and 1.5 mm Eudragit® L100-55 shell.

FIG. 91 shows a photograph of 3D printed theophylline PVA based core (left) and shell-core structure with increasing shell thickness of 0.3, 0.6, 0.9, 1.2 and 1.5 mm Eudragit® L100-55 shell.

Figure 92:
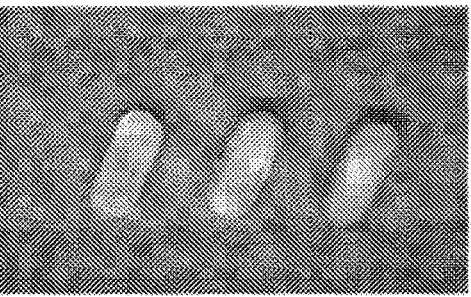
FIG. 92 shows a sectioned core-shell tablet (left) and 100% completed tablets (middle and right).

FIG. 92 shows a sectioned core-shell tablet (left) and 100% completed tablets (middle and right).

Figure 93:
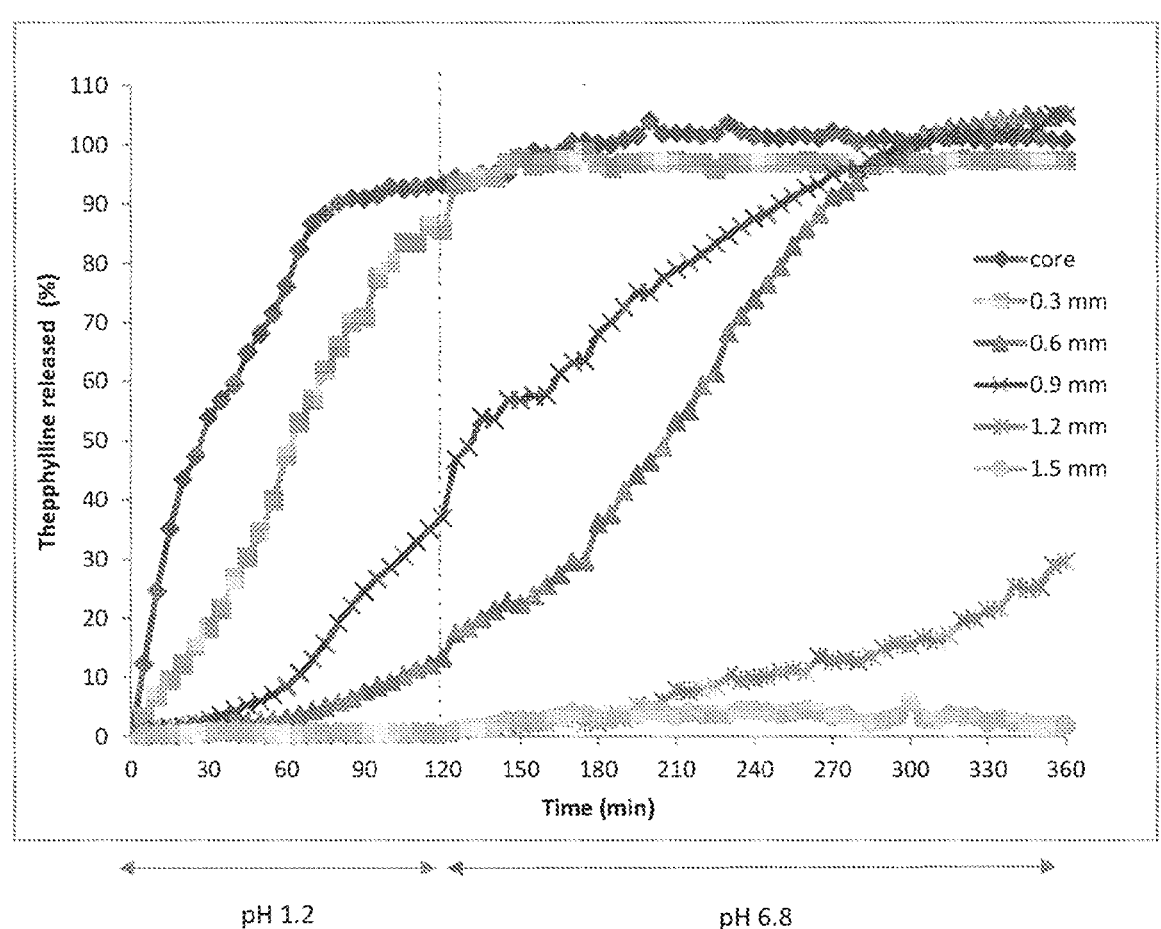
FIG. 93 shows a drug release profile based on in vitro dissolution of core only and a shell-core structures with increasing thickness of enteric shell.

FIG. 93 shows a drug release profile based on in vitro dissolution of core only and a shell-core structures with increasing thickness of enteric shell.

In vitro dissolution tests indicated that shell-core structure appeared to show a pH dependent release profile. The onset of drug release was 30, 60, 180 for shell thicknesses of 0.6, 0.9, 1.2 mm thickness. Despite the spaces between fused polymeric filaments (as previously viewed with SEM) the coating layer managed to suppress drug release from the core. This might be related to the swelling behaviour of Eudragit® polymers in aqueous media, which might have sealed the inter-filament spaces within the shell structure. The coating thickness of 0.3 and 1.5 mm are too thin or too thick for enteric formulation. Fine-tuning and further optimization of shell thickness and the core size will allow the creation of enteric coated extend release (e/c m/r) system.

Example 10—Zero-Order Extended Release Formulation with Shell Structure 10.1—Preparation of Shell-Structure for Zero Order Extended Release.

The filament for the "shell" of the solid form was prepared by mixing together Eudragit® RL, Tec and Talc using a pestle and mortar in the ratio 45%:5%:50% respectively. The feeding temperature into the HME was 130° C. and the filament was extruded at 120° C. with 5 min mixing time (HME nozzle is 1.25 mm).

The filament containing the active was prepared by mixing together PVP, Tec, Talc and Theophylline using pestle and mortar in the ratio 50%:9.5%:30.5%:10% respectively. The feeding temperature in the HME was 100° C. and the filament was extruded at 90° C. after 5 mins mixing time (HME nozzle is 1.25 mm).

Table 41 shows the key parameters used to produce and print the respective filaments.

TABLE 41

| Parameters for preparing and printing core and shell filaments | | |
|---|---|---|
| | Drug | |
| | Shell | core |
| Resolution | Standard | |
| Layer height | 0.3 mm | |
| Infill | 100% | |
| Extruder temperature | 175° C. | 115° C. |
| Plate temperature | 70° C. | |
| 3D Printer Nozzle | 0.4 mm | |

Figure 94:
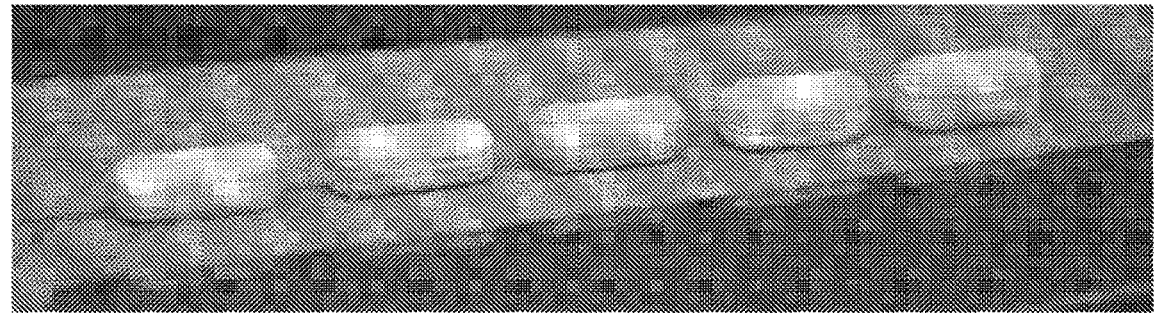
FIG. 94 shows a photograph of PVP-based core (left-most) theophylline tablets and a series of core-shell structures with increasing (right-to-left) shell diameters.

FIG. 94 shows a photograph of PVP-based core (leftmost) theophylline tablets and a series of core-shell structures with increasing (right-to-left) shell diameters as shown.

Figure 95:
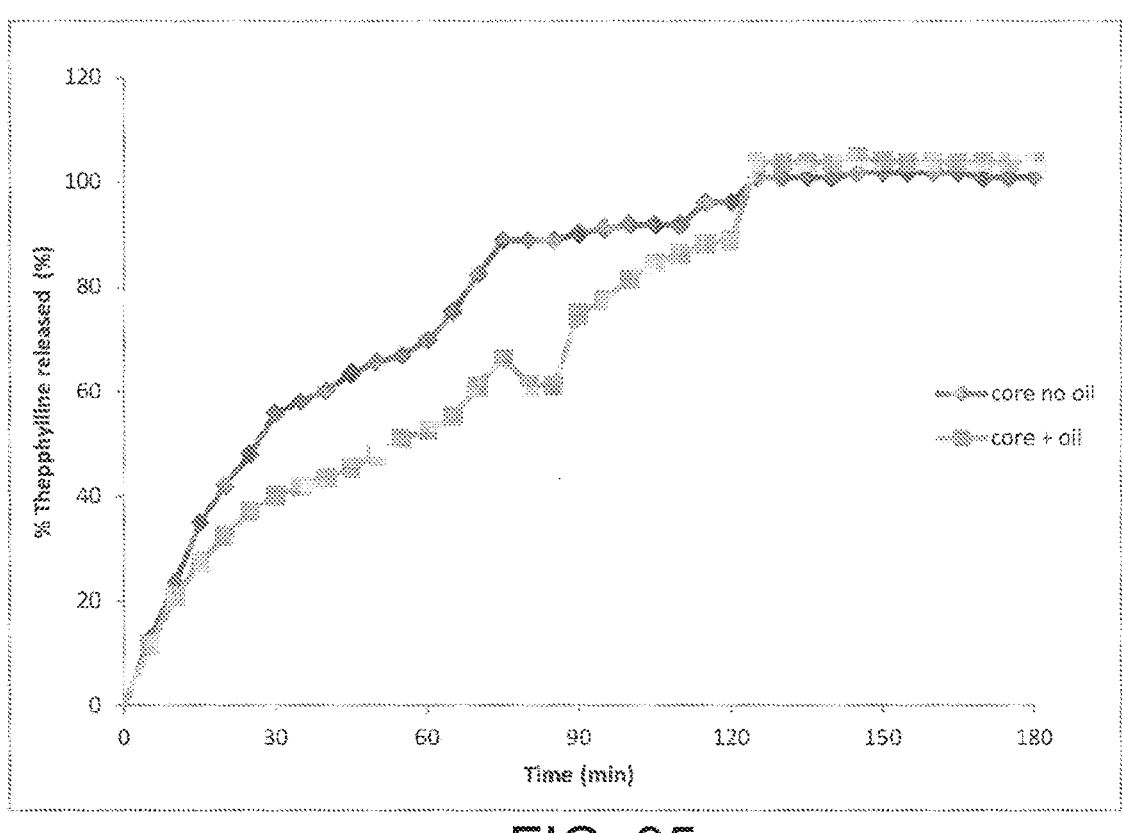
FIG. 95 shows a corresponding drug-release profile for dosage forms with and without oil (in this case Olive Oil BP) applied to the surface of the filament before printing.

FIG. 95 shows a corresponding drug-release profile for dosage forms with and without oil (in this case Olive Oil BP) applied to the surface of the filament before printing.

The result indicated that the application of oil slowed down the release of the drug from the core. This is expected as the oil is likely to render the core more hydrophobic and extend the release time.

Figure 96:
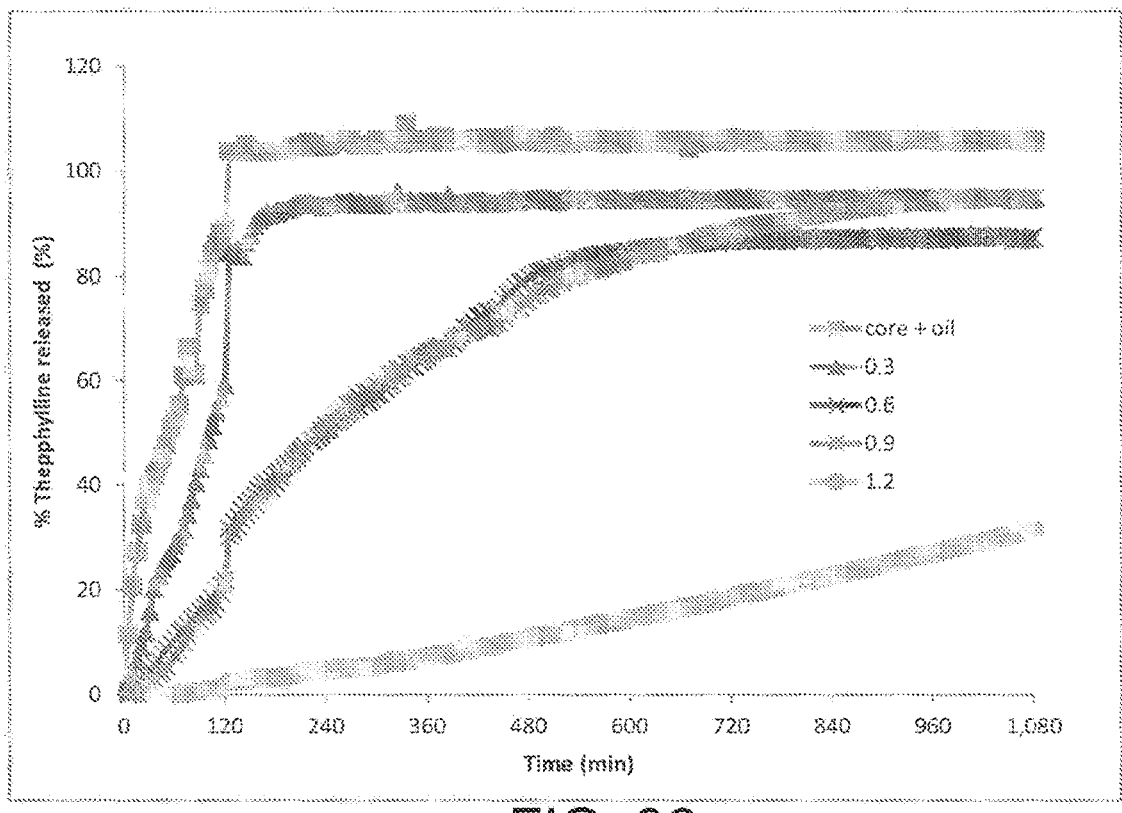
FIG. 96 shows drug release profiles for each of the drugs illustrated in FIG. 94, illustrating that zero-order kinetics are achievable using the 3D printing filaments of the invention.

FIG. 96 shows drug release profiles for each of the drugs illustrated in FIG. 94, illustrating that zero-order kinetics is achievable using the 3D printing filaments of the invention.

The results indicated that the shell-core structures (thickness of 0.3, 0.6 and 0.9 mm) was slightly extended but did not show an extended release pattern. This could be due to the poor physical resistance of the shell which de-capped during the dissolution test, and hence allow the core to dissolve at much faster rate. In case of shell-core (shell thickness of 1.2 mm), zero-order release kinetics were achieved, leaving the shell (membrane) still intact as illustrated by the photographs in FIG. 97.

Figure 97:
FIG. 97 shows photographs of shell-core tablets after 24 dissolution test of the tablets.

FIG. 97 shows photographs of shell-core tablets after 24 dissolution test of the tablets.

What is claimed is:

1. A printer cartridge for a fused filament fabrication (FFF) 3D printer, comprising:

a housing containing an active ingredient-containing printing filament, wherein the active ingredient-containing printing filament consists of, consists essentially of, or comprises an active ingredient-containing filament composition comprising: the active ingredient and an active ingredient carrier;

wherein the printer cartridge is releasably engageable with or releasably installable within the printer;

wherein the printer cartridge further comprises attachment mechanisms;

wherein the printer cartridge further comprises an integral printer nozzle through which the active ingredient-containing printing filament is deliverable during printing.

2. The printer cartridge as claimed in claim 1, wherein the printer nozzle is selectively heatable.

3. The printer cartridge as claimed in claim 2, wherein the printer nozzle is selectively heatable via the printer.

4. The printer cartridge as claimed in claim 1, wherein the printer cartridge further comprises a conveyor mechanism operable to convey the active ingredient-containing printing filament through a printer nozzle during printing.

5. The printer cartridge as claimed in claim 4, wherein the conveyor mechanism comprises a feed channel along which the active ingredient-containing printing filament is feedable during conveyance to the printer nozzle; wherein the feed channel comprises one or more conveyor elements operable to frictionally engage or grip the active ingredient-containing printing filament as the active ingredient-containing printing filament is conveyed.

6. The printer cartridge as claimed in claim 5, wherein one or more of the conveyor elements comprises a roller or set of rollers which engage with or grip the active ingredient-containing printing filament during conveyance thereof.

7. The printer cartridge as claimed in claim 4, wherein the conveyor mechanism is releasably engageable with a mechanical drive mechanism associated with or integral to the printer.

8. The printer cartridge as claimed in claim 1, wherein the printer cartridge is sealed.

9. The printer cartridge as claimed in claim 1, wherein the active ingredient-containing printing filament is formed via hotmelt extrusion of a hotmelt mixture prepared by mixing together at least the pharmaceutical active ingredient and the active ingredient carrier.

10. The printer cartridge as claimed in claim 9, wherein the mixing together is performed at a mixing temperature (T1) that is between 70 and 150° C. and the hotmelt extrusion is performed at a hotmelt extrusion temperature (T2) that is 10 to 50° C. lower than the mixing temperature.

11. The printer cartridge as claimed in claim 10, wherein the active ingredient carrier is a polymer having a glass transition temperature at least 50° C. lower than the melting point of the pharmaceutical active ingredient.

12. The printer cartridge as claimed in claim 1, wherein the active ingredient-containing printing filament comprises a plurality of active ingredients.

13. The printer cartridge as claimed in claim 1, wherein the active ingredient-containing printing filament comprises a disintegrant.

14. The printer cartridge as claimed in claim 1, wherein the active ingredient carrier is selected from the group consisting of:
  an (optionally alkyl-, suitably methyl-or ethyl-) acrylate, methacrylate and/or ethacrylate polymer or copolymer;
  a cellulose or cellulose derivative;
  polyvinyl alcohol (PVA);
  poly (lactic-co-glycolic acid) (PLGA);

a PVP or PVP-based carrier; and
a PEG or PEG-based carrier; and
any combination thereof.

15. The printer cartridge as claimed in claim 1, wherein the active ingredient carrier comprises at least one polymer or co-polymer selected from the group consisting of:
  an acrylate, methacrylate and/or ethacrylate copolymer comprising amine-containing monomeric units;
  an alkyl-acrylate, alkyl-methacrylate and/or alkyl-ethacrylate copolymer comprising amine-containing monomeric units;
  an methyl-acrylate, methyl-methacrylate and/or methyl-ethacrylate copolymer comprising amine-containing monomeric units;
  an ethyl-acrylate, ethyl-methacrylate and/or ethyl-ethacrylate copolymer comprising amine-containing monomeric units;
  an acrylate, methacrylate and/or ethacrylate polymer or copolymer free of any amine-containing monomeric units;
  an alkyl-acrylate, alkyl-methacrylate and/or alkyl-ethacrylate polymer or copolymer free of any amine-containing monomeric units;
  an methyl-acrylate, methyl-methacrylate and/or methyl-ethacrylate polymer or copolymer free of any amine-containing monomeric units;
  an ethyl-acrylate, ethyl-methacrylate and/or ethyl-ethacrylate polymer or copolymer free of any amine-containing monomeric units;
  a cellulose or cellulose derivative;
  a polyvinyl alcohol (PVA); and
  a poly (lactic-co-glycolic acid) (PLGA).

16. The printer cartridge as claimed in claim 1, wherein the active ingredient-containing printing filament further comprises a plasticizer.

17. The printer cartridge as claimed in claim 16, wherein the plasticizer is selected from the group consisting of one or more of triethylcitrate (TEC), glycerol, castor oil, oleic acid, glycerol, triacetin and a polyalkylene glycol.

18. The printer cartridge as claimed in claim 1, wherein the active ingredient-containing printing filament further comprises one or more fillers, where the filler is different from the active ingredient carrier, and wherein the filler has a melting point of at least 200° C.

19. The printer cartridge as claimed in claim 1, wherein the active ingredient-containing printing filament comprises greater than or equal to 5 wt % active ingredient.

20. The printer cartridge as claimed in claim 1, wherein the active ingredient-containing printing filament has a diameter or maximum thickness of between 0.1 mm and 5 mm.

21. The printer cartridge as claimed in claim 1, wherein the printer cartridge is configured for releasable docking within a docking station within the printer.

22. The printer cartridge as claimed in claim 1, wherein the printer cartridge is a disposable printer cartridge.

* * * * *